United States Patent
Brameld et al.

(10) Patent No.: US 9,630,963 B2
(45) Date of Patent: Apr. 25, 2017

(54) QUINOLONE DERIVATIVES AS FIBROBLAST GROWTH FACTOR INHIBITORS

(71) Applicant: Principia Biopharma, Inc., South San Francisco, CA (US)

(72) Inventors: Kenneth Albert Brameld, Menlo Park, CA (US); Erik Verner, Belmont, CA (US)

(73) Assignee: PRINCIPIA BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 14/934,885

(22) PCT Filed: May 7, 2014

(86) PCT No.: PCT/US2014/037173
§ 371 (c)(1),
(2) Date: Nov. 6, 2015

(87) PCT Pub. No.: WO2014/182829
PCT Pub. Date: Nov. 13, 2014

(65) Prior Publication Data
US 2016/0130268 A1 May 12, 2016

Related U.S. Application Data

(60) Provisional application No. 61/821,468, filed on May 9, 2013.

(51) Int. Cl.
*A61K 31/519* (2006.01)
*C07D 471/04* (2006.01)
(52) U.S. Cl.
CPC .................. *C07D 471/04* (2013.01)
(58) Field of Classification Search
USPC .............. 514/228.5, 234.2, 252.16
See application file for complete search history.

(56) References Cited

U.S. PATENT DOCUMENTS 5,620,981 A 4/1997 Blankley et al.
2009/0036472 A1* 2/2009 Palle ................ C07D 471/04
514/264.11

FOREIGN PATENT DOCUMENTS

WO 2005105097 11/2005
WO 2008150260 12/2008

OTHER PUBLICATIONS

Patent Cooperation Treaty, International Search Report for PCT/US2014/037173, mailed Aug. 13, 2014, 4 pages.
Hamby et al., Structure-activity relationships for a novel series of pyrido[2,3-d]pyrimidine tyrosine kinase inhibitors. J Med Chem 40, 2296-303 (1997).
Tan et al., Development of covalent inhibitors that can overcome resistance to first-generation FGFR kinase inhibitors. Proc Natl Acad Sci U S A 111, E4869-E4877 (2014).
Thompson et al., 3-(3,5-Dimethoxyphenyl)-1,6-naphthyridine-2,7-diamines and related 2-urea derivatives are potent and selective inhibitors of the FGF receptor-1 tyrosine kinase. J Med Chem 43, 4200-11 (2000).
Thompson et al., Synthesis and structure-activity relationships of soluble 7-substituted 3-(3,5-dimethoxyphenyl)-1,6-naphthyridin-2-amines and related ureas as dual inhibitors of the fibroblast growth factor receptor-1 and vascular endothelial growth factor receptor-2 tyrosine kinases. J Med Chem 48, 4628-53 (2005).
Zhou et al., A structure-guided approach to creating covalent FGFR inhibitors. Chem Biol 17, 285-95 (2010).

* cited by examiner

*Primary Examiner* — Pancham Bakshi
(74) *Attorney, Agent, or Firm* — Bryan Cave LLP

(57) ABSTRACT

Compounds that are Fibroblast Growth Factor Inhibitors (FGFR) and are therefore useful for the treatment of diseases treatable by inhibition of FGFR are disclosed. Also disclosed are pharmaceutical compositions containing such compounds and processes for preparing such compounds.

14 Claims, 2 Drawing Sheets

QUINOLONE DERIVATIVES AS FIBROBLAST GROWTH FACTOR INHIBITORS

This application claims priority to U.S. Provisional Patent App. No. 61/821,468 filed May 9, 2013, the contents of which are incorporated herein by reference in their entirety.

The present disclosure provides certain compounds that are Fibroblast Growth Factor Inhibitors (FGFR) and are therefore useful for the treatment of diseases treatable by inhibition of FGFR. Also provided are pharmaceutical compositions containing such compounds and processes for preparing such compounds.

Fibroblast growth factors (FGFs) and their receptors (FGFRs) play important roles in physiological processes relating to tissue repair, haematopoiesis, bone growth, angiogenesis and other aspects of embryonic development. Alterations in the FGF signaling pathway have also emerged as important drivers in human disease. FGF signaling can be deregulated through multiple mechanisms, including gene amplification, activating mutations and translocations, overexpression, altered FGFR gene splicing, and autocrine or paracrine overproduction of the ligands of FGFR. Deregulated FGF signaling has been documented in human tumors, including breast (see Ray, M. E., et. al., 2004. Genomic and expression analysis of the 8p11-12 amplicon in human breast cancer cell lines. Cancer Res 64:40-47), multiple myeloma (see Keats, J. J., et. al., 2006. Ten years and counting: so what do we know about t(4; 14)(p16; q32) multiple myeloma. Leuk Lymphoma 47:2289-2300), non-invasive bladder (see Billerey, C., et al. 2001. Frequent FGFR3 mutations in papillary non-invasive bladder (pTa) tumors. Am J Pathol 158:1955-1959 and Williams, S. V., Hurst, C. D., and Knowles, M. A. (2013). Oncogenic FGFR3 gene fusions in bladder cancer. Human molecular genetics 22, 795-803), endometrial (see Pollock, P. M., et al. 2007. Frequent activating FGFR2 mutations in endometrial carcinomas parallel germline mutations associated with craniosynostosis and skeletal dysplasia syndromes. Oncogene 26:7158-7162), gastric (see Jang, J. H., et. al., 2001. Mutations in fibroblast growth factor receptor 2 and fibroblast growth factor receptor 3 genes associated with human gastric and colorectal cancers. Cancer Res 61:3541-3543), prostate cancers (see Sahadevan, K., D et al., 2007. Selective over-expression of fibroblast growth factor receptors 1 and 4 in clinical prostate cancer. J Pathol 213:82-90), lung (see Hammerman P, et al. Genomic characterization and targeted therapeutics in squamous cell lung cancer [abstract]; Proceedings of the 14th World Conference on Lung Cancer; 2011 3-7 July; Aurora (Colo.); and International Association for the Study of Lung Cancer; 2011), esophageal (see Hanada K, et al., Identification of fibroblast growth factor-5 as an overexpressed anti-gen in multiple human adenocarcinomas. Cancer Res 2001; 61: 5511-6), cholioangiosarcoma (see Arai, Y., et al. (2014). Fibroblast growth factor receptor 2 tyrosine kinase fusions define a unique molecular subtype of cholangiocarcinoma. Hepatology 59, 1427-1434 and Borad, M. J., et al. (2014). Integrated genomic characterization reveals novel, therapeutically relevant drug targets in FGFR and EGFR pathways in sporadic intrahepatic cholangiocarcinoma. PLoS genetics 10, e1004135) and glioblastoma (see Rand V., et. al. Sequence survey of receptor tyrosine kinases reveals mutations in glioblastomas. Proc Natl Acad Sci USA 2005; 102: 14344-9 and Parker, et. al. (2014). Emergence of FGFR family gene fusions as therapeutic targets in a wide spectrum of solid tumours. The Journal of pathology 232, 4-15). FGFR1 translocations and FGFR1 fusions are frequently observed in 8p11 myeloproliferative syndromes (Jackson, C. C., Medeiros, L. J., and Miranda, R. N. (2010). 8p11 myeloproliferative syndrome: a review. Human pathology 41, 461-476). Activating mutations in FGFR3 have been shown to cause a number of dwarf syndromes (see Harada, D., et. al., 2009. FGFR3-related dwarfism and cell signaling. J Bone Miner Metab 27:9-15) including achondroplasia (see Bellus, G. A., et. al., 1995. Achondroplasia is defined by recurrent G380R mutations of FGFR3. Am J Hum Genet 56:368-373; Bellus, G. A., et. al., 1995. A recurrent mutation in the tyrosine kinase domain of fibroblast growth factor receptor 3 causes hypochondroplasia. Nat Genet 10:357-359; and Rousseau, F., et. al., 1994. Mutations in the gene encoding fibroblast growth factor receptor-3 in achondroplasia. Nature 371:252-254), Crouzon dermoskeletal syndromes (see Robin, N. H., et. al., 1993. FGFR-Related Craniosynostosis Syndromes), hyopochondroplasia (see Prinos, P., et. al., 1995. A common FGFR3 gene mutation in hypochondroplasia. Hum Mol Genet 4:2097-2101), Muenke syndrome (see Muenke, M., et al. 1997. A unique point mutation in the fibroblast growth factor receptor 3 gene (FGFR3) defines a new craniosynostosis syndrome. Am J Hum Genet 60:555-564), SADDAN (severe achondroplasia with developmental delay and acanthosis nigricans) (see Bellus, G. A., et al. 1999. Severe achondroplasia with developmental delay and acanthosis nigricans (SADDAN): phenotypic analysis of a new skeletal dysplasia caused by a Lys650Met mutation in fibroblast growth factor receptor 3. Am J Med Genet 85:53-65; Tavormina, P. L., et al. 1999. A novel skeletal dysplasia with developmental delay and acanthosis nigricans is caused by a Lys650Met mutation in the fibroblast growth factor receptor 3 gene. Am J Hum Genet 64:722-731), thanatophoric dysplasia (see d'Avis, P. Y., et. al., 1998. Constitutive activation of fibroblast growth factor receptor 3 by mutations responsible for the lethal skeletal dysplasia thanatophoric dysplasia type I. Cell Growth Differ 9:71-78; Kitoh, H., et. al., 1998. Lys650Met substitution in the tyrosine kinase domain of the fibroblast growth factor receptor gene causes thanatophoric dysplasia Type I. Mutations in brief no. 199. Online. Hum Mutat 12:362-363; and Tavormina, P. L., et. al., 1995. Thanatophoric dysplasia (types I and II) caused by distinct mutations in fibroblast growth factor receptor 3. Nat Genet 9:321-328), platyspondylic lethal skeletal dysplasia (see Brodie, S. G., et. al., 1999. Platyspondylic lethal skeletal dysplasia, San Diego type, is caused by FGFR3 mutations. Am J Med Genet 84:476-480), and cervical cancer (see Cappellen, D., et. al., 1999. Frequent activating mutations of FGFR3 in human bladder and cervix carcinomas. Nat Genet 23:18-20). Activating mutations in FGFR4 have been identified in rhabdomyosarcoma (see Shukla, N., et. al., Oncogene mutation profiling of pediatric solid tumors reveals significant subsets of embryonal rhabdomyosarcoma and neuroblastoma with mutated genes in growth signaling pathways. Clin Cancer Res 18:748-757 and Marshall, A. D., et. al., PAX3-FOXO1 and FGFR4 in alveolar rhabdomyosarcoma. Mol Carcinog 51:807-815). For these reasons, FGFRs are attractive therapeutic target for the treatment of diseases.

In a first aspect, provided is a compound of Formula (I'):

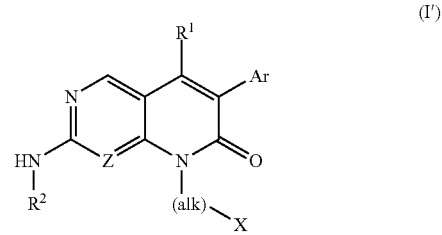

wherein:
Z is N or CH;
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
R¹ is hydrogen, halo, or alkyl;
R² is hydrogen, alkyl, alkynyl, cycloalkyl optionally substituted with amino, alkylamino, or dialkylamino, cycloalkylalkyl, hydroxyalkyl, alkoxyalkyl, aminoalkyl, heterocyclyl (wherein heterocyclyl is optionally substituted with one, two, or three substituents independently selected from alkyl, halo, acyl, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, acyl, halo, hydroxy, hydroxyalkyl, aminoalkyl, optionally substituted aryl, optionally substituted heteroaryl, or optionally substituted heterocyclyl), phenyl, heteroaryl (where phenyl or heteroaryl is optionally substituted with one, two, or three substituents where two of the phenyl or heteroaryl optional substituents are independently selected from alkyl, hydroxy, alkoxy, halo, haloalkyl, haloalkoxy, and cyano and one of the phenyl or heteroaryl optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl), or heteroaralkyl where the heteroaryl ring in heteroaralkyl is optionally substituted with one, two, or three substituents independently selected from halo, alkyl, hydroxy, alkoxy, and haloalkoxy;
alk is alkylene;
X is a group of formula (a) or (b):

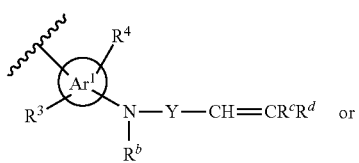

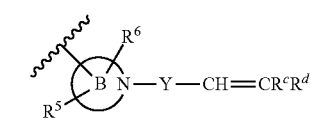

wherein:
Ar¹ is 5- or 6-membered cycloalkylene, phenylene, or 5- or 6-membered heteroarylene;
Ring B is azetidinyl, pyrrolidinyl, or piperidinyl where the nitrogen atom of the azetidinyl, pyrrolidinyl, or piperidinyl ring is attached to Y;
R³ is hydrogen, alkyl, hydroxy, alkoxy, halo, haloalkyl, haloalkoxy, or cyano;
R⁴ is hydrogen, alkyl, cycloalkyl, hydroxy, alkoxy, halo, haloalkyl, haloalkoxy, or cyano;
R⁵ and R⁶ are independently hydrogen, alkyl, or halo;
Y is —CO— or —SO₂—;
$R^b$ is hydrogen or alkyl;
$R^c$ is hydrogen, alkyl, or substituted alkyl; and
$R^d$ is hydrogen or alkyl;
and/or a pharmaceutically acceptable salt thereof;
provided that when (i) Ar¹ is phenylene or 6-membered heteroarylene then alk and —NR^b—Y—CH═CR^cR^d are meta or para to each other and (ii) B is piperidinyl, then alk and —Y—CH═CR^cR^d are meta or para to each other.

In a second aspect, provided is a compound of Formula (I):

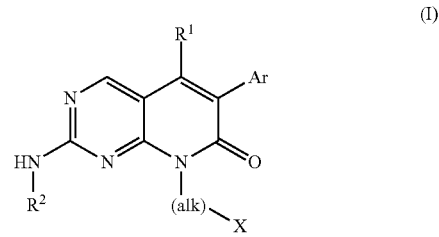

wherein:
Ar is phenyl or heteroaryl, each ring optionally substituted with one, two, three, or four substituents independently selected from alkyl, cycloalkyl, hydroxy, alkoxy, halo, haloalkyl, alkylsulfonyl, haloalkoxy, and cyano;
R¹ is hydrogen, halo, or alkyl;
R² is hydrogen, alkyl, cycloalkyl substituted with amino, alkylamino, or dialkylamino, hydroxyalkyl, alkoxyalkyl, aminoalkyl, heterocyclyl (wherein heterocyclyl is optionally substituted with one or two substituents independently selected from alkyl, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one or two substituents independently selected from alkyl, hydroxyalkyl, aminoalkyl, optionally substituted aryl, optionally substituted heteroaryl, and optionally substituted heterocyclyl), phenyl or heteroaryl where phenyl or heteroaryl is optionally substituted with one, two, or three substituents where two of the phenyl or heteroaryl optional substituents are independently selected from alkyl, hydroxy, alkoxy, halo, haloalkyl, haloalkoxy, and cyano and one of the phenyl or heteroaryl optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl;
alk is alkylene;
X is a group of formula (a) or (b):

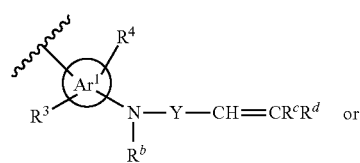

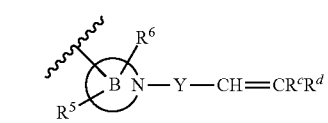

wherein:
Ar¹ is 5- or 6-membered cycloalkylene, phenylene, or 5- or 6-membered heteroarylene;
Ring B is azetidinyl, pyrrolidinyl, or piperidinyl where the nitrogen atom of the azetidinyl, pyrrolidinyl, or piperidinyl ring is attached to Y;

R³ is hydrogen, alkyl, hydroxy, alkoxy, halo, haloalkyl, haloalkoxy, or cyano;

R⁴ is hydrogen, alkyl, cycloalkyl, hydroxy, alkoxy, halo, haloalkyl, haloalkoxy, or cyano;

R⁵ and R⁶ are independently hydrogen, alkyl, or halo;

Y is —CO— or —SO₂—;

$R^b$ is hydrogen or alkyl;

$R^c$ is hydrogen, alkyl, or substituted alkyl; and $R^d$ is hydrogen or alkyl;

and/or a pharmaceutically acceptable salt thereof;

provided that when (i) Ar¹ is phenylene or 6-membered heteroarylene then alk and —NR$^b$—Y—CH=CR$^c$R$^d$ are meta or para to each other and (ii) B is piperidinyl, then alk and —Y—CH=CR$^c$R$^d$ are meta or para to each other. Compounds of Formula (I) is a subset of compounds of Formula (I').

In one embodiment, the compounds of Formulae (I') and (I) and/or a pharmaceutically acceptable salt thereof (and any embodiments thereof disclosed herein) form an irreversible covalent bond with one of Cys488 of FGFR1, Cys491 of FGFR2, Cys482 of FGFR3, and Cys477 of FGFR4.

In another embodiment, the compounds of Formulae (I') and (I) and/or a pharmaceutically acceptable salt thereof (and any embodiments thereof disclosed herein) form an irreversible covalent bond with one of Cys488 of FGFR1, Cys491 of FGFR2, Cys482 of FGFR3, and Cys477 of FGFR4 where the irreversibility of the covalent bond is determined by the Mass Spec. method described in Biological Examples 6 below.

In a third aspect, this disclosure is directed to a pharmaceutical composition comprising a compound of Formula (I') or (I) (or any of the embodiments thereof described herein), and/or a pharmaceutically acceptable salt thereof; and a pharmaceutically acceptable excipient.

In a fourth aspect, this disclosure is directed to a method of treating a disease treatable by inhibition of one or more FGFRs, in particular one or more of FGFR1, 2, and 3, in a patient in recognized need of such treatment which method comprises administering to the patient in recognized need thereof, a pharmaceutical composition comprising a compound of Formula (I') or (I) (or any of the embodiments thereof described herein) and/or a pharmaceutically acceptable salt thereof in a therapeutically effective amount, and a pharmaceutically acceptable excipient. In one embodiment the disease is cancer such as breast cancer, multiple myeloma, bladder cancer, endometrial cancer, gastric cancer, cervical cancer, rhabdomyosarcoma, lung cancer including squamous cell lung cancer, ovarian cancer, esophageal cancer, melanoma, colon cancer, hepatocellular carcinoma, head and neck squamous cell carcinoma, glioblastoma, cholioangiocarcinoma, 8,11 myeloproliferative syndrome, myeloproliferative disorders involving FGFR translocations/fusions, alveolar rhabdomyosarcoma, malignant rhabdoid tumors, and prostate cancers. In another embodiment, the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia.

In a fifth aspect, the disclosure is directed to a compound of Formula (I') or (I) (and any embodiments thereof described herein) and/or a pharmaceutically acceptable salt thereof for use as a medicament. In one embodiment, the compound of Formulae (I') and (I) (and any embodiments thereof described herein) and/or a pharmaceutically acceptable salt thereof is useful for the treatment of cancer such as breast cancer, multiple myeloma, bladder cancer, endometrial cancer, gastric cancer, cervical cancer, rhabdomyosarcoma, lung cancer including squamous cell lung cancer, ovarian cancer, esophageal cancer, melanoma, colon cancer, hepatocellular carcinoma, head and neck squamous cell carcinoma, cholioangiocarcinoma, 8,11 myeloproliferative syndrome, myeloproliferative disorders involving FGFR translocations/fusions, alveolar rhabdomyosarcoma, malignant rhabdoid tumors, glioblastoma, and prostate cancers. In another embodiment, the compound of Formulae (I') and (I) (and any embodiments thereof described herein) and/or a pharmaceutically acceptable salt thereof is useful for the treatment of dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia.

In a sixth aspect provided is the use of a compound of Formula (I') or (I) and/or a pharmaceutically acceptable salt thereof (and any embodiments thereof disclosed herein) in the manufacture of a medicament for treating a disease in a patient in which the activity of FGFR contributes to the pathology and/or symptoms of the disease. In one embodiment the disease is cancer such as breast cancer, multiple myeloma, bladder cancer, endometrial cancer, gastric cancer, cervical cancer, rhabdomyosarcoma, lung cancer including squamous cell lung cancer, ovarian cancer, esophageal cancer, melanoma, colon cancer, hepatocellular carcinoma, head and neck squamous cell carcinoma, cholioangiocarcinoma, 8,11 myeloproliferative syndrome, myeloproliferative disorders involving FGFR translocations/fusions, alveolar rhabdomyosarcoma, malignant rhabdoid tumors, glioblastoma, and prostate cancers. In another embodiment the disease includes dwarf syndromes including achondroplasia, Crouzon dermoskeletal syndromes, hyopochondroplasia, Muenke syndrome, SADDAN (severe achondroplasia with developmental delay and acanthosis nigricans), thanatophoric dysplasia, and platyspondylic lethal skeletal dysplasia.

In any of the aforementioned aspects involving the treatment of cancer, are further embodiments comprising administering the compound of Formula (I') or (I) and/or a pharmaceutically acceptable salt thereof (or any embodiments thereof disclosed herein) in combination with at least one additional anticancer agent. When combination therapy is used, the agents can be administered simultaneously or sequentially.

BRIEF DESCRIPTION OF THE FIGURES

Tumor growth inhibition in a SNU-16 xenograft model conducted as described in Biological Example 4 below for compound of synthetic Example No. 26 is shown in FIG. 1.

pFGFR inhibition in a SNU-16 xenograft model conducted as described in Biological Example 4 below for compound of synthetic Example No. 26 is shown in FIG. 2.

DEFINITIONS

Figure 1:
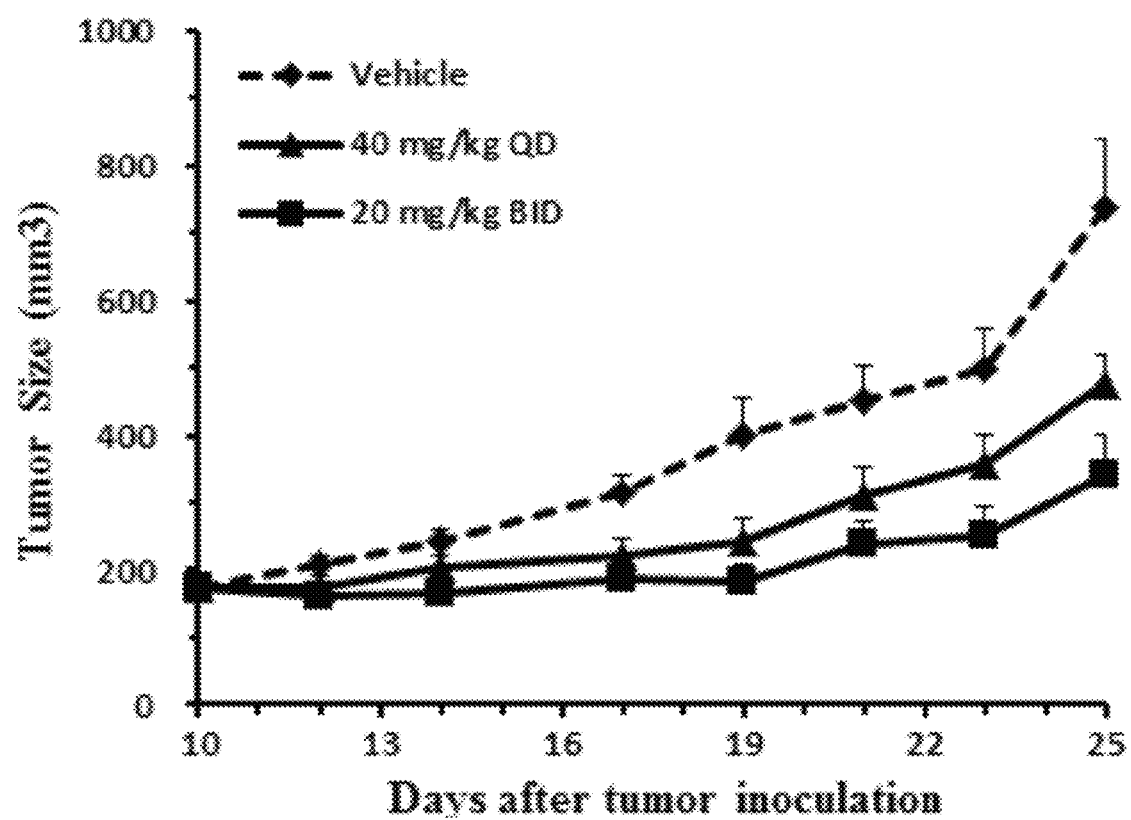

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkynyl" means a linear saturated monovalent hydrocarbon radical of two to six carbon atoms or a branched saturated monovalent hydrocarbon radical of three to six carbon atoms and a triple bond, e.g., ethynyl, propynyl, butynyl, and the like. "Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with —NR'R" where R' and R" are independently hydrogen or alkyl as defined above, e.g., aminomethyl, aminoethyl, methylaminomethyl, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Acyl" means a —C(O)R radical where R is alkyl as defined above, e.g., methylcarbonyl, ethylcarbonyl, and the like.

"Aryl" means a monovalent monocyclic or bicyclic aromatic hydrocarbon radical of 6 to 10 ring atoms e.g., phenyl or naphthyl.

"Cycloalkyl" means a cyclic saturated monovalent hydrocarbon radical of three to ten carbon atoms, e.g., cyclopropyl, cyclobutyl, cyclopentyl, or cyclohexyl, and the like.

"Cycloalkylene" means a divalent cycloalkyl as defined above, unless stated otherwise.

"Cycloalkylalkyl" means a -(alkylene)-R where R is cycloalkyl as defined above, e.g., cyclopropylmethyl, cyclobutylethyl, cyclopentylethyl, or cyclohexylmethyl, and the like.

"Carboxy" means —COOH.

"Dialkylamino" means a —NRR' radical where R and R' are alkyl as defined above, e.g., dimethylamino, methylethylamino, and the like.

"Halo" means fluoro, chloro, bromo, or iodo, preferably fluoro or chloro.

"Haloalkyl" means alkyl radical as defined above, which is substituted with one or more halogen atoms, such as one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, and S(O)$_n$, where n is an integer from 0 to 2, the remaining ring atoms being C. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocyloalkyl" means a -(alkylene)-R radical where R is heterocyclyl ring as defined above e.g., tetraydrofuranylmethyl, piperazinylmethyl, morpholinylethyl, and the like.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocyloamino ring can optionally be substituted with one, two, or three substituents independently selected from alkyl, hydroxyl, alkoxy, amino, alkylamino, and dialkylamino.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

"Heteroaralkyl" or "heterocyloalkyl" means a -(alkylene)-R radical where R is heteroaryl ring as defined above e.g., pyridinylmethyl, imidazolylmethyl, and the like.

The present disclosure also includes protected derivatives of compounds of Formula (I' or I). For example, when compounds of Formula (I' or I') contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I') or (I) can be prepared by methods well known in the art.

The present disclosure also includes polymorphic forms and deuterated forms of the compound of Formula (I' or I) and/or a pharmaceutically acceptable salt thereof.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference in its entirety.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, all mixtures of chiral or diasteromeric forms, and racemic forms are within the scope of this disclosure, unless the specific stereochemistry or isomeric form is specifically indicated.

Certain compounds of Formula (I') or (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of Formula (I') or (I) are within the scope of this disclosure.

"Oxo" or "carbonyl" means =(O) group.

"Optionally substituted aryl" means aryl as defined above that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Phenylene" means a divalent phenyl group.

"Substituted alkyl" means alkyl group as defined herein which is substituted with one, two, or three substituents independently selected from hydroxy, alkoxy, and —NRR' (where R is hydrogen, alkyl, hydroxyalkyl, alkoxyalkyl, or heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino optionally substituted with one, two, or three groups independently selected from alkyl, hydroxyl, alkoxy, and halo.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I') or (I) and/or a pharmaceutically acceptable salt thereof that, when administered to a patient for treating a disease, is sufficient to effect such treatment for the disease. The "therapeutically effective amount" will vary depending on the compound, the disease and its severity and the age, weight, etc., of the mammal to be treated.

EMBODIMENTS

Embodiment (IA)

(IA) In embodiment (IA), the compound of Formula (I') or a salt thereof as defined in the first aspect has the structure (Ia):

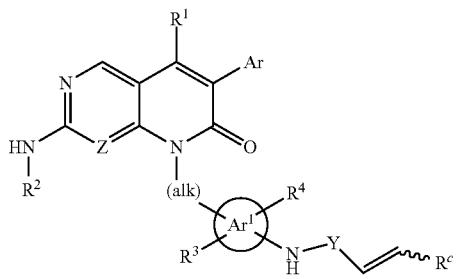

(Ia)

where R² is alkynyl, cycloalkylalkyl, heterocyclyl (wherein heterocyclyl is optionally substituted with one, two, or three substituents independently selected from alkyl, halo, acyl, hydroxy, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one, two, or three substituents independently selected from alkyl, acyl, halo, hydroxy, hydroxyalkyl, aminoalkyl, optionally substituted aryl, optionally substituted heteroaryl, and optionally substituted heterocyclyl), or heteroaralkyl where the heteroaryl ring in heteroaralkyl is optionally substituted with one, two, or three substituents independently selected from halo, alkyl, hydroxy, alkoxy, and haloalkoxy; and the groups are as defined in the first aspect above.

Within embodiment (IA), in one group of compounds R² is alkynyl. Within embodiment (IA), in another group of compounds R² is cycloalkylalkyl. Within embodiment (IA), in another group of compounds R² is heterocyclylalkyl (wherein the heterocyclyl ring in heterocyclylalkyl is optionally substituted with one, two, or three substituents independently selected from alkyl, acyl, halo, hydroxy, hydroxyalkyl, aminoalkyl, optionally substituted aryl, optionally substituted heteroaryl, or optionally substituted heterocyclyl).

Within embodiment (IA), and groups contained therein in one groups of compounds Z is N. Within embodiment (IA), and groups contained therein in one groups of compounds Z is CH.

Embodiment (IB)

(IB) In embodiment (IB), the compound of Formula (I) or a salt thereof as defined in the second aspect has the structure (Ib):

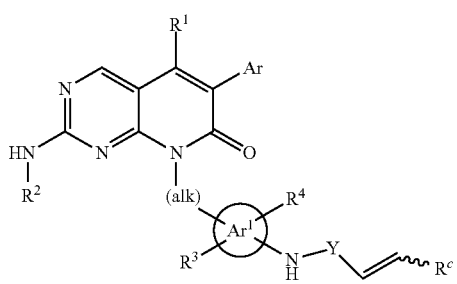

(Ib)

where the groups are as defined in the second aspect above.

Embodiment (IC)

(IC) In embodiment (IC), the compound of Formula (I') or a salt thereof as defined in the first aspect has the structure (Ic):

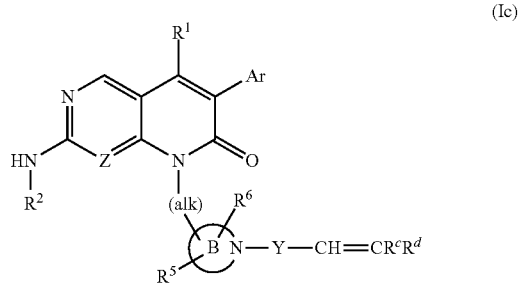

(Ic)

where the groups are as defined in the first aspect above. Within embodiment (IC), in one group of compounds B is piperidin-4-yl. Within embodiment (IC), and groups contained therein in one groups of compounds Z is N. Within embodiment (IC), and groups contained therein in one groups of compounds Z is CH.

Embodiment A

In embodiment A, the compound of Formula (I') and/or a salt thereof as defined in the first aspect, the compound of Formula (I) and/or a salt thereof as defined in the second aspect and the compounds in embodiments (IA), (IB) and (IC) and group contained therein (i.e., groups in embodiment (IA) and (IC)) (each a group within embodiment A) is where R¹ is hydrogen.

Embodiment B

In embodiment B, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC) and (A) and groups contained therein (each a group within embodiment B) is where Ar is phenyl ring optionally substituted with one, two, three, or four substituents independently selected from alkyl, hydroxy, alkoxy, halo, haloalkyl, haloalkoxy, and cyano. Within each of the groups in embodiment B in one group of compounds and/or salts thereof, Ar is a phenyl ring optionally substituted with one, two, three, or four substituents independently selected from methyl, alkoxy, hydroxy, chloro, fluoro, trifluoromethyl, difluoromethyl, trifluoromethoxy, difluoromethoxy, and cyano. Within each the groups in embodiment B, in another group of compounds, Ar is 2-chlorophenyl, 2,6-dichloro-3,5-dimethoxyphenyl, 2-chloro-3,5-dimethoxyphenyl, or 3,5-dimethoxyphenyl. Within each of the groups in embodiment B and groups contained therein, in yet another group of compounds, Ar is 2-chloro-3,5-dimethoxyphenyl, or 3,5-dimethoxyphenyl. Within each of the groups in embodiment B and groups contained therein, in yet another group of compounds and/or salts thereof, Ar is 2-chlorophenyl. Within each of the groups in embodiment B and groups contained therein, in yet another group of compounds and/or salts thereof, Ar is 2,6-dichloro-3,5-dimethoxyphenyl. Within each of the groups in embodiment B and groups contained therein, in yet another group of compounds and/or salts thereof, Ar is 2-chloro-3,5-dimethoxyphenyl.

Embodiment C

In embodiment C, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), and (B) and groups contained therein (each a group within embodiment C) are those where Ar is heteroaryl (such as pyridinyl or thienyl) ring optionally substituted with one, two, or three substituents independently selected from alkyl, hydroxy, alkoxy, halo, haloalkyl, haloalkoxy, and cyano. Within each of the groups in embodiment C and groups contained therein, in one group of compounds, Ar is heteroaryl (such as pyridinyl or thienyl) ring optionally substituted with one, two, or three substituents independently selected from methyl, alkoxy, hydroxy, chloro, fluoro, trifluoromethyl, difluoromethyl, trifluoromethoxy, difluoromethoxy, and cyano.

Embodiment D (Di) In embodiment Di, the compound of Formula (I') and/or a salt thereof as defined in the first aspect, the compound of Formula (I) and/or a salt thereof as defined in the second aspect and the compounds and/or a salt thereof as defined in embodiments (IB), (IC), (A), (B), and (C) and groups contained therein (each a group within embodiment D) are those where $R^2$ is alkyl. Within each of the groups in (Di) and/or salts thereof, and groups contained therein, in one group of compounds $R^2$ is methyl, ethyl, propyl, or butyl. Within each of the groups in (Di) and/or salts thereof and groups contained therein, in another group of compounds $R^2$ is methyl. Within each of the groups in (Di) and/or salts thereof and groups contained therein, in another group of compounds $R^2$ is methyl, ethyl, prop-2-yl, or 2,2-dimethylprop-1-yl.

(Dii) In embodiment Dii, the compound of Formula (I') and/or a salt thereof as defined in the first aspect, the compound of Formula (I) and/or a salt thereof as defined in the second aspect and the compounds and/or a salt thereof as defined in embodiments (IB), (IC), (A), (B), and (C) and groups contained therein (each a group within embodiment D) are those where $R^2$ is hydroxyalkyl or alkoxyalkyl. Within each of the groups in (Dii) and/or salts thereof and groups contained therein, in another group of compounds $R^2$ is 2-hydroxy-2-methylprop-1-yl, 2,3-dihydroxyprop-1-yl, 2-hydroxyethyl, 1,3-dihydroxyprop-2-yl, 3-hydroxy-2-methylprop-2-yl, 3-hydroxy-2,2-dimethylprop-1-yl, 1,3-dihydroxy-2-methylprop-2-yl, or 1,3-dihydroxy-2-ethylprop-2-yl.

(Diii) In embodiment Diii, the compound of Formula (I') and/or a salt thereof as defined in the first aspect, the compound of Formula (I) and/or a salt thereof as defined in the second aspect and the compounds and/or a salt thereof as defined in embodiments (IB), (IC), (A), (B), and (C) and groups contained therein (each a group within embodiment Diii) are those, where $R^2$ is aminoalkyl. Within each of the groups in (Diii) and/or salts in one group of compounds $R^2$ is dimethylamino- or ethylaminoethyl, 3-dimethylamino- or 3-ethylaminopropyl, or 4-dimethylamino- or 4-ethylaminobutyl. Within each of the groups in D(iii) and/or salts in another group of compounds $R^2$ is 4-dimethylaminobutyl or 4-diethylaminobutyl.

(Div) In embodiment Div, the compound of Formula (I') and/or a salt thereof as defined in the first aspect, the compound of Formula (I) and/or a salt thereof as defined in the second aspect and the compounds and/or a salt thereof as defined in embodiments (IB), (IC), (A), (B), and (C) and groups contained therein (each a group within embodiment Div) are those where $R^2$ is heterocyclylalkyl (wherein heterocyclyl ring is optionally substituted with one or two substituents independently selected from with alkyl, hydroxyalkyl, aminoalkyl, optionally substituted aryl, optionally substituted heteroaryl, or optionally substituted heterocyclyl). Within each of the groups in (Div) and/or salts thereof in one group of compounds or salt thereof $R^2$ is ethyl, propyl or butyl substituted with morpholin-4-yl, piperazin-1-yl, 4-methyl or ethylpiperazin-1-yl. Within each of the groups in (Div) and/or salts thereof in one group of compounds or salt thereof $R^2$ is methyl, ethyl, propyl or butyl substituted with morpholin-4-yl, 2,6-dimethylmorpholin-4-yl, piperazin-1-yl, 4-methyl- or 4-ethylpiperazin-1-yl, 4-acetylpiperazin-1-yl, 4-isopropylpiperazin-1-yl, 4-(2-hydroxy-2-methylprop-2-yl)piperazin-1-yl, piperidin-1-yl, 1-methylpiperidin-4-yl, 1,2-dioxothiomorpholin-4-yl, 4-oxetan-3-ylpiperazin-1-yl, 2,6-dimethylpiperazin-1-yl, 3,5-dimethylpiperazin-1-yl, 4-hydroxy-1-methylpiperidin-4-yl, 4,4-difluoropiperidin-1-yl, or 1,4-dimethylpiperidin-4-yl.

Embodiment E

In embodiment E, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), and (E) and groups contained therein (each a group within embodiment E) are those where alk is ethylene.

Embodiment F (Fi) In embodiment Fi, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), and (E) and groups contained therein (each a group within embodiment Fi) are those where $Ar^1$ is phenylene substituted as defined or unsubstituted phenylene. Within the groups of compounds in (Fi) or a salt thereof, in one group of compounds or salt thereof $Ar^1$ is phenylene substituted as defined or unsubstituted phenylene where alk and —NHYCH=CHR$^c$ groups are meta or para to each other on the phenylene ring. Within the groups of compounds in (Fi) or a salt thereof, in one group of compounds or salt thereof $Ar^1$ is phenylene is unsubstituted phenylene where alk and —NHYCH=CHR$^c$ groups are meta or para to each other on the phenylene ring.

(Fii) In embodiment Fii, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), and (E) and groups contained therein (each a group within embodiment Fii) are those where $Ar^1$ is 5- or 6-membered heteroarylene substituted as defined. Within these groups of compounds in (Fii) or a salt thereof, in one group of compounds or salt thereof $Ar^1$ is pyridinylene substituted as defined or unsubstituted pyridinylene. Within these groups of compounds in (Fii) or a salt thereof, in another group of compounds or salt thereof Ar$^1$ is substituted as defined or unsubstituted pyridinylene where alk is attached to the C-2 or C-3 carbon of the pyridinylene ring and the —NHYCH=CHR$^c$ group is attached to the C-6 position of the pyridinylene ring or alk is attached to the C-4 carbon of the pyridinylene ring and the —NHYCH=CHR$^c$ group is at C-2 position of the pyridinylene ring and, the nitrogen atom of the pyridinylene ring being position 1.

Embodiment G

In embodiment G, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), (E), and (F) (and groups contained therein (each a group within embodiment G) are those where Y is —CO—.

Embodiment H (Hi) In embodiment Hi, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), (E), (F) and (G) and groups contained therein (each a group within embodiment Hi) are those where R$^c$ is hydrogen.

(Hii) In embodiment Hii, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), (E), (F) and (G) and groups contained therein (each a group within embodiment Hii) are those where R$^c$ is alkyl. Within compounds in (Hii) or salt thereof in one group of compounds or salt thereof R$^c$ is methyl.

(Hiii) In embodiment Hiii, the compound of Formula (I') and/or a salt thereof as defined in the first aspect, the compound of Formula (I) and/or a salt thereof as defined in the second aspect and the compounds and/or a salt thereof as defined in embodiments (IA), (IB), (IC), (A), (B), (D), (E), (F) and (G) and groups contained therein (each a group within embodiment Hiii) are those R$^c$ is substituted alkyl. Within compounds in (Hiii) or salt thereof in one group of compounds or salt thereof, R$^c$ is —CH$_2$NRR' (where R is hydrogen, alkyl, hydroxyalkyl, alkoxyalkyl, or heterocyclyl optionally substituted with one or two groups independently selected from alkyl, hydroxyl, alkoxy, and halo and R' is hydrogen, alkyl, or cycloalkyl or R and R' together with the nitrogen atom to which they are attached form heterocycloamino). Within compounds in (Hii) or salt thereof in another group of compounds or salt thereof, R$^c$ is:

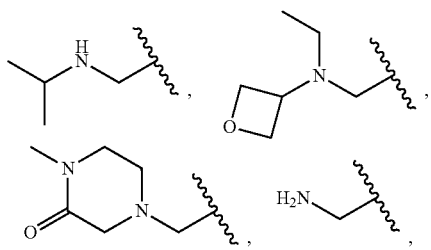

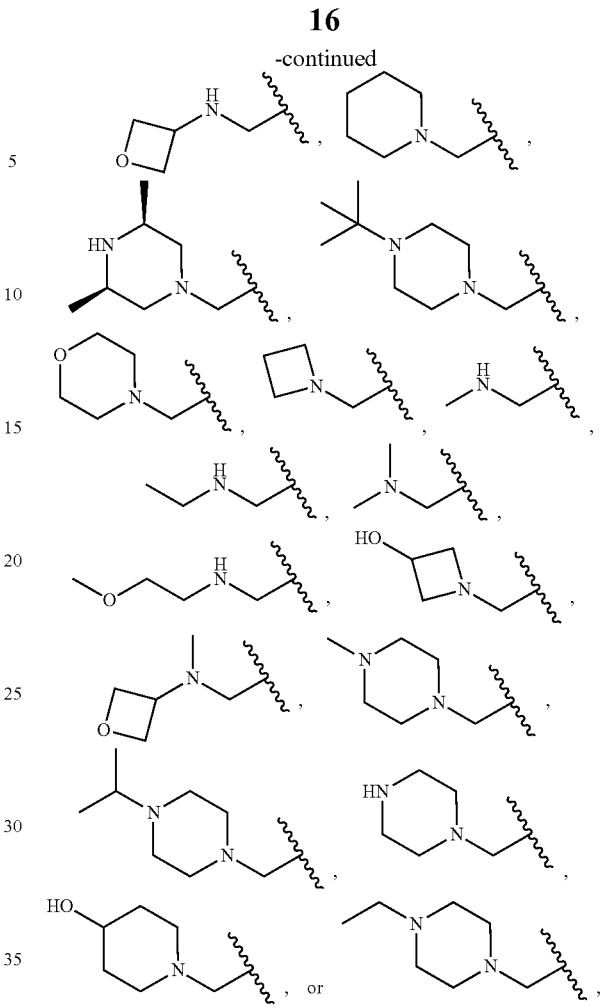

Embodiment (I)

In further embodiments 1-20 below, the present disclosure includes:

1. A compound of Formula (I):

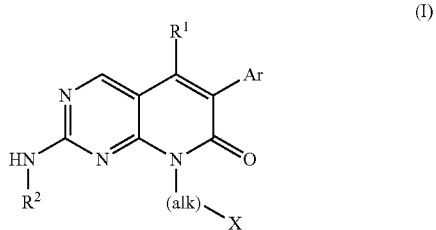

wherein:
Ar is phenyl or heteroaryl each ring optionally substituted with one, two, three, or four substituents independently selected from alkyl, cycloalkyl, hydroxy, alkoxy, halo, haloalkyl, alkylsulfonyl, haloalkoxy, and cyano;
R$^1$ is hydrogen, halo, or alkyl;
R$^2$ is hydrogen, alkyl, cycloalkyl substituted with amino, alkylamino, or dialkylamino, hydroxyalkyl, alkoxyalkyl, aminoalkyl, heterocyclyl (optionally substituted with one two substituents independently selected from alkyl, hydroxyalkyl, alkoxyalkyl, aminoalkyl, optionally substituted aryl, optionally substituted heteroaryl, and optionally substituted heterocyclyl), heterocyclylalkyl (wherein heterocyclyl ring is optionally substituted with one or two substituents independently selected from alkyl, hydroxyalkyl, aminoalkyl, optionally substituted aryl, optionally substituted heteroaryl, and optionally substituted heterocyclyl), phenyl or heteroaryl where phenyl or heteroaryl is optionally substituted with one, two, or three substituents where two of the phenyl or heteroaryl optional substituents are independently selected from alkyl, hydroxy, alkoxy, halo, haloalkyl, haloalkoxy, and cyano and one of the phenyl or heteroaryl optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl;

alk is alkylene;

X is a group of formula (a) or (b):

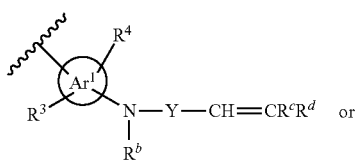

(a)

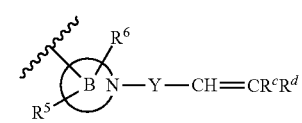

(b)

wherein:

Ar$^1$ is 5- or 6-membered cycloalkylene, phenylene, 5- or 6-membered heteroarylene;

Ring B is azetidinyl, pyrrolidinyl, or piperidinyl where the nitrogen atom of the azetidinyl, pyrrolidinyl, or piperidinyl ring is attached to Y;

R$^3$ is hydrogen, alkyl, hydroxy, alkoxy, halo, haloalkyl, haloalkoxy, or cyano;

R$^4$ is hydrogen, alkyl, cycloalkyl, hydroxy, alkoxy, halo, haloalkyl, haloalkoxy, or cyano;

R$^5$ and R$^6$ are independently hydrogen, alkyl, or halo;

Y is —CO— or —SO$_2$—;

R$^b$ is hydrogen or alkyl;

R$^c$ is hydrogen, alkyl, or substituted alkyl; and

R$^d$ is hydrogen or alkyl;

and/or a pharmaceutically acceptable salt thereof;

provided that when (i) Ar$^1$ is phenylene or 6-membered heteroarylene then alk and —NR$^b$—Y—CH═CR$^c$R$^d$ are meta or para to each other and (ii) B is piperidinyl, then alk and —Y—CH═CR$^c$R$^d$ are meta or para to each other.

2. The compound of embodiment 1 and/or a salt thereof wherein the compound of Formula (I) or the salt thereof has the structure (Ia):

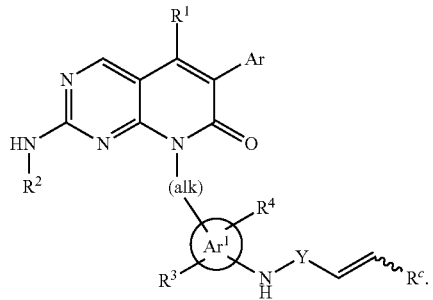

(Ia)

3. The compound of embodiment 1 or 2 and/or salt thereof wherein R$^1$ is hydrogen.

4. The compound of embodiment 1, 2 or 3 and/or salt thereof where Ar is phenyl ring optionally substituted with one, two, three, or four substituents independently selected from alkyl, hydroxy, alkoxy, halo, haloalkyl, haloalkoxy, and cyano.

5. The compound of embodiment 1, 2 or 3 and/or salt thereof where Ar is 2-chloro-3,5-dimethoxy-phenyl, 3,5-dimethoxyphenyl, 2-chlorophenyl, or 2,6-dichloro-3,5-dimethoxyphenyl.

6. The compound of embodiment claim 1, 2 or 3 and/or salt thereof where Ar is heteroaryl ring optionally substituted with one, two, or three substituents independently selected from alkyl, hydroxy, alkoxy, halo, haloalkyl, haloalkoxy, and cyano.

7. The compound of any one of embodiments 1 to 6 and/or salt thereof where R$^2$ is alkyl, hydroxyalkyl, alkoxyalkyl, aminoalkyl, heterocyclyl wherein heterocyclyl is optionally substituted with one two substituents independently selected from alkyl, hydroxyalkyl, alkoxyalkyl, aminoalkyl, optionally substituted aryl, optionally substituted heteroaryl, and optionally substituted heterocyclyl), heterocyclylalkyl wherein the heterocyclyl ring in heterocyclylalkyl is optionally substituted with one or two substituents independently selected from alkyl, hydroxyalkyl, aminoalkyl, optionally substituted aryl, optionally substituted heteroaryl, or optionally substituted heterocyclyl), phenyl or heteroaryl where each ring is optionally substituted with one, two, or three substituents where two of the optional phenyl or heteroaryl substituents are independently selected from alkyl, hydroxy, alkoxy, halo, haloalkyl, haloalkoxy, and cyano and one of the optional phenyl or heteroaryl substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl.

8. The compound of any one of embodiments 1 to 6 and/or salt thereof where R$^2$ is alkyl, preferably, R$^2$ is methyl, ethyl, propyl, or butyl, preferably R$^2$ is methyl.

9. The compound of any one of embodiments 1 to 6 and/or salt thereof where R$^2$ is aminoalkyl 10. The compound of any one of embodiments 1 to 6 and/or salt thereof where R$^2$ is dimethylamino- or ethylaminoethyl, 3-dimethylamino- or 3-ethylaminopropyl, or 4-dimethylamino- or 4-ethylaminobutyl.

11. The compound of any one of embodiments 1 to 6 and/or salt thereof where R$^2$ is 4-dimethylaminobutyl or 4-diethylaminobutyl.

12. The compound of any one of embodiments 1 to 6 and/or salt thereof where R$^2$ is heterocyclylalkyl (wherein heterocyclyl ring is optionally substituted with one or two substituents independently selected from with alkyl, hydroxyalkyl, aminoalkyl, optionally substituted aryl, optionally substituted heteroaryl, and optionally substituted heterocyclyl).

13. The compound of any one of embodiments 1 to 6 and/or salt thereof where $R^2$ is ethyl, propyl or butyl substituted with morpholin-4-yl, piperazin-1-yl, 4-methyl or ethylpiperazin-1-yl.

14. The compound of any one of embodiments 1 to 13 and/or salt thereof where alk is ethylene.

15. The compound of any one of embodiments 1 to 14 and/or salt thereof where $Ar^1$ is phenylene where the alk and —NHYCH=CHR$^c$ group are meta or para to each other on the phenylene ring.

16. The compound of any one of embodiments 1 to 14 and/or a pharmaceutically acceptable salt thereof where $Ar^1$ is pyridinylene and the nitrogen atom of the pyridinylene ring is position #1 and where (i) alk is attached to the C-2 or C-3 carbon of the pyridinylene ring and the —NHYCH=CHR$^c$ group is attached to the C-6 position of the pyridinylene ring or (ii) alk is attached to the C-4 carbon of the pyridinylene ring and the —NHYCH=CHR$^c$ group is at C-2 position of the pyridinylene ring.

17. The compound of any one of embodiments 1 to 16 and/or salt thereof where Y is —CO—.

18. The compound of any one of embodiments 1 to 17 and/or salt thereof where $R^c$ is hydrogen.

19. The compound of any one of embodiments 1 to 17 and/or salt thereof where $R^c$ is alkyl.

20. The compound of any one of embodiments 1 to 17 and/or salt thereof where $R^c$ is —CH$_2$NRR', where R is hydrogen, alkyl, hydroxyalkyl, alkoxyalkyl, or heterocyclyl optionally substituted with one or two groups independently selected from alkyl, hydroxyl, alkoxy, or halo and R' is hydrogen, alkyl, or cycloalkyl or R and R' together with the nitrogen atom to which they are attached form heterocycloamino.

Representative compounds of the disclosure are:
1. N-(4-(2-(6-(2-chlorophenyl)-2-((4-(diethylamino)butyl)amino)-7-oxopyrido[2,3-d]-pyrimidin-8(7H)-yl)ethyl)phenyl)prop-2-enamide;
2. 8-(2-(1-acryloylpiperidin-3-yl)ethyl)-6-(2-chlorophenyl)-2-(4-(diethylamino)butyl-amino)pyrido[2,3-d]pyrimidin-7(8H)-one;
3. N-(3-(2-(6-(2-chlorophenyl)-2-((4-(diethylamino)butyl)amino)-7-oxopyrido[2,3-d]-pyrimidin-8(7H)-yl)ethyl)phenyl)acrylamide;
4. N-(4-(2-(6-(2,6-dichloro-3,5-dimethoxyphenyl)-2-(methylamino)-7-oxopyrido[2,3-d]-pyrimidin-8(7H)-yl)ethyl)phenyl)acrylamide;
5. N-(4-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)acrylamide;
6. N-(3-((6-(2,6-dichloro-3,5-dimethoxyphenyl)-2-((4-(diethylamino)butyl)amino)-7-oxo-pyrido[2,3-d]pyrimidin-8(7H)-yl)methyl)phenyl)acrylamide;
7. N-(3-(2-(6-(2,6-dichloro-3,5-dimethoxyphenyl)-2-((4-(diethylamino)butyl)amino)-7-oxo-pyrido[2,3-d]pyrimidin-8(7H)-yl)ethyl)phenyl)acrylamide;
8. N-(3-(2-(6-(3,5-dimethoxyphenyl)-2-(methylamino)-7-oxopyrido[2,3-d]pyrimidin-8(7H)-yl)ethyl)phenyl)acrylamide;
9. N-(4-(2-(6-(3,5-dimethoxyphenyl)-2-(methylamino)-7-oxopyrido[2,3-d]pyrimidin-8(7H)-yl)ethyl)phenyl)acrylamide;
10. N-(4-(2-(6-(3,5-dimethoxyphenyl)-2-(methylamino)-7-oxopyrido[2,3-d]pyrimidin-8(7H)-yl)ethylpyridinyl-2-yl)acrylamide;
11. N-(6-(2-(6-(3,5-dimethoxyphenyl)-2-(methylamino)-7-oxopyrido[2,3-d]pyrimidin-8(7H)-yl)ethylpyridinyl-2-yl)acrylamide;
12. N-(3-(2-(6-(2-chloro-3,5-dimethoxyphenyl)-2-(methylamino)-7-oxopyrido[2,3-d]-pyrimidin-8(7H)-yl)ethyl)phenyl)acrylamide;
13. N-(4-(2-(6-(2-chloro-3,5-dimethoxyphenyl)-2-(methylamino)-7-oxopyrido[2,3-d]-pyrimidin-8(7H)-yl)ethyl)phenyl)acrylamide;
14. N-(4-(2-(6-(2-chloro-3,5-dimethoxyphenyl)-2-(methylamino)-7-oxopyrido[2,3-d]-pyrimidin-8(7H)-yl)ethyl)pyridin-2-yl)acrylamide;
15. N-(6-(2-(6-(2-chloro-3,5-dimethoxyphenyl)-2-(methylamino)-7-oxopyrido[2,3-d]-pyrimidin-8(7H)-yl)ethyl-pyridin-2-yl)acrylamide;
16. N-(5-(2-(6-(2-chloro-3,5-dimethoxyphenyl)-2-(methylamino)-7-oxopyrido[2,3-d]-pyrimidin-8(7H)-yl)ethyl-pyridin-2-yl)acrylamide;
17. N-(4-(2-(6-(2-chloro-3,5-dimethoxyphenyl)-2-(methylamino)-7-oxopyrido[2,3-d]-pyrimidin-8(7H)-yl)ethyl)phenyl)-N-methylacrylamide;
18. N-(3-(2-(6-(2-chloro-3,5-dimethoxyphenyl)-2-(methylamino)-7-oxopyrido[2,3-d]-pyrimidin-8(7H)-yl)ethyl)phenyl)-N-methylacrylamide;
19. N-(3-((6-(2-chloro-3,5-dimethoxyphenyl)-2-(methylamino)-7-oxopyrido[2,3-d]-pyrimidin-8(7H)-yl)methyl)phenyl)acrylamide;
20. N-(4-(2-(6-(2-chloro-3,5-dimethoxyphenyl)-2-(methylamino)-7-oxopyrido[2,3-d]pyrimidin-8(7H)-yl)ethyl)phenyl)ethenesulfonamide;
21. N-(3-(2-(6-(2-chloro-3,5-dimethoxyphenyl)-2-(methylamino)-7-oxopyrido[2,3-d]-pyrimidin-8(7H)-yl)ethyl)phenyl)ethenesulfonamide;
22. (E)-N-(4-(2-(6-(2-chloro-3,5-dimethoxyphenyl)-2-(methylamino)-7-oxopyrido[2,3-d]-pyrimidin-8(7H)-yl)ethyl)phenyl)-4-(dimethylamino)but-2-enamide;
23. (E)-N-(3-(2-(6-(2-chloro-3,5-dimethoxyphenyl)-2-(methylamino)-7-oxopyrido[2,3-d]-pyrimidin-8(7H)-yl)ethyl)phenyl)-4-(dimethylamino)but-2-enamide;
24. N-(4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)acrylamide;
25. N-(4-(2-(6-(2-chloro-3,5-dimethoxyphenyl)-2-((2-(diethylamino)ethyl)amino)-7-oxo-pyrido[2,3-d]pyrimidin-8(7H)-yl)ethyl)phenyl)acrylamide;
26. N-(4-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide;
27. N-(4-(2-(2-amino-6-(2-chloro-3,5-dimethoxyphenyl)-7-oxopyrido[2,3-d]pyrimidin-8(7H)-yl)ethyl)phenyl)acrylamide;
28. N-(5-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)pyridin-2-yl)acrylamide;
29. N-(5-(2-(6-(2-chloro-3,5-dimethoxyphenyl)-2-((2-(diethylamino)ethyl)amino)-7-oxo-pyrido[2,3-d]pyrimidin-8(7H)-yl)ethyl)pyridin-2-yl)acrylamide;
30. N-(5-(2-(6-(2-chloro-3,5-dimethoxyphenyl)-2-(neopentylamino)-7-oxopyrido[2,3-d]-pyrimidin-8(7H)-yl)ethyl)pyridin-2-yl)acrylamide;
31. N-(5-(2-(6-(2-chloro-3,5-dimethoxyphenyl)-2-(2-morpholinoethylamino)-7-oxopyrido[2,3-d]-pyrimidin-8(7H)-yl)ethyl)pyridin-2-yl)acrylamide;
32. N-(5-(2-(6-(2-chloro-3,5-dimethoxyphenyl)-2-((4-(diethylamino)butyl)amino)-7-oxo-pyrido[2,3-d]pyrimidin-8(7H)-yl)ethyl)pyridin-2-yl)acrylamide;

33. N-(4-(2-(6-(2-chloro-3,5-dimethoxyphenyl)-2-(methylamino)-7-oxopyrido[2,3-d]-pyrimidin-8(7H)-yl)ethyl)thiazol-2-yl)acrylamide;
34. N-(6-(2-(6-(2-chloro-3,5-dimethoxyphenyl)-2-(methylamino)-7-oxopyrido[2,3-d]-pyrimidin-8(7H)-yl)ethyl)pyridin-3-yl)acrylamide;
35. N-(3-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide;
36. N-(3-(2-(6-(2-chloro-3,5-dimethoxyphenyl)-2-((piperidin-1-ylethyl)amino)-7-oxo-pyrido[2,3-d]pyrimidin-8(7H)-yl)ethyl)phenyl)acrylamide;
37. N-(4-(2-(6-(2-chloro-3,5-dimethoxyphenyl)-2-((3-morpholinopropyl)amino)-7-oxo-pyrido[2,3-d]pyrimidin-8(7H)-yl)ethyl)phenyl)acrylamide;
38. N-(6-(2-(6-(2,6-dichloro-3,5-dimethoxyphenyl)-2-(methylamino)-7-oxopyrido[2,3-d]-pyrimidin-8(7H)-yl)ethyl)pyridin-3-yl)acrylamide;
39. N-(6-(2-(6-(2-chloro-3,5-dimethoxyphenyl)-2-((2-morpholinoethyl)amino)-7-oxo-pyrido[2,3-d]pyrimidin-8(7H)-yl)ethyl)pyridin-3-yl)acrylamide;
40. N-(4-(2-(6-(2-chloro-3,5-dimethoxyphenyl)-2-((3-(diethylamino)propyl)amino)-7-oxo-pyrido[2,3-d]pyrimidin-8(7H)-yl)ethyl)phenyl)acrylamide;
41. N-(4-(2-(6-(2,6-dichloro-3,5-dimethoxyphenyl)-2-(methylamino)-7-oxopyrido[2,3-d]-pyrimidin-8(7H)-yl)ethyl)thiazol-2-yl)acrylamide;
42. N-(3-(2-(6-(2-fluoro-3,5-dimethoxyphenyl)-2-(4-diethylaminobutylamino)-7-oxopyrido[2,3-d]pyrimidin-8(7H)-yl)ethyl)phenyl)acrylamide;
43. N-(4-(2-(6-(2-fluoro-3,5-dimethoxyphenyl)-2-((2-morpholinoethyl)amino)-7-oxo-pyrido[2,3-d]pyrimidin-8(7H)-yl)ethyl)phenyl)acrylamide;
44. N-(4-(2-(6-(2,6-dichloro-3,5-dimethoxyphenyl)-2-((2-morpholinoethyl)amino)-7-oxo-pyrido[2,3-d]pyrimidin-8(7H)-yl)ethyl)phenyl)acrylamide;
45. N-(4-(2-(6-(2-chloro-3,5-dimethoxyphenyl)-2-(methylamino)-7-oxopyrido[2,3-d]-pyrimidin-8(7H)-yl)ethyl)phenyl)-2-methylprop-1-ene-1-sulfonamide;
46. N-(5-(2-(6-(2-chloro-3,5-dimethoxyphenyl)-2-(methylamino)-7-oxopyrido[2,3-d]-pyrimidin-8(7H)-yl)ethyl)pyrazin-2-yl)acrylamide;
47. N-(5-(2-(6-(2-chloro-3,5-dimethoxyphenyl)-2-((2-morpholinoethyl)amino)-7-oxo-pyrido[2,3-d]pyrimidin-8(7H)-yl)ethyl)pyrazin-2-yl)acrylamide;
48. N-(1-(2-(6-(2-chloro-3,5-dimethoxyphenyl)-2-(methylamino)-7-oxopyrido[2,3-d]-pyrimidin-8(7H)-yl)ethyl)-1H-imidazol-4-yl)acrylamide;
49. N-(4-(2-(6-(2-chloro-3,5-dimethoxyphenyl)-2-((2-(4-methylpiperazin-1-yl)ethyl)-amino)-7-oxopyrido[2,3-d]pyrimidin-8(7H)-yl)ethyl)phenyl)acrylamide;
50. N-(4-(2-(2-((2-(1H-imidazol-1-yl)ethyl)amino)-6-(2-chloro-3,5-dimethoxyphenyl)-7-oxo-pyrido[2,3-d]pyrimidin-8(7H)-yl)ethyl)phenyl)acrylamide;
51. N-(6-(2-(6-(2,6-dichloro-3,5-dimethoxyphenyl)-2-(2-morpholinoethylamino)-7-oxopyrido[2,3-d]pyrimidin-8(7H)-yl)ethyl)pyridin-3-yl)acrylamide;
52. N-(3-(2-(6-(2-fluoro-3,5-dimethoxyphenyl)-2-((2-morpholin-4-ylethyllamino)-7-oxopyrido[2,3-d]pyrimidin-8(7H)-yl)ethyl)phenyl)acrylamide;
53. N-(2-fluoro-4-(2-(6-(2-fluoro-3,5-dimethoxyphenyl)-2-((2-morpholinoethyl)amino)-7-oxo-pyrido[2,3-d]pyrimidin-8(7H)-yl)ethyl)phenyl)acrylamide;
54. N-(4-(2-(6-(2-chloro-3,5-dimethoxyphenyl)-2-((2-morpholinoethyl)amino)-7-oxo-pyrido-[2,3-d]pyrimidin-8(7H)-yl)ethyl)-2-fluorophenyl)acrylamide;
55. N-(4-(2-(6-(2-chloro-3,5-dimethoxyphenyl)-2-((2-morpholinoethyl)amino)-7-oxopyrido-[2,3-d]pyrimidin-8(7H)-yl)ethyl)-3-fluorophenyl)acrylamide;
56. N-(4-(2-(6-(2-chloro-3,5-dimethoxyphenyl)-2-((2-morpholinoethyl)amino)-7-oxopyrido-[2,3-d]pyrimidin-8(7H)-yl)ethyl)-2-chlorophenyl)acrylamide;
57. N-(4-(2-(6-(2-chloro-3,5-dimethoxyphenyl)-2-((4-isopropylpiperazin-1-ethyl)amino)-7-oxopyrido[2,3-d]pyrimidin-8(7H)-yl)ethyl)-phenyl)acylamide;
58. N-(4-(2-(6-(2-chloro-3,5-dimethoxyphenyl)-2-((2-((2R,6S)-2,6-dimethyl-morpholino)-ethyl)-amino)-7-oxopyrido[2,3-d]pyrimidin-8(7H)-yl)ethyl)phenyl)acrylamide;
59. N-(6-(2-(6-(2-chloro-3,5-dimethoxyphenyl)-7-oxo-2-(prop-2-yn-1-ylamino)pyrido-[2,3-d]-pyrimidin-8(7H)-yl)ethyl)pyridin-3-yl)acrylamide;
60. N-(4-(2-(6-(2-chloro-3,5-dimethoxyphenyl)-2-((2-(4-ethylpiperazin-1-yl)ethyl)-amino)-7-oxopyrido[2,3-d]pyrimidin-8(7H)-yl)ethyl)phenyl)acrylamide;
61. N-(4-(2-(6-(2-chloro-3,5-dimethoxyphenyl)-2-((1-hydroxy-2-methylpropan-2-yl)amino)-7-oxo-pyrido[2,3-d]pyrimidin-8(7H)-yl)ethyl)phenyl)acrylamide;
62. N-(4-(2-(6-(2,6-dichloro-3,5-dimethoxyphenyl)-2-((1-methylpiperidin-4-yl)amino)-7-oxo-pyrido[2,3-d]pyrimidin-8(7H)-yl)ethyl)phenyl)acrylamide;
63. N-(4-(2-(6-(2,6-dichloro-3,5-dimethoxyphenyl)-2-((2,3-dihydroxypropyl)amino)-7-oxo-pyrido[2,3-d]pyrimidin-8(7H)-yl)ethyl)phenyl)acrylamide;
64. N-(4-(2-(6-(2,6-dichloro-3,5-dimethoxyphenyl)-2-((2-hydroxy-2-methylpropyl)-amino)-7-oxopyrido[2,3-d]pyrimidin-8(7H)-yl)ethyl)phenyl)acrylamide;
65. N-(4-(2-(6-(2,6-dichloro-3,5-dimethoxyphenyl)-2-((2-hydroxyethyl)amino)-7-oxo-pyrido[2,3-d]pyrimidin-8(7H)-yl)ethyl)phenyl)acrylamide;
66. N-(4-(2-(2-((2-(4-acetylpiperazin-1-yl)ethyl)amino)-6-(2-chloro-3,5-dimethoxy-phenyl)-7-oxopyrido[2,3-d]pyrimidin-8(7H)-yl)ethyl)phenyl)acrylamide;
67. N-(4-(2-(6-(2-chloro-3,5-dimethoxyphenyl)-2-((2-methyl-1-morpholinopropan-2-yl)-amino)-7-oxopyrido[2,3-d]pyrimidin-8(7H)-yl)ethyl)phenyl)acrylamide;
68. N-(4-(2-(6-(2-chloro-3,5-dimethoxyphenyl)-2-((2-(4-(2-hydroxy-2-methylpropyl)-piperazin-1-yl)ethyl)amino)-7-oxopyrido[2,3-d]pyrimidin-8(7H)-yl)ethyl)-phenyl)acrylamide;
69. N-(4-(2-(6-(2-chloro-3,5-dimethoxyphenyl)-2-((2-hydroxyethyl)amino)-7-oxopyrido[2,3-d]-pyrimidin-8(7H)-yl)ethyl)phenyl)acrylamide;
70. N-(4-(2-(6-(2-chloro-3,5-dimethoxyphenyl)-2-((1-methylpiperidin-4-yl)amino)-7-oxo-pyrido[2,3-d]pyrimidin-8(7H)-yl)ethyl)phenyl)acrylamide;
71. N-(4-(2-(6-(2-chloro-3,5-dimethoxyphenyl)-2-(((1-methylpiperidin-4-yl)methyl)-amino)-7-oxopyrido[2,3-d]pyrimidin-8(7H)-yl)ethyl)phenyl)acrylamide;
72. N-(4-(2-(6-(2-chloro-3,5-dimethoxyphenyl)-2-((1,3-dihydroxypropan-2-yl)amino)-7-oxo-pyrido[2,3-d]pyrimidin-8(7H)-yl)ethyl)phenyl)acrylamide;
73. N-(4-(2-(6-(2-chloro-3,5-dimethoxyphenyl)-2-((2,3-dihydroxypropyl)amino)-7-oxo-pyrido[2,3-d]pyrimidin-8(7H)-yl)ethyl)phenyl)acrylamide;
74. N-(4-(2-(6-(2-chloro-3,5-dimethoxyphenyl)-2-((2-(1,1-dioxidothiomorpholino)-ethyl)amino)-7-oxopyrido[2,3-d]pyrimidin-8(7H)-yl)ethyl)phenyl)acrylamide;
75. N-(4-(2-(6-(2,6-dichloro-3,5-dimethoxyphenyl)-2-(((1-methylpiperidin-4-yl)-methyl)amino)-7-oxopyrido[2,3-d]pyrimidin-8(7H)-yl)ethyl)phenyl)acrylamide;

76. N-(4-(2-(6-(2,6-dichloro-3,5-dimethoxyphenyl)-2-((1,3-dihydroxypropan-2-yl)amino)-7-oxo-pyrido[2,3-d]pyrimidin-8(7H)-yl)ethyl)phenyl)acrylamide;
77. N-(4-(2-(6-(2,6-dichloro-3,5-dimethoxyphenyl)-2-((1-hydroxy-2-methylpropan-2-yl)-amino)-7-oxopyrido[2,3-d]pyrimidin-8(7H)-yl)ethyl)phenyl)acrylamide;
78. N-(4-(2-(6-(2-chloro-3,5-dimethoxyphenyl)-2-((2-(4-(oxetan-3-yl)piperazin-1-yl)-ethyl)amino)-7-oxopyrido[2,3-d]pyrimidin-8(7H)-yl)ethyl)phenyl)acrylamide;
79. N-(6-(2-(6-(2,6-dichloro-3,5-dimethoxyphenyl)-2-(ethylamino)-7-oxopyrido[2,3-d]-pyrimidin-8(7H)-yl)ethyl)pyridin-3-yl)acrylamide;
80. N-(6-(2-(6-(2,6-dichloro-3,5-dimethoxyphenyl)-2-(isopropylamino)-7-oxopyrido[2,3-d]-pyrimidin-8(7H)-yl)ethyl)pyridin-3-yl)acrylamide;
81. N-(6-(2-(6-(2,6-dichloro-3,5-dimethoxyphenyl)-7-oxo-2-((tetrahydro-2H-pyran-4-yl)-amino)-pyrido[2,3-d]pyrimidin-8(7H)-yl)ethyl)pyridin-3-yl)acrylamide;
82. N-(4-(2-(6-(2-chloro-3,5-dimethoxyphenyl)-2-((2-((2R,6S)-2,6-dimethylpiperazin-1-yl)-ethyl)amino)-7-oxopyrido[2,3-d]pyrimidin-8(7H)-yl)ethyl)phenyl)acrylamide;
83. N-(4-(2-(6-(2-chloro-3,5-dimethoxyphenyl)-2-((3-hydroxy-2,2-dimethylpropyl)amino)-7-oxopyrido[2,3-d]pyrimidin-8(7H)-yl)ethyl)phenyl)acrylamide;
84. N-(6-(2-(6-(2,6-dichloro-3,5-dimethoxyphenyl)-2-((2-hydroxy-2-methylpropyl)-amino)-7-oxopyrido[2,3-d]pyrimidin-8(7H)-yl)ethyl)pyridin-3-yl)acrylamide;
85. N-(4-(2-(6-(2-chloro-3,5-dimethoxyphenyl)-2-((2-((3S,5R)-3,5-dimethylpiperazin-1-yl)-ethyl)amino)-7-oxopyrido[2,3-d]pyrimidin-8(7H)-yl)ethyl)phenyl)acrylamide;
86. N-(6-(2-(6-(2,6-dichloro-3,5-dimethoxyphenyl)-2-((2-hydroxyethyl)amino)-7-oxo-pyrido[2,3-d]pyrimidin-8(7H)-yl)ethyl)pyridin-3-yl)acrylamide;
87. N-(6-(2-(6-(2,6-dichloro-3,5-dimethoxyphenyl)-2-((1,3-dihydroxypropan-2-yl)amino)-7-oxopyrido[2,3-d]pyrimidin-8(7H)-yl)ethyl)pyridin-3-yl)acrylamide;
88. N-(6-(2-(6-(2,6-dichloro-3,5-dimethoxyphenyl)-2-((2,3-dihydroxypropyl)amino)-7-oxo-pyrido[2,3-d]pyrimidin-8(7H)-yl)ethyl)pyridin-3-yl)acrylamide;
89. N-(4-(2-(6-(2,6-dichloro-3,5-dimethoxyphenyl)-7-oxo-2-((tetrahydro-2H-pyran-4-yl)-amino)pyrido[2,3-d]pyrimidin-8 (7H)-yl)ethyl)phenyl)acrylamide;
90. N-(4-(2-(2-(((cyclopropylmethyl)amino)-6-(2,6-dichloro-3,5-dimethoxyphenyl)-7-oxo-pyrido[2,3-d]pyrimidin-8(7H)-yl)ethyl)phenyl)acrylamide;
91. N-(4-(2-(6-(2,6-dichloro-3,5-dimethoxyphenyl)-2-((1,3-dihydroxy-2-methylpropan-2-yl)amino)-7-oxopyrido[2,3-d]pyrimidin-8(7H)-yl)ethyl)phenyl)acrylamide;
92. N-(4-(2-(6-(2,6-dichloro-3,5-dimethoxyphenyl)-2-((1-hydroxy-2-(hydroxymethyl)-butan-2-yl)-amino)-7-oxopyrido[2,3-d]pyrimidin-8(7H)-yl)ethyl)phenyl)acrylamide;
93. N-(4-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)phenyl)acrylamide;
94. N-(6-(2-(6-(2,6-dichloro-3,5-dimethoxyphenyl)-2-((1-hydroxy-2-methylpropan-2-yl)-amino)-7-oxopyrido[2,3-d]pyrimidin-8(7H)-yl)ethyl)pyridin-3-yl)acrylamide;
95. N-(4-(2-(6-(2-chloro-3,5-dimethoxyphenyl)-2-((1,3-dihydroxy-2-methylpropan-2-yl)-amino)-7-oxopyrido[2,3-d]pyrimidin-8(7H)-yl)ethyl)phenyl)acrylamide;
96. N-(4-(2-(6-(2-chloro-3,5-dimethoxyphenyl)-2-(((4-hydroxy-1-methylpiperidin-4-yl)-methyl)-amino)-7-oxopyrido[2,3-d]pyrimidin-8(7H)-yl)ethyl)phenyl)acrylamide;
97. N-(6-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)pyridin-3-yl)acrylamide;
98. N-(4-(2-(6-(2,6-dichloro-3,5-dimethoxyphenyl)-2-(((4-hydroxy-1-methylpiperidin-4-yl)-methyl)-amino)-7-oxopyrido[2,3-d]pyrimidin-8(7H)-yl)ethyl)phenyl)acrylamide;
99. N-(6-(2-(6-(2,6-dichloro-3,5-dimethoxyphenyl)-2-((1,3-dihydroxy-2-methylpropan-2-yl)amino)-7-oxopyrido[2,3-d]pyrimidin-8(7H)-yl)ethyl)pyridin-3-yl)acrylamide;
100. N-(6-(2-(6-(2,6-dichloro-3,5-dimethoxyphenyl)-2-((1-hydroxy-2-(hydroxymethyl)-butan-2-yl)amino)-7-oxopyrido[2,3-d]pyrimidin-8(7H)-yl)ethyl)pyridin-3-yl)acrylamide;
101. N-(6-(2-(6-(2,6-dichloro-3,5-dimethoxyphenyl)-7-oxo-2-(prop-2-yn-1-ylamino)pyrido[2,3-d]pyrimidin-8(7H)-yl)ethyl)pyridin-3-yl)acrylamide;
102. N-(3-((6-(2-chloro-3,5-dimethoxyphenyl)-2-((2-morpholinoethyl)amino)-7-oxopyrido[2,3-d]pyrimidin-8(7H)-yl)methyl)phenyl)acrylamide;
103. N-(6-(2-(6-(2-chloro-3,5-dimethoxyphenyl)-2-((cyclopropylmethyl)amino)-7-oxopyrido-[2,3-d]pyrimidin-8(7H)-yl)ethyl)pyridin-3-yl)acrylamide;
104. N-(6-(2-(6-(2-chloro-3,5-dimethoxyphenyl)-2-((2-hydroxyethyl)amino)-7-oxopyrido[2,3-d]pyrimidin-8(7H)-yl)ethyl)pyridin-3-yl)acrylamide;
105. N-(4-(2-(6-(2,6-dichloro-3,5-dimethoxyphenyl)-2-((4-methylpiperazin-1-yl)amino)-7-oxopyrido[2,3-d]pyrimidin-8(7H)-yl)ethyl)phenyl)acrylamide;
106. N-(4-(2-(6-(2,6-dichlorophenyl)-2-(methylamino)-7-oxopyrido[2,3-d]pyrimidin-8(7H)-yl)ethyl)phenyl)acrylamide;
107. N-(6-(2-(6-(2,6-dichlorophenyl)-2-(methylamino)-7-oxopyrido[2,3-d]pyrimidin-8(7H)-yl)ethyl)pyridin-3-yl)acrylamide;
108. N-(6-(2-(6-(2-chloro-3,5-dimethoxyphenyl)-7-oxo-2-(pyridin-2-ylamino)pyrido[2,3-d]pyrimidin-8(7H)-yl)ethyl)pyridin-3-yl)acrylamide;
109. N-(6-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)pyridin-3-yl)acrylamide;
110. N-(4-(2-(6-(2-chloro-3,5-dimethoxyphenyl)-2-((2-methyl-2-morpholinopropyl)-amino)-7-oxopyrido[2,3-d]pyrimidin-8(7H)-yl)ethyl)phenyl)acrylamide;
111. N-(4-(2-(6-(2-chloro-3,5-dimethoxyphenyl)-2-((2-(4,4-difluoropiperidin-1-yl)ethyl)amino)-7-oxopyrido[2,3-d]pyrimidin-8(7H)-yl)ethyl)phenyl)acrylamide;
112. N-(4-(2-(6-(2-chloro-3,5-dimethoxyphenyl)-2-(((1,4-dimethylpiperidin-4-yl)methyl)-amino)-7-oxopyrido[2,3-d]pyrimidin-8(7H)-yl)ethyl)phenyl)acrylamide;
113. N-(4-(1-(6-(2-chloro-3,5-dimethoxyphenyl)-2-(methylamino)-7-oxopyrido[2,3-d]-pyrimidin-8(7H)-yl)-2-methylpropan-2-yl)phenyl)acrylamide; or
114. (E)-N-(4-(2-(6-(2,6-dichloro-3,5-dimethoxyphenyl)-2-(methylamino)-7-oxopyrido-[2,3-d]pyrimidin-8(7H)-yl)ethyl)phenyl)-4-(dimethylamino)but-2-enamide;
an individual E or Z isomer thereof;
and/or a pharmaceutically acceptable salt of any of the above compounds.

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I') where X is a group of formula (a) can be prepared as illustrated and described in Scheme 1 below.

Scheme 1

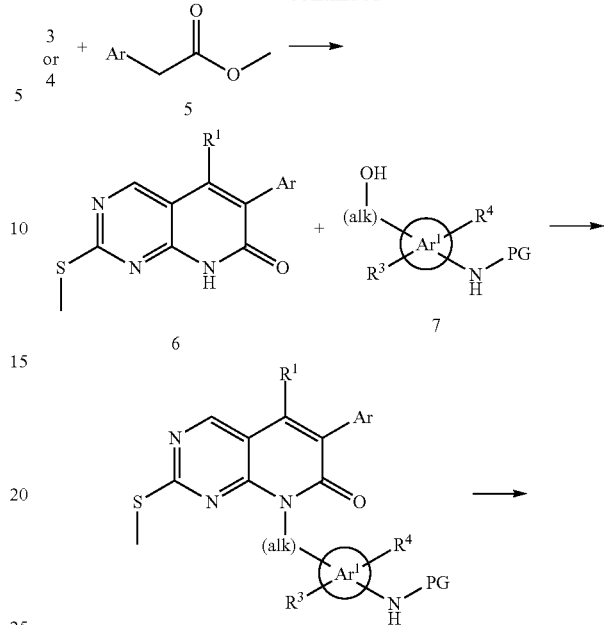

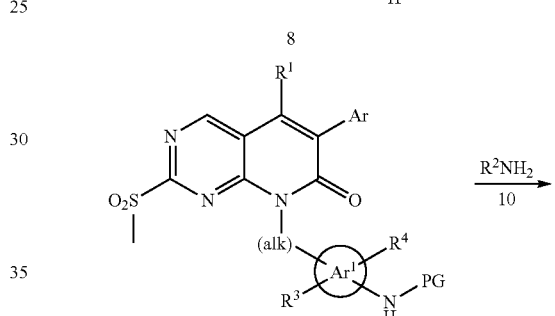

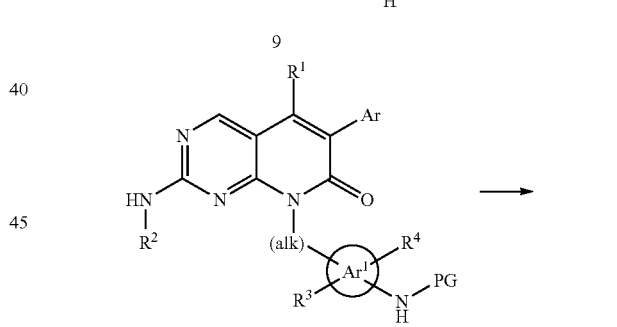

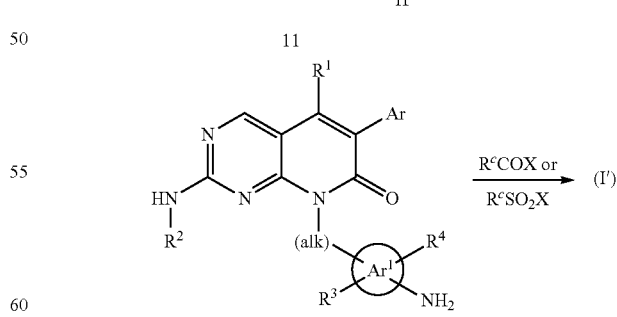

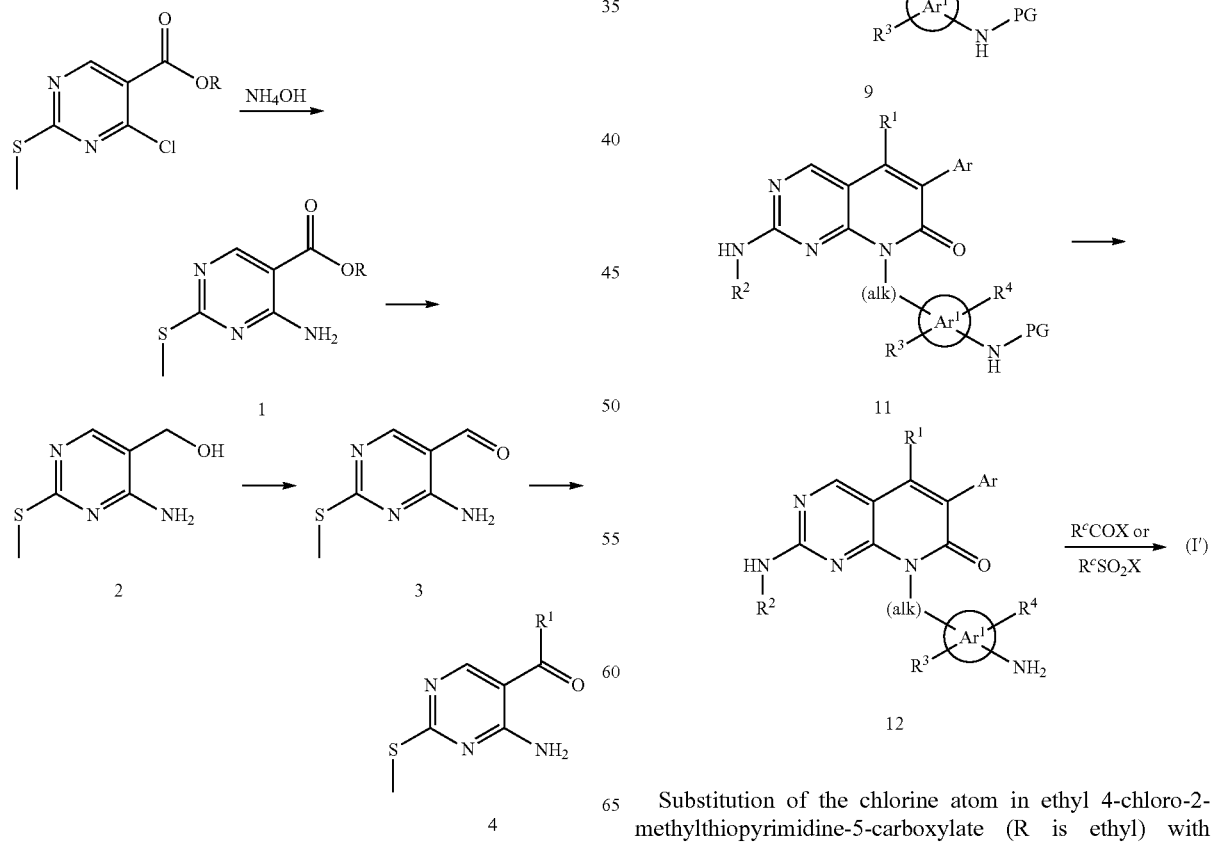

Substitution of the chlorine atom in ethyl 4-chloro-2-methylthiopyrimidine-5-carboxylate (R is ethyl) with ammonia in an organic solvent such as dichloromethane, tetrahydrofuran (THF), N,N-dimethylformamide (DMF), N-methylpyrrolidine (NMP), methyl alcohol, and the like, provides an amino compound of formula 1. Reduction of the ester group to an alcohol can be performed with a reducing agent such as lithium aluminum hydride in a solvent such as THF or diethyl ether at 0° C. to room temperature to provide a compound of formula 2.

Oxidation of the alcohol group in 2 provides an aldehyde of formula 3. The reaction is carried out under standard oxidation conditions well known in the art such as manganese dioxide ($MnO_2$) in solvents such as dichloromethane at 0° C. to 60° C. For compounds of Formula (I') where $R^1$ is alkyl, compound 3 can be treated with an alkyl lithium or alkyl magnesium halide in a solvent such as THF to generate a secondary alcohol which can then oxidized under standard oxidation reaction conditions to provide a compound of formula 4.

Coupling of compound 3 or 4 with an ester of formula 5 where Ar is as defined in the Summary provides a quinolone compound of formula 6 where $R^1$ is hydrogen or alkyl, respectively. The coupling reaction is carried out in solvents such as N,N-dimethylformamide (DMF), N-methylpyrrolidine (NMP), and the like, using a base such as sodium hydride, sodium bicarbonate, lithium bicarbonate, potassium bicarbonate or triethylamine, and the like, at room temperature to 150° C. Compounds of formula 5 are either commercially available or can be readily prepared by methods well known in the art.

Reaction of a compound of formula 6 with a compound of formula 7 where alk, $Ar^1$, $R^3$, and $R^4$ are as defined in the Summary and PG is a suitable nitrogen protecting group under standard Mitsunobu reaction conditions (e.g. triphenylphosphine, diisopropylazo-dicarboxylate in solvents such as THF, DCM or DMF provides a compound of formula 8. Compounds of formula 7 are either commercially available e.g. tert-butyl (3-(2-hydroxyethyl)phenyl)carbamate, tert-butyl (4-(2-hydroxyethyl)phenyl)carbamate, tert-butyl (3-(hydroxymethyl)phenyl)carbamate or can be readily prepared by methods well known in the art. Alternatively, the hydroxy group in 7 can be converted to a suitable leaving group such as tosylate, mesylate, or halo and then reacted with compound 6 in the presence of an organic base such as triethylamine, pyridine, and the like, to give a compound of formula 8.

Oxidation of the methylthio group in compound 8 provides sulfone of formula 9, utilizing oxidizing agents such as 3-chloroperbenzoic acid (MCPBA) in dichloromethane or Oxone® in methanol, aqueous ethanol or aqueous tetrahydrofuran at 0° C. to room temperature. Alternatively, the oxidation may be carried out under catalytic conditions with rhenium/peroxide reagents, see ("Oxidation of Sulfoxides by Hydrogen Peroxide, Catalyzed by Methyltrioxorhenium (VII)", Lahi, David W.; Espenson, James H, Inorg. Chem (2000) 39(10) pp. 2164-2167; "Rhenium oxo complexes in catalytic oxidations, Catal. Today (2000) 55(4), pp 317-363 and "A Simple and Efficient Method for the Preparation of Pyridine N-Oxides", Coperet, Christophe; Adolfsson, Hans; Khuong, Tinh-Alfredo V.; Yudin, Andrei K.; Sharpless, K. Barry, J. Org. Chem. (1998) 63(5), pp 1740-1741).

Coupling of the sulfone compound 9 with an amine of formula 10 where $R^2$ is as defined in the Summary in a solvent such as DMF or NMP at temperatures of 80° C. to 150° C. provides a compound of formula 11. Compounds of formula 10 are either commercially available e.g., methylamine, $N^1,N^1$-diethylbutane-1,4-diamine or can be readily prepared by methods well known in the art.

Removal of the amino protecting group provides a compound of formula 12. The reaction conditions depend on nature of the amino protecting group. For example, when PG is Boc, it can be removed by treating a compound of formula 11 with an acid e.g hydrogen chloride or trifluoroacetic acid in solvents such as DCM.

Compound 12 can be then converted to a compound of Formula (I') by methods well known in the art. For example, reacting 12 with an acyl halide of formula $R^cCOX$ or $R^cSO_2X$ where $R^c$ is as defined in the Summary and X is halo under standard acylating or sulfonylating conditions i.e., in the presence of a base such as TEA or DIEA in solvents such as THF or DCM provides a compound of Formula (I').

It will be apparent to a person of ordinary skill in the art that compounds of Formula (I') where X is a group of formula (b) can be readily prepared by a method disclosed above. A representative example of such preparation is provided in Working Examples below.

Testing

The FGFR kinase inhibitory activity of the compounds of the present disclosure can be tested using the in vitro and in vivo assays described in Biological Examples 1-4 below and the residence time of the compound FGFR bound complex can be tested using the Biological Examples 7 and 8 below. A determination of kinase inhibitory activity by any of those assays is considered to be kinase inhibitory activity within the scope of this disclosure even if any or all of the other assays do not result in a determination of kinase inhibitory activity. The ability of the compound of the disclosure to form an irreversible covalent bond with Cys488 of FGFR1 (UniprotKB Sequence ID P11362), Cys491 (UniprotKB Sequence ID P21802) of FGFR2, Cys482 (UniprotKB Sequence ID P22607) of FGFR3, and Cys477 (UniprotKB Sequence ID P22455) and the olefinic bond in the compound of the disclosure, can be determined by the assays described in Biological Example 6 below. The ability of the compound of the disclosure to form an irreversible covalent bond with FGFR 1-4 and the olefinic bond in the compound of the disclosure can be determined by the assays described in Biological Examples 5-9 below. A determination of the irreversibility of the covalent bond between the cysteine residue and the olefinic bond of the compound of the disclosure by any of Biological Examples 5-9 below is considered within the scope of this disclosure even if one or more of the other methods does not result in a determination of binding irreversibility of the covalent bond.

Administration and Pharmaceutical Composition

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of this disclosure) in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. For example, the compound is present at a level of about 1-80 wt %.

The compounds of this disclosure may be used in combination with one or more other drugs in the treatment of diseases or conditions for which compounds of this disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of this disclosure not only with one other active compound, but also with two or more other active compounds. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyhol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of this disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; Mtor inhibitors; and antibodies (e.g., rituxan).

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitocycin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula (I') or (I) include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maytansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of this disclosure include but are not limited to vinca alkaloids (e.g., diethylstil, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of this disclosure) include, but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Noscapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desacetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

SYNTHETIC EXAMPLES

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof. The  line at the alkene carbon, in the compounds below denotes that the compounds are isolated as an undefined mixture of (E) and (Z) isomers.

Reference 1

Synthesis of 6-(2-chlorophenyl)-2-(methylthio)pyrido[2,3-d]pyrimidin-7(8H)-one

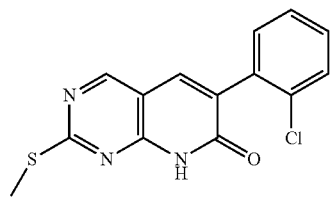 [SMILES: CSc1ncc2cc(-c3ccccc3Cl)c(=O)[nH]c2n1]

Step 1

To a solution of ethyl 4-chloro-2-(methylthio)pyrimidine-5-carboxylate (30 g, 129.3 mmol, 1.00 equiv) and Et₃N (51 mL) in THF (225 mL) was added NH₃.H₂O (300 mL). The resulting mixture was stirred at rt overnight. The mixture was concentrated and diluted with EtOAc. The organic phase was washed with sat. NaHCO₃ solution and brine, dried over anhydrous sodium sulfate. The solids were filtered and concentrated under vacuum to give 26.8 g (97%) of ethyl 4-amino-2-(methylthio)pyrimidine-5-carboxylate as a white solid.

Step 2

To a suspension of LiAlH₄ (10.53 g, 277.0 mmol, 2.2 equiv) in THF (500 mL) was added dropwise ethyl 4-amino-2-(methylthio)pyrimidine-5-carboxylate (26.8 g, 126.0 mmol, 1.0 equiv) in THF (500 mL) at 0° C. The resulting mixture was stirred at 0° C. for 5 h. The reaction was quenched with 15% NaOH solution. The mixture was stirred for 1 h. The white precipitate was removed by filtration, washing with EtOAc. The filtrate was concentrated under vacuum to give 22 g (crude) of (4-amino-2-(methylthio)pyrimidin-5-yl)methanol as a white solid.

Step 3

To a solution of (4-amino-2-(methylthio)pyrimidin-5-yl)methanol (11 g, 63 mmol, 1.0 equiv) in CHCl₃ (900 mL) was added MnO₂ (43.85 g, 504 mmol, 8.0 equiv). The suspension was stirred overnight at rt. The resulting mixture was filtration and washing with CHCl₃. The filtrate was concentrated under vacuum to give 10 g (94%) of 4-amino-2-(methylthio)pyrimidine-5-carbaldehyde as a white solid.

Step 4

A solution of 4-amino-2-(methylthio)pyrimidine-5-carbaldehyde (20 g, 119 mmol, 1.0 equiv), K₂CO₃ (49.26 g, 357 mmol, 3.0 equiv) and methyl 2-(2-chlorophenyl)acetate (32.84 g, 178.5 mmol, 1.5 equiv) in NMP (130 ml) was stirred at 110° C. overnight. The reaction was diluted with EtOAc and water and extracted with EtOAc. The organic phase washed with brine, dried and concentrated. The residue was purified by column chromatography using EtOAc/PE (1/3) to give. 19 g (53%) of 6-(2-chlorophenyl)-2-(methylthio)pyrido[2,3-d]pyrimidin-7(8H)-one as a yellow solid.

Example 1

Synthesis of N-(4-[2-[6-(2-chlorophenyl)-2-[[4-(diethylamino)butyl]amino]-7-oxo-7H,8H-pyrido[2,3-d]pyrimidin-8-yl]ethyl]phenyl)prop-2-enamide

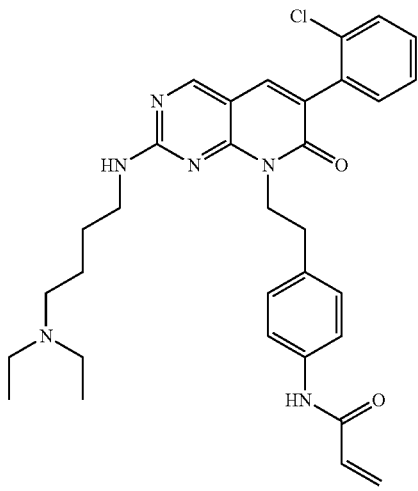 [SMILES: C=CC(=O)Nc1ccc(CCn2c(=O)c(-c3ccccc3Cl)cc3cnc(NCCCCN(CC)CC)nc32)cc1]

Step 1

Into a 100-mL 3-necked round-bottom flask, was placed 6-(2-chlorophenyl)-2-(methylsulfanyl)-7H,8H-pyrido[2,3-d]pyrimidin-7-one (3.03 g, 9.97 mmol, 1.00 equiv), tert-butyl N-[4-(2-hydroxyethyl)phenyl]carbamate (2.61 g, 10.99 mmol, 1.10 equiv), PPh$_3$ (5.24 g, 19.98 mmol, 2.00 equiv), N,N-dimethylformamide (30 mL). After the mixture was stirred for 3 min, DIAD (4.04 g, 19.98 mmol, 2.00 equiv) was dropped into with stirring at 0° C. under N$_2$. The resulting solution was stirred for 4 h at 0° C. in a water/ice bath. The resulting solution was diluted with H$_2$O and extracted with ethyl acetate and the organic layers combined. The resulting mixture was washed with water and dried over anhydrous sodium sulfate. The residue was applied onto a silica gel column with ethyl acetate/petroleum ether (1:10-1:5) to give 3.15 g of tert-butylN-(4-[2-[6-(2-chlorophenyl)-2-(methylsulfanyl)-7-oxo-7H,8H-pyrido[2,3-d]pyrimidin-8-yl]ethyl]phenyl)-carbamate as an off-white solid (yield 60%).

Step 2

Into a 500-mL round-bottom flask, was placed tert-butyl N-(4-[2-[6-(2-chlorophenyl)-2-(methylsulfanyl)-7-oxo-7H,8H-pyrido[2,3-d]pyrimidin-8-yl]ethyl]phenyl)carbamate (2.85 g, 5.45 mmol, 1.00 equiv), CHCl$_3$ (150 mL and, m-CPBA (85%, 2.82 g, 3.00 equiv) was added slowly with stirring. The resulting solution was stirred for 3 h at room temperature and then diluted with DCM. The resulting mixture was washed with saturated potassium carbonate solution and saturated sodium chloride solution. The mixture was dried over anhydrous sodium sulfate and concentrated under vacuum to give 3.40 g (crude) of tert-butyl N-(4-[2-[6-(2-chlorophenyl)-2-methanesulfonyl-7-oxo-7H,8H-pyrido[2,3-d]pyrimidin-8-yl]ethyl]phenyl)carbamate as a light brown solid.

Step 3

Into a 250-mL round-bottom flask, was placed tert-butyl N-(4-[2-[6-(2-chlorophenyl)-2-methanesulfonyl-7-oxo-7H,8H-pyrido[2,3-d]pyrimidin-8-yl]ethyl]phenyl)carbamate (3.20 g, 5.77 mmol, 1.00 equiv), (4-aminobutyl)diethylamine (1.67 g, 11.58 mmol, 2.00 equiv), pyridine (40 mL). The resulting solution was stirred for 2 h at 80° C. in an oil bath. The resulting mixture was concentrated under vacuum. The residue was applied onto a silica gel column with methanol: EtOAc (EtOAc-1:30-1:20). The collected fractions were combined and concentrated under vacuum. This resulted in 2.80 g (crude) of tert-butyl N-(4-[2-[6-(2-chlorophenyl)-2-[[4-(diethylamino)butyl]amino]-7-oxo-7H,8H-pyrido[2,3-d]pyrimidin-8-yl]ethyl]phenyl)carbamate as a brown solid.

Step 4

Into a 250-mL round-bottom flask, was placed tert-butyl N-(4-[2-[6-(2-chlorophenyl)-2-[[4-(diethylamino)butyl]amino]-7-oxo-7H,8H-pyrido[2,3-d]pyrimidin-8-yl]ethyl]phenyl)-carbamate (1.00 g, 1.61 mmol, 1.00 equiv) and dichloromethane (30 mL). Trifluoroacetic acid (8 mL) was dropped into slowly at 0° C. with stirring. The resulting solution was stirred for 2 h at room temperature and then concentrated under vacuum. The residue was diluted with DCM and washed with saturated potassium carbonate solution. The mixture was dried over anhydrous sodium sulfate and concentrated under vacuum to give 803 mg (96%) of 8-[2-(4-aminophenyl)-ethyl]-6-(2-chlorophenyl)-2-[[4-(diethylamino)butyl]amino]-7H,8H-pyrido[2,3-d]pyrimidin-7-one as a brown solid.

Step 5

Into a 100-mL 3-necked round-bottom flask, was placed 8-[2-(4-aminophenyl)ethyl]-6-(2-chlorophenyl)-2-[[4-(diethylamino)butyl]amino]-7H,8H-pyrido[2,3-d]pyrimidin-7-one (400 mg, 0.77 mmol, 1.00 equiv) and dichloromethane (30 mL). Prop-2-enoyl chloride (140 mg, 1.55 mmol, 2.01 equiv) was added dropwise with stirring at −20° C. The resulting solution was stirred for 2 h at −20° C. and then quenched with 2 mL of methanol. The resulting mixture was concentrated under vacuum. The residue was applied onto a silica gel column and eluted with EtOAc:Methanol (5:1). The collected fractions were combined and concentrated under vacuum. The residue was dissolved in 4 mL of methanol. The crude product (100 mg) was purified by Prep-HPLC with the following conditions (1#-Pre-HPLC-005(Waters)): Column, SunFire Prep C18 19*150 mm 5 um; mobile phase, water with 0.05% TFA and CH$_3$CN (10% CH$_3$CN up to 30% in 10 min); Detector, 254 nm to give 64.1 mg (15%) of the title as an off-white solid. LCMS (ESI, pos. ion) m/z: 573 (M+1).

Example 2

Synthesis of 8-(2-(1-acryloylpiperidin-3-yl)ethyl)-6-(2-chlorophenyl)-2-(4-(diethylamino)-butylamino)pyrido[2,3-d]pyrimidin-7(8H)-one

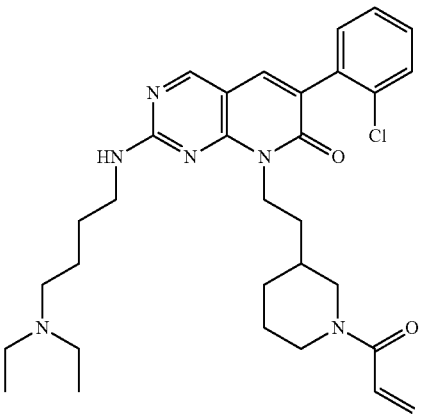 [SMILES: C=CC(=O)N1CCCC(CCn2c(=O)c(-c3ccccc3Cl)cc3cnc(NCCCCN(CC)CC)nc32)C1]

Step 1

To a mixture of 6-(2-chlorophenyl)-2-(methylthio)pyrido[2,3-d]pyrimidin-7(8H)-one (3.03 g, 10 mmol, 1.0 equiv), tert-butyl 3-(2-hydroxyethyl)piperidine-1-carboxylate (2.52 g, 11 mmol, 1.1 equiv) and PPh₃ (5.24 g, 20 mmol, 2.0 equiv) in DMF (30 mL) was added dropwise DIAD (4.04 g, 20 mmol, 2.0 equiv) at 0° C. under N₂. The mixture was stirred at rt overnight. The resulting mixture was poured into water and extracted with EtOAc, washed with water, dried over anhydrous sodium sulfate and concentrated under vacuum. The residue was purified by column chromatography using PE/EtOAc (10/1 to 3/1). This resulted in 5.15 g (60%) of tert-butyl 3-(2-(6-(2-chlorophenyl)-2-(methylthio)-7-oxopyrido[2,3-d]pyrimidin-8(7H)-yl)ethyl)piperidine-1-carboxylate as a white solid.

Step 2

To a mixture of tert-butyl 3-(2-(6-(2-chlorophenyl)-2-(methylthio)-7-oxopyrido[2,3-d]pyrimidin-8(7H)-yl)ethyl)piperidine-1-carboxylate (3.09 g, 6 mmol, 1 equiv) in CHCl₃ (150 mL) was added slowly portionwise mCPBA (85%, 3.65 g, 18 mmol, 3.0 equiv). The reaction was stirred at rt overnight. The mixture was washed with sat. NaHCO₃ solution and brine, dried over anhydrous sodium sulfate. The solids were filtered and concentrated under vacuum to give 4.1 g (crude) of tert-butyl 3-(2-(6-(2-chlorophenyl)-2-(methylsulfonyl)-7-oxopyrido[2,3-d]pyrimidin-8(7H)-yl)ethyl)piperidine-1-carboxylate as a brown oil.

Step 3

A solution of tert-butyl 3-(2-(6-(2-chlorophenyl)-2-(methylsulfonyl)-7-oxopyrido[2,3-d]-pyrimidin-8(7H)-yl)ethyl)piperidine-1-carboxylate (3.27 g, 6 mmol, 1.0 equiv) and N¹,N¹-diethylbutane-1,4-diamine (2.6 g, 18 mmol, 3.0 equiv) in Py (20 mL) was heated to 80° C. for 2 h. The mixture was poured into water and extracted with EtOAc. The organic layer was washed with brine, dried over anhydrous sodium sulfate. The solids were filtered and concentrated under vacuum. The residue was purified by column chromatography using EtOAc/MeOH (30/1 to 5/1). This resulted in 2.2 g (60%) of tert-butyl 3-(2-(6-(2-chlorophenyl)-2-(4-(diethylamino)butyl-amino)-7-oxopyrido[2,3-d]pyrimidin-8(7H)-yl)ethyl)piperidine-1-carboxylate as a brown solid.

Step 4

To a mixture of tert-butyl 3-(2-(6-(2-chlorophenyl)-2-(4-(diethylamino)butylamino)-7-oxopyrido[2,3-d]pyrimidin-8(7H)-yl)ethyl)piperidine-1-carboxylate (0.8 g, 1.3 mmol, 1.0 equiv) in DCM (8 mL) was added TFA (2 mL). The reaction was stirred overnight at rt. The solution was concentrated and to the residue was added sat.Na₂CO₃ solution. The resulting mixture was extracted with EtOAc. The organic layer was washed with brine, dried over anhydrous sodium sulfate and concentrated under vacuum to give 0.62 g (93%) of 6-(2-chlorophenyl)-2-(4-(diethylamino)butylamino)-8-(2-(piperidin-3-yl)ethyl)pyrido[2,3-d]pyrimidin-7(8H)-one as a brown solid.

Step 5

To a mixture of 6-(2-chlorophenyl)-2-(4-(diethylamino)butylamino)-8-(2-(piperidin-3-yl)ethyl)pyrido[2,3-d]pyrimidin-7(8H)-one (409 mg, 0.8 mmol, 1.0 equiv) in DCM (20 mL) was added dropwise acryloyl chloride (144 mg, 1.6 mmol, 2.0 equiv) at −20° C. under N₂. The resulting mixture was stirred at this temperature for 30 min, then the reaction was quenched with MeOH (5 mL). The mixture was concentrated. The crude product was purified by prep-HPLC with the following conditions (IntelFlash-1): Column, C18 silica gel; mobile phase, CH₃CN/H₂O (0.05% TFA)=5/100 increasing to CH₃CN/H₂O (0.05% TFA)=40/100 within 20 min; Detector, UV 254 nm. After removing off MeCN, The pH of the aqueous phase was adjusted to 9 and extracted with DCM. The organic layers were combined, washed with brine, dried over sodium sulfate, filtrate and concentrated to give the title compound 28.6 mg (6.4%) as a white solid. LCMS (ESI, pos. ion) m/z: 565.45 (M+1).

Example 3

Synthesis of N-(3-(2-(6-(2-chlorophenyl)-2-(4-(diethylamino)butylamino)-7-oxopyrido[2,3-d]-pyrimidin-8(7H)-yl)ethyl)phenyl)acrylamide

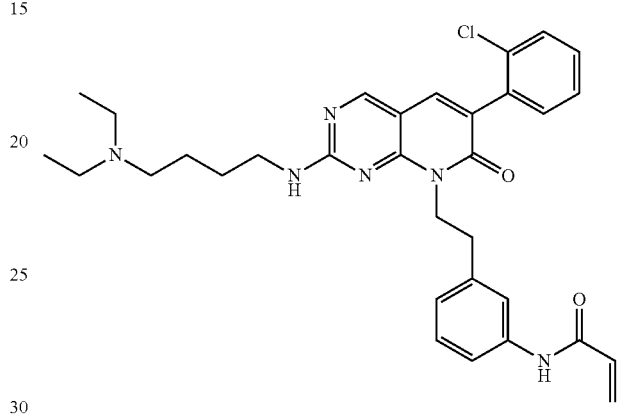

Step 1

To a mixture of 6-(2-chlorophenyl)-2-(methylthio)pyrido[2,3-d]pyrimidin-7(8H)-one (3.03 g, 10 mmol, 1.0 equiv), tert-butyl 3-(2-hydroxyethyl)phenylcarbamate (2.61 g, 11 mmol, 1.1 equiv) and PPh₃ (5.24 g, 20 mmol, 2.0 equiv) in DMF (30 mL) was added dropwise DIAD (4.04 g, 20 mmol, 2.0 equiv) at 0° C. under N₂. The mixture was stirred at rt overnight. The resulting mixture was poured into water and extracted with EtOAc, washed with water, dried over anhydrous sodium sulfate and concentrated under vacuum. The residue was purified by column chromatography using EtOAc/PE (1/10 to 1/3) to give 3.66 g (70%) of tert-butyl 3-(2-(6-(2-chlorophenyl)-2-(methylthio)-7-oxopyrido[2,3-d]pyrimidin-8(7H)-yl)ethyl)phenylcarbamate as a white solid.

Step 2

To a mixture of tert-butyl 3-(2-(6-(2-chlorophenyl)-2-(methylthio)-7-oxopyrido[2,3-d]-pyrimidin-8(7H)-yl)ethyl)phenylcarbamate (3.13 g, 6 mmol, 1.0 equiv) in CHCl₃ (150 mL) was added slowly portionwise mCPBA (85%, 3.65 g, 18 mmol, 3.0 equiv). The reaction was stirred at rt overnight. The mixture was washed with sat. NaHCO₃ solution and brine, dried over anhydrous sodium sulfate. The solids were filtered and concentrated under vacuum to give in 4 g (crude) of tert-butyl 3-(2-(6-(2-chlorophenyl)-2-(methylsulfonyl)-7-oxopyrido[2,3-d]pyrimidin-8(7H)-yl)ethyl)phenylcarbamate as a brown oil.

Step 3

Proceeding under conditions similar to those described in Example 1, Step 3 above but substituting tert-butyl N-(4-[2-[6-(2-chlorophenyl)-2-methanesulfonyl-7-oxo-7H,8H-pyrido[2,3-d]pyrimidin-8-yl]ethyl]phenyl)-carbamate with tert-butyl 3-(2-(6-(2-chlorophenyl)-2-(methylsulfonyl)-7-oxopyrido[2,3-d]-pyrimidin-8(7H)-yl)ethyl)phenylcarbamate, tert-butyl 3-(2-(6-(2-chlorophenyl)-2-(4-(diethylamino)butylamino)-7-oxopyrido[2,3-d]pyrimidin-8(7H)-yl)

ethyl)phenylcarbamate was prepared. tert Butyl 3-(2-(6-(2-chlorophenyl)-2-(4-(diethyl-amino)butylamino)-7-oxopyrido[2,3-d]pyrimidin-8(7H)-yl)ethyl)phenylcarbamate was then converted to 8-(3-aminophenethyl)-6-(2-chlorophenyl)-2-(4-(diethylamino)butylamino)pyrido-[2,3-d]-pyrimidin-7(8H)-one by proceeding under conditions similar to those described in Example 1, Step 4 above.

Step 5

To a mixture of 8-(3-aminophenethyl)-6-(2-chlorophenyl)-2-(4-(diethylamino)butylamino)pyrido[2,3-d]pyrimidin-7(8H)-one (414.4 mg, 0.8 mmol, 1.0 equiv) in DCM (20 mL) was added dropwise acryloyl chloride (144 mg, 1.6 mmol, 2.0 equiv) at −20° C. under N$_2$. The resulting mixture was stirred at this temperature for 30 min. The mixture was concentrated. The crude product was purified by prep-HPLC. The resulting solution was diluted with sat.Na$_2$CO$_3$ solution, extracted with DCM. The combined organic layer was washed with brine, dried over anhydrous sodium sulfate and concentrated under vacuum to give 68.5 mg (15%) of the title compound as a white solid. LCMS (ESI, pos. ion) m/z: 573.2 (M+1).

Example 4

Synthesis of N-(4-(2-(6-(2,6-dichloro-3,5-dimethoxyphenyl)-2-(methylamino)-7-oxopyrido[2,3-d]pyrimidin-8(7H)-yl)ethyl)phenyl)acrylamide

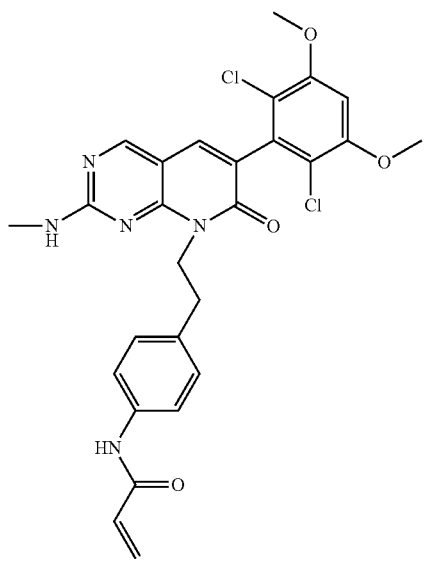

Step 1

Into a 500-mL 3-necked round-bottom flask, which was purged and maintained with an inert atmosphere of nitrogen, was placed a solution of 1,3-dimethoxy-5-methylbenzene (5 g, 32.85 mmol, 1.00 equiv) in dichloromethane (150 mL). This was followed by the addition of sulfuroyl dichloride (8.869 g, 65.71 mmol, 2.00 equiv) dropwise with stirring at 0° C. The resulting solution was stirred overnight at room temperature. The pH value of the solution was adjusted to 8 with sodium carbonate (sat. aq.). The resulting solution was extracted with dichloromethane, and the combined organic layers were concentrated under vacuum. The resulting mixture was washed with hexane to give 5.36 g (74%) of 2,4-dichloro-1,5-dimethoxy-3-methylbenzene as a white solid.

Step 2

Into a 1 L round-bottom flask, was placed a solution of 2,4-dichloro-1,5-dimethoxy-3-methylbenzene (35 g, 158.31 mmol, 1.00 equiv) in tetrachloromethane (600 mL). NBS (31 g, 174.18 mmol, 1.10 equiv) and AIBN (3.5 g, 21.31 mmol, 0.13 equiv) were added to the reaction mixture. The resulting solution was heated to reflux for 3 h. The reaction was then quenched by the addition of sodium carbonate (sat. aq.). The organic layer was washed with sodium chloride (sat.). The resulting mixture was concentrated under vacuum to give 38 g (80%) of 3-(bromomethyl)-2,4-dichloro-1,5-dimethoxybenzene as a yellow solid.

Step 3

Into a 1 L round-bottom flask, was placed a solution of 3-(bromomethyl)-2,4-dichloro-1,5-dimethoxybenzene (47 g, 156.68 mmol, 1.00 equiv) in DMSO (500 mL). Sodium cyanide (8.445 g, 172.32 mmol, 1.10 equiv) was added to the reaction mixture. The resulting solution was stirred overnight at 35° C. The reaction was then quenched with sodium bicarbonate (sat. aq.). The resulting solution was extracted with ethyl acetate, The combined organic layers were washed with water and concentrated. The residue was applied onto a silica gel column with ethyl acetate/petroleum ether (1:10) as eluent to yield 20 g (52%) of 2-(2,6-dichloro-3,5-dimethoxy-phenyl)acetonitrile as a white solid.

Step 4

Into a 100-mL round-bottom flask, was placed a solution of 4-amino-2-(methylsulfanyl)-pyrimidine-5-carbaldehyde (2.0 g, 11.82 mmol, 1.00 equiv) in DMF (40 mL). 2-(2,6-Dichloro-3,5-dimethoxyphenyl)acetonitrile (4.08 g, 16.58 mmol, 1.40 equiv), and potassium carbonate (4.90 g, 35.20 mmol, 3.00 equiv) were added and the resulting solution was stirred for 12 h at 100° C. in an oil bath, and then it was quenched with water. The resulting solution was extracted with ethyl acetate, and the combined organic layers were dried over anhydrous sodium sulfate and concentrated under vacuum. The residue was applied onto a silica gel column with ethyl acetate/petroleum ether (1:2) as eluent to yield 1.65 g (35%) of 6-(2,6-dichloro-3,5-dimethoxy-phenyl)-2-(methylsulfanyl)-7H,8H-pyrido[2,3-d]pyrimidin-7-imine as a yellow solid.

Step 5

Into a 50-mL round-bottom flask, was placed a solution of 6-(2,6-dichloro-3,5-dimethoxy-phenyl)-2-(methylsulfanyl)-7H,8H-pyrido[2,3-d]pyrimidin-7-imine (1.60 g, 4.03 mmol, 1.00 equiv) in acetic acid (40 mL). NaNO$_2$ (1.50 g, 21.74 mmol, 5.00 equiv) was added to the reaction mixture. The resulting solution was stirred for 2 h at 70° C., and then it was quenched with water. The solids were collected by filtration to give 1.25 g (78%) of 6-(2,6-dichloro-3,5-dimethoxy-phenyl)-2-(methylsulfanyl)-7H,8H-pyrido[2,3-d]pyrimidin-7-one as a yellow solid.

Step 6

Into a 250-mL round-bottom flask, was placed a solution of 6-(2,6-dichloro-3,5-dimethoxyphenyl)-2-(methylsulfanyl)-7H,8H-pyrido[2,3-d]pyrimidin-7-one (1.5 g, 3.77 mmol, 1.00 equiv) in acetone (100 mL). Potassium carbonate (3.123 g, 22.43 mmol, 6.00 equiv), and tert-butyl N-[4-(2-iodoethyl)phenyl]carbamate (1.962 g, 5.65 mmol, 1.50 equiv) were added and the resulting solution was heated to reflux overnight, and then concentrated under vacuum. The reaction was then quenched with water and then extracted with ethyl acetate, and the combined organic layers were concentrated under vacuum. The residue was applied onto a silica gel column with ethyl acetate/petroleum ether (1:2) as eluent. The collected fractions were combined and concentrated under vacuum to yield 1.7 g (73%) of tert-butyl N-(4-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)-carbamate as a yellow solid.

Step 7

Into a 500-mL round-bottom flask, was placed a solution of tert-butyl N-(4-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)carbamate (1.7 g, 2.75 mmol, 1.00 equiv) in chloroform (200 mL). m-CPBA (1.187 g, 6.88 mmol, 2.50 equiv) was added to the reaction mixture. The resulting solution was stirred overnight at room temperature. The pH value of the solution was adjusted to 8 with sodium bicarbonate solution (sat.). The resulting solution was extracted with dichloromethane, and the combined organic layers were washed with brine, and concentrated under vacuum. The residue was applied onto a silica gel column with ethyl acetate/petroleum ether (1:1) as eluent. The collected fractions were combined and concentrated under vacuum to yield 1.49 g (83%) of tert-butyl N-(4-[2-[6-(2,6-dichloro-3,5-dimethoxyphenyl)-2-methanesulfonyl-7-oxo-7H,8H-pyrido[2,3-d]pyrimidin-8-yl]ethyl]phenyl)carbamate as a light yellow solid.

Step 8

Into a 50-mL round-bottom flask, was placed a solution of tert-butyl N-(4-[2-[6-(2,6-dichloro-3,5-dimethoxyphenyl)-2-methanesulfonyl-7-oxo-7H,8H-pyrido[2,3-d]pyrimidin-8-yl]ethyl]phenyl)carbamate (160 mg, 0.25 mmol, 1.00 equiv) in DMSO (5 mL). TEA (124.6 mg, 1.23 mmol, 5.00 equiv), and methanamine hydrochloride (33.4 mg, 0.49 mmol, 2.00 equiv) were added and the resulting solution was stirred overnight at 50° C., and then it was diluted with H$_2$O. The resulting solution was extracted with ethyl acetate, and the combined organic layers were washed with brine, concentrated under vacuum to give 120 mg (81%) of tert-butyl N-(4-[2-[6-(2,6-dichloro-3,5-dimethoxyphenyl)-2-(methylamino)-7-oxo-7H,8H-pyrido[2,3-d]pyrimidin-8-yl]ethyl]phenyl)carbamate as a brown solid.

Step 9

Into a 50-mL round-bottom flask, was placed a solution of tert-butyl N-(4-[2-[6-(2,6-dichloro-3,5-dimethoxyphenyl)-2-(methylamino)-7-oxo-7H,8H-pyrido[2,3-d]pyrimidin-8-yl]ethyl]phenyl)carbamate (120 mg, 0.20 mmol, 1.00 equiv) in dichloromethane (10 mL) and trifluoroacetic acid (5 mL). The resulting solution was stirred for 3 h at room temperature. The pH value of the solution was adjusted to 8 with sodium bicarbonate (sat.). The aqueous layer was extracted with dichloromethane, and the combined organic layers were concentrated under vacuum to give 95 mg (95%) of 8-[2-(4-aminophenyl)ethyl]-6-(2,6-dichloro-3,5-dimethoxyphenyl)-2-(methylamino)-7H,8H-pyrido[2,3-d]pyrimidin-7-one as a brown solid.

Step 10

Into a 25-mL round-bottom flask, was placed a solution of 8-[2-(4-aminophenyl)ethyl]-6-(2,6-dichloro-3,5-dimethoxyphenyl)-2-(methylamino)-7H,8H-pyrido[2,3-d]pyrimidin-7-one (90 mg, 0.18 mmol, 1.00 equiv) in N,N-dimethylformamide (5 mL). TEA (54.6 mg, 0.54 mmol, 3.00 equiv), prop-2-enoic acid (14.3 mg, 0.20 mmol, 1.10 equiv) and HATU (102.6 mg, 0.27 mmol, 1.50 equiv) were added to the reaction mixture. The resulting solution was stirred overnight at room temperature, and then it was diluted with H$_2$O. The resulting solution was extracted with ethyl acetate, and the combined organic layers were concentrated under vacuum. The crude product (100 mg) was purified by Prep-HPLC with the following conditions (2#-AnalyseHPLC-SHIMADZU(HPLC-10)): Column, SunFire Prep C18 OBD Column, 5 um, 19*150 mm; mobile phase, water with 0.1% HCOOH and MeCN (48.0% MeCN up to 58.0% in 8 min, up to 100.0% in 2 min, down to 48.0% in 1 min); Detector, Waters2545 UvDector 254&220 nm. This resulted in 22 mg (22%) of the title compound as a light yellow solid. LC-MS m/z: 554 [M+1].

Example 5

Synthesis of N-(4-(2-(6-(2,6-dichloro-3,5-dimethoxyphenyl)-2-(4-(diethylamino)butylamino)-7-oxopyrido[2,3-d]pyrimidin-8(7H)-yl)ethyl)phenyl) acrylamide hydrochloride

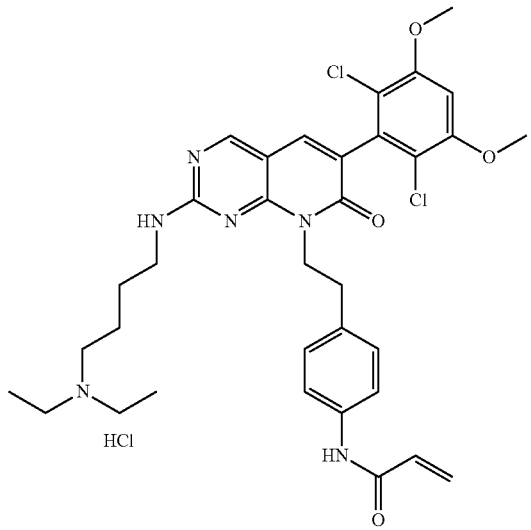 [SMILES: C=CC(=O)Nc1ccc(CCn2c(=O)c(-c3c(Cl)c(OC)cc(OC)c3Cl)cc3cnc(NCCCCN(CC)CC)nc32)cc1 ; Cl]

Step 1

Into a 100-mL round-bottom flask, was placed a solution of tert-butyl N-(4-[2-[6-(2,6-dichloro-3,5-dimethoxyphenyl)-2-methanesulfonyl-7-oxo-7H,8H-pyrido[2,3-d]pyrimidin-8-yl]ethyl]phenyl)carbamate (1.02 g, 1.57 mmol, 1.00 equiv) in DMSO (30 mL). TEA (477 mg, 4.71 mmol, 3.00 equiv) and (4-aminobutyl)diethylamine (340 mg, 2.36 mmol, 1.50 equiv) were added and the resulting solution was stirred for 4 h at 50° C., and then it was diluted with water. The resulting solution was extracted with ethyl acetate, and the combined organic layers were washed with brine and concentrated under vacuum. This resulted in 1.1 g (98%) of tert-butyl N-(4-[2-[6-(2,6-dichloro-3,5-dimethoxyphenyl)-2-[[4-(diethylamino)butyl]amino]-7-oxo-7H,8H-pyrido[2,3-d]pyrimidin-8-yl]ethyl]phenyl)carbamate as a brown solid which was converted to 8-[2-(4-aminophenyl)ethyl]-6-(2,6-dichloro-3,5-dimethoxyphenyl)-2-[[4-(diethylamino)butyl]amino]-7H,8H-pyrido[2,3-d]pyrimidin-7-one under conditions similar to those described in Example 4, Step 9 above.

Step 2

8-[2-(4-Aminophenyl)ethyl]-6-(2,6-dichloro-3,5-dimethoxyphenyl)-2-[[4-(diethylamino)butyl]amino]-7H,8H-pyrido[2,3-d]pyrimidin-7-one was converted to the title compound as described in Example 4, Step 10 above. The crude product (100 mg) was purified by Prep-HPLC with the following conditions (2#-AnalyseHPLC-SHIMADZU (HPLC-10)): Column, SunFire Prep C18 OBD Column, 5 um, 19*150 mm; mobile phase, water with 0.1% HCOOH and MeCN (22% MeCN up to 36% in 8 min, up to 100% in 2 min, down to 22% in 1 min); Detector, Waters2545 UvDector 254&220 nm. LC-MS m/z: 667.4 [M+1-HCl]+

Example 6

Synthesis of N-(3-[[6-(2,6-dichloro-3,5-dimethoxyphenyl)-2-[[4-(diethylamino)butyl]-amino]-7-oxo-7H,8H-pyrido[2,3-d]pyrimidin-8-yl]methyl]phenyl)acrylamide

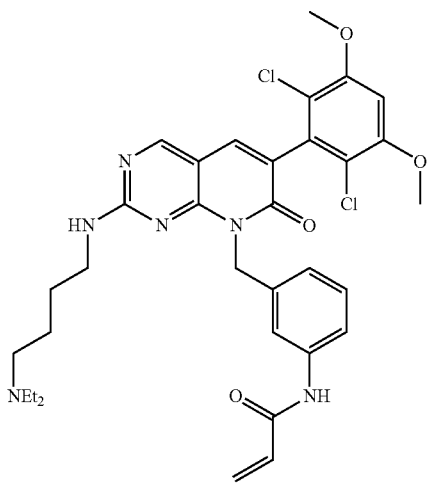

Step 1

Into a 250-mL round-bottom flask, was placed a solution of (3-aminophenyl)methanol (5 g, 40.60 mmol, 1.00 equiv) and di-tert-butyl dicarbonate (9.60 g, 43.99 mmol, 1.08 equiv) in tetrahydrofuran (150 mL). The resulting solution was stirred overnight at room temperature. The resulting mixture was concentrated under vacuum. The residue was applied onto a silica gel column with ethyl acetate/petroleum ether (1:10) to yield 8.92 g (98%) of tert-butyl N-[3-(hydroxymethyl)phenyl]carbamate as a white solid.

Step 2

Into a 250-mL round-bottom flask, was placed a solution of tert-butyl N-[3-(hydroxymethyl)phenyl]carbamate (4.46 g, 19.98 mmol, 1.00 equiv) in dichloromethane (150 mL). Triphenylphosphine (6.70 g, 25.54 mmol, 1.28 equiv), 1H-imidazole (2.244 g, 32.96 mmol, 1.65 equiv), and iodine (6.10 g, 24.03 mmol, 1.20 equiv) were added to the reaction mixture. The resulting solution was stirred for 1.5 h at room temperature, and then it was quenched with water. The resulting solution was extracted with dichloromethane, and the combined organic layers were dried over anhydrous sodium sulfate and concentrated under vacuum. The residue was applied onto a silica gel column with ethyl acetate/petroleum ether (1:50) as eluent to give 4.7 g (71%) of tert-butyl N-[3-(iodomethyl)phenyl]carbamate as a white solid.

Step 3

Into a 100-mL round-bottom flask, was placed a solution of tert-butyl N-[3-(iodomethyl)-phenyl]carbamate (503 mg, 1.51 mmol, 1.50 equiv), 6-(2,6-dichloro-3,5-dimethoxyphenyl)-2-(methylsulfanyl)-7H,8H-pyrido[2,3-d]pyrimidin-7-one (400 mg, 1.00 mmol, 1.00 equiv), and potassium carbonate (834 mg, 6.04 mmol, 6.00 equiv) in acetone (50 mL). The resulting solution was stirred for 8 h at 55° C. in an oil bath. The reaction was then quenched with water. The resulting solution was extracted with dichloromethane and the combined organic layers were dried over anhydrous sodium sulfate and concentrated under vacuum. The residue was applied onto a silica gel column with ethyl acetate/petroleum ether (1:4) as eluent to give 382 mg (63%) of tert-butyl N-(3-[[6-(2,6-dichloro-3,5-dimethoxyphenyl)-2-(methylsulfanyl)-7-oxo-7H,8H-pyrido[2,3-d]pyrimidin-8-yl]methyl]phenyl)carbamate as a yellow solid.

Step 4

Into a 50-mL round-bottom flask, was placed a solution of tert-butyl N-(3-[[6-(2,6-dichloro-3,5-dimethoxyphenyl)-2-(methylsulfanyl)-7-oxo-7H,8H-pyrido[2,3-d]pyrimidin-8-yl]methyl]phenyl)carbamate (380 mg, 0.63 mmol, 1.00 equiv) in chloroform (25 mL). m-CPBA (326 mg, 1.89 mmol, 3.00 equiv) was added to the reaction. The resulting solution was stirred for 12 h at room temperature, and then it was quenched with 5 mL of Na$_2$SO$_3$ (sat.). The resulting solution was extracted with dichloromethane, and the combined organic layers were dried over anhydrous sodium sulfate and concentrated under vacuum. This resulted in 390 mg (97%) of tert-butyl N-(3-[[6-(2,6-dichloro-3,5-dimethoxyphenyl)-2-methanesulfonyl-7-oxo-7H,8H-pyrido[2,3-d]pyrimidin-8-yl]methyl]phenyl)carbamate as a yellow solid.

Step 5

Into a 50-mL round-bottom flask, was placed a solution of tert-butyl N-(3-[[6-(2,6-dichloro-3,5-dimethoxyphenyl)-2-methanesulfonyl-7-oxo-7H,8H-pyrido[2,3-d]pyrimidin-8-yl]methyl]phenyl)carbamate (360 mg, 0.57 mmol, 1.00 equiv) in DMSO (30 mL). (4-Aminobutyl)diethylamine (122.6 mg, 0.85 mmol, 1.50 equiv) and triethylamine (172.4 mg, 1.70 mmol, 3.00 equiv) were added to the reaction mixture. The resulting solution was stirred for 5 h at 50° C., and then it was quenched with water. The resulting solution was extracted with ethyl acetate, and the combined organic layers were dried over anhydrous sodium sulfate and concentrated under vacuum. This resulted in 396 mg (100%) of tert-butyl N-(3-[[6-(2,6-dichloro-3,5-dimethoxyphenyl)-2-[[4-(diethylamino)butyl]amino]-7-oxo-7H,8H-pyrido[2,3-d]pyrimidin-8-yl]methyl]phenyl)carbamate as a yellow solid.

Step 6

Into a 50-mL round-bottom flask, was placed a solution of tert-butyl N-(3-[[6-(2,6-dichloro-3,5-dimethoxyphenyl)-2-[[4-(diethylamino)butyl]amino]-7-oxo-7H,8H-pyrido[2,3-d]pyrimidin-8-yl]methyl]phenyl)carbamate (428 mg, 0.61 mmol, 1.00 equiv) in dichloromethane (10 mL) and trifluoroacetic acid (5 mL). The resulting solution was stirred for 5 h at room temperature, and then it was quenched by the addition of 10 mL of sodium carbonate (sat.). The resulting solution was extracted with 5×10 mL of dichloromethane, and the combined organic layers were dried over anhydrous sodium sulfate and concentrated under vacuum. This resulted in 340 mg (93%) of 8-[(3-aminophenyl)methyl]-6-(2,6-dichloro-3,5-dimethoxyphenyl)-2-[[4-(diethylamino)butyl]amino]-7H,8H-pyrido[2,3-d]pyrimidin-7-one as a yellow solid.

Step 7

Into a 50-mL round-bottom flask, was placed a solution of 8-[(3-aminophenyl)methyl]-6-(2,6-dichloro-3,5-dimethoxyphenyl)-2-[[4-(diethylamino)butyl]amino]-7H,8H-pyrido[2,3-d]pyrimidin-7-one (150 mg, 0.25 mmol, 1.00 equiv) in DMF (10 mL). Acrylic acid (25.3 mg, 0.35 mmol, 1.40 equiv), HATU (143 mg, 0.38 mmol, 1.50 equiv) and DIPEA (97.1 mg, 0.75 mmol, 3.00 equiv) were added to the reaction mixture. The resulting solution was stirred for 5 h at room temperature, and then quenched with water. The resulting solution was extracted with ethyl acetate and the combined organic layers were dried over anhydrous sodium sulfate and concentrated under vacuum. The crude product (100 mg) was purified by Prep-HPLC with the following conditions (2#-AnalyseHPLC-SHIMADZU(HPLC-10)): Column, SunFire Prep C18 OBD Column, 5 um, 19*150 mm; mobile phase, water with 0.1% TFA and MeCN (18% MeCN up to 30% in 11 min, up to 100% in 2 min, down to 18% in 1 min); Detector, Waters2545 UvDector 254&220 nm to give the title compound as a light yellow solid. LC-MS (m/z): 653.3 [M+1].

Example 7

Synthesis of N-(3-(2-(6-(2,6-dichloro-3,5-dimethoxyphenyl)-2-(4-(diethylamino)butylamino)-7-oxopyrido[2,3-d]pyrimidin-8(7H)-yl)ethyl)phenyl) acrylamide hydrochloride

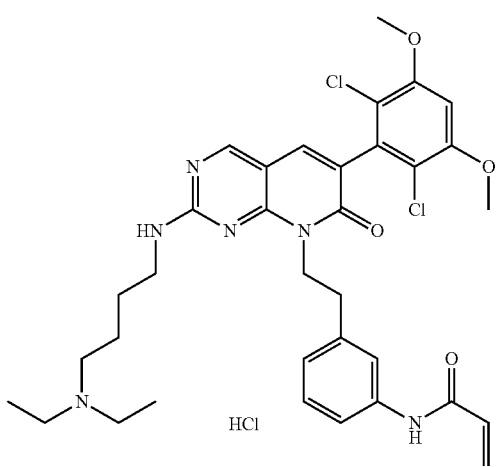 [SMILES: C=CC(=O)Nc1cccc(CCn2c(=O)c(-c3c(Cl)c(OC)cc(OC)c3Cl)cc3cnc(NCCCCN(CC)CC)nc32)c1 ; Cl]

Step 1

Into a 50-mL round-bottom flask, was placed a mixture of 2-(3-nitrophenyl)acetonitrile (4 g, 24.67 mmol, 1.00 equiv), water (8 mL), sulfuric acid (8 mL), and acetic acid (8 mL). The resulting solution was stirred overnight at 110° C., and then it was diluted with water. The resulting solution was extracted with ethyl acetate, and the combined organic layers were concentrated under vacuum to yield 4.2 g (94%) of 2-(3-nitrophenyl)acetic acid as a yellow solid.

Step 2

Into a 500-mL three neck round-bottom flask, was placed a solution of 2-(3-nitro-phenyl)acetic acid (2 g, 11.04 mmol, 1.00 equiv) in tetrahydrofuran (150 mL). This was followed by the addition of BH$_3$.SMe$_2$ (10M, 1.2 mL, 12.15 mmol, 1.10 equiv) drop wise with stirring, while the temperature was maintained at reflux over 10 min. The resulting solution was heated to reflux overnight. The pH value of the solution was adjusted to 8 with sodium bicarbonate (aq). The resulting solution was extracted DCM/MeOH (10:1) and the combined organic layers were concentrated under vacuum. The residue was applied onto a silica gel column with ethyl acetate/petroleum ether (1:2) as eluent to yield 1.1 g (60%) of 2-(3-nitrophenyl)ethan-1-ol as a brown oil.

Step 3

Into a 250-mL round-bottom flask, was placed a solution of 2-(3-nitrophenyl)ethan-1-ol (1.1 g, 6.58 mmol, 1.00 equiv) in ethanol (100 mL). 10% Palladium on carbon (500 mg) was added to the reaction mixture. The resulting solution was stirred overnight at room temperature under hydrogen atmosphere. The solids were filtered out. The filtrate was concentrated under vacuum to yield 800 mg (89%) of 2-(3-aminophenyl)ethan-1-ol as a brown oil.

Step 4

Into a 100-mL round-bottom flask, was placed a solution of 2-(3-aminophenyl)ethan-1-ol (800 mg, 5.83 mmol, 1.00 equiv) in a solvent mixture of water (15 mL) and 1,4-dioxane (30 mL). Sodium hydroxide (240 mg, 6.00 mmol, 1.00 equiv) and di-tert-butyl dicarbonate (1.4 g, 6.41 mmol, 1.10 equiv) were added to the reaction mixture. The resulting solution was stirred overnight at room temperature, and then it was diluted with water. The resulting solution was extracted with ethyl acetate and the combined organic layers were concentrated under vacuum. The residue was applied onto a silica gel column with ethyl acetate/petroleum ether (1:3) as eluent to yield 1.1 g (79%) of tert-butyl N-[3-(2-hydroxyethyl)phenyl]carbamate as a light yellow solid which was converted to tert-butyl N-[3-(2-iodoethyl)phenyl] carbamate under conditions similar to those described Example 6, Step 2 above. tert-Butyl N-[3-(2-iodoethyl) phenyl]carbamate was reacted with 6-(2,6-dichloro-3,5-dimethoxyphenyl)-2-(methylsulfanyl)-7H,8H-pyrido[2,3-d] pyrimidin-7-one under conditions similar to those described in Example 6, Step 3 above to give tert-butyl N-(3-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)carbamate.

Step 5

Proceeding under conditions similar to those described in Example 4, Step 7 above, tert-butyl N-(3-[2-[6-(2,6-dichloro-3,5-dimethoxyphenyl)-2-(methylsulfanyl)-7-oxo-7H,8H-pyrido[2,3-d]pyrimidin-8-yl]ethyl]phenyl)carbamate (600 mg was converted to tert-butyl N-(3-[2-[6-(2,6-dichloro-3,5-dimethoxyphenyl)-2-methanesulfonyl-7-oxo-7H,8H-pyrido[2,3-d]pyrimidin-8-yl]ethyl]phenyl) carbamate 607 mg (96%) as a brown solid.

Step 6

Proceeding under conditions similar to those described in Example 4, Step 8 above, tert-butyl N-(3-[2-[6-(2,6-dichloro-3,5-dimethoxyphenyl)-2-methanesulfonyl-7-oxo-7H,8H-pyrido[2,3-d]pyrimidin-8-yl]-phenyl)carbamate (400 mg) was converted to tert-butyl N-(3-[2-[6-(2,6-dichloro-3,5-dimethoxyphenyl)-2-[[4-(diethylamino)butyl] amino]-7-oxo-7H,8H-pyrido[2,3-d]pyrimidin-8-yl]ethyl] phenyl)carbamate 420 mg (96%) as a brown solid by substituting methamine with (4-aminobutyl)diethylamine.

Step 7

Into a 50-mL round-bottom flask, was placed a solution of tert-butyl N-(3-[2-[6-(2,6-dichloro-3,5-dimethoxyphenyl)-2-[[4-(diethylamino)butyl]amino]-7-oxo-7H,8H-pyrido[2,3-d]pyrimidin-8-yl]ethyl]phenyl)carbamate (420 mg, 0.59 mmol, 1.00 equiv) in dichloromethane (10 mL) and trifluoroacetic acid (4 mL). The resulting solution was stirred overnight at room temperature. The pH value of the solution was adjusted to 9 with sodium carbonate (aq). The resulting solution was extracted with DCM/MeOH (10:1) and the combined organic layers were concentrated under vacuum to furnish 350 mg (97%) of 8-[2-(3-aminophenyl)ethyl]-6-(2, 6-dichloro-3,5-dimethoxyphenyl)-2-[[4-(diethylamino)butyl]amino]-7H,8H-pyrido[2,3-d]pyrimidin-7-one as a brown solid.

Step 8

Proceeding under conditions similar to those described in Example 4, Step 10 above, 8-[2-(3-aminophenyl)ethyl]-6-(2,6-dichloro-3,5-dimethoxyphenyl)-2-[[4-(diethylamino)butyl]amino]-7H,8H-pyrido[2,3-d]pyrimidin-7-one (160 mg) was converted to the title compound 13.1 mg (7%) as a light yellow solid. LC-MS m/z: 667 [M+1]$^+$ Example 8

Synthesis of N-(3-(2-(6-(3,5-dimethoxyphenyl)-2-(methylamino)-7-oxopyrido[2,3-d]pyrimidin-8(7H)-yl)ethyl)phenyl)acrylamide

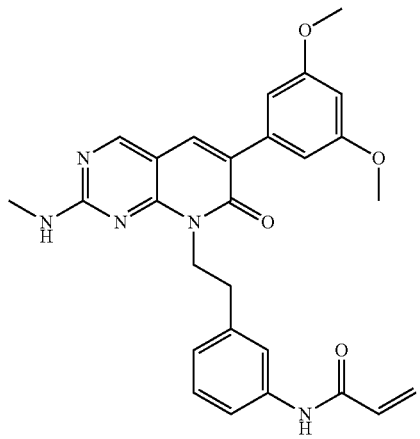 [SMILES: C=CC(=O)Nc1cccc(CCn2c(=O)c(-c3cc(OC)cc(OC)c3)cc3cnc(NC)nc32)c1]

Step 1

To a solution of 2-(3,5-dimethoxyphenyl)acetic acid (7.5 g, 38.2 mmol) in MeOH (30 mL) was added SOCl$_2$ (1 mL) at 0° C. The mixture was stirred at room temperature for 2 h, and then it was concentrated under vacuum to give a residue. The residue was re-dissolved in EtOAc (100 mL), and the mixture was washed NaHCO$_3$, the organic layer was dried over Na$_2$SO$_4$, filtered and concentrated to give methyl 2-(3,5-dimethoxyphenyl)acetate (8.1 g, 100%) as a colorless oil.

Step 2

To a solution of methyl 2-(3,5-dimethoxyphenyl)acetate (3.38 g, 20 mmol), and 4-amino-2-(methylthio)pyrimidine-5-carbaldehyde (6.3 g, 30 mmol) in NMP (20 mL) was added K$_2$CO$_3$ (5.5 g, 40 mmol) and the mixture was stirred at 70° C. overnight. H$_2$O (50 mL) was added and the mixture was filtered, the filtered cake was washed with EtOAc and dried to give 6-(3,5-dimethoxyphenyl)-2-(methylthio)pyrido[2,3-d]pyrimidin-7(8H)-one (6.5 g, 99%) as a light yellow solid.

Step 3

To a solution of 6-(3,5-dimethoxyphenyl)-2-(methylthio)pyrido[2,3-d]pyrimidin-7(8H)-one (1.2 g, 3.6 mmol) and tert-butyl (3-(2-iodoethyl)phenyl)carbamate (1.4 g, 4.0 mmol) in DMF (15 mL) was added K$_2$CO$_3$ (1.5 g, 10.8 mmol), the mixture was stirred at 85° C. for 3 h, then it was cooled to room temperature and poured into water. The light yellow solid was collected and dried to give tert-butyl (3-(2-(6-(3,5-dimethoxyphenyl)-2-(methylthio)-7-oxopyrido[2,3-d]pyrimidin-8(7H)-yl)ethyl)phenyl)carbamate (1.7 g, 88%) which was used in the next step without further purification.

Step 4

To a solution of tert-butyl (3-(2-(6-(3,5-dimethoxyphenyl)-2-(methylthio)-7-oxopyrido[2,3-d]pyrimidin-8(7H)-yl)ethyl)phenyl)carbamate (1.7 g, 3.1 mmol) in DCM (20 mL) was added m-CPBA (0.7 g, 6.2 mmol). The mixture was stirred at room temperature for 1 h, then washed by NaHSO$_3$ (aq) and NaHCO$_3$ (aq). The organic phase was dried and concentrated to give tert-butyl (3-(2-(6-(3,5-dimethoxyphenyl)-2-(methylsulfinyl)-7-oxopyrido[2,3-d]pyrimidin-8(7H)-yl)ethyl)phenyl)carbamate (1.5 g, crude) as a light yellow oil which was used in the next Step without further purification.

Step 5

To a solution of tert-butyl (3-(2-(6-(3,5-dimethoxyphenyl)-2-(methylsulfinyl)-7-oxopyrido[2,3-d]pyrimidin-8(7H)-yl)ethyl)phenyl)carbamate (1.5 g, 2.6 mmol) in DMSO (10 mL) was added DIPEA (1.0 g, 8.0 mmol) and MeNH$_2$.HCl (540 mg, 8.0 mmol). The mixture was stirred at 100° C. for 0.5 h, then it was cooled to room temperature and poured into water. The light yellow solid was collected and dried to give tert-butyl (3-(2-(6-(3,5-dimethoxyphenyl)-2-(methylamino)-7-oxopyrido[2,3-d]pyrimidin-8(7H)-yl)ethyl)phenyl)carbamate (1.1 g, crude) which was used in the next step without further purification.

Step 6

Proceeding under conditions similar to those described in Example 4, Step 9 above, tert-butyl (3-(2-(6-(3,5-dimethoxyphenyl)-2-(methylamino)-7-oxopyrido[2,3-d]pyrimidin-8(7H)-yl)ethyl)phenyl)carbamate (1.1 g) was converted to 8-(3-aminophenethyl)-6-(3,5-dimethoxyphenyl)-2-(methylamino)pyrido[2,3-d]pyrimidin-7(8H)-one (085 g, 95%) as a light yellow solid.

Step 7

To a solution of 8-(3-aminophenethyl)-6-(3,5-dimethoxyphenyl)-2-(methylamino)pyrido[2,3-d]pyrimidin-7(8H)-one (200 mg, 0.46 mmol), DIPEA (119 mg, 0.92 mmol) in DCM (4 mL) was added acryloyl chloride (47 mg, 0.52 mmol) in DCM (4 mL) dropwise. The mixture was stirred at 0° C. for 10 min, and then DCM was added and washed with brine. The organic layer was dried over Na$_2$SO$_4$, filtered and concentrated. The residue was purified by column chromatography (silica gel, DCM:MeOH=50:1) to give the title compound (150 mg, 66%) as a white solid. LC-MS m/z: 485.8 [M+1]$^+$ Example 9

Synthesis of N-(4-(2-(6-(3,5-dimethoxyphenyl)-2-(methylamino)-7-oxopyrido[2,3-d]pyrimidin-8(7H)-yl)ethyl)phenyl)acrylamide

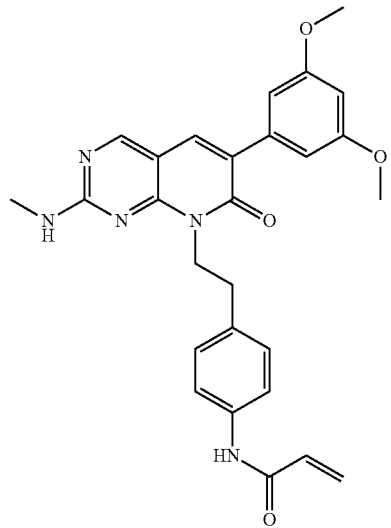

Step 1

Proceeding under conditions similar to those described in Example 8, Step 3 above, but substituting tert-butyl (3-(2-iodoethyl)phenyl)carbamate with tert-butyl (4-(2-iodoethyl)phenyl)carbamate, tert-butyl (4-(2-(6-(3,5-dimethoxyphenyl)-2-(methylthio)-7-oxopyrido[2,3-d]pyrimidin-8(7H)-yl)ethyl)phenyl)carbamate (160 mg, crude) was prepared and was used for the next step without further purification.

Step 2

Proceeding under conditions similar to those described in Example 8, Step 4 above, tert-butyl (4-(2-(6-(3,5-dimethoxyphenyl)-2-(methylsulfinyl)-7-oxopyrido[2,3-d]pyrimidin-8(7H)-yl)ethyl)phenyl)carbamate (160 mg, crude) was prepared which was used in the next step without further purification.

Step 3

Proceeding under conditions similar to those described in Example 8, Step 5 above, tert-butyl (4-(2-(6-(3,5-dimethoxyphenyl)-2-(methylamino)-7-oxopyrido[2,3-d]pyrimidin-8(7H)-yl)ethyl)phenyl)carbamate (120 mg, 80%) was prepared which was used in the next step without further purification.

Step 4

Proceeding under conditions similar to those described in Example 4, Step 9 above, tert-butyl (4-(2-(6-(3,5-dimethoxyphenyl)-2-(methylamino)-7-oxopyrido[2,3-d]pyrimidin-8(7H)-yl)ethyl)phenyl)carbamate (120 mg) was converted to 8-(4-aminophenethyl)-6-(3,5-dimethoxyphenyl)-2-(methyl-amino)pyrido[2,3-d]pyrimidin-7(8H)-one (95 mg, 100%) as a light yellow solid.

Step 5

A mixture of 8-(4-aminophenethyl)-6-(3,5-dimethoxyphenyl)-2-(methylamino)pyrido[2,3-d]pyrimidin-7(8H)-one (200 mg, 0.46 mmol), acrylic acid (50.4 mg, 0.70 mmol), HBTU (223 mg, 0.70 mmol) and DIPEA (258 mg, 0.92 mmol) in DCM (1 mL) was stirred at room temperature overnight. EtOAc (200 mL) was added, washed with water (50 mL) and brine. The organic layer was dried over $Na_2SO_4$, filtered and concentrated, and the residue was purified by Prep-HPLC to give the title compound (20 mg, 8.9%) as a white solid. LC-MS m/z: 486.2 $[M+1]^+$ Example 10

Synthesis of N-(4-(2-(6-(3,5-dimethoxyphenyl)-2-(methylamino)-7-oxopyrido[2,3-d]pyrimidin-8(7H)-yl)ethyl)pyridin-2-yl)acrylamide

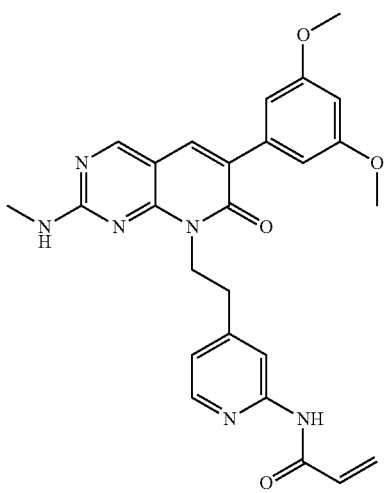 [SMILES: C=CC(=O)Nc1cc(CCn2c(=O)c(-c3cc(OC)cc(OC)c3)cc3cnc(NC)nc32)ccn1]

Step 1

To a solution of 2-chloro-4-methylpyridine (10 g, 78 mmol) in THF (100 mL) was added dropwise LDA (78 mL, 156 mmol, 2M in THF) at −78° C. under a nitrogen atmosphere. The mixture was warmed to 0° C. for 0.5 h, then it was cooled to −78° C. and diethyl carbonate (11 g, 94 mmol) was added dropwise. The mixture was stirred at −78° C. for 0.5 h and then it was warmed to r.t. Water was added and the product was extracted with EtOAc. The organic phase was washed with brine, dried over $Na_2SO_4$ and concentrated under vacuum. The residue was purified by column chromatography (silica gel, PE:EtOAc=6:1) to give ethyl 2-(2-chloropyridin-4-yl)acetate (5.9 g, 38%) as a colorless oil.

Step 2

A mixture of ethyl 2-(2-chloropyridin-4-yl)acetate (5.9 g, 29.8 mmol), tert-butyl carbamate (7.0 g, 59.6 mmol), Xantphos (0.86 g, 1.5 mmol), $Pd_2(dba)_3$ (0.68 g, 0.75 mmol) and $Cs_2CO_3$ (14.6 g, 44.7 mmol) in THF (60 mL) was stirred at reflux for 16 h under nitrogen atmosphere, then cooled and concentrated. The residue was diluted with EtOAc and washed with water and brine, dried over $Na_2SO_4$, and concentrated under vacuum. The residue was purified by column chromatography (silica gel, PE:EtOAc=10:1) to give ethyl 2-(2-((tert-butoxycarbonyl)amino)pyridin-4-yl)acetate (4.4 g, 53%) as a white solid.

Step 3

To a solution of ethyl 2-(2-((tert-butoxycarbonyl)amino)pyridin-4-yl)acetate (4.4 g, 15.8 mmol) in THF (50 mL) was added $LiBH_4$ (688 mg, 31.6 mmol) at r.t. The reaction solution was stirred at room temperature for 16 h, then $CH_3OH$ (10 mL) was added and the resulting solution was stirred at reflux for 1 h and then concentrated. The residue was diluted with EtOAc, washed with water and brine. The organic phase was concentrated to give tert-butyl (4-(2-hydroxyethyl)pyridin-2-yl)carbamate (3 g, 80%) as a white solid.

Step 4

To a solution of tert-butyl (4-(2-hydroxyethyl)pyridin-2-yl)carbamate (400 mg, 1.7 mmol) and triethylamine (340 mg, 3.4 mmol) in DCM (5 mL) was added dropwise methanesulfonyl chloride (212 mg, 1.9 mmol) at 0° C. The reaction solution was stirred at 0° C. for 1 h, then water was added and washed with brine. The organic phase was dried over $Na_2SO_4$ and concentrated to give 2-(2-((tert-butoxycarbonyl)amino)pyridin-4-yl)ethyl methanesulfonate (530 mg, 99%) as a white solid.

Step 5

To a solution of 6-(3,5-dimethoxyphenyl)-2-(methylthio)pyrido[2,3-d]pyrimidin-7(8H)-one (464 mg, 1.4 mmol) and $K_2CO_3$ (353 g, 2.6 mmol) in DMF (5 mL) was added dropwise 2-(2-((tert-butoxycarbonyl)amino)pyridin-4-yl)ethyl methanesulfonate (494 mg, 1.5 mmol) at 85° C. The mixture was stirred for 1 h at 85° C., then cooled to room temperature and poured into water. The light yellow solid was collected and dried to give tert-butyl(4-(2-(6-(3,5-dimethoxyphenyl)-2-(methylthio)-7-oxopyrido[2,3-d]pyrimidin-8(7H)-yl)ethyl)pyridin-2-yl)carbamate (650 mg, 84%) as a white solid.

Step 6

Proceeding under conditions similar to those described in Example 8, Step 4 above, tert-butyl (4-(2-(6-(3,5-dimethoxyphenyl)-2-(methylthio)-7-oxopyrido[2,3-d]pyrimidin-8(7H)-yl)ethyl)pyridin-2-yl)carbamate (650 mg, 1.2 mmol) was converted to tert-butyl(4-(2-(6-(3,5-dimethoxyphenyl)-

2-(methylsulfinyl)-7-oxopyrido[2,3-d]pyrimidin-8(7H)-yl) ethyl)pyridin-2-yl)carbamate (668 mg, 100%) as an off-white solid.

Step 7

Proceeding under conditions similar to those described in Example 8, Step 5 above, tert-butyl (4-(2-(6-(3,5-dimethoxyphenyl)-2-(methylsulfanyl)-7-oxopyrido[2,3-d]pyrimidin-8(7H)-yl)ethyl)pyridin-2-yl)carbamate (668 mg, 1.2 mmol) was converted to tert-butyl (4-(2-(6-(3,5-dimethoxyphenyl)-2-(methylamino)-7-oxopyrido[2,3-d]pyrimidin-8 (7H)-yl)ethyl)pyridin-2-yl)carbamate (564 mg, 90%) as an off-white solid.

Step 8

Proceeding under conditions similar to those described in Example 4, Step 9 above, tert-butyl (4-(2-(6-(3,5-dimethoxyphenyl)-2-(methylamino)-7-oxopyrido[2,3-d]pyrimidin-8(7H)-yl)ethyl)pyridin-2-yl)carbamate (564 mg, 1.1 mmol) was converted to 8-(2-(2-aminopyridin-4-yl)ethyl)-6-(3,5-dimethoxyphenyl)-2-(methylamino)pyrido-[2,3-d]pyrimidin-7(8H)-one (350 mg, 76%) as a white solid.

Step 9

Proceeding under conditions similar to those described in Example 8, Step 7 above, 8-(2-(2-aminopyridin-4-yl)ethyl)-6-(3,5-dimethoxyphenyl)-2-(methylamino)pyrido[2,3-d]pyrimidin-7(8H)-one (65 mg, 0.15 mmol was converted to the title compound (15 mg, 20%) as a yellow solid. LC-MS m/z: 487.2 [M+1]$^+$ Example 11

Synthesis of N-(6-(2-(6-(3,5-dimethoxyphenyl)-2-(methylamino)-7-oxopyrido[2,3-d]pyrimidin-8(7H)-yl)ethyl)pyridin-2-yl)acrylamide

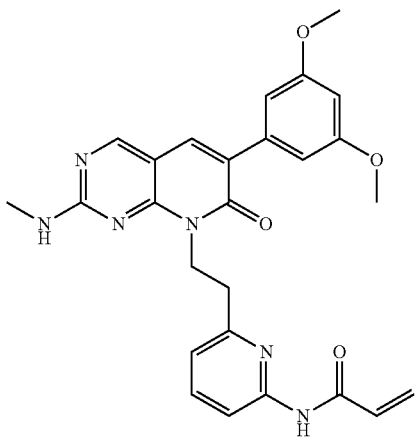 [SMILES: C=CC(=O)Nc1cccc(CCn2c(=O)c(-c3cc(OC)cc(OC)c3)cc3cnc(NC)nc32)n1]

Step 1

To a solution of 6-methylpyridin-2-amine (20 g, 0.18 mol) in t-BuOH (200 mL) was added TEA (22 g, 0.22 mol) and (Boc)$_2$O (48 g, 0.22 mol), the mixture was stirred at 50° C. overnight and then concentrated and the residue was purified by column chromatography (silica gel, PE:EtOAc=10:1) to give tert-butyl (6-methylpyridin-2-yl)carbamate (35 g, 90%) as a white solid.

Step 2

To a solution of tert-butyl (6-methylpyridin-2-yl)carbamate (10 g, 48 mmol) in THF (100 mL) was added LDA (96 mL, 192 mmol) at −78° C. The reaction solution was stirred at −78° C. for 0.5 h, diethyl carbonate (11.3 g, 96 mmol) was added to the above solution at −78° C. and the reaction mixture stirred for 20 min, warmed to 0° C. and stirred for 2 h. The reaction mixture was quenched by NH$_4$Cl (aq), extracted with EtOAc, and concentrated. The residue was purified by column chromatography (silica gel, PE:EtOAc=10:1) to give ethyl 2-(6-((tert-butoxy-carbonyl) amino)pyridin-2-yl)acetate (3.8 g, 28%) as a white solid.

Step 3

To a solution of ethyl 2-(6-((tert-butoxycarbonyl)amino) pyridin-2-yl)acetate (3.5 g, 12.4 mmol) in THF (40 mL) was added LiBH$_4$ (820 mg, 37.4 mmol) at 0° C. The reaction solution was stirred at room temperature for 3 h and then it was quenched by H$_2$O and concentrated to give tert-butyl (6-(2-hydroxyethyl)pyridin-2-yl)carbamate (2.4 g, 80%) as light yellow oil which was used in the next step without further purification.

Step 4

To a solution of I$_2$ (3.2 g, 12.6 mmol), PPh$_3$ (3.3 g, 12.6 mmol) and 1H-imidazole (857 mg, 12.6 mmol) in CH$_2$Cl$_2$ (20 mL) was added tert-butyl (6-(2-hydroxyethyl)pyridin-2-yl)carbamate (2 g, 8.4 mmol) at 0° C. The reaction solution was stirred at room temperature for 1 h, concentrated and the residue was purified by column chromatography (silica gel, PE:EtOAc=5:1) to give tert-butyl (6-(2-iodoethyl)pyridin-2-yl)carbamate (0.6 g, 21%) as a white solid.

Step 5

To a solution of 6-(3,5-dimethoxyphenyl)-2-(methylthio) pyrido[2,3-d]pyrimidin-7(8H)-one (0.8 g, 2.43 mmol) and tert-butyl (6-(2-iodoethyl)pyridin-2-yl)carbamate (1.02 g, 2.92 mmol) in DMF (20 mL) was added K$_2$CO$_3$ (1.0 g, 7.29 mmol). The mixture was stirred at 85° C. for 1 h, then cooled to room temperature and poured into water. The light yellow solid was collected and dried to give tert-butyl (6-(2-(6-(3,5-dimethoxyphenyl)-2-(methylthio)-7-oxopyrido[2,3-d]-pyrimidin-8(7H)-yl)ethyl)pyridin-2-yl)carbamate (1.3 g, crude) which was used in the next step without further purification.

Step 6

Proceeding under conditions similar to those described in Example 8, Step 4 above, tert-butyl (6-(2-(6-(3,5-dimethoxyphenyl)-2-(methylthio)-7-oxopyrido[2,3-d]pyrimidin-8(7H)-yl)ethyl)pyridin-2-yl)carbamate (1.3 g, 2.4 mmol) was converted to tert-butyl(6-(2-(6-(3,5-dimethoxyphenyl)-2-(methylsulfinyl)-7-oxopyrido[2,3-d]pyrimidin-8(7H)-yl) ethyl)pyridin-2-yl)carbamate (1.3 g, crude) and was used in the next step without further purification.

Step 7

Proceeding under conditions similar to those described in Example 8, Step 5 above, tert-butyl (6-(2-(6-(3,5-dimethoxyphenyl)-2-(methylsulfinyl)-7-oxopyrido[2,3-d]pyrimidin-8(7H)-yl)ethyl)pyridin-2-yl)carbamate (1.3 g, 2.4 mmol) was converted to tert-butyl (6-(2-(6-(3,5-dimethoxyphenyl)-2-(methylamino)-7-oxopyrido[2,3-d]pyrimidin-8 (7H)-yl)ethyl)pyridin-2-yl)carbamate (1.0 g, crude) which was used in the next step without further purification.

Step 8

Proceeding under conditions similar to those described in Example 4, Step 9 above, tert-butyl (6-(2-(6-(3,5-dimethoxyphenyl)-2-(methylamino)-7-oxopyrido[2,3-d]pyrimidin-8(7H)-yl)ethyl)pyridin-2-yl)carbamate (1.0 g, 1.9 mmol) was converted to 8-(2-(6-aminopyridin-2-yl)ethyl)-6-(3,5-dimethoxyphenyl)-2-(methylamino)pyrido[2,3-d]pyrimidin-7(8H)-one (0.6 g, 74%) as a light yellow solid.

Step 9

Proceeding under conditions similar to those described in Example 8, Step 7 above, 8-(2-(6-aminopyridin-2-yl)ethyl)-6-(3,5-dimethoxyphenyl)-2-(methylamino)pyrido-[2,3-d] pyrimidin-7(8H)-one (110 mg, 0.25 mmol) was converted to the title compound (32 mg, 26%) as a white solid. LC-MS m/z: 487.1 [M+1]$^+$

Example 12

Synthesis of N-(3-(2-(6-(2-chloro-3,5-dimethoxyphenyl)-2-(methylamino)-7-oxopyrido[2,3-d]pyrimidin-8(7H)-yl)ethyl)phenyl)acrylamide

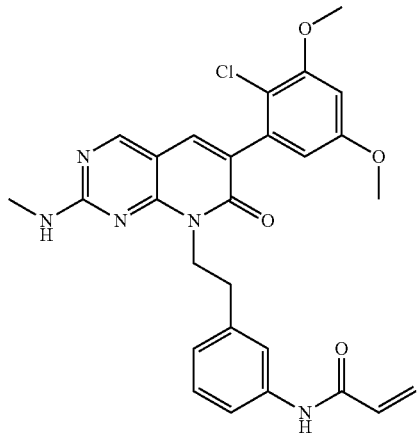 [SMILES: C=CC(=O)Nc1cccc(CCn2c(=O)c(-c3cc(OC)cc(OC)c3Cl)cc3cnc(NC)nc32)c1]

Step 1

To a solution of 2-(3,5-dimethoxyphenyl)acetic acid (25 g, 127.6 mmol) in H₂O/MeCN (200/200 mL) was added Oxone (78.5 g, 127.6 mmol) and KCl (9.5 g, 127.6 mmol), and the mixture was stirred at room temperature for 2 h. The mixture was filtered, EtOAc was added to the filtrate, and the H₂O layer was separated. The organic layer was concentrated to give a residue, which was dissolved in NaOH, washed with EtOAc, then the H₂O layer was adjusted to pH=5-6 with concentrated HCl (aq). The solid was filtered and the filtered cake was dried to give 2-(2-chloro-3,5-dimethoxyphenyl)acetic acid (26.5 g, 90%) as a light yellow solid.

Step 2

To a solution of 2-(2-chloro-3,5-dimethoxyphenyl)acetic acid (26.5 g, 114.9 mmol) in MeOH (100 mL) was added SOCl₂ (2 mL) at 0° C. The mixture was stirred at room temperature for 2 h, and then concentrated under vacuum to give a residue. The residue was re-dissolved in EtOAc, and the mixture was washed NaHCO₃. The organic layer was dried over Na₂SO₄, filtered and concentrated to give methyl 2-(2-chloro-3,5-dimethoxyphenyl)acetate (28.1 g, 100%) as a white solid.

Step 3

To a solution of 4-amino-2-(methylthio)pyrimidine-5-carbaldehyde (12.5 g, 74 mmol), and methyl 2-(2-chloro-3,5-dimethoxyphenyl)acetate (28 g, 114.5 mmol) in NMP (30 mL) was added K₂CO₃ (20.5 g, 148 mmol) and the mixture was stirred at 70° C. overnight. H₂O was added, the mixture was filtered and the filtered cake was washed with EtOAc. The filtered cake was dried to give 6-(2-chloro-3,5-dimethoxyphenyl)-2-(methylthio)pyrido[2,3-d]pyrimidin-7(8H)-one (14.8 g, 55%) as an off-white solid.

Step 4

Proceeding under conditions similar to those described in Example 8, Step 3 above, 6-(2-chloro-3,5-dimethoxyphenyl)-2-(methylthio)pyrido[2,3-d]pyrimidin-7(8H)-one (1.1 g, 3.0 mmol) was converted to tert-butyl (3-(2-(6-(2-chloro-3,5-dimethoxyphenyl)-2-(methylthio)-7-oxopyrido[2,3-d]pyrimidin-8(7H)-yl)ethyl)phenyl)carbamate (1.4 g, crude) which was used in the next step without further purification.

Step 5

Proceeding under conditions similar to those described in Example 8, Step 4 above, tert-butyl (3-(2-(6-(2-chloro-3,5-dimethoxyphenyl)-2-(methylthio)-7-oxopyrido[2,3-d]pyrimidin-8(7H)-yl)ethyl)phenyl)carbamate (1.4 g, 2.4 mmol) was converted to tert-butyl (3-(2-(6-(2-chloro-3,5-dimethoxyphenyl)-2-(methylsulfinyl)-7-oxopyrido[2,3-d]pyrimidin-8(7H)-yl)ethyl)-phenyl)carbamate (1.2 g, crude) which was used in the next step without further purification.

Step 6

To a solution of tert-butyl (3-(2-(6-(2-chloro-3,5-dimethoxyphenyl)-2-(methylsulfinyl)-7-oxopyrido[2,3-d]pyrimidin-8(7H)-yl)ethyl)phenyl)carbamate (1.1 g, 1.8 mmol) in DMSO (15 mL) was added DIPEA (700 mg, 5.4 mmol) and MeNH₂.HCl (375 mg, 5.4 mmol). The mixture was stirred at 85° C. for 0.5 h, then it was cooled to room temperature and poured into water. The light yellow solid was collected and dried to give tert-butyl (3-(2-(6-(2-chloro-3,5-dimethoxy-phenyl)-2-(methylamino)-7-oxopyrido[2,3-d]pyrimidin-8(7H)-yl)ethyl)phenyl)carbamate (880 mg, crude) which was used in the next step without further purification.

Step 7

Proceeding under conditions similar to those described in Example 4, Step 9 above, tert-butyl (3-(2-(6-(2-chloro-3,5-dimethoxyphenyl)-2-(methylamino)-7-oxopyrido[2,3-d]pyrimidin-8(7H)-yl)ethyl)phenyl)carbamate (880 mg, 1.6 mmol) in DCM (10 mL) was converted to 8-(3-aminophenethyl)-6-(2-chloro-3,5-dimethoxyphenyl)-2-(methylamino)pyrido[2,3-d]pyrimidin-7(8H)-one (0.72 g, 100%) as a light yellow solid.

Step 8

To a solution of 8-(3-aminophenethyl)-6-(2-chloro-3,5-dimethoxyphenyl)-2-(methylamino)pyrido[2,3-d]pyrimidin-7(8H)-one (230 mg, 0.5 mmol), DIPEA (260 mg, 2 mmol) in DMF (4 mL) was added acryloyl chloride (45 mg, 0.5 mmol) in DMF (4 mL) dropwise. The mixture was stirred at room temperature for 1 h, and then EtOAc was added. The mixture was washed with water, brine and then the organic layer was dried over NaSO₄, filtered and concentrated. The residue was purified by column chromatography (silica gel, DCM:MeOH=50:1) to give N-(3-(2-(6-(2-chloro-3,5-dimethoxyphenyl)-2-(methylamino)-7-oxopyrido[2,3-d]pyrimidin-8(7H)-yl)ethyl)phenyl)acrylamide (85 mg, 33%) as a white solid. LC-MS m/z: 520.1 [M+1]⁺

Example 13

Synthesis of N-(4-(2-(6-(2-chloro-3,5-dimethoxyphenyl)-2-(methylamino)-7-oxopyrido[2,3-d]pyrimidin-8(7H)-yl)ethyl)phenyl)acrylamide

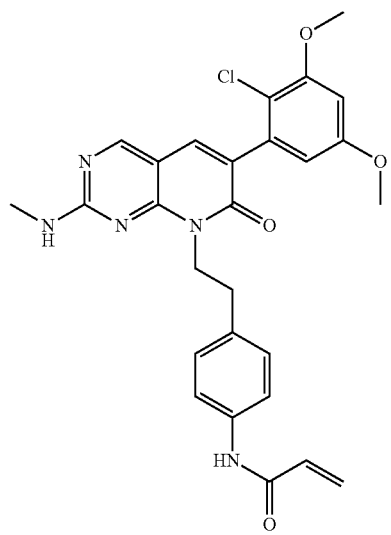

Step 1

Proceeding under conditions similar to those described in Example 8, Step 3 above, 6-(2-chloro-3,5-dimethoxyphenyl)-2-(methylthio)pyrido[2,3-d]pyrimidin-7(8H)-one (1.1 g, 3.0 mmol) was reacted with tert-butyl (4-(2-iodoethyl)phenyl)carbamate (1.2 g, 3.3 mmol) to give tert-butyl (4-

(2-(6-(2-chloro-3,5-dimethoxyphenyl)-2-(methylthio)-7-oxopyrido[2,3-d]pyrimidin-8(7H)-yl)ethyl)phenyl)carbamate (1.5 g, 85%) which was used in the next step without further purification.
Step 2
Proceeding under conditions similar to those described in Example 8, Step 4 above, tert-butyl (4-(2-(6-(2-chloro-3,5-dimethoxyphenyl)-2-(methylthio)-7-oxopyrido[2,3-d]pyrimidin-8(7H)-yl)ethyl)phenyl)carbamate (1.5 g, 2.6 mmol) was converted to tert-butyl (4-(2-(6-(2-chloro-3,5-dimethoxyphenyl)-2-(methylsulfinyl)-7-oxopyrido[2,3-d]pyrimidin-8(7H)-yl)ethyl)-phenyl)carbamate (1.4 g, 90%) which was used in the next step without further purification.
Step 3
Proceeding under conditions similar to those described in Example 8, Step 5 above tert-butyl (4-(2-(6-(2-chloro-3,5-dimethoxyphenyl)-2-(methylsulfinyl)-7-oxopyrido[2,3-d]pyrimidin-8(7H)-yl)ethyl)phenyl)carbamate (1.4 g, 2.3 mmol) was converted to tert-butyl (4-(2-(6-(2-chloro-3,5-dimethoxyphenyl)-2-(methylamino)-7-oxopyrido[2,3-d]pyrimidin-8(7H)-yl)ethyl)-phenyl)carbamate (1.1 g, 85%) which was used in the next step without further purification.
Step 4
Proceeding under conditions similar to those described in Example 4, Step 9 above, tert-butyl (4-(2-(6-(2-chloro-3,5-dimethoxyphenyl)-2-(methylamino)-7-oxopyrido[2,3-d]pyrimidin-8(7H)-yl)ethyl)phenyl)carbamate (1.1 g, 1.9 mmol) in DCM (20 mL) was converted to 8-(4-aminophenethyl)-6-(2-chloro-3,5-dimethoxyphenyl)-2-(methylamino)-pyrido[2,3-d]pyrimidin-7(8H)-one (820 mg, 90%) as a light yellow solid.
Step 5
Proceeding under conditions similar to those described in Example 12, Step 8 above, 8-(4-aminophenethyl)-6-(2-chloro-3,5-dimethoxyphenyl)-2-(methylamino)pyrido[2,3-d]pyrimidin-7(8H)-one (232 mg, 0.5 mmol) was converted to N-(4-(2-(6-(2-chloro-3,5-dimethoxyphenyl)-2-(methylamino)-7-oxopyrido[2,3-d]pyrimidin-8(7H)-yl)ethyl)phenyl)acrylamide (70 mg, 27%) as a white solid. LC-MS m/z: 520.1 [M+1]$^+$ Example 14

Synthesis of N-(4-(2-(6-(2-chloro-3,5-dimethoxyphenyl)-2-(methylamino)-7-oxopyrido[2,3-d]pyrimidin-8(7H)-yl)ethyl)pyridin-2-yl)acrylamide

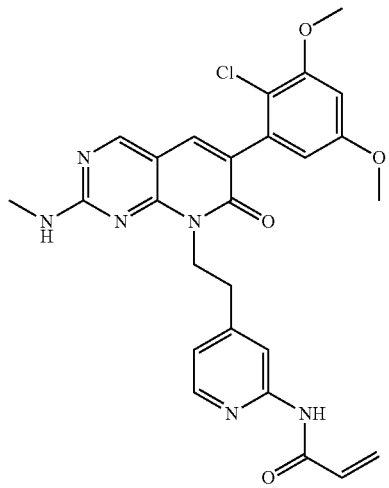

Step 1
Proceeding under conditions similar to those described in Example 10, Step 5 above, 6-(2-chloro-3,5-dimethoxyphenyl)-2-(methylthio)pyrido[2,3-d]pyrimidin-7(8H)-one (525 mg, 1.5 mmol) was reacted with 2-(2-((tert-butoxycarbonyl)amino)pyridin-4-yl)ethyl methanesulfonate (480 mg, 1.5 mmol) to give tert-butyl (4-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (600 mg, 71%) as a white solid.
Step 2
Proceeding under conditions similar to those described in Example 8, Step 4 above, tert-butyl (4-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (600 mg, 1.0 mmol) was converted to tert-butyl (4-(2-(6-(2-chloro-3,5-dimethoxyphenyl)-2-(methylsulfinyl)-7-oxopyrido[2,3-d]pyrimidin-8(7H)-yl)ethyl)pyridin-2-yl)carbamate (617 mg, crude) as an off-white solid.
Step 3
Proceeding under conditions similar to those described in Example 8, Step 5 above, tert-butyl (4-(2-(6-(2-chloro-3,5-dimethoxyphenyl)-2-(methylsulfinyl)-7-oxopyrido[2,3-d]pyrimidin-8(7H)-yl)ethyl)pyridin-2-yl)carbamate (617 mg, 1 mmol) was converted to tert-butyl (4-(2-(6-(2-chloro-3,5-dimethoxy-phenyl)-2-(methylamino)-7-oxopyrido[2,3-d]pyrimidin-8(7H)-yl)ethyl)pyridin-2-yl)carbamate (457 mg, 78%) as an off-white solid.
Step 4
Proceeding under conditions similar to those described in Example 4, Step 9 above, tert-butyl (4-(2-(6-(2-chloro-3,5-dimethoxyphenyl)-2-(methylamino)-7-oxopyrido[2,3-d]pyrimidin-8(7H)-yl)ethyl)pyridin-2-yl)carbamate (457 mg, 0.8 mmol) was converted to 8-(2-(2-aminopyridin-4-yl)ethyl)-6-(2-chloro-3,5-dimethoxyphenyl)-2-(methyl-amino)pyrido[2,3-d]pyrimidin-7(8H)-one (260 mg, 70%) as a white solid.
Step 5
Proceeding under conditions similar to those described in Example 8, Step 7 above, 8-(2-(2-aminopyridin-4-yl)ethyl)-6-(2-chloro-3,5-dimethoxyphenyl)-2-(methylamino)pyrido[2,3-d]pyrimidin-7(8H)-one (120 mg, 0.25 mmol) was converted to the title compound (10 mg, 7%) as a white solid. LC-MS m/z: 521.1 [M+1]$^+$ Example 15

Synthesis of N-(6-(2-(6-(2-chloro-3,5-dimethoxyphenyl)-2-(methylamino)-7-oxopyrido[2,3-d]pyrimidin-8(7H)-yl)ethyl)pyridin-2-yl)acrylamide

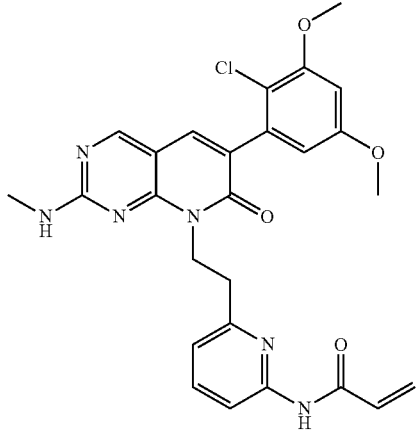 [SMILES: C=CC(=O)Nc1cccc(CCn2c(=O)c(-c3cc(OC)cc(OC)c3Cl)cc3cnc(NC)nc32)n1]

Step 1
Proceeding under conditions similar to those described in Example 11, Step 5 above, 6-(2-chloro-3,5-dimethoxyphenyl)-2-(methylthio)pyrido[2,3-d]pyrimidin-7(8H)-one (100 mg, 0.3 mmol) and tert-butyl (6-(2-iodoethyl)pyridin-2-yl)carbamate (116 g, 0.33 mmol) were reacted to give tert-butyl (6-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (145 mg, 90%) which was used in the next step without further purification.
Step 2
Proceeding under conditions similar to those described in Example 8, Step 4 above, tert-butyl (6-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (145 mg, 0.25 mmol) was converted to tert-butyl (6-(2-(6-(2-chloro-3,5-dimethoxyphenyl)-2-(methylsulfinyl)-7-oxopyrido[2,3-d]pyrimidin-8(7H)-yl)ethyl)pyridin-2-yl)carbamate (150 mg, crude) which was used in the next step without further purification.
Step 3
Proceeding under conditions similar to those described in Example 8, Step 5 above, tert-butyl (6-(2-(6-(2-chloro-3,5-dimethoxyphenyl)-2-(methylsulfinyl)-7-oxopyrido[2,3-d]pyrimidin-8(7H)-yl)ethyl)pyridin-2-yl)carbamate (150 mg, 0.25 mmol) was converted to tert-butyl (6-(2-(6-(2-chloro-3,5-dimethoxyphenyl)-2-(methylamino)-7-oxopyrido[2,3-d]pyrimidin-8(7H)-yl)ethyl)pyridin-2-yl)carbamate (110 mg, 80%) which was used in the next step without further purification.
Step 4
Proceeding under conditions similar to those described in Example 4, Step 9 above, tert-butyl (6-(2-(6-(2-chloro-3,5-dimethoxyphenyl)-2-(methylamino)-7-oxopyrido[2,3-d]pyrimidin-8(7H)-yl)ethyl)pyridin-2-yl)carbamate (110 mg, 0.2 mmol) was converted to 8-(2-(6-aminopyridin-2-yl)ethyl)-6-(2-chloro-3,5-dimethoxy-phenyl)-2-(methylamino)pyrido[2,3-d]pyrimidin-7(8H)-one (90 mg, 100%) as a light yellow solid.
Step 5
Proceeding under conditions similar to those described in Example 12, Step 8 above, 8-(2-(6-aminopyridin-2-yl)ethyl)-6-(2-chloro-3,5-dimethoxyphenyl)-2-(methylamino)pyrido[2,3-d]pyrimidin-7(8H)-one (100 mg, 0.2 mmol) was converted to the title compound (21.7 mg, 20%) as a white solid. LC-MS m/z: 521.1 [M+1]$^+$ Example 16

Synthesis of N-(5-(2-(6-(2-chloro-3,5-dimethoxyphenyl)-2-(methylamino)-7-oxopyrido[2,3-d]pyrimidin-8(7H)-yl)ethyl)pyridin-2-yl)acrylamide

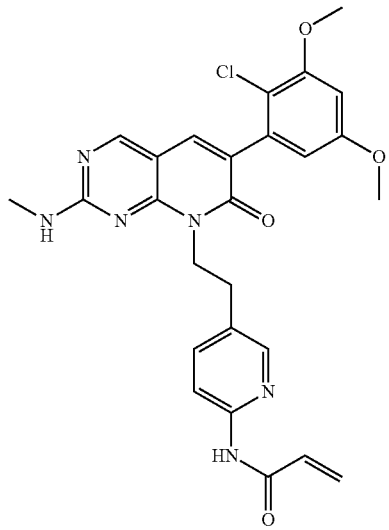

Step 1
A mixture of tert-butyl ethyl malonate (25 g, 130 mmol) and NaH (9.8 g, 130 mmol) in DMF (300 mL) was stirred at r.t. for 1 h under $N_2$ atmosphere, and then 5-bromo-2-nitropyridine (22 g, 110 mmol) was added. The resulting solution was stirred at r.t. overnight and then the mixture was quenched with water and extracted with EtOAc. The organic phase was concentrated to give 1-tert-butyl 3-ethyl 2-(6-nitropyridin-3-yl)malonate (16 g, crude) which was used in the next step without further purification.
Step 2
A solution of 1-tert-butyl 3-ethyl 2-(6-nitropyridin-3-yl)malonate (16 g, 51.6 mmol) in $CH_2Cl_2$ (200 mL)/TFA (100 mL) was refluxed for 3 h, then the solvent was concentrated and the residue was diluted with water, adjusted to pH=9 with $NaHCO_3$ (aq), and the $H_2O$ layer was extracted with EtOAc. The organic phase was concentrated and the residue was purified by column chromatography (silica gel, PE:EtOAc=10:1) to give ethyl 2-(6-nitropyridin-3-yl)acetate (2.2 g, 20%) as a light yellow solid.
Step 3
To a solution of ethyl 2-(6-nitropyridin-3-yl)acetate (2.2 g, 10.5 mmol) in $CH_3OH$ (200 mL) was added Pd/C (250 mg). The mixture was stirred at r.t. under $H_2$ atmosphere overnight and then the mixture was filtered and the filtrate was concentrated to give ethyl 2-(6-aminopyridin-3-yl)acetate (1.7 g, crude) which was used in the next step without further purification.
Step 4
To a solution of ethyl 2-(6-aminopyridin-3-yl)acetate (1.7 g, 9.4 mmol) in t-BuOH (25 mL) was added TEA (1.1 g, 11.3 mmol) and $(Boc)_2O$ (2.5 g, 11.3 mol). The mixture was stirred at 50° C. for 3 h and then the reaction mixture was concentrated and the residue was purified by column chromatography (silica gel, PE:EtOAc=10:1) to give ethyl 2-(6-((tert-butoxy-carbonyl)amino)pyridin-3-yl)acetate (1.9 g, 73%) as a white solid.
Step 5
To a solution of ethyl 2-(6-((tert-butoxycarbonyl)amino)pyridin-3-yl)acetate (1.9 g, 6.8 mmol) in THF (20 mL) was added $LiBH_4$ (450 mg, 20.4 mmol) at 0° C. The reaction solution was stirred at room temperature overnight and then $CH_3OH$ (20 mL) was added, and the resulting solution was refluxed for 1 h. The reaction mixture was concentrated, and the residue was diluted with EtOAc, washed with $H_2O$ and brine. The organic phase was concentrated to give tert-butyl (5-(2-hydroxyethyl)pyridin-2-yl)carbamate (1.4 g, 90%) as a light yellow oil which was used in the next step without further purification.
Step 6
Proceeding under conditions similar to those described in Example 11, Step 4 above, tert-butyl (5-(2-hydroxyethyl)pyridin-2-yl)carbamate (250 mg, 1.1 mmol) was converted to tert-butyl (5-(2-iodoethyl)pyridin-2-yl)carbamate (130 mg, 36%) as a white solid.
Step 7
Proceeding under conditions similar to those described in Example 11, Step 5 above, 6-(2-chloro-3,5-dimethoxyphenyl)-2-(methylthio)pyrido[2,3-d]pyrimidin-7(8H)-one (0.4 g, 1.1 mmol) and tert-butyl (5-(2-iodoethyl)pyridin-2-yl)carbamate (0.42 g, 1.2 mmol) were reacted to give tert-butyl (5-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (580 mg, 90%) which was used in the next step without further purification.

Step 8

Proceeding under conditions similar to those described in Example 8, Step 4 above, tert-butyl (5-(2-(6-(2-chloro-3,5-dimethoxyphenyl)-2-(methylthio)-7-oxopyrido[2,3-d]pyrimidin-8(7H)-yl)ethyl)pyridin-2-yl)carbamate (580 mg, 1.0 mmol) was converted to tert-butyl (5-(2-(6-(2-chloro-3,5-dimethoxyphenyl)-2-(methylsulfinyl)-7-oxopyrido[2,3-d]pyrimidin-8(7H)-yl)ethyl)pyridin-2-yl)carbamate (0.6 g, crude) as a light yellow oil which was used in the next step without further purification.

Step 9

Proceeding under conditions similar to those described in Example 8, Step 5 above, tert-butyl (5-(2-(6-(2-chloro-3,5-dimethoxyphenyl)-2-(methylsulfinyl)-7-oxopyrido-[2,3-d]pyrimidin-8(7H)-yl)ethyl)pyridin-2-yl)carbamate (600 mg, 1 mmol) was converted to tert-butyl (5-(2-(6-(2-chloro-3,5-dimethoxyphenyl)-2-(methylamino)-7-oxopyrido[2,3-d]pyrimidin-8(7H)-yl)ethyl)pyridin-2-yl)carbamate (500 mg, crude) which was used in the next step without further purification.

Step 10

Proceeding under conditions similar to those described in Example 4, Step 9 above, tert-butyl (5-(2-(6-(2-chloro-3,5-dimethoxyphenyl)-2-(methylamino)-7-oxopyrido[2,3-d]pyrimidin-8(7H)-yl)ethyl)pyridin-2-yl)carbamate (500 mg, 0.88 mmol) was converted to 8-(2-(6-aminopyridin-3-yl)ethyl)-6-(2-chloro-3,5-dimethoxy-phenyl)-2-(methylamino)pyrido[2,3-d]pyrimidin-7(8H)-one (410 mg, 100%) as a light yellow solid.

Step 11

Proceeding under conditions similar to those described in Example 8, Step 7 above, 8-(2-(6-aminopyridin-3-yl)ethyl)-6-(2-chloro-3,5-dimethoxyphenyl)-2-(methylamino)-pyrido[2,3-d]pyrimidin-7(8H)-one (100 mg, 0.23 mmol) was converted to the title compound (20 mg, 16.5%) as a white solid. LC-MS m/z: 521.1 [M+1]+

Example 17

Synthesis of N-(4-(2-(6-(2-chloro-3,5-dimethoxyphenyl)-2-(methylamino)-7-oxopyrido[2,3-d]pyrimidin-8(7H)-yl)ethyl)phenyl)-N-methylacrylamide

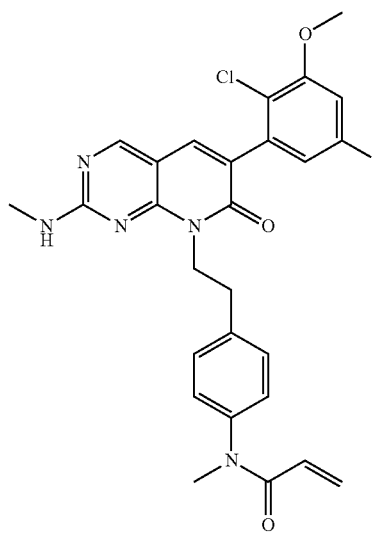

Step 1

To a solution of tert-butyl (4-(2-hydroxyethyl)phenyl) carbamate (6.90 g, 30 mmol) and imidazole (2.45 g, 36 mmol) in DCM (100 mL), was added dropwise chlorotriisopropylsilane (6.36 g, 33 mmol) at rt. The reaction mixture was stirred for 1 h and then water was added. The organic layer was washed with brine dried over $Na_2SO_4$ and concentrated under vacuum. The residue was purified by column chromatography (silica gel, DCM) to afford tert-butyl (4-(2-((triisopropylsilyl)oxy)ethyl)phenyl)carbamate (11.7 g, 99%) as a white solid.

Step 2

To a solution of tert-butyl (4-(2-((triisopropylsilyl)oxy) ethyl)phenyl)carbamate (11.7 g, 30 mmol) in DMF (140 mL), was added NaH (1.8 g, 60% dispersion in mineral oil, 45 mmol) at 0° C. The reaction mixture was stirred at rt for 0.5 h and then iodomethane (6.4 g, 45 mmol) was added at 0° C. The reaction mixture was stirred at rt for 0.5 h and then water was added, extracted with EtOAc, washed with brine, dried over $Na_2SO_4$ and concentrated. The residue was purified by flash chromatography (silica gel, DCM) to afford tert-butyl methyl (4-(2-((triisopropylsilyl)oxy)-ethyl)phenyl)carbamate (10.8 g, 90%) as a white solid.

Step 3

To a solution of tert-butyl methyl (4-(2-((triisopropylsilyl) oxy)ethyl)phenyl)carbamate (10.8 g, 26.5 mmol) in THF (150 mL) was added TBAF (40 mL, 1M in THF, 40 mmol) at rt. The reaction mixture was stirred at rt for 2 and then water was added, extracted with EtOAc, washed with brine, dried over $Na_2SO_4$ and concentrated. The residue was purified by flash chromatography (silica gel, DCM:EtOH=50:1) to afford tert-butyl (4-(2-hydroxyethyl)-phenyl)(methyl)carbamate (6.5 g, 97%) as a colorless oil which was covered to the title compound as described in Example 13 above. LCMS (ESI, pos. ion) m/z: 534.0 (M+1).

Example 18

Synthesis of N-(3-(2-(6-(2-chloro-3,5-dimethoxyphenyl)-2-(methylamino)-7-oxopyrido[2,3-d]pyrimidin-8(7H)-yl)ethyl)phenyl)-N-methylacrylamide

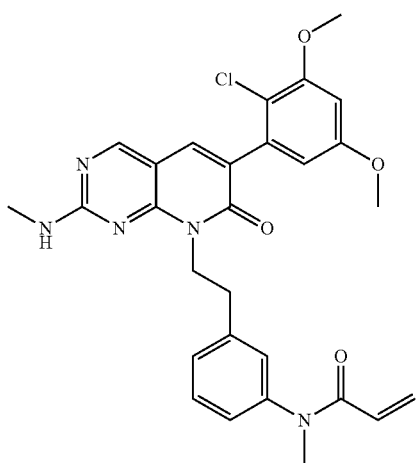 [SMILES: C=CC(=O)N(C)c1cccc(CCn2c(=O)c(-c3cc(OC)cc(OC)c3Cl)cc3cnc(NC)nc32)c1]

Step 1

To a solution of 2-(3-aminophenyl)ethanol (4.11 g, 30 mmol) in THF (100 mL) was added DIPEA (7.74 g, 60 mmol) and (Boc)$_2$O (7.85 g, 36 mmol). The reaction mixture was stirred at ambient temperature for 3 h and then concentrated. The residue was dissolved with ethyl acetate, washed with brine and water. The organic layer was dried over anhydrous $Na_2SO_4$, filtered and evaporated to afford tert-butyl (3-(2-hydroxyethyl)phenyl)carbamate as a colorless oil (7.2 g, crude) which was covered to the title compound as described in Example 13 above. LCMS (ESI, pos. ion) m/z: 534.0 (M+1).

Example 19

Synthesis of N-(3-((6-(2-chloro-3,5-dimethoxyphenyl)-2-(methylamino)-7-oxopyrido[2,3-d]pyrimidin-8(7H)-yl)methyl)phenyl)acrylamide

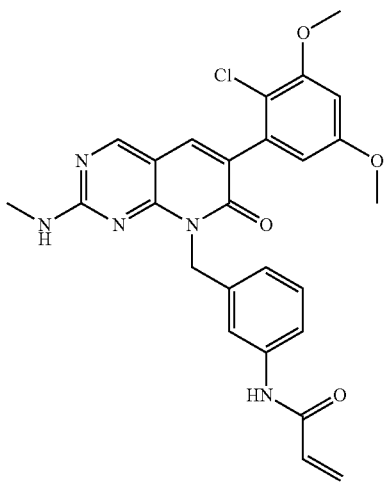

Step 1

To a solution of (3-aminophenyl)methanol (1.23 g, 10 mmol) in THF (100 mL) was added $Boc_2O$ (2.62 g, 1.2 mmol) and DIPEA (2.58 g, 2 mmol). The reaction mixture was stirred at 50° C. for 2 h before cooling to ambient temperature. The reaction mixture was poured into water (100 mL) and exacted with ethyl acetate. The organic layer was dried over anhydrous $Na_2SO_4$, filtered and concentrated. The residue was purified by flash chromatography (silica gel, petroleum ether/ethyl acetate=10:1) to afford tert-butyl (3-(hydroxymethyl)phenyl)carbamate as a white solid (2.16 g, 97%).

Step 2

To a solution of tert-butyl (3-(hydroxymethyl)phenyl)carbamate (2.16 g, 9.7 mmol) in DCM (100 mL) was added perbromomethane (4.97 g, 15 mmol), TPP (3.93 g, 15 mmol) and imidazole (1.0 g, 1.5 mmol). The reaction mixture was stirred at ambient temperature for 3 h before diluting with DCM (150 mL). The reaction mixture was washed with brine and the organic layer was dried over anhydrous $Na_2SO_4$, filtered and concentrated to afford tert-butyl (3-(bromomethyl)phenyl)carbamate as a white solid (4.0 g, crude) which was converted to the title compound as described Example 12 above. LCMS (ESI, pos. ion) m/z: 506.0 (M+1).

Example 20

Synthesis of N-(4-(2-(6-(2-chloro-3,5-dimethoxyphenyl)-2-(methylamino)-7-oxopyrido[2,3-d]pyrimidin-8(7H)-yl)ethyl)phenyl)ethenesulfonamide

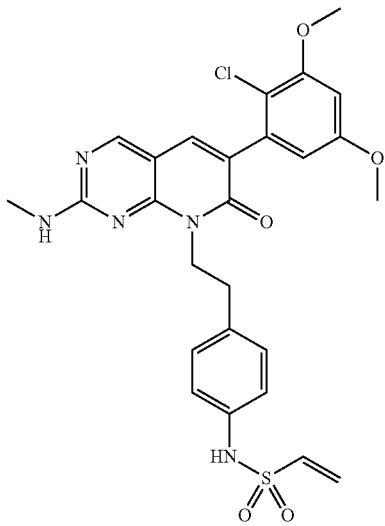

To a solution of 8-(4-aminophenethyl)-6-(2-chloro-3,5-dimethoxyphenyl)-2-(methyl-amino)pyrido[2,3-d]pyrimidin-7(8H)-one (76. mg, 0.16 mmol)), DIPEA (0.04 mL, 0.21 mmol) and DCM (5 mL) was added 2-chloroethanesulfonyl chloride (31.91 mg, 0.20 mmol)). The solution was stirred at room temperature for 3 hr and then concentrated. The residue was purified by chromatography to afford N-(4-(2-(6-(2-chloro-3,5-dimethoxyphenyl)-2-(methylamino)-7-oxopyrido[2,3-d]pyrimidin-8(7H)-yl)ethyl)phenyl)ethenesulfonamide (7 mg, 7%). LCMS (ESI, pos. ion) m/z: 556.2 (M+1).

Example 21

Synthesis of N-(3-(2-(6-(2-chloro-3,5-dimethoxyphenyl)-2-(methylamino)-7-oxopyrido[2,3-d]pyrimidin-8(7H)-yl)ethyl)phenyl)ethenesulfonamide

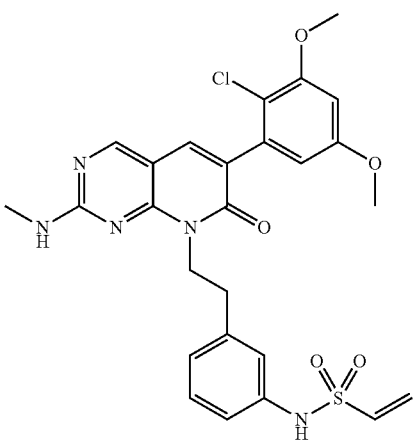 [SMILES: C=CS(=O)(=O)Nc1cccc(CCn2c(=O)c(-c3cc(OC)cc(OC)c3Cl)cc3cnc(NC)nc32)c1]

The compound was prepared as described in Example 20 using 8-(3-aminophenethyl)-6-(2-chloro-3,5-dimethoxyphenyl)-2-(methylamino)pyrido[2,3-d]pyrimidin-7(8H)-one. LCMS (ESI, pos. ion) m/z: 556.2 (M+1).

Example 22

Synthesis of (E)-N-(4-(2-(6-(2-chloro-3,5-dimethoxyphenyl)-2-(methylamino)-7-oxopyrido[2,3-d]pyrimidin-8(7H)-yl)ethyl)phenyl)-4-(dimethylamino)but-2-enamide

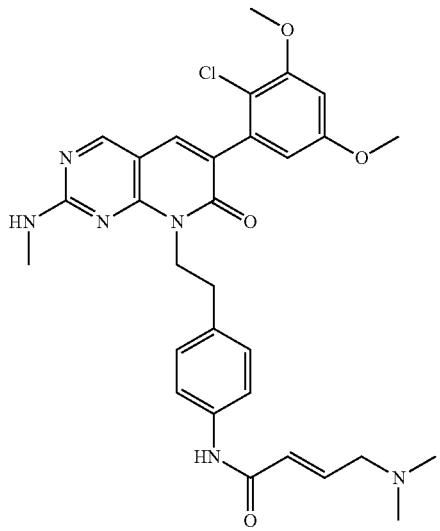 [SMILES: CNc1ncc2cc(-c3cc(OC)cc(OC)c3Cl)c(=O)n(CCc3ccc(NC(=O)/C=C/CN(C)C)cc3)c2n1]

To a solution of 8-(4-aminophenethyl)-6-(2-chloro-3,5-dimethoxyphenyl)-2-(methylamino)pyrido[2,3-d]pyrimidin-7(8H)-one (200 mg, 0.43 mmol) in NMP (5 mL) was added (E)-4-(dimethylamino)but-2-enoyl chloride (95 mg, 0.65 mmol) at 0° C. The reaction mixture was stirred at ambient temperature for 0.5 h before quenching with water. The reaction mixture was exacted with ethyl acetate and washed with sat. NaHCO₃. The organic layer was dried over anhydrous Na₂SO₄, filtered and concentrated to afford (E)-N-(4-(2-(6-(2-chloro-3,5-dimethoxyphenyl)-2-(methylamino)-7-oxopyrido[2,3-d]pyrimidin-8(7H)-yl)ethyl)phenyl)-4-(dimethylamino)but-2-enamide get the desired product as a white solid (50 mg, 20%) after purification by Prep-HPLC. LCMS (ESI, pos. ion) m/z: 576.9 (M+1).

Example 23

Synthesis of (E)-N-(3-(2-(6-(2-chloro-3,5-dimethoxyphenyl)-2-(methylamino)-7-oxopyrido[2,3-d]pyrimidin-8(7H)-yl)ethyl)phenyl)-4-(dimethylamino)but-2-enamide

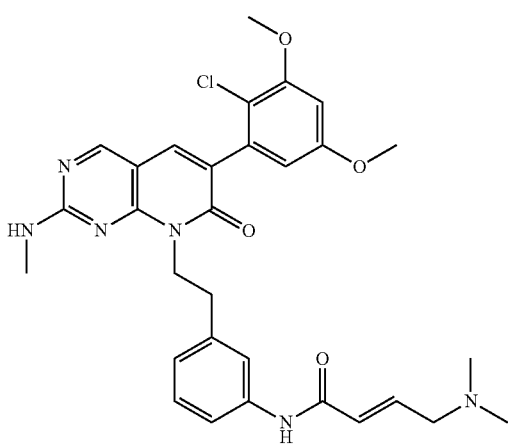 [SMILES: CNc1ncc2cc(-c3cc(OC)cc(OC)c3Cl)c(=O)n(CCc3cccc(NC(=O)/C=C/CN(C)C)c3)c2n1]

The compound was prepared as described in Example 22 using 8-(3-aminophenethyl)-6-(2-chloro-3,5-dimethoxyphenyl)-2-(methylamino)pyrido[2,3-d]pyrimidin-7(8H)-one. LCMS (ESI, pos. ion) m/z: 576.9 (M+1).

Example 24

Synthesis of N-(4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)acrylamide

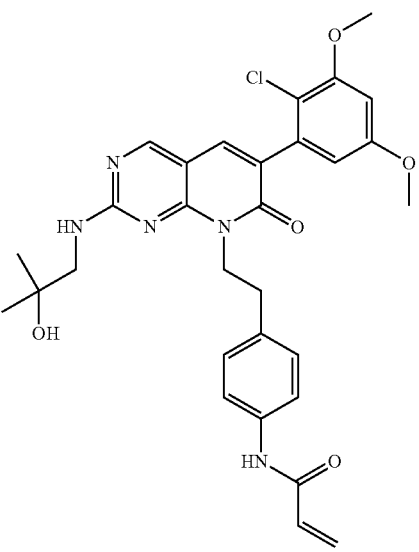 [SMILES: C=CC(=O)Nc1ccc(CCn2c(=O)c(-c3cc(OC)cc(OC)c3Cl)cc3cnc(NCC(C)(C)O)nc32)cc1]

Step 1

To a solution of tert-butyl (4-(2-(6-(2-chloro-3,5-dimethoxyphenyl)-2-(methylsulfinyl)-7-oxopyrido[2,3-d]pyrimidin-8(7H)-yl)ethyl)phenyl)carbamate (0.48 g, 0.73 mmol) in DMSO (5 mL) was added DIPEA (0.19 g, 1.46 mmol) and 1-amino-2-methylpropan-2-ol (0.13 g, 1.46 mmol). The reaction mixture was stirred at 80° C. for 30 min and then cooled to ambient temperature, poured into water, exacted with ethyl acetate and washed with brine. The organic layer was dried over anhydrous Na₂SO₄, filtered and evaporated to afford tert-butyl (4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)carbamate as a yellow oil (458 mg, crude).

Step 2

To a solution of tert-butyl (4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)carbamate (457 mg, 0.73 mmol) in DCM (6 mL) was added TFA (2 mL). The reaction mixture was stirred at ambient temperature for 1 h and then concentrated. The residue was poured into brine, exacted with DCM and washed with aq. NaHCO₃. The organic layer was dried over anhydrous sodium sulfate, filtered and concentrated to afford 8-(4-aminophenethyl)-6-(2-chloro-3,5-dimethoxy-phenyl)-2-((2-hydroxy-2-methylpropyl)amino)-pyrido[2,3-d]pyrimidin-7(8H)-one as a white solid (150 mg, 39%) after purification by flash chromatography (silica gel, DCM/MeOH=20:1).

Step 3

To a solution of 8-(4-aminophenethyl)-6-(2-chloro-3,5-dimethoxyphenyl)-2-((2-hydroxy-2-methylpropyl)amino) pyrido[2,3-d]pyrimidin-7(8H)-one (150 mg, 0.29 mmol) in DCM (10 mL) was added DIPEA (374 mg, 2.9 mmol) and acrylic anhydride (180 mg, 1.43 mmol). The reaction mixture was stirred at ambient temperature for 3 h and then poured into water, extracted with DCM and washed with aq. sodium bicarbonate. The organic layer was dried over anhydrous $Na_2SO_4$, filtered and concentrated to afford N-(4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)acrylamide as a white solid (30 mg, 18%) after purification by prep-TLC (silica gel, DCM/MeOH=20:1). LCMS (ESI, pos. ion) m/z: 578.2 (M+1).

Example 25

Synthesis of N-(4-(2-(6-(2-chloro-3,5-dimethoxyphenyl)-2-((2-(diethylamino)ethyl)amino)-7-oxopyrido[2,3-d]pyrimidin-8(7H)-yl)ethyl)phenyl)acrylamide

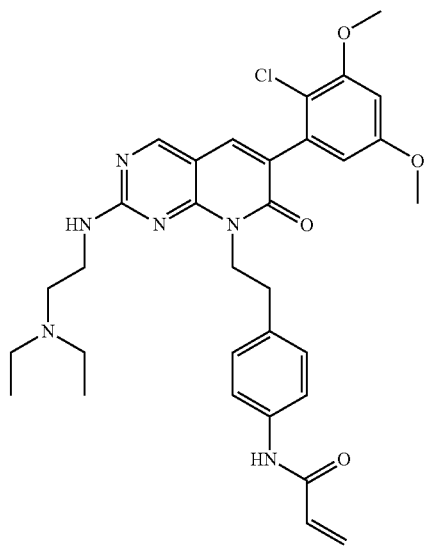 [SMILES: C=CC(=O)Nc1ccc(CCn2c(=O)c(-c3cc(OC)cc(OC)c3Cl)cc3cnc(NCCN(CC)CC)nc32)cc1]

The compound was prepared as described in Example 13 except $N^1,N^1$-diethylethane-1,2-diamine was used in Step 3. LCMS (ESI, pos. ion) m/z: 605.1 (M+1).

Example 26

Synthesis of N-(4-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide

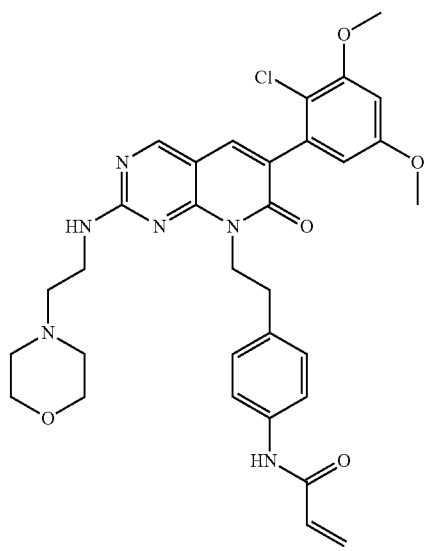 [SMILES: C=CC(=O)Nc1ccc(CCn2c(=O)c(-c3cc(OC)cc(OC)c3Cl)cc3cnc(NCCN4CCOCC4)nc32)cc1]

The compound was prepared as described in Example 13 above, except 2-morpholinoethanamine was used in Step 3. LCMS (ESI, pos. ion) m/z: 619.1 (M+1).

Example 27

Synthesis of N-(4-(2-(2-amino-6-(2-chloro-3,5-dimethoxyphenyl)-7-oxopyrido[2,3-d]pyrimidin-8(7H)-yl)ethyl)phenyl)acrylamide

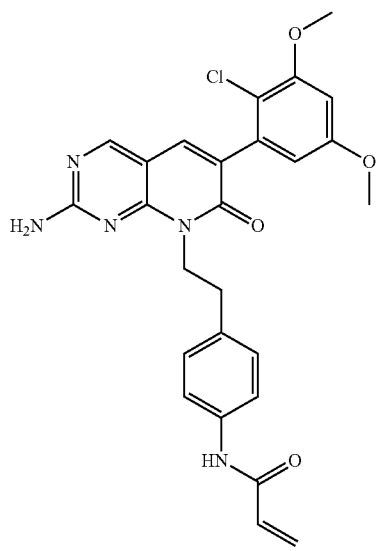 [SMILES: C=CC(=O)Nc1ccc(CCn2c(=O)c(-c3cc(OC)cc(OC)c3Cl)cc3cnc(N)nc32)cc1]

The compound was prepared as described in Example 13 except $NH_3$/THF (2M) was used in Step 3. LCMS (ESI, pos. ion) m/z: 505.9 (M+1).

Example 28

Synthesis of N-(5-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)pyridin-2-yl)acrylamide

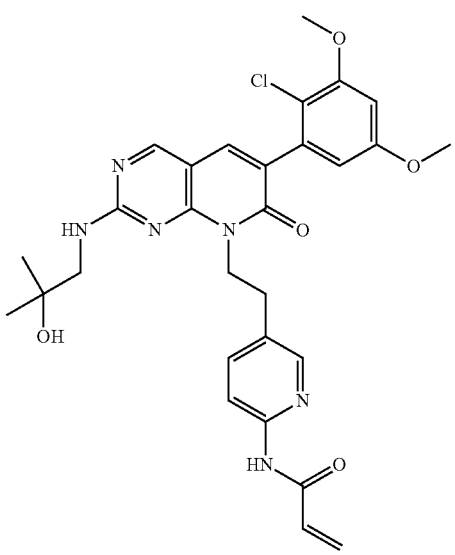 [SMILES: C=CC(=O)Nc1ccc(CCn2c(=O)c(-c3cc(OC)cc(OC)c3Cl)cc3cnc(NCC(C)(C)O)nc32)cn1]

The compound was prepared as described in Example 16 above except 1-amino-2-methylpropan-2-ol was used in Step 9. LCMS (ESI, pos. ion) m/z: 579.1 (M+1).

Example 29

Synthesis of N-(5-(2-(6-(2-chloro-3,5-dimethoxyphenyl)-2-((2-(diethylamino)ethyl)amino)-7-oxopyrido[2,3-d]pyrimidin-8(7H)-yl)ethyl)pyridin-2-yl)acrylamide

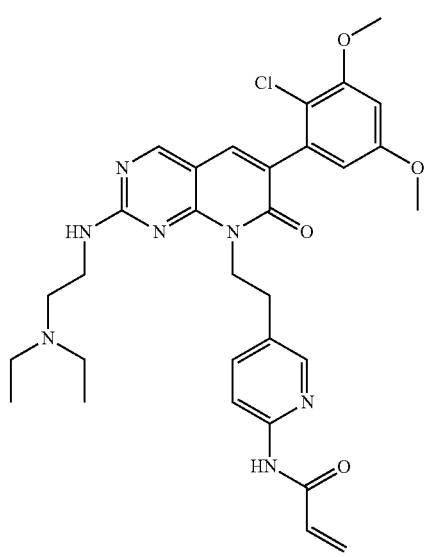 [SMILES: C=CC(=O)Nc1ccc(CCn2c(=O)c(-c3cc(OC)cc(OC)c3Cl)cc3cnc(NCCN(CC)CC)nc32)cn1]

The compound was prepared as described in Example 16 above except N$^1$,N$^1$-diethylethane-1,2-diamine was used in Step 9. LCMS (ESI, pos. ion) m/z: 606.1 (M+1).

Example 30

Synthesis of N-(5-(2-(6-(2-chloro-3,5-dimethoxyphenyl)-2-(neopentylamino)-7-oxopyrido[2,3-d]pyrimidin-8(7H)-yl)ethyl)pyridin-2-yl)acrylamide

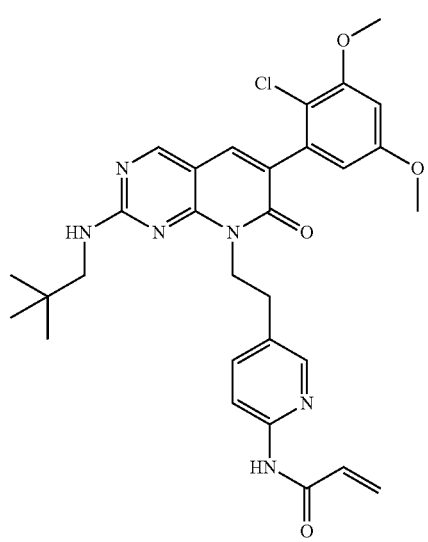 [SMILES: C=CC(=O)Nc1ccc(CCn2c(=O)c(-c3cc(OC)cc(OC)c3Cl)cc3cnc(NCC(C)(C)C)nc32)cn1]

The compound was prepared as described in Example 16, except 2,2-dimethylpropan-1-amine was used in Step 9. LCMS (ESI, pos. ion) m/z: 577.2 (M+1).

Example 31

Synthesis of N-(5-(2-(6-(2-chloro-3,5-dimethoxyphenyl)-2-(2-morpholinoethylamino)-7-oxopyrido[2,3-d]pyrimidin-8(7H)-yl)ethyl)pyridin-2-yl)acrylamide

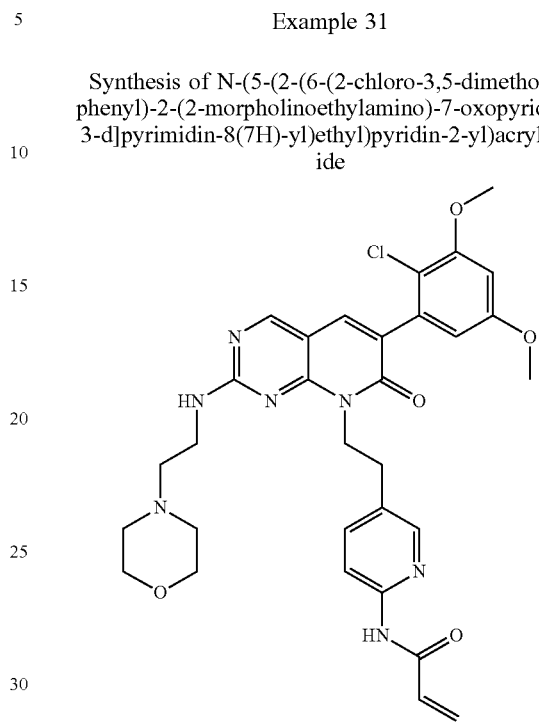

The compound was prepared as described in Example 16 except 2-morpholinoethanamine was used in Step 9. LCMS (ESI, pos. ion) m/z: 620.2 (M+1).

Example 32

Synthesis of N-(5-(2-(6-(2-chloro-3,5-dimethoxyphenyl)-2-((4-(diethylamino)butyl)amino)-7-oxopyrido[2,3-d]pyrimidin-8(7H)-yl)ethyl)pyridin-2-yl)acrylamide

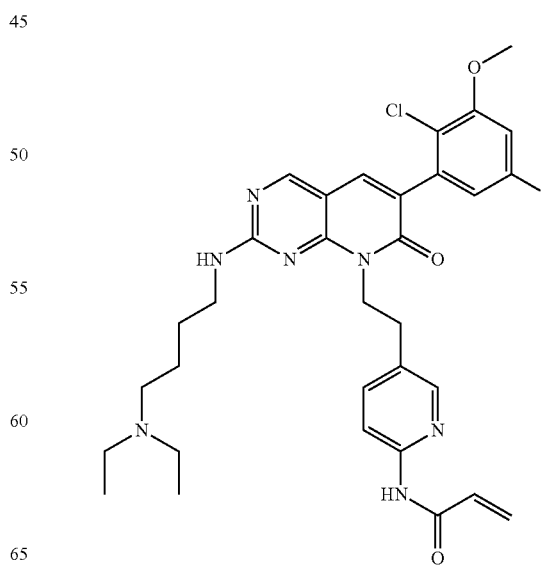

The compound was prepared as described in Example 16 except N¹,N¹-diethethylbutane-1,4-diamine was used in Step 9. LCMS (ESI, pos. ion) m/z: 634.0 (M+1).

Example 33

Synthesis of N-(4-(2-(6-(2-chloro-3,5-dimethoxyphenyl)-2-(methylamino)-7-oxopyrido[2,3-d]-pyrimidin-8(7H)-yl)ethyl)thiazol-2-yl)acrylamide

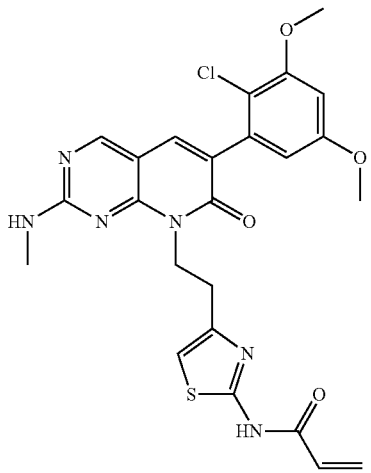 [SMILES: C=CC(=O)Nc1nc(CCn2c(=O)c(-c3cc(OC)cc(OC)c3Cl)cc3cnc(NC)nc32)cs1]

Step 1

To a solution of ethyl 2-(2-aminothiazol-4-yl)acetate (6 g, 32.2 mmol) in DCM (140 mL) was added DMAP (0.59 g, 4.8 mmol) and Boc₂O (7.7 g, 35.4 mmol). The reaction mixture was stirred at ambient temperature overnight. The reaction mixture was washed with aq. sodium bicarbonate and water. The organic layer was dried over anhydrous Na₂SO₄, filtered and concentrated to afford ethyl 2-(2-((tert-butoxycarbonyl)amino)thiazol-4-yl)acetate as a colorless oil (7.6 g, 82%) after purification by flash chromatography (silica gel, petroleum ether/ethyl acetate=5:1).

Step 2

To a solution of ethyl 2-(2-((tert-butoxycarbonyl)amino) thiazol-4-yl)acetate (2 g, 7 mmol) in THF (50 mL) was added LiBH₄ (0.305 g, 14 mmol) at ambient temperature. The reaction mixture was stirred at for 16 h and then MeOH (10 mL) was added to the reaction mixture and refluxed for 1 h. The reaction mixture was poured into water and exacted with ethyl acetate. The organic layer was washed with brine, dried over anhydrous Na₂SO₄, filtered and concentrated to afford tert-butyl (4-(2-hydroxyethyl)thiazol-2-yl)carbamate as a white solid (1.5 g, 88%).

Step 3

To a solution of tert-butyl (4-(2-hydroxyethyl)thiazol-2-yl)carbamate (1.5 g, 6.14 mmol) in DCM (15 mL) was added TEA (1.24 g, 12.3 mmol) and MsCl (0.77 g, 6.76 mmol) dropwise at 0° C. The reaction mixture was stirred at 0° C. for 1 h and then H₂O was added to the reaction mixture and exacted with DCM. The organic layer was dried over anhydrous Na₂SO₄, filtered and concentrated to afford 2-(2-((tert-butoxycarbonyl)amino)thiazol-4-yl)ethyl methanesulfonate as a red oil (2.1 g, crude) which was covered to the title compound using appropriate starting materials as described in Example 10, Steps 5 to 9. LCMS (ESI, pos. ion) m/z: 527.0 (M+1).

Example 34

Synthesis of N-(6-(2-(6-(2-chloro-3,5-dimethoxyphenyl)-2-(methylamino)-7-oxopyrido[2,3-d]pyrimidin-8(7H)-yl)ethyl)pyridin-3-yl)acrylamide

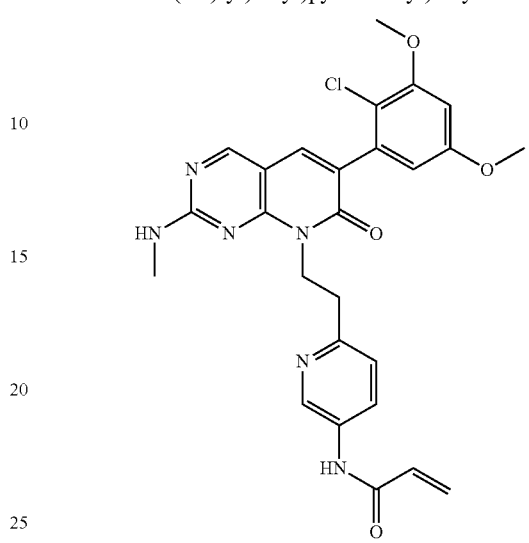

Step 1

A mixture of 2-chloro-5-nitropyridine (10 g, 63.07 mmol), 1,3-diethyl propanedioate (20 g, 124.87 mmol), potassium carbonate (26 g, 188.12 mmol) and DMF (50 mL) was stirred overnight at 70° C. The solids were filtered was concentrated. The residue was purified by chromatography (ethyl acetate/petroleum ether (1:20)) to afford 20 g (crude) of 1,3-diethyl 2-(5-nitropyridin-2-yl)propanedioate as a brown solid.

Step 2

A solution of 1,3-diethyl 2-(5-nitropyridin-2-yl)propanedioate (20 g, 70.86 mmol), sodium chloride (4.2 g), water (2 mL, 1.50 equiv) and DMSO (200 mL) was stirred overnight at 120° C. The reaction was then quenched with 100 mL of water/ice. The resulting solution was extracted with ethyl acetate and the organic layer was washed with sat. NaCl. The mixture was dried over anhydrous Na₂SO₄, filtered and concentrated. The residue was purified by chromatography (ethyl acetate/petroleum ether (1:10)) to afford 10 g (67%) of ethyl 2-(5-nitropyridin-2-yl)acetate as a colorless oil.

Step 3

A mixture of ethyl 2-(5-nitropyridin-2-yl)acetate (11 g, 49.06 mmol), Pd on carbon (2 g), and ethanol (200 mL) over hydrogen atmosphere was stirred overnight at room temperature. The solids were filtered and the filtrate was concentrated to afford 8.6 g (90%) of ethyl 2-(5-aminopyridin-2-yl)acetate as a light yellow oil.

Step 4

A solution of ethyl 2-(5-aminopyridin-2-yl)acetate (4 g, 22.20 mmol) and Boc₂O (12 g, 54.98 mmol) in THF (100 mL) was stirred overnight at 70° C. The reaction was concentrated and the residue was purified by chromatography (ethyl acetate/petroleum ether (1:5)) to afford 5 g (80%) of ethyl 2-(5-[[(tert-butoxy)carbonyl]amino]pyridin-2-yl) acetate as a light yellow oil.

Step 5

To a mixture of LiAlH₄ (2.5 g, 65.88 mmol) in THF (50 mL) was added a solution of ethyl 2-(5-[[(tert-butoxy) carbonyl]amino]pyridin-2-yl)acetate (5.5 g, 19.62 mmol, 1.00 equiv) in tetrahydrofuran (50 mL) dropwise with stirring at 0° C. The resulting solution was stirred for 4 h at 80°

C. and the reaction was then quenched by the addition of 5 g of Na$_2$SO$_4$.10H$_2$O. The solids were filtered and the filtrate was concentrated to afford 3 g (64%) of tert-butyl N-[6-(2-hydroxyethyl)pyridin-3-yl]carbamate as colorless oil.

Step 6

To a solution of tert-butyl (6-(2-hydroxyethyl)pyridin-3-yl)carbamate (1.7 g, 7.1 mmol) in DCM at 0° C. (15 mL) was added DIPEA (1.8 g, 14.2 mmol) and MsCl (1.1 g, 9.2 mmol) dropwise. The reaction mixture was stirred at ambient temperature for 1 h and then water was added. The reaction mixture was exacted with DCM, washed with brine, dried over anhydrous Na$_2$SO$_4$, filtered and concentrated to afford 2-(5-((tert-butoxycarbonyl)amino)pyridin-2-yl)ethyl methanesulfonate (1.3 g, 58%) as a yellow oil Step 7

To a solution of 6-(2-chloro-3,5-dimethoxyphenyl)-2-(methylthio)pyrido[2,3-d]pyrimidin-7(8H)-one (1.1 g, 3.1 mmol) in DMF (10 mL) was added 2-(5-((tert-butoxycarbonyl)amino)-pyridin-2-yl)ethyl methanesulfonate (1.3 g, 4.1 mmol) and K$_2$CO$_3$ (856 mg, 6.2 mmol). The reaction mixture was stirred at 85° C. for 1 h before cooling to ambient temperature and adding water. The solid was collected by filtration and the filtrated cake was dried to afford tert-butyl (6-(2-(6-(2-chloro-3,5-dimethoxyphenyl)-2-(methylthio)-7-oxopyrido[2,3-d]pyrimidin-8(7H)-yl)ethyl)pyridin-3-yl)carbamate (1.6 g, 88%) as a yellow solid.

Step 8

To a solution of tert-butyl (6-(2-(6-(2-chloro-3,5-dimethoxyphenyl)-2-(methylthio)-7-oxopyrido[2,3-d]pyrimidin-8(7H)-yl)ethyl)pyridin-3-yl)carbamate (1.6 g, 2.7 mmol) in DCM (10 mL) was added m-CPBA (663 mg, 2.7 mmol, 70%). The reaction mixture was stirred at ambient temperature for 30 min then sat. Na$_2$S$_2$O$_3$ was added. The reaction mixture was exacted with DCM, washed with brine, dried over anhydrous sodium sulfate, filtered and concentrated to afford tert-butyl (6-(2-(6-(2-chloro-3,5-dimethoxyphenyl)-2-(methylsulfinyl)-7-oxopyrido[2,3-d]pyrimidin-8(7H)-yl)ethyl)pyridin-3-yl)carbamate (1.5 g, 92%) as a yellow solid.

Step 9

To a solution of tert-butyl (6-(2-(6-(2-chloro-3,5-dimethoxyphenyl)-2-(methylsulfinyl)-7-oxopyrido[2,3-d]pyrimidin-8(7H)-yl)ethyl)pyridin-3-yl)carbamate (1.5 g, 2.5 mmol) in DMSO (10 mL) was added CH$_3$NH$_2$—HCl (503 mg, 7.5 mmol). The reaction mixture was stirred at 85° C. for 30 min and then cooled to ambient temperature. The reaction mixture was exacted with ethyl acetate, washed with brine, dried over anhydrous Na$_2$SO$_4$, filtered and concentrated to afford tert-butyl (6-(2-(6-(2-chloro-3,5-dimethoxyphenyl)-2-(methylamino)-7-oxopyrido[2,3-d]pyrimidin-8(7H)-yl)ethyl)pyridin-3-yl)carbamate (1.2 g, 84%) as a yellow solid.

Step 10

To a solution of tert-butyl (6-(2-(6-(2-chloro-3,5-dimethoxyphenyl)-2-(methylamino)-7-oxopyrido[2,3-d]pyrimidin-8(7H)-yl)ethyl)pyridin-3-yl)carbamate (1.2 g, 2.1 mmol) in DCM (10 mL) was added TFA (5 mL). The reaction mixture was stirred at ambient temperature for 3 h and then concentrated. The reaction mixture was diluted with ethyl acetate (100 mL), washed with aq. NaHCO$_3$ and brine, dried over anhydrous Na$_2$SO$_4$, filtered and concentrated to afford 8-(2-(5-aminopyridin-2-yl)ethyl)-6-(2-chloro-3,5-dimethoxyphenyl)-2-(methylamino)pyrido[2,3-d]pyrimidin-7(8H)-one (800 mg, 82%) as a light yellow solid.

Step 11

To a solution of 8-(2-(5-aminopyridin-2-yl)ethyl)-6-(2-chloro-3,5-dimethoxyphenyl)-2-(methylamino)pyrido[2,3-d]pyrimidin-7(8H)-one (300 mg, 0.64 mmol) in DCM (3 mL) at −40° C. was added TEA (129 mg, 1.28 mmol) and acryloyl chloride (63 mg, 0.70 mmol). The reaction mixture was stirred for 10 min and then filtered through a short silica gel column and concentrated. The residue was purified by prep-HPLC to afford N-(6-(2-(6-(2-chloro-3,5-dimethoxyphenyl)-2-(methylamino)-7-oxopyrido[2,3-d]pyrimidin-8(7H)-yl)ethyl)pyridin-3-yl)acrylamide (35 mg, 11%) as a light yellow solid. LCMS (ESI, pos. ion) m/z: 521.1 (M+1).

Example 35

Synthesis of N-(3-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide

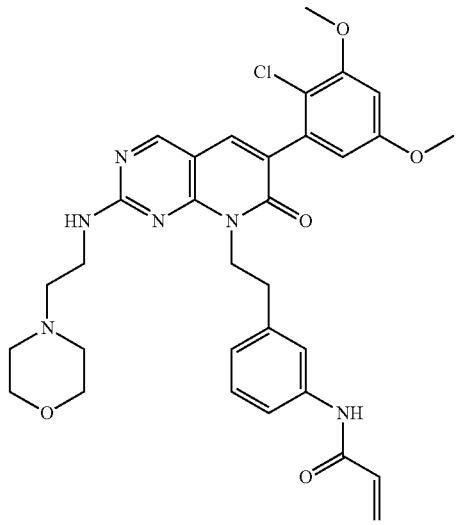 [SMILES: C=CC(=O)Nc1cccc(CCn2c(=O)c(-c3cc(OC)cc(OC)c3Cl)cc3cnc(NCCN4CCOCC4)nc32)c1]

The compound was prepared as described in Example 12, except 2-morpholinoethanamine was used in Step 6. LCMS (ESI, pos. ion) m/z: 619.1 (M+1).

Example 36

Synthesis of N-(3-(2-(6-(2-chloro-3,5-dimethoxyphenyl)-2-((2-piperidin-1-ylethyl)amino)-7-oxopyrido[2,3-d]pyrimidin-8(7H)-yl)ethyl)phenyl)acrylamide

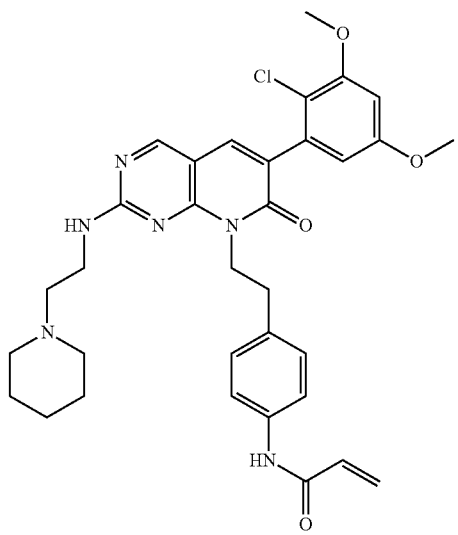 [SMILES: C=CC(=O)Nc1ccc(CCn2c(=O)c(-c3cc(OC)cc(OC)c3Cl)cc3cnc(NCCN4CCCCC4)nc32)cc1]

The compound was prepared as described in Example 13 except 2-(piperidin-1-yl)ethanamine was used in Step 3. LCMS (ESI, pos. ion) m/z: 617.3 (M+1).

Example 37

Synthesis of N-(4-(2-(6-(2-chloro-3,5-dimethoxyphenyl)-2-(3-morpholinopropyl)amino)-7-oxopyrido[2,3-d]pyrimidin-8(7H)-yl)ethyl)phenyl)acrylamide

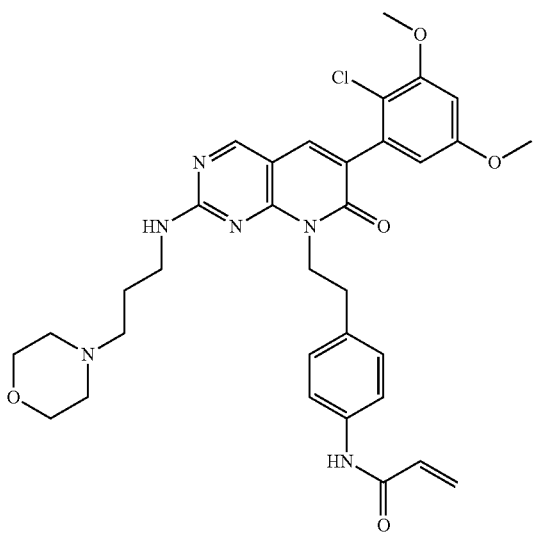 [SMILES: C=CC(=O)Nc1ccc(CCn2c(=O)c(-c3cc(OC)cc(OC)c3Cl)cc3cnc(NCCCN4CCOCC4)nc32)cc1]

The compound was prepared as described in Example 13 except 3-morpholinopropan-1-amine was used in Step 3. LCMS (ESI, pos. ion) m/z: 633.2 (M+1).

Example 38

Synthesis of N-(6-(2-(6-(2,6-dichloro-3,5-dimethoxyphenyl)-2-(methylamino)-7-oxopyrido[2,3-d]pyrimidin-8(7H)-yl)ethyl)pyridin-3-yl)acrylamide

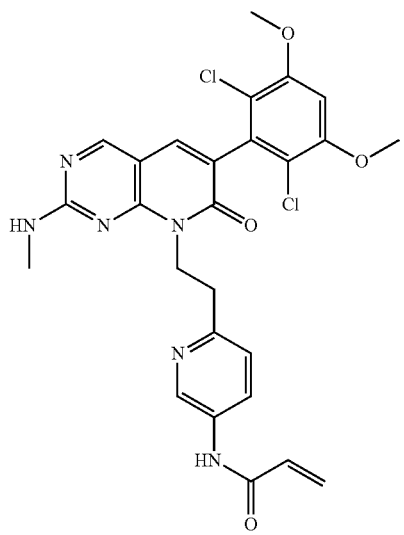

Step 1

A solution of tert-butyl N-[6-(2-hydroxyethyl)pyridin-3-yl]carbamate (3.5 g, 14.69 mmol), $I_2$ (11.2 g), imidazole (3.5 g) and $PPh_3$ (11.5 g, 43.84 mmol) in DCM (150 mL) was stirred for 5 h at room temperature. The solids were filtered and the filtrate was concentrated. The residue was purified by chromatography (ethyl acetate/petroleum ether (1:20)) to afford 4.5 g (88%) of tert-butyl N-[6-(2-iodoethyl)pyridin-3-yl]carbamate as a light yellow oil.

Step 2

A mixture of 6-(2,6-dichloro-3,5-dimethoxyphenyl)-2-(methylsulfanyl)-7H,8H-pyrido[2,3-d]pyrimidin-7-one (700 mg, 1.76 mmol), tert-butyl N-[4-(2-iodoethyl)phenyl]-carbamate (1.3 g, 3.74 mmol) and $K_2CO_3$ (1.2 g, 5.00 equiv) in acetone (20 mL) was stirred overnight at 55° C. The resulting mixture was concentrated and the residue was purified by chromatography (ethyl acetate/petroleum ether (1:5)) to afford 1 g (92%) of tert-butyl N-(6-[2-[6-(2,6-dichloro-3,5-dimethoxyphenyl)-2-(methylsulfanyl)-7-oxo-7H,8H-pyrido[2,3-d]pyrimidin-8-yl]ethyl]pyridin-3-yl)carbamate as a brown solid.

Step 3

A solution of tert-butyl N-(6-[2-[6-(2,6-dichloro-3,5-dimethoxyphenyl)-2-(methylsulfanyl)-7-oxo-7H,8H-pyrido[2,3-d]pyrimidin-8-yl]ethyl]pyridin-3-yl)carbamate (200 mg, 0.32 mmol) and m-CPBA (55 mg, 0.32 mmol, 1.00 equiv) in DCM (20 mL) was stirred for 3 h at room temperature. The reaction was then quenched with sat. $NaHCO_3$ and washed with water and sat. NaCl. The organic layer was dried over anhydrous $Na_2SO_4$ and concentrated to afford 180 mg (86%) 5-((tert-butoxycarbonyl)amino)-2-(2-(6-(2,6-dichloro-3,5-dimethoxyphenyl)-2-(methylsulfinyl)-7-oxopyrido[2,3-d]pyrimidin-8(7H)-yl)ethyl)pyridine 1-oxide as a light yellow solid.

Step 4

A solution of 5-((tert-butoxycarbonyl)amino)-2-(2-(6-(2,6-dichloro-3,5-dimethoxyphenyl)-2-(methylsulfinyl)-7-oxopyrido[2,3-d]pyrimidin-8(7H)-yl)ethyl)pyridine 1-oxide (180 mg, 0.28 mmol) and $CH_3NH_2$/THF (2.0 M, 0.5 mL) in DMSO (5 mL) was stirred for 2 h at 55° C. The resulting solution was diluted with DCM and washed with water and sat. NaCl. The mixture was dried over anhydrous $Na_2SO_4$ and concentrated to afford 120 mg (70%) of 5-((tert-butoxycarbonyl)amino)-2-(2-(6-(2,6-dichloro-3,5-dimethoxyphenyl)-2-(methylamino)-7-oxopyrido[2,3-d]pyrimidin-8(7H)-yl)ethyl)pyridine 1-oxide as a brown solid.

Step 5

A solution of 5-((tert-butoxycarbonyl)amino)-2-(2-(6-(2,6-dichloro-3,5-dimethoxy-phenyl)-2-(methylamino)-7-oxopyrido[2,3-d]pyrimidin-8(7H)-yl)ethyl)pyridine 1-oxide (120 mg, 0.19 mmol) and Fe (200 mg) in EtOH (10 mL) and sat. $NH_4Cl$ (1 mL) was stirred overnight at 90° C. The solids were filtered and the filtrate was concentrated. The residue was purified by chromatography (DCM/MeOH (20:1)) to afford 100 mg (86%) of tert-butyl N-(6-[2-[6-(2,6-dichloro-3,5-dimethoxyphenyl)-2-(methylamino)-7-oxo-7H,8H-pyrido[2,3-d]pyrimidin-8-yl]ethyl]pyridin-3-yl)carbamate as a yellow solid.

Step 6

A solution of tert-butyl N-(6-[2-[6-(2,6-dichloro-3,5-dimethoxyphenyl)-2-(methylamino)-7-oxo-7H,8H-pyrido[2, 3-d]pyrimidin-8-yl]ethyl]pyridin-3-yl)carbamate (400 mg, 0.67 mmol) and TFA (4 mL) in DCM (15 mL) was stirred overnight at room temperature.

The resulting mixture was concentrated and then diluted with 4M HCl/dioxane (10 mL). Then the resulting mixture was concentrated again to afford 250 mg (70%) of 8-[2-(5-aminopyridin-2-yl)ethyl]-6-(2,6-dichloro-3,5-dimethoxyphenyl)-2-(methylamino)-7H,8H-pyrido[2,3-d]pyrimidin-7-one hydrochloride as a brown solid.

Step 7

A solution of 8-[2-(5-aminopyridin-2-yl)ethyl]-6-(2,6-dichloro-3,5-dimethoxyphenyl)-2-(methylamino)-7H,8H-pyrido[2,3-d]pyrimidin-7-one hydrochloride (200 mg, 0.37 mmol), prop-2-enoic acid (27 mg, 0.37 mmol) and HATU (280 mg, 0.74 mmol) in DMF (5 mL) and TEA (0.25 mL) was stirred overnight at room temperature. The resulting mixture was concentrated and the crude product (200 mg) was purified by Prep-HPLC to afford 23 mg (11%) of N-(6-[2-[6-(2,6-dichloro-3,5-dimethoxyphenyl)-2-(methylamino)-7-oxo-7H,8H-pyrido[2,3-d]pyrimidin-8-yl]ethyl]pyridin-3-yl)prop-2-enamide as a white solid. LCMS (ESI, pos. ion) m/z: 555.2 (M+1).

Example 39

Synthesis of N-(6-(2-(6-(2-chloro-3,5-dimethoxyphenyl)-2-((2-morpholinoethyl)amino)-7-oxopyrido[2,3-d]pyrimidin-8(7H)-yl)ethyl)pyridin-3-yl)acrylamide

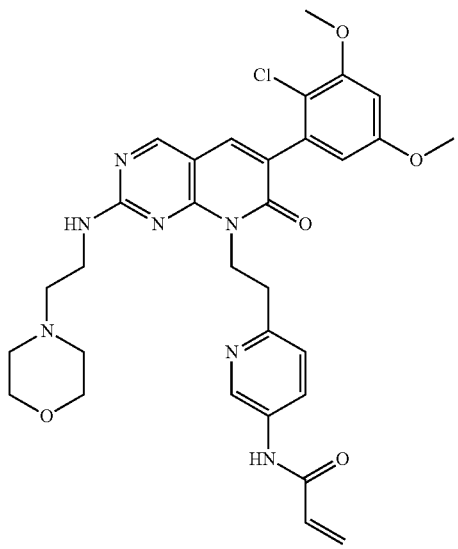 [SMILES: C=CC(=O)Nc1ccc(CCn2c(=O)c(-c3cc(OC)cc(OC)c3Cl)cc3cnc(NCCN4CCOCC4)nc32)nc1]

The compound was prepared as described in Example 34 except 2-morpholinoethanamine was used in Step 9. LCMS (ESI, pos. ion) m/z: 620.2 (M+1).

Example 40

Synthesis of N-(4-(2-(6-(2-chloro-3,5-dimethoxyphenyl)-2-((3-(diethylamino)propyl)amino)-7-oxopyrido[2,3-d]pyrimidin-8(7H)-yl)ethyl)phenyl)acrylamide

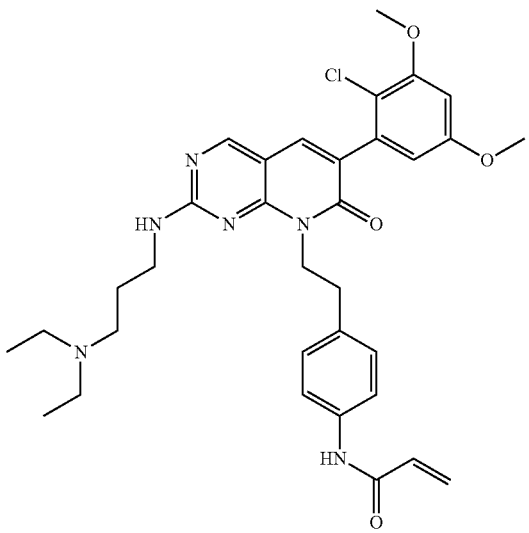 [SMILES: C=CC(=O)Nc1ccc(CCn2c(=O)c(-c3cc(OC)cc(OC)c3Cl)cc3cnc(NCCCN(CC)CC)nc32)cc1]

The compound was prepared as Example 13 except N¹,N¹-diethylpropane-1,3-diamine was used in Step 3. LCMS (ESI, pos. ion) m/z: 619.1 (M+1).

Example 41

Synthesis of N-(4-(2-(6-(2,6-dichloro-3,5-dimethoxyphenyl)-2-(methylamino)-7-oxopyrido[2,3-d]pyrimidin-8(7H)-yl)ethyl)thiazol-2-yl)acrylamide

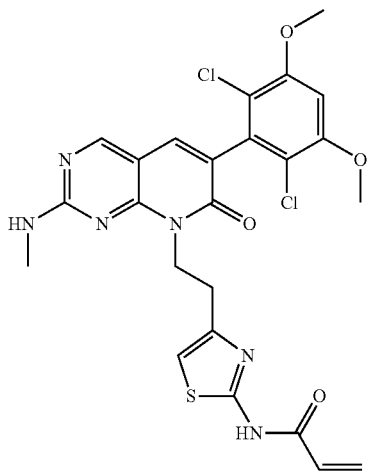 [SMILES: C=CC(=O)Nc1nc(CCn2c(=O)c(-c3c(Cl)c(OC)cc(OC)c3Cl)cc3cnc(NC)nc32)cs1]

Prepared as described in Example 33 except 6-(2,6-dichloro-3,5-dimethoxy-phenyl)-2-(methylamino)pyrido[2,3-d]pyrimidin-7(8H)-one was used. LCMS (ESI, pos. ion) m/z: 561.2 (M+1).

Example 42

Synthesis of N-(3-(2-(6-(2-fluoro-3,5-dimethoxyphenyl)-2-(4-diethylaminobutylamino)-7-oxopyrido[2,3-d]pyrimidin-8(7H)-yl)ethyl)phenyl)acrylamide

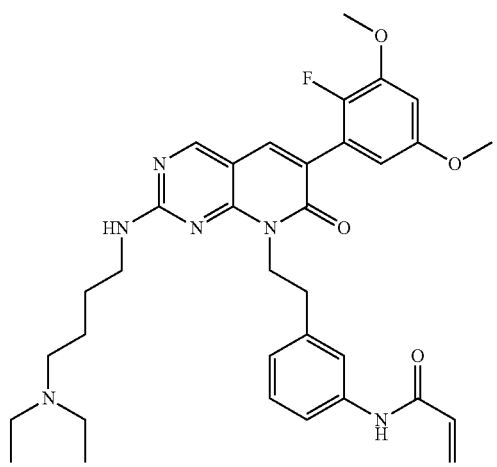 [SMILES: C=CC(=O)Nc1cccc(CCn2c(=O)c(-c3cc(OC)cc(OC)c3F)cc3cnc(NCCCCN(CC)CC)nc32)c1]

Step 1

A solution of 6-(2-fluoro-3,5-dimethoxyphenyl)-2-(methylsulfanyl)-7H,8H-pyrido[2,3-d]pyrimidin-7-one (500 mg, 1.44 mmol) (prepared as described in Example 12 except Selectfluor was used in Step 1), $K_2CO_3$ (590 mg, 4.24 mmol) and 1-(2-iodoethyl)-3-nitrobenzene (590 mg, 2.13 mmol) in acetone (50 mL) was heated to reflux overnight. The resulting solution was diluted with water and then extracted with DCM/MeOH (10:1). The organic layer was concentrated to afford 540 mg (76%) of 6-(2-fluoro-3,5-dimethoxyphenyl)-2-(methylsulfanyl)-8-[2-(3-nitrophenyl)ethyl]-7H,8H-pyrido[2,3-d]pyrimidin-7-one as a gray crude solid.

Step 2

A solution of 6-(2-fluoro-3,5-dimethoxyphenyl)-2-(methylsulfanyl)-8-[2-(3-nitrophenyl)ethyl]-7H,8H-pyrido[2,3-d]pyrimidin-7-one (540 mg, 1.09 mmol) and mCPBA (560 mg) in $CHCl_3$ (50 mL) was stirred for 1.5 h at room temperature. The reaction was quenched with sat. $NaHCO_3$ and extracted with DCM. The organic layer was washed with water and the organic layer was concentrated to afford 420 mg (73%) of 6-(2-fluoro-3,5-dimethoxyphenyl)-2-methanesulfonyl-8-[2-(3-nitrophenyl)ethyl]-7H,8H-pyrido[2,3-d]pyrimidin-7-one as a yellow solid.

Step 3

A solution of 6-(2-fluoro-3,5-dimethoxyphenyl)-2-methanesulfonyl-8-[2-(3-nitrophenyl)ethyl]-7H,8H-pyrido[2,3-d]pyrimidin-7-one (420 mg, 0.79 mmol), TEA (250 mg, 2.47 mmol) and (4-aminobutyl)diethylamine (115 mg, 0.80 mmol) in 2-methylpropan-2-ol (50 mL) was stirred overnight at 55° C. The resulting solution was diluted with water and extracted with DCM/MeOH (10:1). The organic layer was concentrated to afford 400 mg (85%) of 2-[[4-(diethylamino)butyl]amino]-6-(2-fluoro-3,5-dimethoxyphenyl)-8-[2-(3-nitrophenyl)ethyl]-7H,8H-pyrido[2,3-d]pyrimidin-7-one as a yellow solid.

Step 4

A mixture of 2-[[4-(diethylamino)butyl]amino]-6-(2-fluoro-3,5-dimethoxyphenyl)-8-[2-(3-nitrophenyl)ethyl]-7H,8H-pyrido[2,3-d]pyrimidin-7-one (400 mg, 0.67 mmol) and Raney-Ni (1.5 g) in tert-butanol (50 mL) was stirred under an $H_2$ atmosphere for 2 h at room temperature. The solids were then filtered and the filtrate was concentrated to afford 320 mg (84%) of 8-[2-(3-aminophenyl)ethyl]-2-[[4-(diethylamino)butyl]amino]-6-(2-fluoro-3,5-dimethoxyphenyl)-7H,8H-pyrido[2,3-d]pyrimidin-7-one as a yellow solid.

Step 5

A solution of 8-[2-(3-aminophenyl)ethyl]-2-[[4-(diethylamino)butyl]amino]-6-(2-fluoro-3,5-dimethoxyphenyl)-7H,8H-pyrido[2,3-d]pyrimidin-7-one (320 mg, 0.57 mmol), TEA (0.4 mL) and prop-2-enoyl chloride (0.4 mL) in DCM (15 mL) and MeOH (15 mL) was stirred overnight at room temperature. The solution was diluted with DCM and the solids were filtered and the filtrate was concentrated. The crude product was purified by Prep-HPLC to afford 49.9 mg (14%) of the title compound as an off-white solid. LCMS (ESI, pos. ion) m/z: 617.5 (M+1).

Example 43

Synthesis of N-(4-(2-(6-(2-fluoro-3,5-dimethoxyphenyl)-2-((2-morpholinoethyl)amino)-7-oxopyrido[2,3-d]pyrimidin-8(7H)-yl)ethyl)phenyl)acrylamide

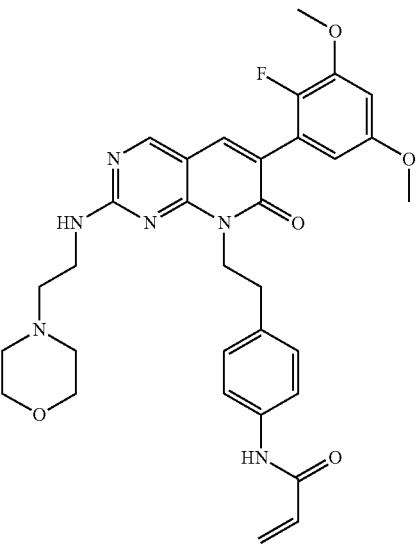 [SMILES: C=CC(=O)Nc1ccc(CCn2c(=O)c(-c3cc(OC)cc(OC)c3F)cc3cnc(NCCN4CCOCC4)nc32)cc1]

The compound was prepared as described in Example 42 except 1-(2-iodoethyl)-4-nitrobenzene was used in Step 1 and 2-morpholinoethanamine was used in Step 3. LCMS (ESI, pos. ion) m/z: 603.4 (M+1).

Example 44

Synthesis of N-(4-(2-(6-(2,6-dichloro-3,5-dimethoxyphenyl)-2-((2-morpholinoethyl)amino)-7-oxopyrido[2,3-d]pyrimidin-8(7H)-yl)ethyl)phenyl)acrylamide

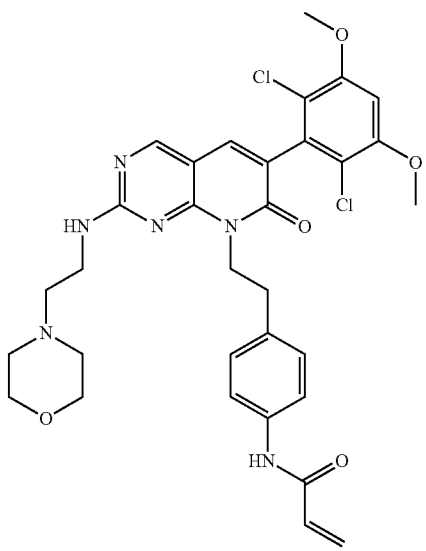 [SMILES: C=CC(=O)Nc1ccc(CCn2c(=O)c(-c3c(Cl)c(OC)cc(OC)c3Cl)cc3cnc(NCCN4CCOCC4)nc32)cc1]

The compound was prepared as described in Example 4 except 2-morpholinoethanamine was used in Step 8. LCMS (ESI, pos. ion) m/z: 653.4 (M+1).

Example 45

Synthesis of N-(4-(2-(6-(2-chloro-3,5-dimethoxyphenyl)-2-(methylamino)-7-oxopyrido[2,3-d]pyrimidin-8(7H)-yl)ethyl)phenyl)-2-methylprop-1-ene-1-sulfonamide

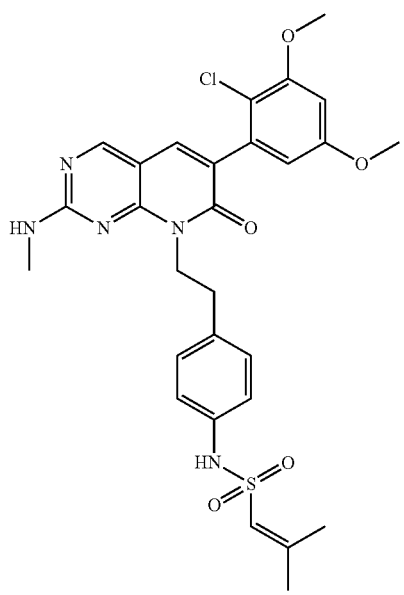 [SMILES: CNc1ncc2cc(-c3cc(OC)cc(OC)c3Cl)c(=O)n(CCc3ccc(NS(=O)(=O)C=C(C)C)cc3)c2n1]

Step 1

To a solution of 1-bromo-2-methylprop-1-ene (1.35 g, 10 mmol) in THF (30 mL) at −78° C. was added t-BuLi (15 mL, 20 mmol, 1.3 M). The solution was stirred for 30 min, then $SO_2Cl_2$ (1.76 g, 13 mmol) was added dropwise. The solution was warmed to ambient temperature and stirred overnight. The solution was concentrated to afford 2-methylprop-1-ene-1-sulfonyl chloride as a light green oil which was used directly in the next step.

Step 2

To a solution of 8-(4-aminophenethyl)-6-(2-chloro-3,5-dimethoxyphenyl)-2-(methyl-amino)pyrido[2,3-d]pyrimidin-7(8H)-one (380 mg, 0.81 mmol) in pyridine/DMF (2 mL/5 mL) was added DMAP (100 mg, 0.81 mmol) and 2-methylprop-1-ene-1-sulfonyl chloride (500 mg, 10 mmol). The reaction mixture was stirred at 60° C. for 6 h before cooling to ambient temperature. The reaction mixture was exacted with ethyl acetate, washed with sat. $NH_4Cl$ and brine. The organic layer was dried over anhydrous $Na_2SO_4$, filtered, and concentrated to afford the title compound as a light yellow solid (38 mg, 8%) after purification by prep-HPLC. LCMS (ESI, pos. ion) m/z: 584.0 (M+1).

Example 46

Synthesis of N-(5-(2-(6-(2-chloro-3,5-dimethoxyphenyl)-2-(methylamino)-7-oxopyrido[2,3-d]pyrimidin-8(7H)-yl)ethyl)pyrazin-2-yl)acrylamide

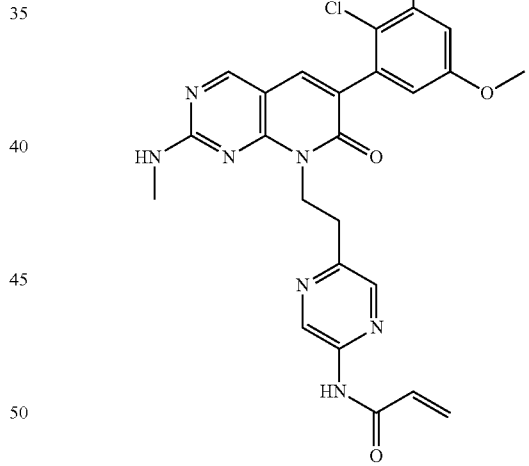

Step 1

To a solution of pyrazin-2-amine (30 g, 0.32 mmol) in DCM (900 mL) at 0° C. was added NBS (56 g, 0.32 mmol). The reaction mixture was stirred at ambient temperature for 3 h and then washed with sat. $NaHCO_3$ and brine. The organic layer was dried over anhydrous $Na_2SO_4$, filtered and concentrated to afford 5-bromopyrazin-2-amine (38 g, 70%) as a white solid which was used directly in the next step.

Step 2

To a solution of 5-bromopyrazin-2-amine (20 g, 0.12 mol) in DCM (200 mL) at 0° C. was added DIPEA (46 g, 0.36 mol), DMAP (15 g, 0.12 mol) and $(Boc)_2O$ (63 g, 0.29 mol). The reaction mixture was stirred at ambient temperature overnight and then concentrated. The residue was purified by chromatography (silica gel, pet.ether/ethyl acetate=5:1) to afford tert-butyl (5-bromopyrazin-2-yl)carbamate as a white solid (24 g, 55%).

Step 3

To a solution of tert-butyl (5-bromopyrazin-2-yl)carbamate (17 g, 45.6 mmol) in dioxane (250 mL) was added dimethylmalonate (18 g, 137 mmol), picolinic acid (1.1 g, 9.1 mmol), CuI (3.5 g, 18.2 mmol) and cesium carbonate (44.6 g, 137 mmol). The reaction mixture was stirred at 95° C. for 72 h before cooling to ambient temperature. The reaction mixture was diluted with ethyl acetate and washed with brine. The organic layer was dried over anhydrous $Na_2SO_4$, filtered and concentrated to afford methyl 2-(5-((tert-butoxycarbonyl)amino)pyrazin-2-yl)acetate product as a yellow solid (5.1 g, 30%).

Step 4

To a solution of methyl 2-(5-((tert-butoxycarbonyl)amino)pyrazin-2-yl)acetate (2.5 g, 6.8 mmol) in THF (35 mL) was added $LiAlH_4$ (770 mg, 20.4 mmol). The reaction mixture was refluxed overnight before cooling to the ambient temperature and adding MeOH (5 mL). The residue was concentrated and purified by flash chromatography (silica gel, pet. ether/ethyl acetate=1:1 to ethyl acetate) to afford tert-butyl (5-(2-hydroxyethyl)pyrazin-2-yl)carbamate as a light yellow oil (250 mg, 16%).

Step 5

To a solution of tert-butyl (5-(2-hydroxyethyl)pyrazin-2-yl)carbamate (0.25 g, 1.0 mmol) in DCM (10 mL) at 0° C. was added DIPEA (0.39 g, 3.0 mmol), and MsCl (0.17 g, 1.5 mmol). The reaction mixture was stirred at ambient temperature for 1 h and then water was added. The reaction mixture was exacted with DCM, washed with aq. $NaHCO_3$ and brine. The organic layer was dried over anhydrous $Na_2SO_4$, filtered and concentrated to afford 2-(5-((tert-butoxycarbonyl)amino)pyrazin-2-yl)ethyl methanesulfonate as a yellow solid (0.31 g, crude) which was converted to the title compound as described in Example 10 except 6-(2-chloro-3,5-dimethoxyphenyl)-2-(methylthio)pyrido[2,3-d]pyrimidin-7(8H)-one was used. LCMS (ESI, pos. ion) m/z: 522.1 (M+1).

Example 47

Synthesis of N-(5-(2-(6-(2-chloro-3,5-dimethoxyphenyl)-2-((2-morpholinoethyl)amino)-7-oxopyrido[2,3-d]pyrimidin-8(7H)-yl)ethyl)pyrazin-2-yl)acrylamide

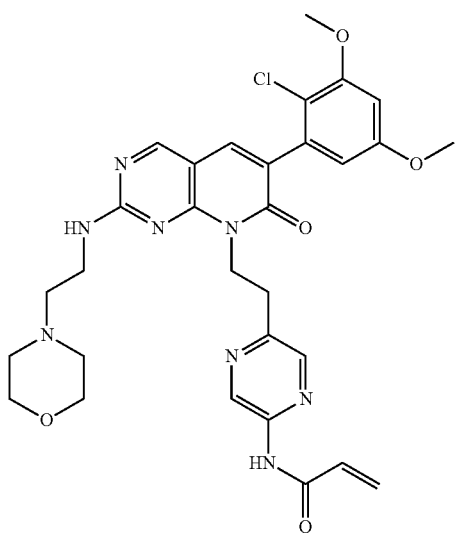 [SMILES: C=CC(=O)Nc1cnc(CCn2c(=O)c(-c3cc(OC)cc(OC)c3Cl)cc3cnc(NCCN4CCOCC4)nc32)cn1]

The compound was prepared as described in Example 46, except 2-morpholinoethanamine was used. LCMS (ESI, pos. ion) m/z: 621.1 (M+1).

Example 48

Synthesis of N-(1-(2-(6-(2-chloro-3,5-dimethoxyphenyl)-2-(methylamino)-7-oxopyrido[2,3-d]-pyrimidin-8(7H)-yl)ethyl)-1H-imidazol-4-yl)acrylamide

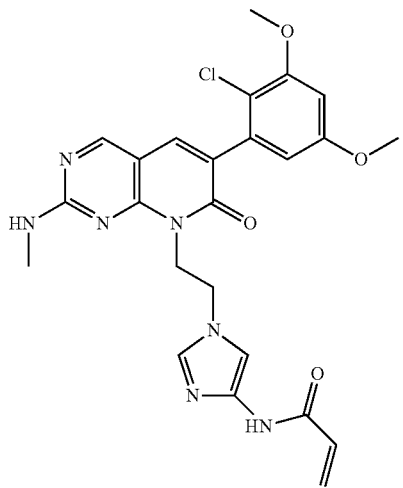 [SMILES: C=CC(=O)Nc1cn(CCn2c(=O)c(-c3cc(OC)cc(OC)c3Cl)cc3cnc(NC)nc32)cn1]

Step 1

To a solution of ethyl 2-(4-nitro-1H-imidazol-1-yl)acetate (2 g, 10 mmol) in MeOH (20 mL) was added Pd/C (10%) (0.2 g). The reaction mixture was stirred at ambient temperature under an $H_2$ atmosphere for 24 h and then filtered through celite. The filtrated was concentrated to afford ethyl 2-(4-amino-1H-imidazol-1-yl)acetate (1.2 g, 71%) as a yellow oil.

Step 2

To a solution of ethyl 2-(4-amino-1H-imidazol-1-yl)acetate (1.2 g, 7.1 mmol) in MeOH (12 mL) was added DIPEA (1.83 g, 14.2 mmol) and $Boc_2O$ (1.86 g, 8.52 mmol). The reaction mixture was stirred at ambient temperature for 3 h and then poured into water, exacted with ethyl acetate and washed with brine. The organic layer was dried over anhydrous $Na_2SO_4$, filtered and concentrated to afford ethyl 2-(4-((tert-butoxycarbonyl)amino)-1H-imidazol-1-yl)acetate (1 g, 52%) as a white solid after purification by flash chromatography (silica gel, petroleum ether/ethyl acetate=2:1).

Step 3

To a solution of ethyl 2-(4-((tert-butoxycarbonyl)amino)-1H-imidazol-1-yl)acetate (1 g, 3.72 mmol) in THF (15 mL) was added $LiBH_4$ (0.16 g, 7.43 mmol). The reaction mixture was stirred at ambient temperature for 16 h and then MeOH (5 mL) was added. The reaction mixture was stirred at refluxed temperature for 1 h before cooling to ambient temperature and then poured into water, exacted with ethyl acetate and washed with brine. The organic layer was dried over anhydrous $Na_2SO_4$, filtered and concentrated to afford tert-butyl (1-(2-hydroxyethyl)-1H-imidazol-4-yl)carbamate as a white solid (380 mg, 45%) which was converted to the title compound as described in Example 46. LCMS (ESI, pos. ion) m/z: 510.1 (M+1).

Example 49

Synthesis of N-(4-(2-(6-(2-chloro-3,5-dimethoxy-phenyl)-2-((2-(4-methylpiperazin-1-yl)ethyl)-amino)-7-oxopyrido[2,3-d]pyrimidin-8(7H)-yl)ethyl)phenyl)acrylamide

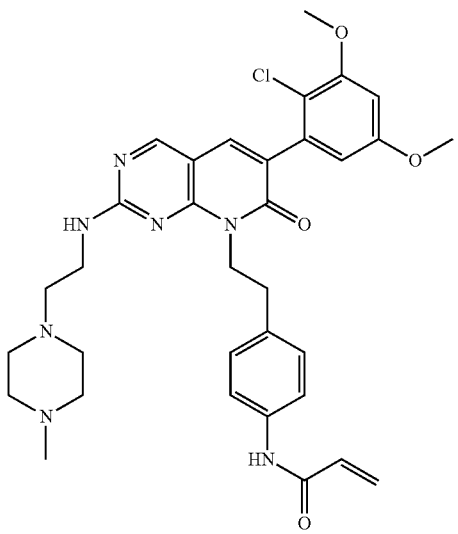 [SMILES: C=CC(=O)Nc1ccc(CCn2c(=O)c(-c3cc(OC)cc(OC)c3Cl)cc3cnc(NCCN4CCN(C)CC4)nc32)cc1]

The compound was prepared as described in Example 13 except 2-(4-methylpiperazin-1-yl)ethanamine was used in Step 3. LCMS (ESI, pos. ion) m/z: 632.3 (M+1).

Example 50

Synthesis of N-(4-(2-(2-((2-(1H-imidazol-1-yl)ethyl)amino)-6-(2-chloro-3,5-dimethoxyphenyl)-7-oxopyrido[2,3-d]pyrimidin-8(7H)-yl)ethyl)phenyl)acrylamide

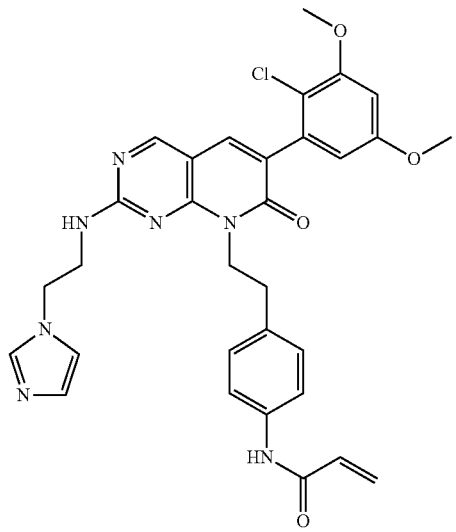 [SMILES: C=CC(=O)Nc1ccc(CCn2c(=O)c(-c3cc(OC)cc(OC)c3Cl)cc3cnc(NCCn4ccnc4)nc32)cc1]

The compound was prepared as described in Example 13 except 2-(1H-imidazol-1-yl)ethanamine was used in Step 3. LCMS (ESI, pos. ion) m/z: 600.0 (M+1).

Example 51

Synthesis of N-(6-(2-(6-(2,6-dichloro-3,5-dimethoxyphenyl)-2-(2-morpholinoethylamino)-7-oxopyrido[2,3-d]pyrimidin-8(7H)-yl)ethyl)pyridin-3-yl)acrylamide

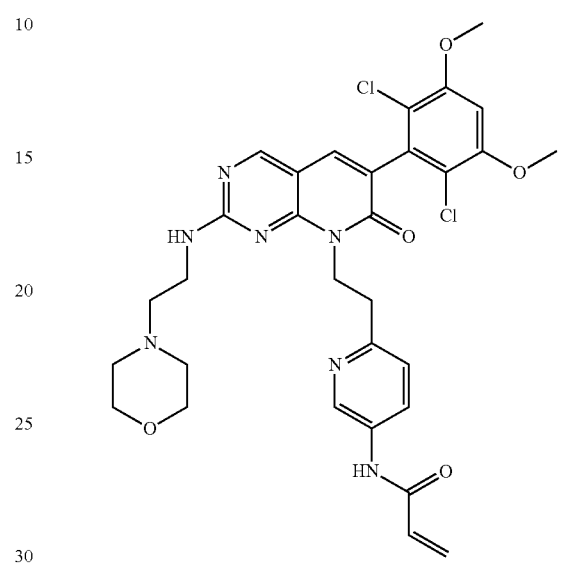

The compound was prepared as described in Example 38 except 2-morpholinoethanamine was used in Step 4. LCMS (ESI, pos. ion) m/z: 656.4 (M+1).

Example 52

Synthesis of N-(3-(2-(6-(2-fluoro-3,5-dimethoxyphenyl)-2-(2-morpholin-4-ylethyllamino)-7-oxopyrido[2,3-d]pyrimidin-8(7H)-yl)ethyl)phenyl)acrylamide

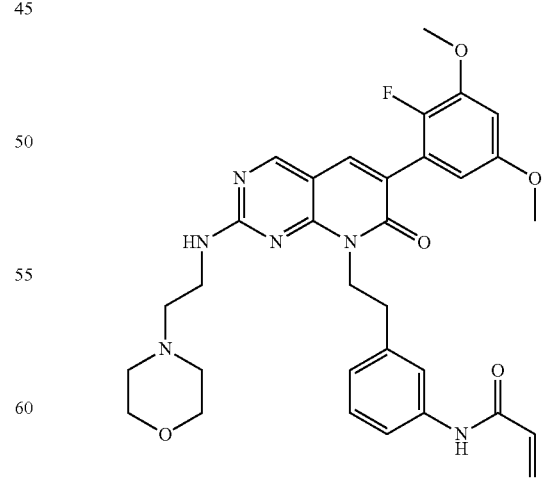

The compound was prepared as described in Example 42 except 2-morpholinoethanamine was used in Step 3. LCMS (ESI, pos. ion) m/z: 603.1 (M+1).

Example 53

Synthesis of N-(2-fluoro-4-(2-(6-(2-fluoro-3,5-dimethoxyphenyl)-2-((2-morpholinoethyl)amino)-7-oxopyrido[2,3-d]pyrimidin-8(7H)-yl)ethyl)phenyl)acrylamide

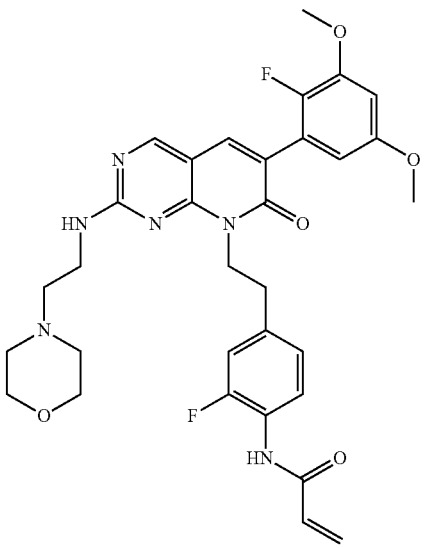 [SMILES: C=CC(=O)Nc1ccc(CCn2c(=O)c(-c3cc(OC)cc(OC)c3F)cc3cnc(NCCN4CCOCC4)nc32)cc1F]

Step 1

To a solution of nitric acid (1.6 mL) was added a solution of 2-(3-fluorophenyl)acetic acid (6 g, 38.93 mmol) in sulfuric acid (12 mL) dropwise with stirring at 0° C. in 30 min. The resulting solution was stirred for 3 h at room temperature and then water/ice was added. The resulting solution was extracted with of ethyl acetate and the organic layers combined and dried over anhydrous $Na_2SO_4$ and concentrated. The residue was purified by chromatography (ethyl acetate/petroleum ether (1:3)) to afford 5 g (65%) of 2-(3-fluoro-4-nitrophenyl)acetic acid as a yellow solid.

Step 2

To a solution of 2-(3-fluoro-4-nitrophenyl)acetic acid (5 g, 25.11 mmol) in THF (150 mL) was added (methylsulfanyl)methane borane (5 mL) dropwise with stirring at 0° C. The resulting solution was stirred for 2 h at 60° C. and then concentrated. The reaction was then quenched by the addition of $NH_4Cl(aq)$. The resulting solution was extracted with of ethyl acetate and the organic layers combined and dried over anhydrous $Na_2SO_4$ and concentrated to afford 5 g (crude) of 2-(3-fluoro-4-nitrophenyl)ethan-1-ol as yellow oil.

Step 3

To a solution of 2-(3-fluoro-4-nitrophenyl)ethan-1-ol (5 g, 27.00 mmol) in EtOH (200 mL) was added of Raney Ni (3 g). The resulting mixture was stirred overnight under an $H_2$ atmosphere. The solids were filtered and the filtrate was concentrated to afford 4 g (95%) of 2-(4-amino-3-fluorophenyl)ethan-1-ol as brown oil.

Step 4

To a solution of 2-(4-amino-3-fluorophenyl)ethan-1-ol (4 g, 25.78 mmol) in $THF/H_2O$ (100/100 mL) was added $NaHCO_3$ (6.5 g, 77.37 mmol) and di-tert-butyl dicarbonate (6.7 g, 30.70 mmol). The resulting solution was stirred for 5 h at room temperature and then water was added. The resulting solution was extracted with of ethyl acetate and the organic layers combined, dried over anhydrous $Na_2SO_4$ and concentrated to afford 6 g (91%) of tert-butyl N-[2-fluoro-4-(2-hydroxyethyl)phenyl]carbamate as a light yellow solid.

Step 5

To a solution of tert-butyl N-[2-fluoro-4-(2-hydroxyethyl)phenyl]carbamate (2 g, 7.83 mmol) in DCM (200 mL) was added imidazole (0.8 g), triphenylphosphane (3.1 g, 11.82 mmol) and $I_2$ (3 g). The resulting solution was stirred overnight at room temperature and then water was added. The resulting solution was extracted with DCM and the organic layers combined and dried over anhydrous $Na_2SO_4$ and concentrated. The residue was purified by chromatography (ethyl acetate/pet. ether (1:50)) to afford 1.8 g (63%) of tert-butyl N-[2-fluoro-4-(2-iodoethyl)phenyl]-carbamate as a yellow solid.

The title compound was prepared as described in Example 13 except 6-(2-fluoro-3,5-dimethoxyphenyl)-2-(methylthio)pyrido[2,3-d]pyrimidin-7(8H)-one was used in Step 1 and 2-morpholinoethanamine was used in Step 3. LCMS (ESI, pos. ion) m/z: 621.4 (M+1).

Example 54

Synthesis of N-(4-(2-(6-(2-chloro-3,5-dimethoxyphenyl)-2-((2-morpholinoethyl)amino)-7-oxopyrido[2,3-d]pyrimidin-8(7H)-yl)ethyl)-2-fluorophenyl)acrylamide

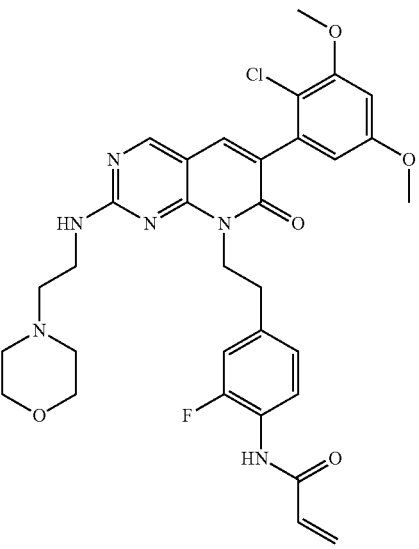 [SMILES: C=CC(=O)Nc1ccc(CCn2c(=O)c(-c3cc(OC)cc(OC)c3Cl)cc3cnc(NCCN4CCOCC4)nc32)cc1F]

The title compound was prepared as described in Example 53 except 6-(2-chloro-3,5-dimethoxyphenyl)-2-(methylthio)pyrido[2,3-d]pyrimidin-7(8H)-one was used in Step 1 and 2-morpholinoethanamine was used in Step 3. LCMS (ESI, pos. ion) m/z: 637.2 (M+1).

Example 55

Synthesis of N-(4-(2-(6-(2-chloro-3,5-dimethoxyphenyl)-2-((2-morpholinoethyl)amino)-7-oxopyrido[2,3-d]pyrimidin-8(7H)-yl)ethyl)-3-fluorophenyl)acrylamide

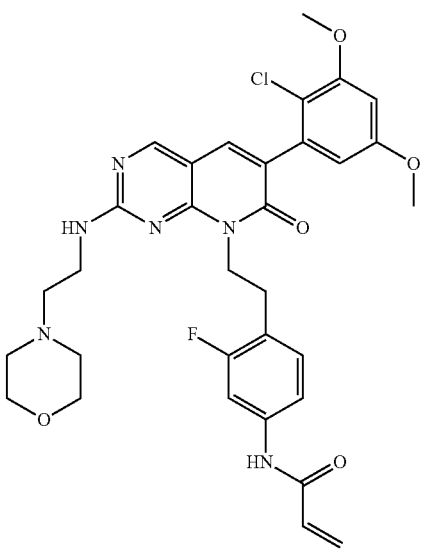 [SMILES: C=CC(=O)Nc1ccc(CCn2c(=O)c(-c3cc(OC)cc(OC)c3Cl)cc3cnc(NCCN4CCOCC4)nc32)c(F)c1]

Step 1

A mixture of 1,3-diethyl propanedioate (7.55 g, 47.14 mmol), $K_2CO_3$ (8.7 g, 62.95 mmol) and 1,2-difluoro-4-nitrobenzene (5 g, 31.43 mmol) in DMF (30 mL) heated to 50° C. for 5 h at 50° C. The resulting mixture was extracted with ethyl acetate and the organic layers were combined and washed with water and (sat.) NaCl. The organic layer was dried over anhydrous $Na_2SO_4$ and concentrated. The residue was purified by chromatography (ethyl acetate/petroleum ether (1:100)) to afford 7.5 g (80%) of 1,3-diethyl 2-(2-fluoro-4-nitrophenyl)propanedioate as a yellow liquid.

Step 2

A solution of 1,3-diethyl 2-(2-fluoro-4-nitrophenyl)propanedioate (7.5 g, 25.06 mmol) and NaCl (1.47 g, 25.13 mmol) in DMSO (30 mL) and water (0.5 mL) was stirred overnight at 120° C. The resulting solution was diluted with ethyl acetate and then washed with of water and (sat.) NaCl. The mixture was dried over anhydrous $Na_2SO_4$ and concentrated. The residue was purified by chromatography (ethyl acetate/petroleum ether (1:50)) to afford 3.07 g (54%) of ethyl 2-(2-fluoro-4-nitrophenyl)acetate as a yellow solid.

Step 3

A solution of ethyl 2-(2-fluoro-4-nitrophenyl)acetate (3.07 g, 13.51 mmol) and $NaBH_4$ (2.06 g, 54.45 mmol) in MeOH (50 mL) was stirred at 70° C. for 16 h. The reaction was then quenched with sat. $NH_4Cl$ and extracted with of ethyl acetate. The organic layers were combined, washed with water and sat. NaCl and then dried over anhydrous $Na_2SO_4$ and concentrated. The residue was purified by chromatography (ethyl acetate/petroleum ether (1:20)) to afford 1.89 g (76%) of 2-(2-fluoro-4-nitrophenyl)ethan-1-ol as a yellow liquid.

Step 4

A solution of 2-(2-fluoro-4-nitrophenyl)ethan-1-ol (1.89 g, 10.21 mmol), $PPh_3$ (16.06 g, 61.23 mmol), imidazole (4.17 g, 61.32 mmol) and $I_2$ (15.57 g, 61.30 mmol) in ACN (15 mL) and ether (45 mL) was stirred for 4 h at room temperature. The reaction was then quenched with sat. $Na_2S_2O_3$ and extracted with ethyl acetate. The organic layers were combined, washed with 10% HCl, sat. $NaHCO_3$ and sat. NaCl. The organic layer was dried over anhydrous $Na_2SO_4$ and concentrated. The residue was purified by chromatography (pet. ether) to afford 2.1 g (70%) of 2-fluoro-1-(2-iodoethyl)-4-nitrobenzene as a yellow solid.

The compound was prepared as described in Example 42 except 6-(2-chloro-3,5-dimethoxyphenyl)-2-(methylthio)pyrido[2,3-d]pyrimidin-7(8H)-one was used in Step 1 and 2-morpholinoethanamine is used in Step 3. LCMS (ESI, pos. ion) m/z: 637.3 (M+1).

Example 56

Synthesis of N-(4-(2-(6-(2-chloro-3,5-dimethoxyphenyl)-2-((2-morpholinoethyl)amino)-7-oxopyrido[2,3-d]pyrimidin-8(7H)-yl)ethyl)-2-chlorophenyl)acrylamide

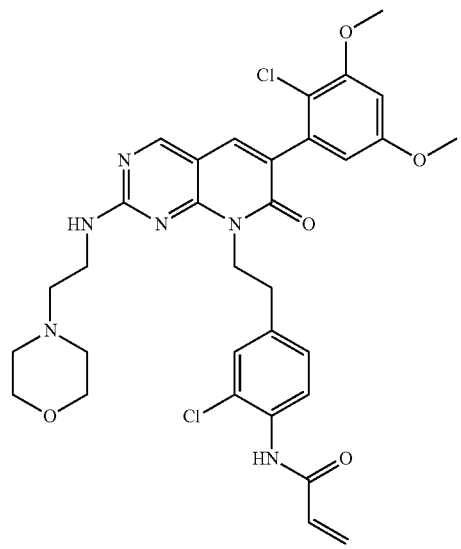 [SMILES: C=CC(=O)Nc1ccc(CCn2c(=O)c(-c3cc(OC)cc(OC)c3Cl)cc3cnc(NCCN4CCOCC4)nc32)cc1Cl]

The title compound was prepared as described in Example 53 except 2-(3-chlorophenyl)acetic acid was used in Step 1. LCMS (ESI, pos. ion) m/z: 653.5 (M+1).

Example 57

Synthesis of N-(4-(2-(6-(2-chloro-3,5-dimethoxy-phenyl)-2-((4-isopropylpiperazin-1-yl-ethyl)amino)-7-oxopyrido[2,3-d]pyrimidin-8(7H)-yl)ethyl)phenyl)acylamide

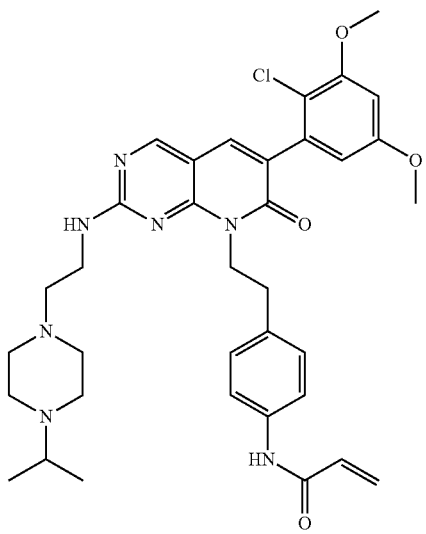 [SMILES: C=CC(=O)Nc1ccc(CCn2c(=O)c(-c3cc(OC)cc(OC)c3Cl)cc3cnc(NCCN4CCN(C(C)C)CC4)nc32)cc1]

The title compound was prepared as described in Example 13 except 2-(4-isopropylpiperazin-1-yl)ethanamine was used in Step 3. LCMS (ESI, pos. ion) m/z: 660.3 (M+1).

Example 58

Synthesis of N-(4-(2-(6-(2-chloro-3,5-dimethoxy-phenyl)-2-((2-((2R,6S)-2,6-dimethyl-morpholino)ethyl)-amino)-7-oxopyrido[2,3-d]pyrimidin-8(7H)-yl)ethyl)phenyl)acrylamide

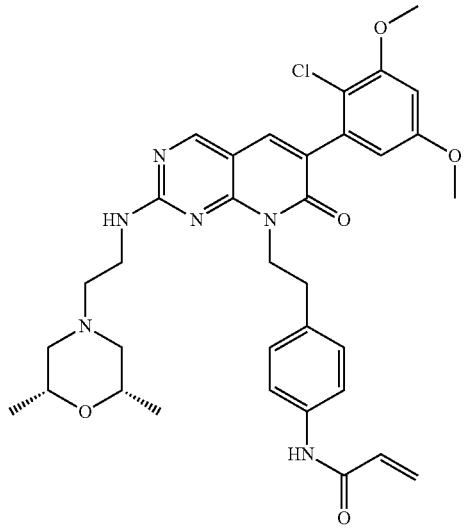

The title compound was prepared as described in Example 13, except 2-(2,6-dimethylmorpholin-4-yl)ethanamine was used in Step 3. LCMS (ESI, pos. ion) m/z: 647.2 (M+1).

Example 59

Synthesis of N-(6-(2-(6-(2-chloro-3,5-dimethoxy-phenyl)-7-oxo-2-(prop-2-yn-1-ylamino)pyrido-[2,3-d]pyrimidin-8(7H)-yl)ethyl)pyridin-3-yl)acrylamide

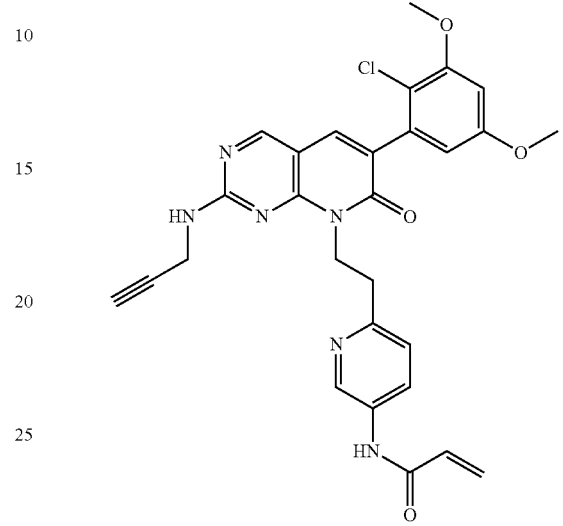

The title compound was prepared as described in Example 34 except prop-2-yn-1-amine was used in Step 9. LCMS (ESI, pos. ion) m/z: 545.1 (M+1).

Example 60

Synthesis of N-(4-(2-(6-(2-chloro-3,5-dimethoxy-phenyl)-2-((2-(4-ethylpiperazin-1-yl)ethyl)-amino)-7-oxopyrido[2,3-d]pyrimidin-8(7H)-yl)ethyl)phenyl)acrylamide

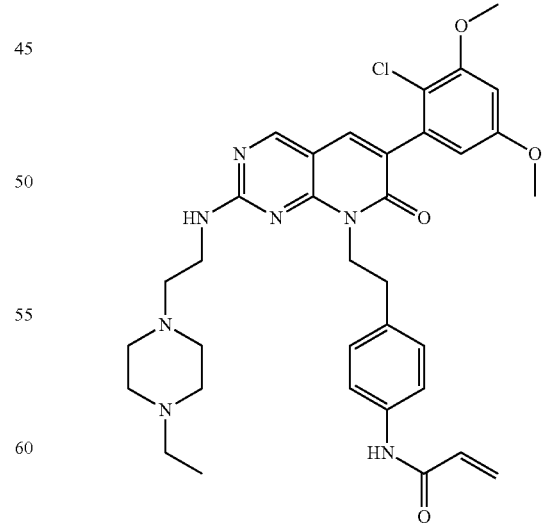

The compound was prepared as described in Example 13 except 2-(4-ethyl-piperazin-1-yl)ethanamine was used in Step 3. LCMS (ESI, pos. ion) m/z: 646.2 (M+1).

Example 61

Synthesis of N-(4-(2-(6-(2-chloro-3,5-dimethoxyphenyl)-2-((1-hydroxy-2-methylpropan-2-yl)amino)-7-oxopyrido[2,3-d]pyrimidin-8(7H)-yl)ethyl)phenyl)acrylamide

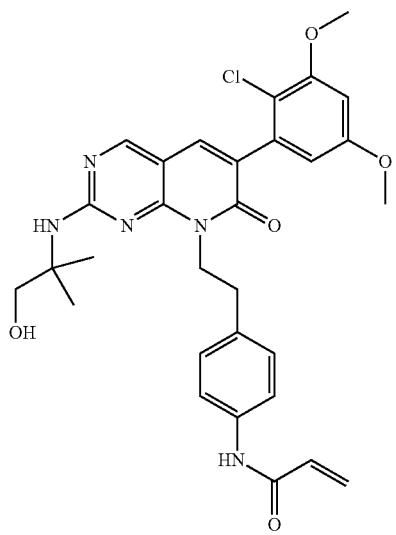 [SMILES: C=CC(=O)Nc1ccc(CCn2c(=O)c(-c3cc(OC)cc(OC)c3Cl)cc3cnc(NC(C)(C)CO)nc32)cc1]

The title compound was prepared as described in Example 13 except 2-amino-2-methylpropan-1-ol was used in Step 3. LCMS (ESI, pos. ion) m/z: 578.2 (M+1).

Example 62

Synthesis of N-(4-(2-(6-(2,6-dichloro-3,5-dimethoxyphenyl)-2-((1-methylpiperidin-4-yl)amino)-7-oxopyrido[2,3-d]pyrimidin-8(7H)-yl)ethyl)phenyl)acrylamide

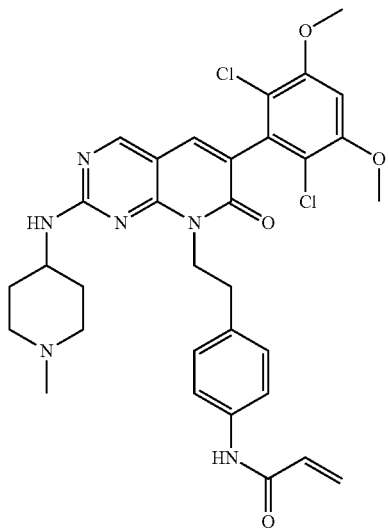

The title compound was prepared as described in Example 4 except 1-methylpiperidin-4-amine was used in Step 8. LCMS (ESI, pos. ion) m/z: 637.5 (M+1).

Example 63

Synthesis of N-(4-(2-(6-(2,6-dichloro-3,5-dimethoxyphenyl)-2-((2,3-dihydroxypropyl)amino)-7-oxopyrido[2,3-d]pyrimidin-8(7H)-yl)ethyl)phenyl)acrylamide

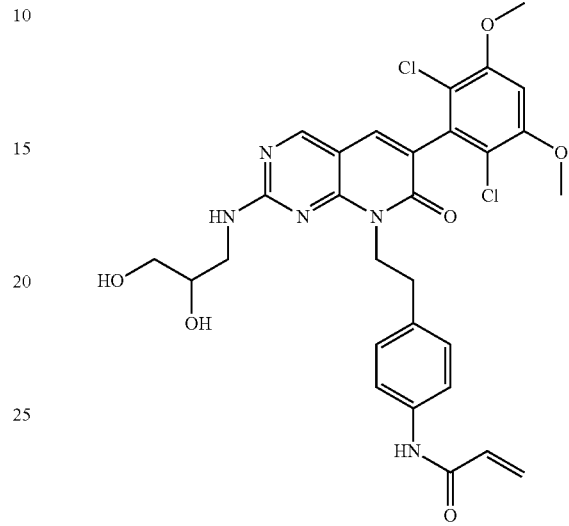

The title compound was prepared as described in Example 4 except 3-aminopropane-1,2-diol was used in Step 8. LCMS (ESI, pos. ion) m/z: 614.4 (M+1).

Example 64

Synthesis of N-(4-(2-(6-(2,6-dichloro-3,5-dimethoxyphenyl)-2-((2-hydroxy-2-methylpropyl)amino)-7-oxopyrido[2,3-d]pyrimidin-8(7H)-yl)ethyl)phenyl)acrylamide

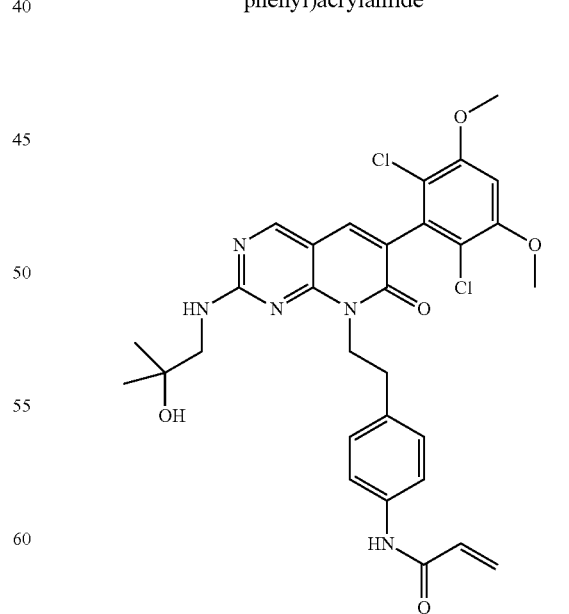

The compound was prepared as described in Example 4 except 1-amino-2-methylpropan-2-ol was used in Step 8. LCMS (ESI, pos. ion) m/z: 612.4 (M+1).

Example 65

Synthesis of N-(4-(2-(6-(2,6-dichloro-3,5-dimethoxyphenyl)-2-((2-hydroxyethyl)amino)-7-oxopyrido[2,3-d]pyrimidin-8(7H)-yl)ethyl)phenyl)acrylamide

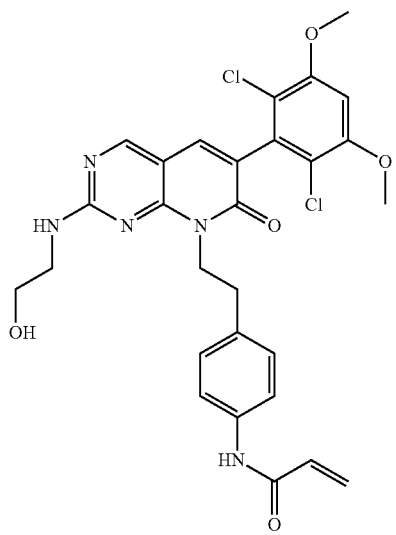 [SMILES: C=CC(=O)Nc1ccc(CCn2c(=O)c(-c3c(Cl)c(OC)cc(OC)c3Cl)cc3cnc(NCCO)nc32)cc1]

The title compound was prepared as described in Example 4 except 2-aminoethanol was used in Step 8. LCMS (ESI, pos. ion) m/z: 584.3 (M+1).

Example 66

Synthesis of N-(4-(2-(2-((2-(4-acetylpiperazin-1-yl)ethyl)amino)-6-(2-chloro-3,5-dimethoxy-phenyl)-7-oxopyrido[2,3-d]pyrimidin-8(7H)-yl)ethyl)phenyl)acrylamide

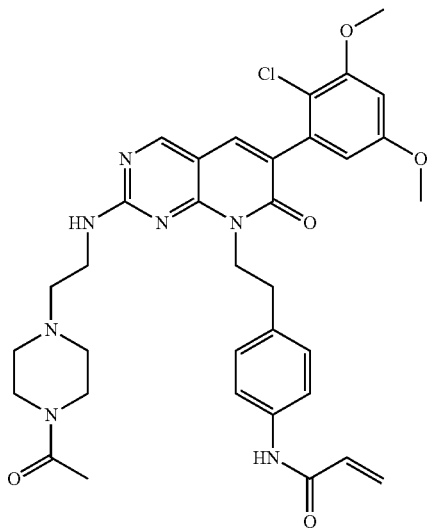 [SMILES: C=CC(=O)Nc1ccc(CCn2c(=O)c(-c3cc(OC)cc(OC)c3Cl)cc3cnc(NCCN4CCN(C(C)=O)CC4)nc32)cc1]

The title compound was prepared as described in Example 13 except 1-(4-(2-aminoethyl)piperazin-1-yl)ethanone was used in Step 3. LCMS (ESI, pos. ion) m/z: 660.2 (M+1).

Example 67

Synthesis of N-(4-(2-(6-(2-chloro-3,5-dimethoxyphenyl)-2-((2-methyl-1-morpholinopropan-2-yl)amino)-7-oxopyrido[2,3-d]pyrimidin-8(7H)-yl)ethyl)phenyl)acrylamide

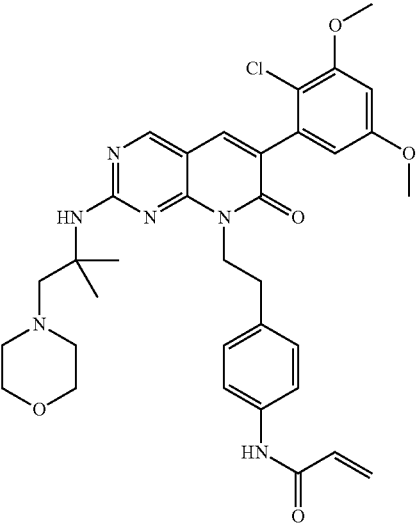 [SMILES: C=CC(=O)Nc1ccc(CCn2c(=O)c(-c3cc(OC)cc(OC)c3Cl)cc3cnc(NC(C)(C)CN4CCOCC4)nc32)cc1]

The title compound was prepared as described in Example 13 except 2-methyl-1-morpholinopropan-2-amine was used in Step 3. LCMS (ESI, pos. ion) m/z: 647.2 (M+1).

Example 68

Synthesis of N-(4-(2-(6-(2-chloro-3,5-dimethoxyphenyl)-2-((2-(4-(2-hydroxy-2-methylpropyl)-piperazin-1-yl)ethyl)amino)-7-oxopyrido[2,3-d]pyrimidin-8(7H)-yl)ethyl)phenyl)acrylamide

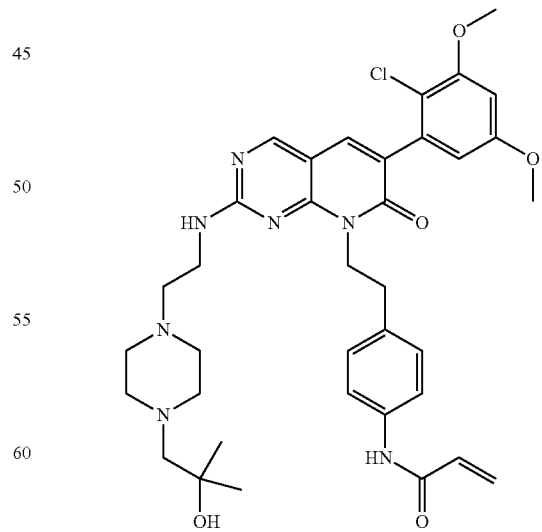

Step 1

To a solution of tert-butyl (2-(piperazin-1-yl)ethyl)carbamate (1 g, 4.4 mmol) in DMF (15 mL) was added 1-chloro-2-methylpropan-2-ol (1.89 g, 17.4 mmol), $K_2CO_3$ (1.8 g, 13.1 mmol) and NaI (1.31 g, 8.7 mmol). The reaction was stirred at 70-80° C. for 24 h, cooled to room temperature, and poured into water. The reaction mixture was extracted with ethyl acetate, and the organic layers were combined, washed with brine, dried ($Na_2SO_4$), filtered and concentrated. The crude residue was chromatographed (silica gel, DCM:MeOH=40:1) to afford tert-butyl (2-(4-(2-hydroxy-2-methylpropyl)piperazin-1-yl)ethyl)carbamate as an oil (0.95 g, 73%).

Step 2

To a solution of tert-butyl (2-(4-(2-hydroxy-2-methylpropyl)piperazin-1-yl)ethyl)-carbamate (0.95 g, 0.3.16 mmol) in dioxane (10 mL) was added conc. HCl (5 mL). The reaction mixture was stirred at ambient temperature for 2 h before concentrating. The residue was adjusted to pH=7 with aq. $NaHCO_3$ and evaporated under vacuum. The resultant mixture was diluted with ethanol, and filtered to remove formed NaCl and the filtrate was dried over $Na_2SO_4$, filtered and concentrated to afford 1-(4-(2-aminoethyl)piperazin-1-yl)-2-methylpropan-2-ol as an oil (0.5 g, crude).

The title compound was then prepared as described in Example 13 except 1-(4-(2-aminoethyl)piperazin-1-yl)-2-methylpropan-2-ol was used in Step 3. LCMS (ESI, pos. ion) m/z: 690.2 (M+1).

Example 69

Synthesis of N-(4-(2-(6-(2-chloro-3,5-dimethoxyphenyl)-2-((2-hydroxyethyl)amino)-7-oxopyrido[2,3-d]pyrimidin-8(7H)-yl)ethyl)phenyl)acrylamide

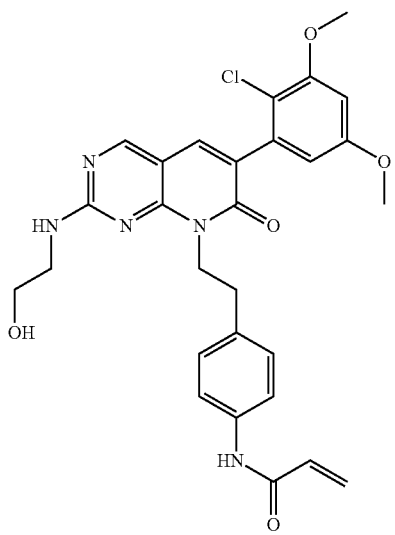 [SMILES: C=CC(=O)Nc1ccc(CCn2c(=O)c(-c3cc(OC)cc(OC)c3Cl)cc3cnc(NCCO)nc32)cc1]

The title compound was prepared as described in Example 13 except 2-aminoethanol was used in Step 3. LCMS (ESI, pos. ion) m/z: 550.1 (M+1).

Example 70

Synthesis of N-(4-(2-(6-(2-chloro-3,5-dimethoxyphenyl)-2-(((1-methylpiperidin-4-yl)amino)-7-oxopyrido[2,3-d]pyrimidin-8(7H)-yl)ethyl)phenyl)acrylamide

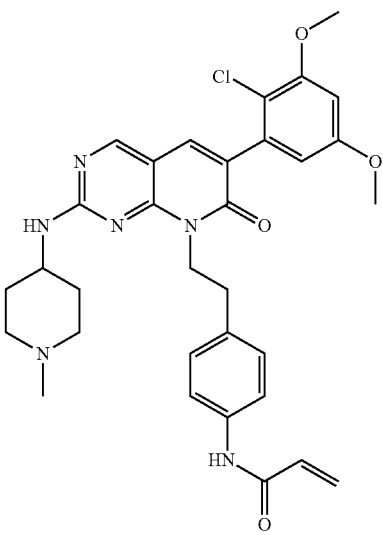 [SMILES: C=CC(=O)Nc1ccc(CCn2c(=O)c(-c3cc(OC)cc(OC)c3Cl)cc3cnc(NC4CCN(C)CC4)nc32)cc1]

The title compound was prepared as described in Example 13 except 1-methylpiperidin-4-amine was used in Step 3. LCMS (ESI, pos. ion) m/z: 603.2 (M+1).

Example 71

Synthesis of N-(4-(2-(6-(2-chloro-3,5-dimethoxyphenyl)-2-(((1-methylpiperidin-4-yl)methyl)-amino)-7-oxopyrido[2,3-d]pyrimidin-8(7H)-yl)ethyl)phenyl)acrylamide

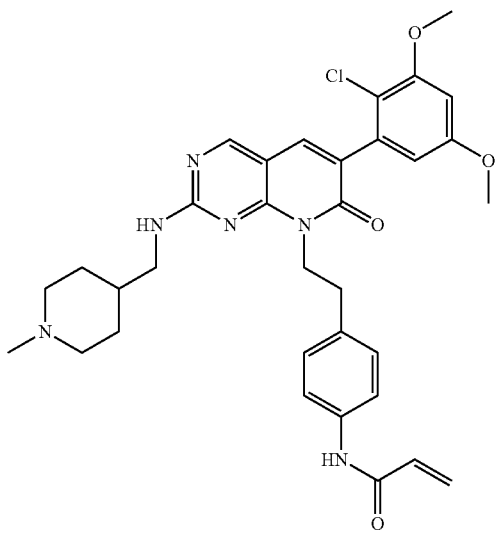

The title compound was prepared as described in Example 13 except (1-methylpiperidin-4-yl)methanamine was used in Step 3. LCMS (ESI, pos. ion) m/z: 617.2 (M+1).

Example 72

Synthesis of N-(4-(2-(6-(2-chloro-3,5-dimethoxy-phenyl)-2-((1,3-dihydroxypropan-2-yl)amino)-7-oxopyrido[2,3-d]pyrimidin-8(7H)-yl)ethyl)phenyl)acrylamide

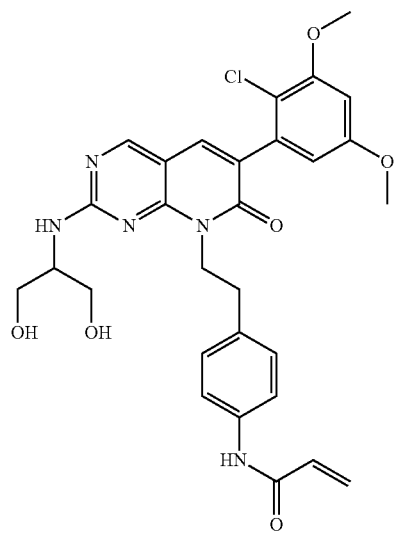 [SMILES: C=CC(=O)Nc1ccc(CCn2c(=O)c(-c3cc(OC)cc(OC)c3Cl)cc3cnc(NC(CO)CO)nc32)cc1]

The title compound was prepared as described in Example 13 except 2-aminopropane-1,3-diol was used in Step 3. LCMS (ESI, pos. ion) m/z: 580.1 (M+1).

Example 73

Synthesis of N-(4-(2-(6-(2-chloro-3,5-dimethoxy-phenyl)-2-((2,3-dihydroxypropyl)amino)-7-oxopyrido[2,3-d]pyrimidin-8(7H)-yl)ethyl)phenyl)acrylamide

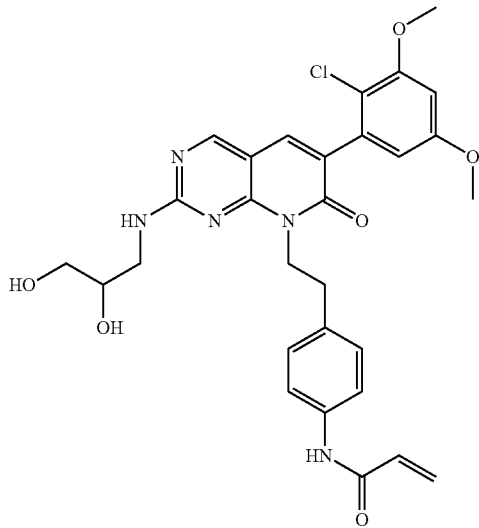 [SMILES: C=CC(=O)Nc1ccc(CCn2c(=O)c(-c3cc(OC)cc(OC)c3Cl)cc3cnc(NCC(O)CO)nc32)cc1]

The title compound was prepared as described in Example 13 except 3-aminopropane-1,2-diol was used in Step 3. LCMS (ESI, pos. ion) m/z: 580.1 (M+1).

Example 74

Synthesis of N-(4-(2-(6-(2-chloro-3,5-dimethoxy-phenyl)-2-((2-(1,1-dioxidothiomorpholino)-ethyl)amino)-7-oxopyrido[2,3-d]pyrimidin-8(7H)-yl)ethyl)phenyl)acrylamide

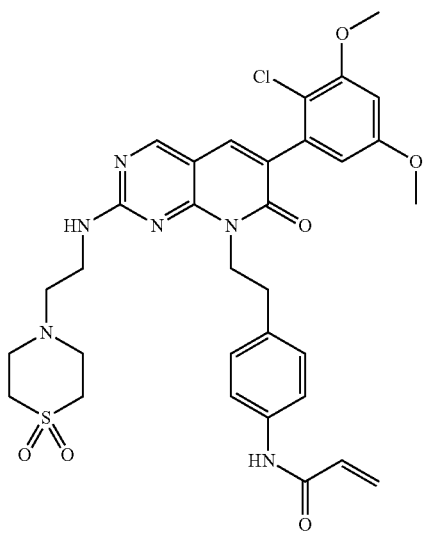 [SMILES: C=CC(=O)Nc1ccc(CCn2c(=O)c(-c3cc(OC)cc(OC)c3Cl)cc3cnc(NCCN4CCS(=O)(=O)CC4)nc32)cc1]

The title compound was prepared as described in Example 13 except 4-(2-aminoethyl)thiomorpholine 1,1-dioxide was used in Step 3. LCMS (ESI, pos. ion) m/z: 666.6 (M+1).

Example 75

Synthesis of N-(4-(2-(6-(2,6-dichloro-3,5-dimethoxyphenyl)-2-(((1-methylpiperidin-4-yl)methyl)-amino)-7-oxopyrido[2,3-d]pyrimidin-8(7H)-yl)ethyl)phenyl)acrylamide

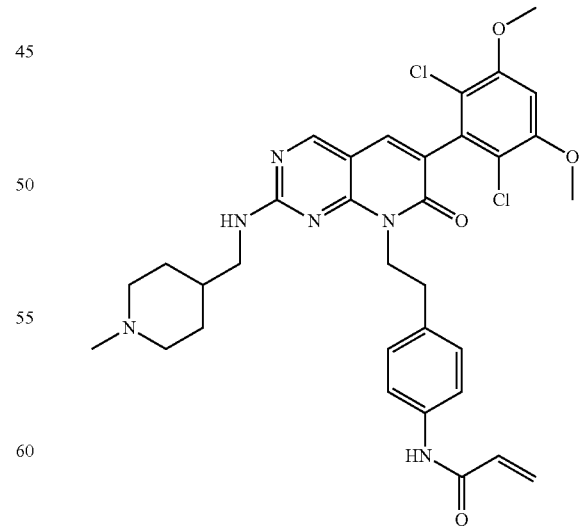

The title compound was prepared as described in Example 4 except (1-methylpiperidin-4-yl)methanamine was used in Step 8. LCMS (ESI, pos. ion) m/z: 651.2 (M+1).

Example 76

Synthesis of N-(4-(2-(6-(2,6-dichloro-3,5-dimethoxyphenyl)-2-((1,3-dihydroxypropan-2-yl)-amino)-7-oxopyrido[2,3-d]pyrimidin-8(7H)-yl)ethyl)phenyl)acrylamide

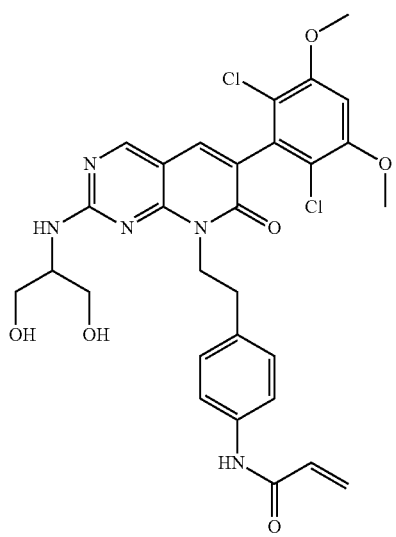 [SMILES: C=CC(=O)Nc1ccc(CCn2c(=O)c(-c3c(Cl)c(OC)cc(OC)c3Cl)cc3cnc(NC(CO)CO)nc32)cc1]

The title compound was prepared as described in Example 4 except 2-aminopropane-1,3-diol was used in Step 8. LCMS (ESI, pos. ion) m/z: 614.3 (M+1).

Example 77

Synthesis of N-(4-(2-(6-(2,6-dichloro-3,5-dimethoxyphenyl)-2-((1-hydroxy-2-methylpropan-2-yl)amino)-7-oxopyrido[2,3-d]pyrimidin-8(7H)-yl)ethyl)phenyl)acrylamide

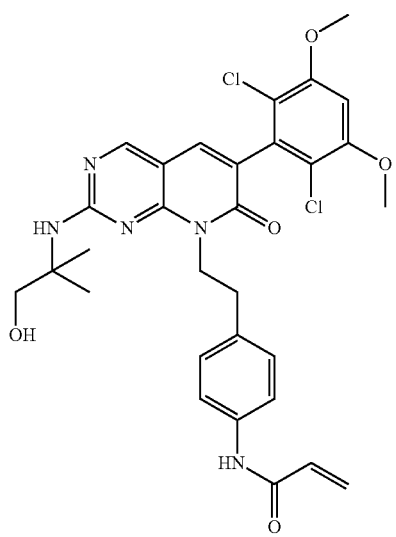 [SMILES: C=CC(=O)Nc1ccc(CCn2c(=O)c(-c3c(Cl)c(OC)cc(OC)c3Cl)cc3cnc(NC(C)(C)CO)nc32)cc1]

The title compound was prepared as described in Example 4 except 2-amino-2-methylpropan-1-ol was used in Step 8. LCMS (ESI, pos. ion) m/z: 612.2 (M+1).

Example 78

Synthesis of N-(4-(2-(6-(2-chloro-3,5-dimethoxyphenyl)-2-((2-(4-(oxetan-3-yl)piperazin-1-yl)ethyl)amino)-7-oxopyrido[2,3-d]pyrimidin-8(7H)-yl)ethyl)phenyl)acrylamide

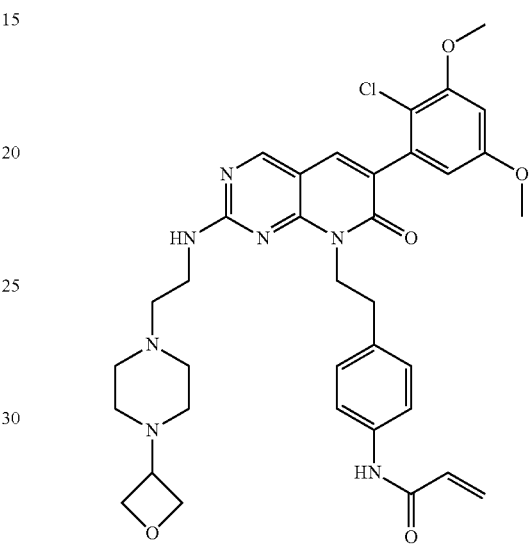

Step 1

To a solution of tert-butyl (2-(piperazin-1-yl)ethyl)carbamate (1.15 g, 5 mmol) and oxetan-3-one (1.8 g, 25 mmol) in MeOH (30 mL) was added ZnCl$_2$ (3.4 g, 25 mmol). The mixture was stirred at room temperature for 3 h, and then NaBH$_3$CN (950 mg, 15 mmol) was added. The mixture was stirred at room temperature overnight and then filtered and the filtrate was concentrated to afford tert-butyl (2-(4-(oxetan-3-yl)piperazin-1-yl)ethyl)carbamate (1.3 g, crude) as a light yellow oil which was used for next step without further purification.

Step 2

To a solution of tert-butyl (2-(4-(oxetan-3-yl)piperazin-1-yl)ethyl)carbamate (0.5 g, 1.75 mmol) in DCM (10 mL) was added TFA (5 mL). The reaction mixture was stirred at room temperature for 2 h and more DCM (30 mL) was added, and the reaction mixture was washed with NaHCO$_3$ and brine. The organic layer was dried over Na$_2$SO$_4$, filtered and concentrated to afford 2-(4-(oxetan-3-yl)piperazin-1-yl)ethanamine (300 mg, 93%) as a light yellow semi-solid. The compound was prepared as described in Example 13 except 2-(4-(oxetan-3-yl)piperazin-1-yl)ethanamine was used in Step 3. LCMS (ESI, pos. ion) m/z: 673.7 (M+1).

Example 79

Synthesis of N-(6-(2-(6-(2,6-dichloro-3,5-dimethoxyphenyl)-2-(ethylamino)-7-oxopyrido[2,3-d]pyrimidin-8(7H)-yl)ethyl)pyridin-3-yl)acrylamide

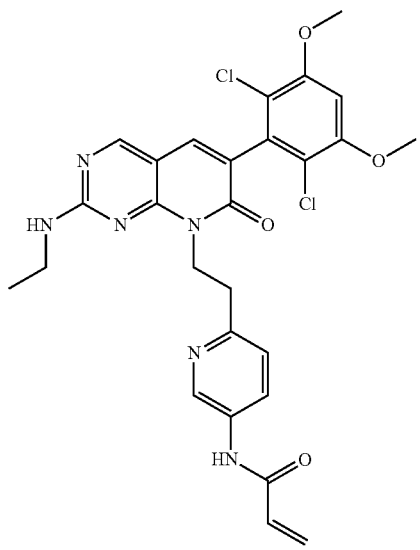 [SMILES: C=CC(=O)Nc1ccc(CCn2c(=O)c(-c3c(Cl)c(OC)cc(OC)c3Cl)cc3cnc(NCC)nc32)nc1]

The compound was prepared as described in Example 38 except ethanamine was used in Step 4. LCMS (ESI, pos. ion) m/z: 569.1 (M+1).

Example 80

Synthesis of N-(6-(2-(6-(2,6-dichloro-3,5-dimethoxyphenyl)-2-(isopropylamino)-7-oxopyrido[2,3-d]pyrimidin-8(7H)-yl)ethyl)pyridin-3-yl)acrylamide

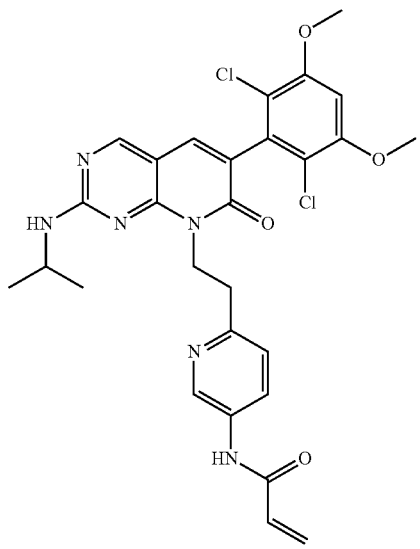 [SMILES: C=CC(=O)Nc1ccc(CCn2c(=O)c(-c3c(Cl)c(OC)cc(OC)c3Cl)cc3cnc(NC(C)C)nc32)nc1]

The title compound was prepared as described in Example 38 except propan-2-amine was used in Step 4. LCMS (ESI, pos. ion) m/z: 583.2 (M+1).

Example 81

Synthesis of N-(6-(2-(6-(2,6-dichloro-3,5-dimethoxyphenyl)-7-oxo-2-((tetrahydro-2H-pyran-4-yl)amino)-pyrido[2,3-d]pyrimidin-8(7H)-yl)ethyl)pyridin-3-yl)acrylamide

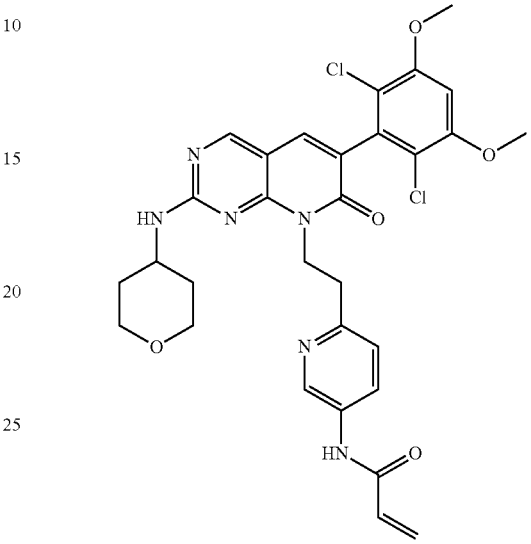

The title compound was prepared as described in Example 38 except tetrahydro-2H-pyran-4-amine was used in Step 4. LCMS (ESI, pos. ion) m/z: 625.1 (M+1).

Example 82

Synthesis of N-(4-(2-(6-(2-chloro-3,5-dimethoxyphenyl)-2-((2-((2R,6S)-2,6-dimethylpiperazin-1-yl)ethyl)amino)-7-oxopyrido[2,3-d]pyrimidin-8(7H)-yl)ethyl)phenyl)acrylamide

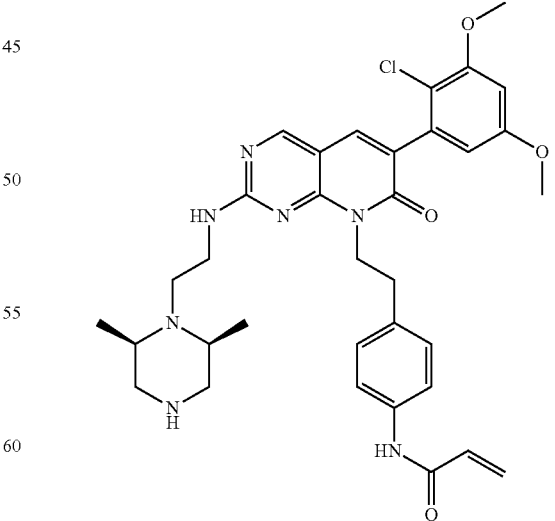

Step 1

To a solution of (3R,5S)-tert-butyl 3,5-dimethylpiperazine-1-carboxylate (2 g, 9 mmol) in DMF (20 mL) was added benzyl (2-bromoethyl)carbamate (3.2 g, 11 mmol), $K_2CO_3$ (2.5 g, 18 mmol) and NaI (1.0 g). The reaction was stirred at 70-80° C. for 24 h, cooled to room temperature, and poured into water (60 mL). The reaction mixture was extracted with ethyl acetate, and the organic layers were combined, washed with brine, dried ($Na_2SO_4$), filtered, and evaporated. The crude residue was chromatographed (silica gel, DCM:MeOH=20:1) to afford (3R,5S)-tert-butyl 4-(2-(((benzyloxy)carbonyl)amino)ethyl)-3,5-dimethylpiperazine-1-carboxylate as a yellow oil (2.2 g, 60%).

Step 2

To a solution of (3R,5S)-tert-butyl 4-(2-(((benzyloxy)carbonyl)amino)ethyl)-3,5-dimethylpiperazine-1-carboxylate (2.2 g, 5.6 mmol) in $CH_3OH$ (50 mL) was added Pd/C (200 mg). The reaction mixture was stirred at RT for overnight under an $H_2$ atmosphere, then filtered and evaporated to give (3R,5S)-tert-butyl 4-(2-aminoethyl)-3,5-dimethylpiperazine-1-carboxylate. The residue (1.3 g) was used in next step without further purification.

The title compound was prepared as described in Example 13 except (3R,5S)-tert-butyl 4-(2-aminoethyl)-3,5-dimethylpiperazine-1-carboxylate was used in Step 3. LCMS (ESI, pos. ion) m/z: 646.2 (M+1).

Example 83

Synthesis of N-(4-(2-(6-(2-chloro-3,5-dimethoxyphenyl)-2-((3-hydroxy-2,2-dimethyl-propyl)amino)-7-oxopyrido[2,3-d]pyrimidin-8(7H)-yl)ethyl)phenyl)acrylamide

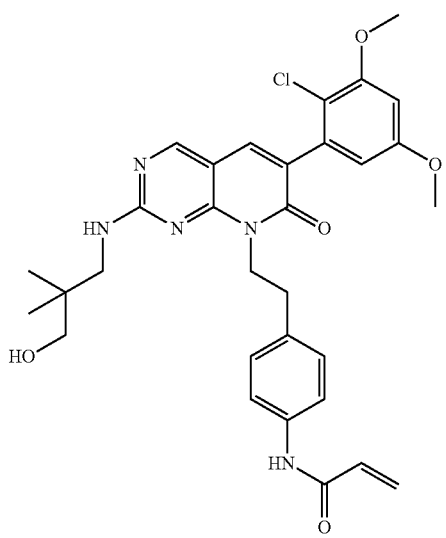 [SMILES: C=CC(=O)Nc1ccc(CCn2c(=O)c(-c3cc(OC)cc(OC)c3Cl)cc3cnc(NCC(C)(C)CO)nc32)cc1]

The title compound was prepared as described in Example 13 except 3-amino-2,2-dimethylpropan-1-ol was used in Step 3. LCMS (ESI, pos. ion) m/z: 592.2 (M+1).

Example 84

Synthesis of N-(6-(2-(6-(2,6-dichloro-3,5-dimethoxyphenyl)-2-((2-hydroxy-2-methylpropyl)amino)-7-oxopyrido[2,3-d]pyrimidin-8(7H)-yl)ethyl)pyridin-3-yl)acrylamide

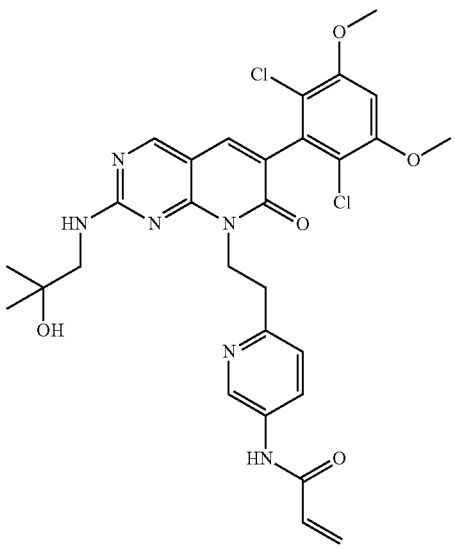 [SMILES: C=CC(=O)Nc1ccc(CCn2c(=O)c(-c3c(Cl)c(OC)cc(OC)c3Cl)cc3cnc(NCC(C)(C)O)nc32)nc1]

The title compound was prepared as described in Example 38 except 1-amino-2-methylpropan-2-ol was used in Step 4. LCMS (ESI, pos. ion) m/z: 613.1 (M+1).

Example 85

Synthesis of N-(4-(2-(6-(2-chloro-3,5-dimethoxyphenyl)-2-((2-((3S,5R)-3,5-dimethylpiperazin-1-yl)ethyl)amino)-7-oxopyrido[2,3-d]pyrimidin-8(7H)-yl)ethyl)phenyl)acrylamide

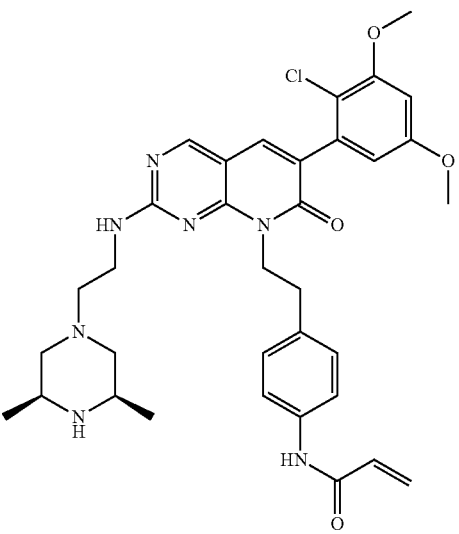

Step 1

To a solution of (2S,6R)-tert-butyl 2,6-dimethylpiperazine-1-carboxylate (1.5 g, 7 mmol) in DMF (10 mL) was added K₂CO₃ (1.9 g, 14 mmol) and 2-chloroacetonitrile (1 g, 14 mmol). The reaction mixture was stirred at 40° C. overnight, cooled and then EtOAc (100 mL) was added to the reaction mixture. The mixture was washed with brine, dried over Na₂SO₄, filtered and concentrated to afford (2S,6R)-tert-butyl 4-(cyanomethyl)-2,6-dimethylpiperazine-1-carboxylate (1.5 g, 85%, crude) as a light yellow oil.

Step 2

To a solution of (2S,6R)-tert-butyl 4-(cyanomethyl)-2,6-dimethylpiperazine-1-carboxylate (1.5 g, 5.9 mmol) in MeOH (30 mL) was added R—Ni (1 g). The reaction mixture was stirred at 40° C. under H₂ (4 atm) overnight. The mixture was filtered and concentrated to afford (2S,6R)-tert-butyl 4-(2-aminoethyl)-2,6-dimethylpiperazine-1-carboxylate (0.8 g, 53%, crude) as a light yellow solid. The title compound was prepared as described in Example 13 except (2S,6R)-tert-butyl 4-(2-aminoethyl)-2,6-dimethylpiperazine-1-carboxylate was used in Step 3. LCMS (ESI, pos. ion) m/z: 646.2 (M+1).

Example 86

Synthesis of N-(6-(2-(6-(2,6-dichloro-3,5-dimethoxyphenyl)-2-((2-hydroxyethyl)amino)-7-oxopyrido[2,3-d]pyrimidin-8(7H)-yl)ethyl)pyridin-3-yl)acrylamide

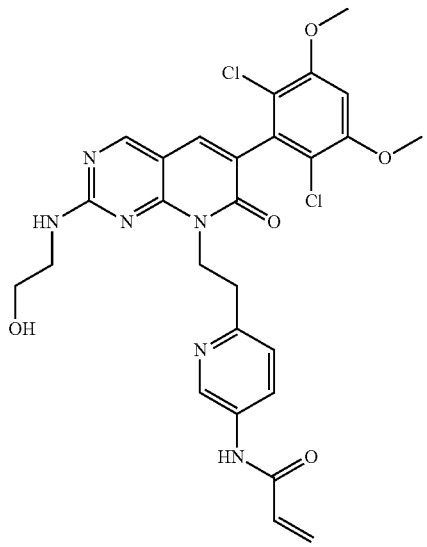 [SMILES: C=CC(=O)Nc1ccc(CCn2c(=O)c(-c3c(Cl)c(OC)cc(OC)c3Cl)cc3cnc(NCCO)nc32)nc1]

The title compound was prepared as described in Example 38 except 2-aminoethanol was used in Step 4. LCMS (ESI, pos. ion) m/z: 585.1 (M+1).

Example 87

Synthesis of N-(6-(2-(6-(2,6-dichloro-3,5-dimethoxyphenyl)-2-((1,3-dihydroxypropan-2-yl)amino)-7-oxopyrido[2,3-d]pyrimidin-8(7H)-yl)ethyl)pyridin-3-yl)acrylamide

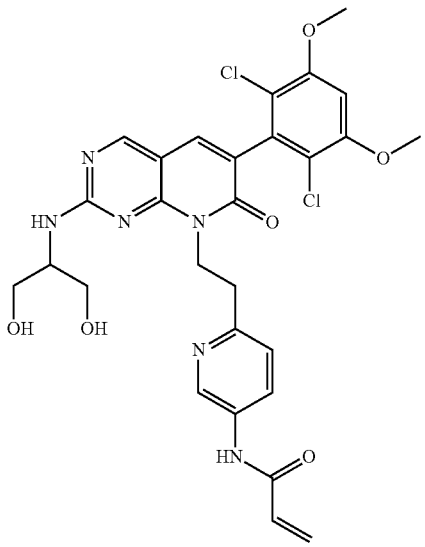 [SMILES: C=CC(=O)Nc1ccc(CCn2c(=O)c(-c3c(Cl)c(OC)cc(OC)c3Cl)cc3cnc(NC(CO)CO)nc32)nc1]

The title compound was prepared as described in Example 38 except 2-aminopropane-1,3-diol was used in Step 4. LCMS (ESI, pos. ion) m/z: 615.1 (M+1).

Example 88

Synthesis of N-(6-(2-(6-(2,6-dichloro-3,5-dimethoxyphenyl)-2-((2,3-dihydroxypropyl)amino)-7-oxopyrido[2,3-d]pyrimidin-8(7H)-yl)ethyl)pyridin-3-yl)acrylamide

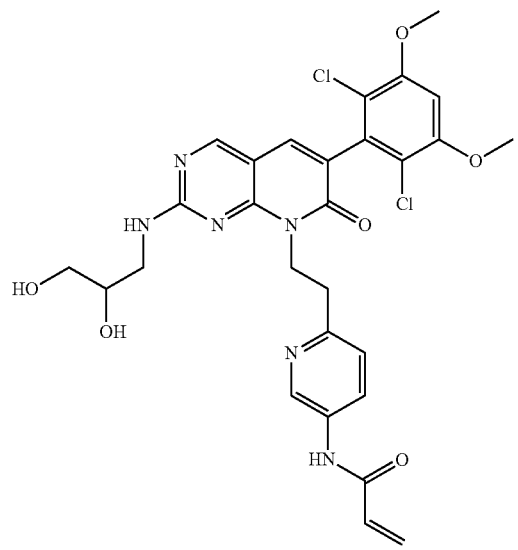 [SMILES: C=CC(=O)Nc1ccc(CCn2c(=O)c(-c3c(Cl)c(OC)cc(OC)c3Cl)cc3cnc(NCC(O)CO)nc32)nc1]

The title compound was prepared as described in Example 38 except 3-aminopropane-1,2-diol was used in Step 4. LCMS (ESI, pos. ion) m/z: 615.1 (M+1).

Example 89

Synthesis of N-(4-(2-(6-(2,6-dichloro-3,5-dimethoxyphenyl)-7-oxo-2-((tetrahydro-2H-pyran-4-yl)amino)pyrido[2,3-d]pyrimidin-8(7H)-yl)ethyl)phenyl)acrylamide

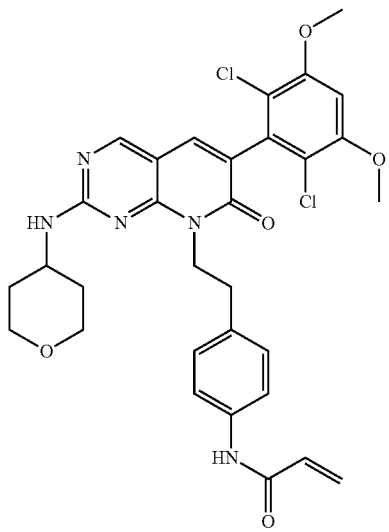

The title compound was prepared as described in Example 4 except tetrahydro-2H-pyran-4-amine was used in Step 8. LCMS (ESI, pos. ion) m/z: 624.3 (M+1).

Example 90

Synthesis of N-(4-(2-(2-((cyclopropylmethyl)amino)-6-(2,6-dichloro-3,5-dimethoxyphenyl)-7-oxopyrido[2,3-d]pyrimidin-8(7H)-yl)ethyl)phenyl)acrylamide

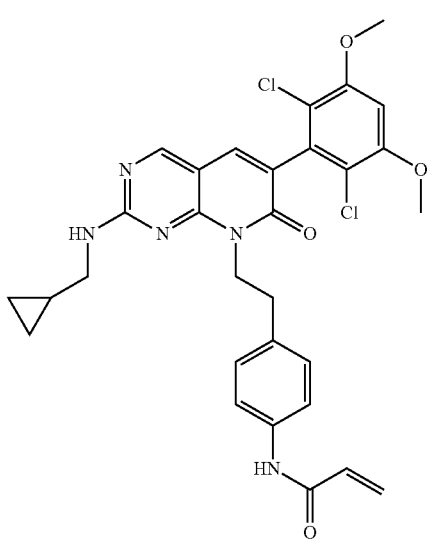 [SMILES: C=CC(=O)Nc1ccc(CCn2c(=O)c(-c3c(Cl)c(OC)cc(OC)c3Cl)cc3cnc(NCC4CC4)nc32)cc1]

The title compound was prepared as described in Example 4 except cyclopropylmethanamine was used in Step 8. LCMS (ESI, pos. ion) m/z: 594.1 (M+1).

Example 91

Synthesis of N-(4-(2-(6-(2,6-dichloro-3,5-dimethoxyphenyl)-2-((1,3-dihydroxy-2-methylpropan-2-yl)amino)-7-oxopyrido[2,3-d]pyrimidin-8(7H)-yl)ethyl)phenyl)acrylamide

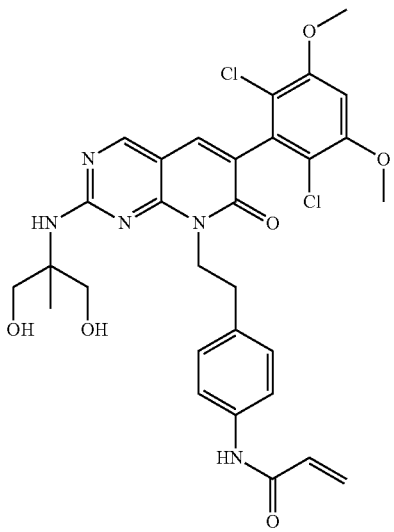 [SMILES: C=CC(=O)Nc1ccc(CCn2c(=O)c(-c3c(Cl)c(OC)cc(OC)c3Cl)cc3cnc(NC(C)(CO)CO)nc32)cc1]

The title compound was prepared as described in Example 4 except 2-amino-2-methylpropane-1,3-diol was used in Step 8. LCMS (ESI, pos. ion) m/z: 628.1 (M+1).

Example 92

Synthesis of N-(4-(2-(6-(2,6-dichloro-3,5-dimethoxyphenyl)-2-((1-hydroxy-2-(hydroxymethyl)-butan-2-yl)amino)-7-oxopyrido[2,3-d]pyrimidin-8(7H)-yl)ethyl)phenyl)acrylamide

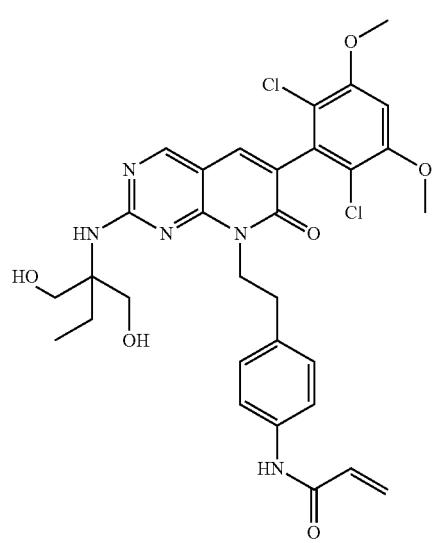 [SMILES: C=CC(=O)Nc1ccc(CCn2c(=O)c(-c3c(Cl)c(OC)cc(OC)c3Cl)cc3cnc(NC(CC)(CO)CO)nc32)cc1]

The title compound was prepared as described in Example 4 except 2-amino-2-ethylpropane-1,3-diol was used in Step 8. LCMS (ESI, pos. ion) m/z: 642.1 (M+1).

Example 93

Synthesis of N-(4-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)phenyl)acrylamide

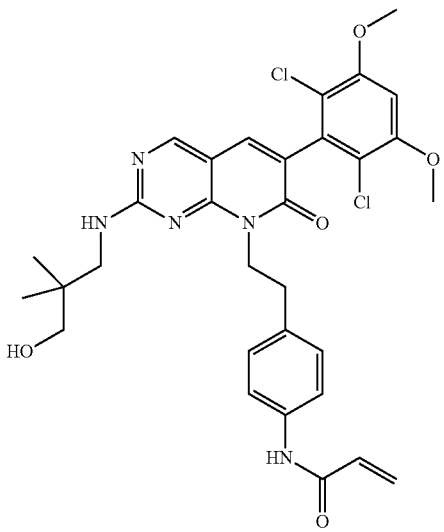 [SMILES: C=CC(=O)Nc1ccc(CCn2c(=O)c(-c3c(Cl)c(OC)cc(OC)c3Cl)cc3cnc(NCC(C)(C)CO)nc32)cc1]

The title compound was prepared as described in Example 4 except 3-amino-2,2-dimethylpropan-1-ol was used in Step 8. LCMS (ESI, pos. ion) m/z: 626.5 (M+1).

Example 94

Synthesis of N-(6-(2-(6-(2,6-dichloro-3,5-dimethoxyphenyl)-2-((1-hydroxy-2-methylpropan-2-yl)amino)-7-oxopyrido[2,3-d]pyrimidin-8(7H)-yl)ethyl)pyridin-3-yl)acrylamide

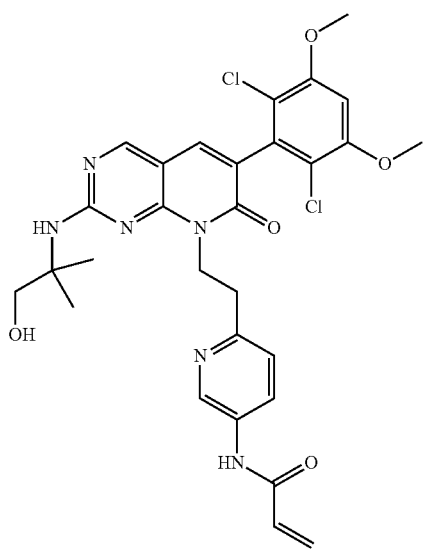 [SMILES: C=CC(=O)Nc1ccc(CCn2c(=O)c(-c3c(Cl)c(OC)cc(OC)c3Cl)cc3cnc(NC(C)(C)CO)nc32)nc1]

The title compound was prepared as described in Example 38 except 2-amino-2-methylpropan-1-ol was used in Step 4. LCMS (ESI, pos. ion) m/z: 613.1 (M+1).

Example 95

Synthesis of N-(4-(2-(6-(2-chloro-3,5-dimethoxyphenyl)-2-((1,3-dihydroxy-2-methylpropan-2-yl)amino)-7-oxopyrido[2,3-d]pyrimidin-8(7H)-yl)ethyl)phenyl)acrylamide

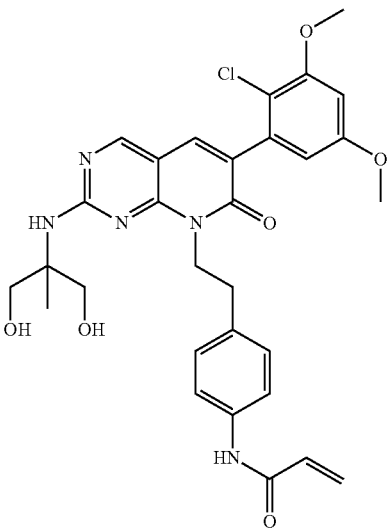 [SMILES: C=CC(=O)Nc1ccc(CCn2c(=O)c(-c3cc(OC)cc(OC)c3Cl)cc3cnc(NC(C)(CO)CO)nc32)cc1]

The title compound was prepared as described in Example 13 except 2-amino-2-methylpropane-1,3-diol was used in Step 3. LCMS (ESI, pos. ion) m/z: 594.0 (M+1).

Example 96

Synthesis of N-(4-(2-(6-(2-chloro-3,5-dimethoxyphenyl)-2-(((4-hydroxy-1-methylpiperidin-4-yl)methyl)-amino)-7-oxopyrido[2,3-d]pyrimidin-8(7H)-yl)ethyl)phenyl)acrylamide

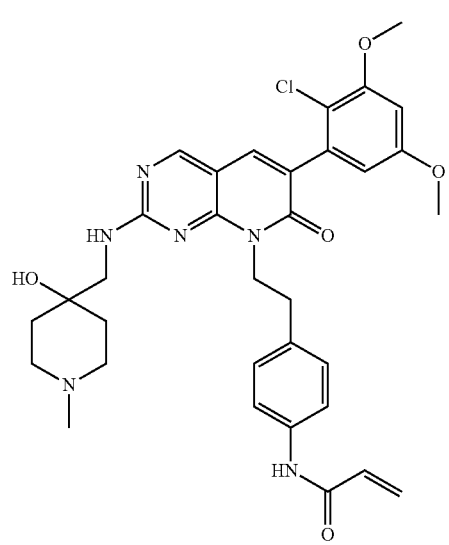 [SMILES: C=CC(=O)Nc1ccc(CCn2c(=O)c(-c3cc(OC)cc(OC)c3Cl)cc3cnc(NCC4(O)CCN(C)CC4)nc32)cc1]

The title compound was prepared as described in Example 13 except 4-(aminomethyl)-1-methylpiperidin-4-ol was used in Step 3. LCMS (ESI, pos. ion) m/z: 633.1 (M+1).

Example 97

Synthesis of N-(6-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)pyridin-3-yl)acrylamide

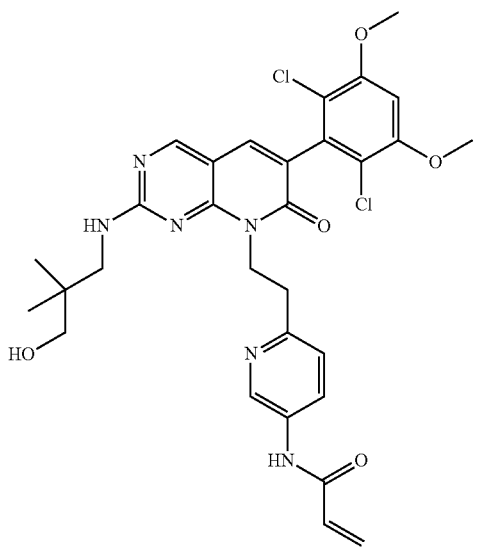 [SMILES: C=CC(=O)Nc1ccc(CCn2c(=O)c(-c3c(Cl)c(OC)cc(OC)c3Cl)cc3cnc(NCC(C)(C)CO)nc32)nc1]

The title compound was prepared as described in Example 38 except 3-amino-2,2-dimethylpropan-1-ol was used in Step 4. LCMS (ESI, pos. ion) m/z: 627.1 (M+1).

Example 98

Synthesis of N-(4-(2-(6-(2,6-dichloro-3,5-dimethoxyphenyl)-2-(((4-hydroxy-1-methylpiperidin-4-yl)methyl)-amino)-7-oxopyrido[2,3-d]pyrimidin-8(7H)-yl)ethyl)phenyl)acrylamide

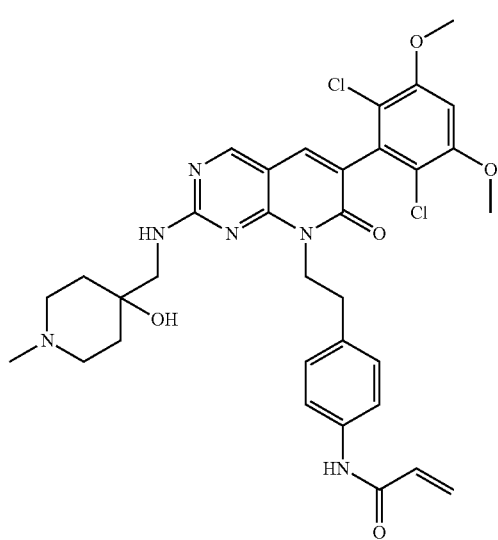

Step 1

To a solution of 1-methylpiperidin-4-one (2 g, 17.67 mmol) in EtOH (10 mL) was added nitromethane (1.5 g, 24.57 mmol) and methoxysodium (47 mg, 0.87 mmol). The resulting solution was stirred overnight at room temperature and then the solids were filtered and the filtrate was concentrated to afford 1.4 g (45%) of 1-methyl-4-(nitromethyl)piperidin-4-ol as a colorless oil.

Step 2

To a solution of 1-methyl-4-(nitromethyl)piperidin-4-ol (1.4 g, 8.04 mmol) in MeOH (20 mL) was added Raney Ni (0.5 g). The resulting mixture was stirred overnight at room temperature under an $H_2$ atmosphere. The solids were then filtered and the filtrate was concentrated. The residue was purified by chromatography (DCM/MeOH (5:1)) to afford 0.8 g (69%) of 4-(aminomethyl)-1-methylpiperidin-4-ol as a colorless oil.

The compound was prepared as described in Example 4 except 4-(aminomethyl)-1-methylpiperidin-4-ol was used in Step 8. LCMS (ESI, pos. ion) m/z: 667.6 (M+1).

Example 99

Synthesis of N-(6-(2-(6-(2,6-dichloro-3,5-dimethoxyphenyl)-2-((1,3-dihydroxy-2-methylpropan-2-yl)-amino)-7-oxopyrido[2,3-d]pyrimidin-8(7H)-yl)ethyl)pyridin-3-yl)acrylamide

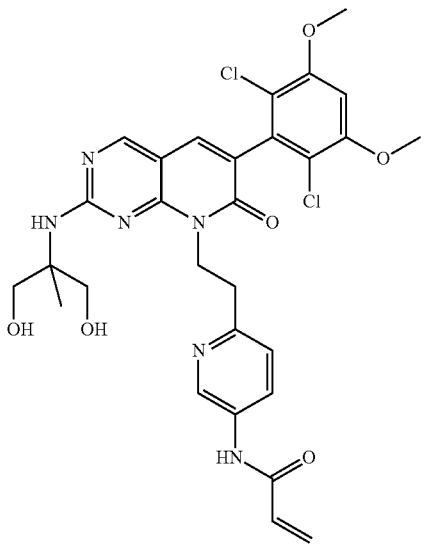 [SMILES: C=CC(=O)Nc1ccc(CCn2c(=O)c(-c3c(Cl)c(OC)cc(OC)c3Cl)cc3cnc(NC(C)(CO)CO)nc32)nc1]

The title compound was prepared as described in Example 38 except 2-amino-2-methylpropane-1,3-diol was used in Step 4. LCMS (ESI, pos. ion) m/z: 629.1 (M+1).

Example 100

Synthesis of N-(6-(2-(6-(2,6-dichloro-3,5-dimethoxyphenyl)-2-((1-hydroxy-2-(hydroxymethyl)-butan-2-yl)amino)-7-oxopyrido[2,3-d]pyrimidin-8(7H)-yl)ethyl)pyridin-3-yl)acrylamide

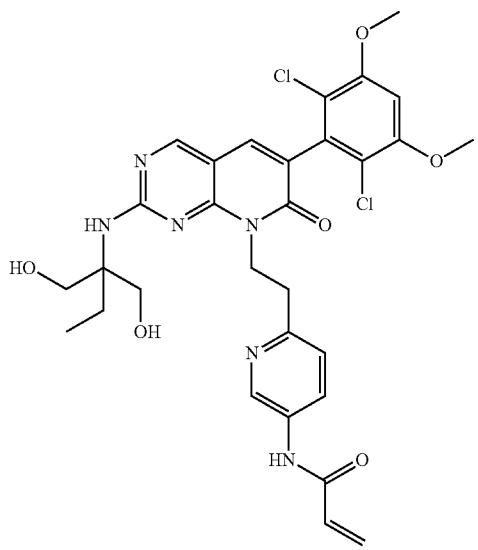 [SMILES: C=CC(=O)Nc1ccc(CCn2c(=O)c(-c3c(Cl)c(OC)cc(OC)c3Cl)cc3cnc(NC(CC)(CO)CO)nc32)nc1]

The title compound was prepared as described in Example 38 except 2-amino-2-ethylpropane-1,3-diol was used in Step 4. LCMS (ESI, pos. ion) m/z: 643.1 (M+1).

Example 101

Synthesis of N-(6-(2-(6-(2,6-dichloro-3,5-dimethoxyphenyl)-7-oxo-2-(prop-2-yn-1-ylamino)-pyrido[2,3-d]pyrimidin-8(7H)-yl)ethyl)pyridin-3-yl)acrylamide

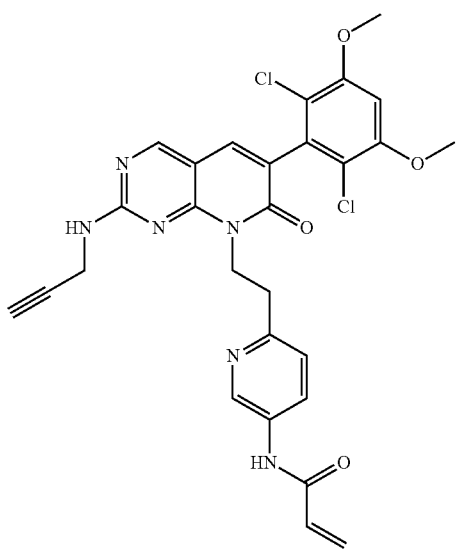 [SMILES: C#CCNc1ncc2cc(-c3c(Cl)c(OC)cc(OC)c3Cl)c(=O)n(CCc3ccc(NC(=O)C=C)cn3)c2n1]

The title compound was prepared as described in Example 38 except prop-2-yn-1-amine was used in Step 4. LCMS (ESI, pos. ion) m/z: 579.0 (M+1).

Example 102

Synthesis of N-(3-(((6-(2-chloro-3,5-dimethoxyphenyl)-2-((2-morpholinoethyl)amino)-7-oxopyrido[2,3-d]pyrimidin-8(7H)-yl)methyl)phenyl)acrylamide

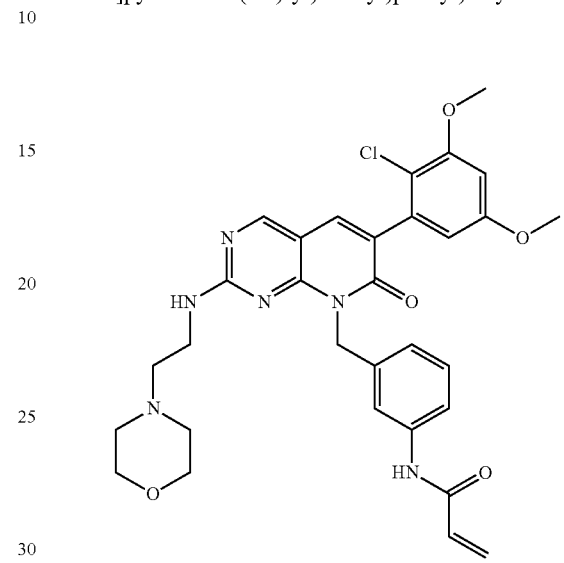

The compound was prepared as described in Example 12 except tert-butyl (3-(bromomethyl)phenyl)-carbamate was used in Step 4 and 2-morpholinoethanamine was used in Step 6. LCMS (ESI, pos. ion) m/z: 605.2 (M+1).

Example 103

Synthesis of N-(6-(2-(6-(2-chloro-3,5-dimethoxyphenyl)-2-((cyclopropylmethyl)amino)-7-oxopyrido[2,3-d]pyrimidin-8(7H)-yl)ethyl)pyridin-3-yl)acrylamide

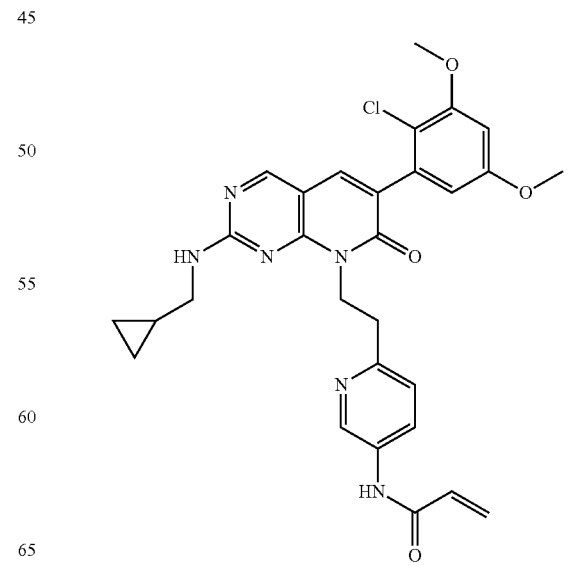

The compound was prepared as described in Example 34 except cyclopropylmethanamine was used in Step 9. LCMS (ESI, pos. ion) m/z: 561.1 (M+1).

Example 104

Synthesis of N-(6-(2-(6-(2-chloro-3,5-dimethoxyphenyl)-2-((2-hydroxyethyl)amino)-7-oxopyrido[2,3-d]pyrimidin-8(7H)-yl)ethyl)pyridin-3-yl)acrylamide

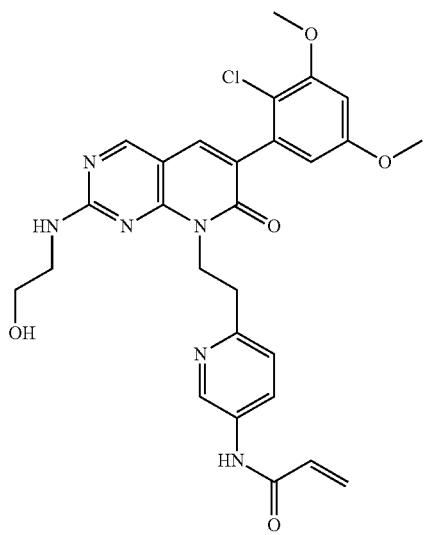 [SMILES: C=CC(=O)Nc1ccc(CCn2c(=O)c(-c3cc(OC)cc(OC)c3Cl)cc3cnc(NCCO)nc32)nc1]

The compound was prepared as described in Example 34 except 2-aminoethanol was used in Step 9. LCMS (ESI, pos. ion) m/z: 551.1 (M+1).

Example 105

Synthesis of N-(4-(2-(6-(2,6-dichloro-3,5-dimethoxyphenyl)-2-((4-methylpiperazin-1-yl)amino)-7-oxopyrido[2,3-d]pyrimidin-8(7H)-yl)ethyl)phenyl)acrylamide

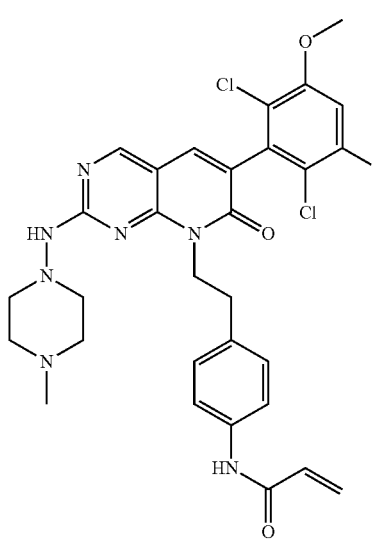

The title compound was prepared as described in Example 4 except 4-methylpiperazin-1-amine was used in Step 8. LCMS (ESI, pos. ion) m/z: 638.1 (M+1).

Example 106

Synthesis of N-(4-(2-(6-(2,6-dichlorophenyl)-2-(methylamino)-7-oxopyrido[2,3-d]pyrimidin-8(7H)-yl)ethyl)phenyl)acrylamide

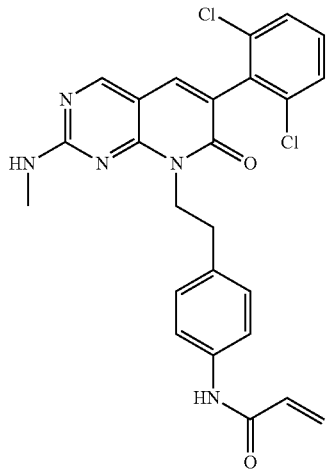 [SMILES: C=CC(=O)Nc1ccc(CCn2c(=O)c(-c3c(Cl)cccc3Cl)cc3cnc(NC)nc32)cc1]

The title compound was prepared as described in Example 4 except 1,3-dichloro-2-methylbenzene was used in Step 2. LCMS (ESI, pos. ion) m/z: 494.0 (M+1).

Example 107

Synthesis of N-(6-(2-(6-(2,6-dichlorophenyl)-2-(methylamino)-7-oxopyrido[2,3-d]pyrimidin-8(7H)-yl)ethyl)pyridin-3-yl)acrylamide

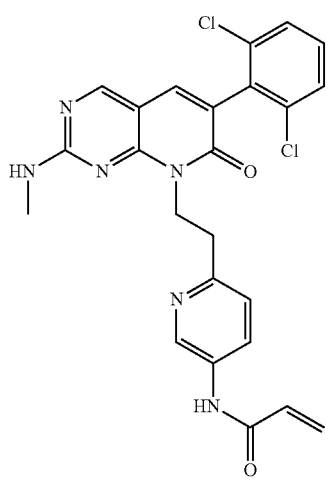 [SMILES: C=CC(=O)Nc1ccc(CCn2c(=O)c(-c3c(Cl)cccc3Cl)cc3cnc(NC)nc32)nc1]

The title compound was prepared as described in Example 4 except 1,3-dichloro-2-methylbenzene was used in Step 2 and tert-butyl (6-(2-iodoethyl)pyridin-3-yl)carbamate was used in Step 6. LCMS (ESI, pos. ion) m/z: 495.0 (M+1).

Example 108

Synthesis of N-(6-(2-(6-(2-chloro-3,5-dimethoxy-phenyl)-7-oxo-2-(pyridin-2-ylamino)pyrido[2,3-d]pyrimidin-8(7H)-yl)ethyl)pyridin-3-yl)acrylamide

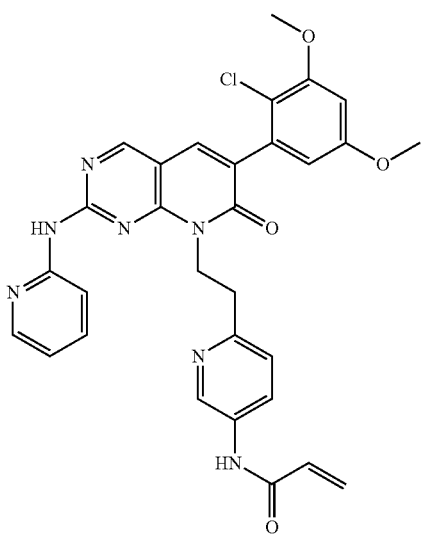 [SMILES: C=CC(=O)Nc1ccc(CCn2c(=O)c(-c3cc(OC)cc(OC)c3Cl)cc3cnc(Nc4ccccn4)nc32)nc1]

The title compound was prepared as described in Example 34 except pyridin-2-amine was used in Step 9. LCMS (ESI, pos. ion) m/z: 583.1 (M+1).

Example 109

Synthesis of N-(6-(2-(6-(2-chloro-3,5-dimethoxy-phenyl)-2-((2-hydroxy-2-methylpropyl)amino)-7-oxopyrido[2,3-d]pyrimidin-8(7H)-yl)ethyl)pyridin-3-yl)acrylamide

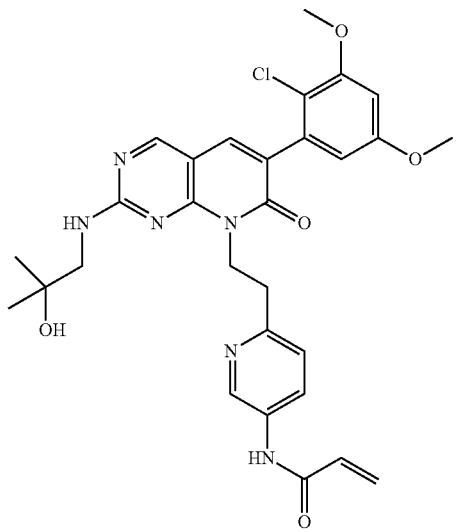 [SMILES: C=CC(=O)Nc1ccc(CCn2c(=O)c(-c3cc(OC)cc(OC)c3Cl)cc3cnc(NCC(C)(C)O)nc32)nc1]

The title compound was prepared as described in Example 34 except 1-amino-2-methylpropan-2-ol was used in Step 9. LCMS (ESI, pos. ion) m/z: 579.2 (M+1).

Example 110

Synthesis of N-(4-(2-(6-(2-chloro-3,5-dimethoxy-phenyl)-2-((2-methyl-2-morpholinopropyl)-amino)-7-oxopyrido[2,3-d]pyrimidin-8(7H)-yl)ethyl)phenyl)acrylamide

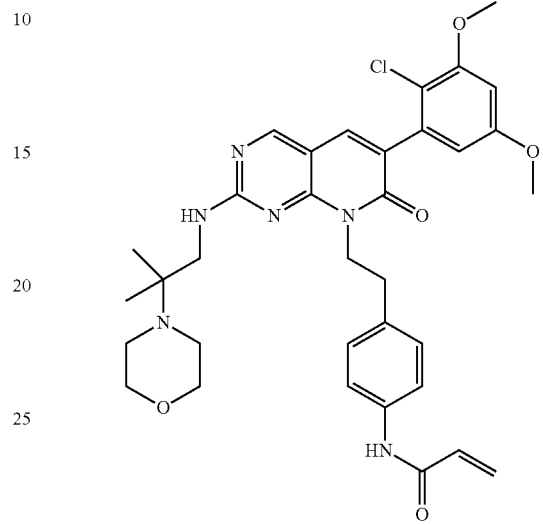

The title compound was prepared as described in Example 13 except 2-methyl-2-morpholinopropan-1-amine was used in Step 3. LCMS (ESI, pos. ion) m/z: 647.0 (M+1).

Example 111

Synthesis of N-(4-(2-(6-(2-chloro-3,5-dimethoxy-phenyl)-2-((2-(4,4-difluoropiperidin-1-yl)-ethyl)amino)-7-oxopyrido[2,3-d]pyrimidin-8(7H)-yl)ethyl)phenyl)acrylamide

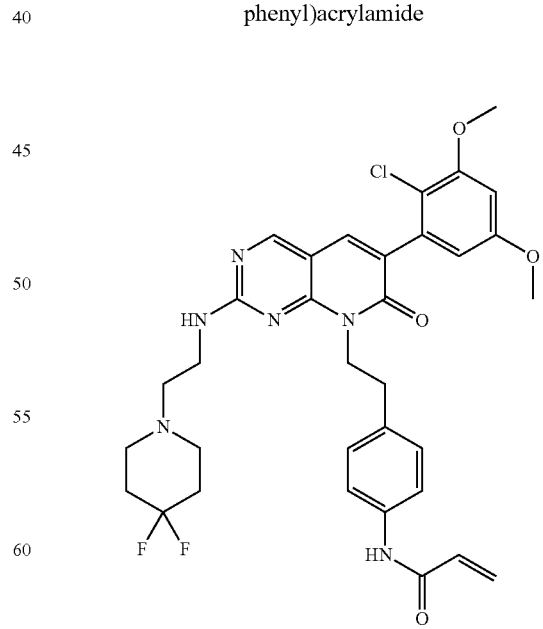

Step 1

A mixture of 4,4-difluoropiperidine hydrochloride (500 mg, 3.2 mmol), $K_2CO_3$ (873 mg, 6.3 mmol) and 2-bromoacetonitrile (384 mg, 3.2 mmol) in ACN (8 mL) was heated to 70° C. overnight. After cooling to room temperature, the reaction mixture was concentrated to give a residue which was diluted with H₂O, and extracted with EtOAc. The organic extract was dried and concentrated to afford 2-(4,4-difluoropiperidin-1-yl)acetonitrile (480 mg, 93%) which was used in next step without further purification.

Step 2

To a solution of 2-(4,4-difluoropiperidin-1-yl)acetonitrile (480 mg, 3.0 mmol) in THF (10 mL) at ambient temperature was added LAH (228 mg, 6.0 mmol). The reaction mixture was stirred at ambient temperature overnight before quenching with H₂O and aq. NaOH (15%, 10 mL). The resultant mixture was filtered and the filtrate was concentrated to give a residue which was purified by chromatography (DCM:MeOH=10:1) to afford 2-(4,4-difluoropiperidin-1-yl)ethanamine (400 mg, 80%) as a yellow oil.

The compound title was prepared as described in Example 34 except 2-(4,4-difluoropiperidin-1-yl)ethanamine was used in Step 9. LCMS (ESI, pos. ion) m/z: 653.1 (M+1).

Example 112

Synthesis of N-(4-(2-(6-(2-chloro-3,5-dimethoxyphenyl)-2-(((1,4-dimethylpiperidin-4-yl)methyl)amino)-7-oxopyrido[2,3-d]pyrimidin-8(7H)-yl)ethyl)phenyl)acrylamide

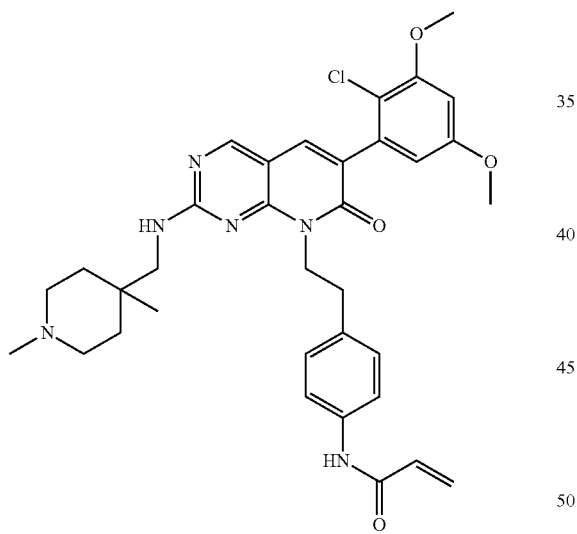

Step 1

To a solution of ethyl 1-methylpiperidine-4-carboxylate (3.42 g, 20 mmol) in THF (100 m L) at −78° C. was added drop wise LDA (30.0 mL, 1M, 30.0 mmol). After stirring for 0.5 h, CH₃I (4.26 g, 30.0 mmol) was added dropwise to the reaction mixture at −78° C. The reaction was warmed to room temperature and stirred for 1 h. The solution was diluted with water and extracted with EtOAc. The organic phase was dried and concentrated to afford ethyl 1,4-dimethylpiperidine-4-carboxylate (2.7 g, 70%).

Step 2

To a solution of ethyl 1,4-dimethylpiperidine-4-carboxylate (1.1 g, 6.0 mmol) in THF (4 mL), H₂O (2 ml) and MeOH (1 mL) was added NaOH (480 mg, 12 mmol). The reaction mixture was heated to 50° C. for 1 h and then concentrated to afford 1,4-dimethylpiperidine-4-carboxylic acid (1.6 g, crude).

Step 3

A solution of 1,4-dimethylpiperidine-4-carboxylic acid (1.6 g, crude) in SOCl₂ (20.0 mL) was heated to reflux for 16 h. The solvent was then removed to afford 1,4-dimethylpiperidine-4-carbonyl chloride (2.0 g, crude).

Step 4

To a mixture of 1,4-dimethylpiperidine-4-carbonyl chloride (2.0 g, crude) in DCM (5.0 mL) was bubbled with NH₃ (gas) for 6 min at room temperature. The solvent was removed to afford 1,4-dimethylpiperidine-4-carboxamide (1.8 g, crude).

Step 5

A mixture of LiAlH₄ (4.3 g, 115 mmol) in THF (50 mL) was added dropwise to a solution of 1,4-dimethylpiperidine-4-carboxamide (1.8 g, crude) in THF (20 mL) at 0° C. The reaction mixture was heated to reflux for 1 h before cooling to 0° C. and then quenched with H₂O and 15% NaOH (4.3 mL). The reaction mixture was stirred for 1 h and filtered. The filtrate was concentrated to afford 1,4-dimethylpiperidin-4-yl)methanamine (600 mg, 72%, 4 steps).

The title compound was prepared as described in Example 34 except 1,4-dimethylpiperidin-4-yl)methanamine was used in Step 9. LCMS (ESI, pos. ion) m/z: 631.0 (M+1).

Example 113

Synthesis of N-(4-(1-(6-(2-chloro-3,5-dimethoxyphenyl)-2-(methylamino)-7-oxopyrido[2,3-d]pyrimidin-8(7H)-yl)-2-methylpropan-2-yl)phenyl)acrylamide

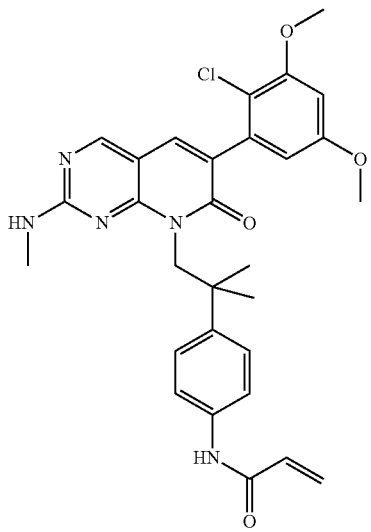 [SMILES: C=CC(=O)Nc1ccc(C(C)(C)Cn2c(=O)c(-c3cc(OC)cc(OC)c3Cl)cc3cnc(NC)nc32)cc1]

Step 1

A solution of ethyl 2-(4-nitrophenyl)acetate (3.41 g, 16.3 mmol) in DMF (30 mL) was added dropwise to a suspension of NaH (2.28 g, 57 mmol, 60%) in DMF (30 mL) with ice-cooling. CH₃I (6.24 g, 44 mmol) was added and the reaction mixture was stirred at r.t. for 24 h before cooling in an ice-bath, and followed by the dropwise addition of water with vigorous stirring. The mixture was partitioned between water and EtOAc. The aqueous phase was extracted with EtOAc and the combined organics was washed with water, dried over anhydrous MgSO₄ and concentrated to afford ethyl 2-methyl-2-(4-nitrophenyl)propanoate (1.1 g, 28%) as a yellow oil.

Step 2

To a solution of ethyl 2-methyl-2-(4-nitrophenyl)propanoate (1.1 g, 4.6 mmol) in THF (20 mL) was added LiBH₄ (408 mg, 18.6 mmol). The reaction mixture was stirred at ambient temperature overnight and then MeOH was added (10 mL). After stirring at 50° C. for 1 h, the solution was concentrated to give a residue which was re-dissolved in ethyl acetate and washed with aq. NaHCO₃ and brine, dried over anhydrous Na₂SO₄ and concentrated to afford 2-methyl-2-(4-nitrophenyl)propan-1-ol (0.49 g, 40%) as a brown oil.

Step 3

To a solution of 2-methyl-2-(4-nitrophenyl)propan-1-ol (0.49 g, 2.5 mmol) in DCM (15 mL) at 0° C. was added Et₃N (0.38 g, 3.8 mmol) and MsCl (0.32 g, 2.8 mmol). The reaction mixture was stirred at ambient temperature for 1 h before quenching with water. The reaction mixture was extracted with DCM and the organics were washed with brine, dried over anhydrous Na₂SO₄, filtered and concentrated to afford 2-methyl-2-(4-nitrophenyl)propyl methanesulfonate (0.5 g, 73%) as a yellow solid.

Step 4

To a solution of 6-(2-chloro-3,5-dimethoxyphenyl)-2-(methylthio)pyrido[2,3-d]pyrimidin-7(8H)-one (550 mg, 1.52 mmol) in DMF (10 mL) was added 2-methyl-2-(4-nitrophenyl)propyl methanesulfonate (500 mg, 1.83 mmol) and K₂CO₃ (420 mg, 3.04 mmol). The reaction mixture was stirred at 105° C. for 1 h before cooling to ambient temperature, followed by addition of water. The participated solid was collected by filtration and dried to afford 6-(2-chloro-3,5-dimethoxyphenyl)-8-(2-methyl-2-(4-nitrophenyl)propyl)-2-(methylthio)pyrido[2,3-d]pyrimidin-7(8H)-one (247 mg, 30%) as a yellow solid.

Step 5

To a solution of 6-(2-chloro-3,5-dimethoxyphenyl)-8-(2-methyl-2-(4-nitrophenyl)propyl)-2-(methylthio)pyrido[2,3-d]pyrimidin-7(8H)-one (247 g, 0.46 mmol) in DCM (10 mL) was added m-CPBA (126 mg, 0.55 mmol, 70%). The reaction mixture was stirred at ambient temperature for 0.5 h and then sat. Na₂S₂O₃ and aq. Na₂CO₃ was added. The reaction mixture was extracted with DCM. The organics were washed with brine, dried over anhydrous Na₂SO₄, filtered and concentrated to afford 6-(2-chloro-3,5-dimethoxyphenyl)-8-(2-methyl-2-(4-nitrophenyl)propyl)-2-(methylsulfinyl)pyrido[2,3-d]pyrimidin-7(8H)-one (200 mg, 79%) as a yellow solid.

Step 6

To a solution of 6-(2-chloro-3,5-dimethoxyphenyl)-8-(2-methyl-2-(4-nitrophenyl)propyl)-2-(methylsulfinyl)pyrido[2,3-d]pyrimidin-7(8H)-one (200 mg, 0.36 mmol) in DMSO (4 mL) was added CH₃NH₂—HCl (73 mg, 1.08 mmol). The reaction mixture was stirred at 85° C. for 0.5 h before cooling to ambient temperature, followed by addition of water. The solids were collected by filtration and dried to afford 6-(2-chloro-3,5-dimethoxyphenyl)-8-(2-methyl-2-(4-nitrophenyl)propyl)-2-(methylamino)pyrido[2,3-d]pyrimidin-7(8H)-one (164 mg, 87%) as a yellow solid.

Step 7

To a solution of 6-(2-chloro-3,5-dimethoxyphenyl)-8-(2-methyl-2-(4-nitrophenyl)propyl)-2-(methylamino)pyrido[2,3-d]pyrimidin-7(8H)-one (164 mg, 0.31 mmol) in EtOH (10 mL) and aq. NH₄Cl (1 mL) was added Fe powder (105 mg, 1.88 mmol). The reaction mixture was stirred at 78° C. for 2 h before concentrating to give a residue which was diluted with THF and filtered. The filtrate was concentrated to afford 8-(2-(4-aminophenyl)-2-methylpropyl)-6-(2-chloro-3,5-dimethoxyphenyl)-2-(methylamino)pyrido[2,3-d]pyrimidin-7(8H)-one which was used for next step directly.

Step 8

To a solution of 8-(2-(4-aminophenyl)-2-methylpropyl)-6-(2-chloro-3,5-dimethoxy-Stepphenyl)-2-(methylamino)pyrido[2,3-d]pyrimidin-7(8H)-one in THF (20 mL) at 0° C. was added aq. NaHCO₃ (2 mL) and acryloyl chloride (28 mg, 0.31 mmol). The reaction mixture was stirred at 0° C. for 1 h before extraction with ethyl acetate. The organic was dried over anhydrous sodium sulfate, filtered and concentrated. The residue was purified by Prep-HPLC to afford N-(4-(1-(6-(2-chloro-3,5-dimethoxyphenyl)-2-(methylamino)-7-oxopyrido[2,3-d]-pyrimidin-8(7H)-yl)-2-methylpropan-2-yl)phenyl)acrylamide (43 mg, 25% for two steps). LCMS (ESI, pos. ion) m/z: 548.2 (M+1).

Example 114

Synthesis of (E)-N-(4-(2-(6-(2,6-dichloro-3,5-dimethoxyphenyl)-2-(methylamino)-7-oxopyrido-[2,3-d]pyrimidin-8(7H)-yl)ethyl)phenyl)-4-(dimethylamino)but-2-enamide

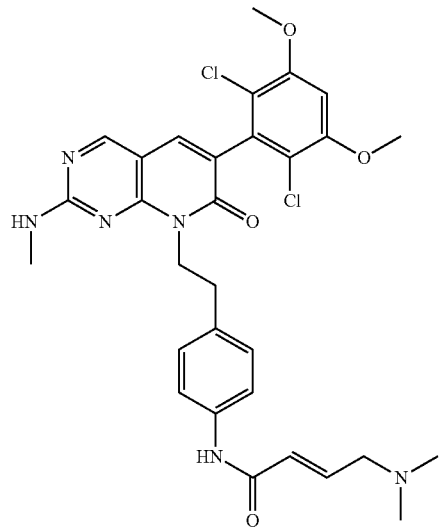 [SMILES: CNc1ncc2cc(-c3c(Cl)c(OC)cc(OC)c3Cl)c(=O)n(CCc3ccc(NC(=O)/C=C/CN(C)C)cc3)c2n1]

To a solution of 8-(4-aminophenethyl)-6-(2,6-dichloro-3,5-dimethoxyphenyl)-2-(methylamino)pyrido[2,3-d]pyrimidin-7(8H)-one (140 mg, 0.28 mmol) in NMP (10 mL) at 0° C. was added (E)-4-(dimethylamino)but-2-enoyl chloride (50 mg, 0.34 mmol). The reaction mixture was stirred at ambient temperature for 0.5 h and then water was added. The reaction mixture was extracted with ethyl acetate and the organics were washed with sat. NaHCO₃ (50 mL), dried over anhydrous Na₂SO₄, filtered and concentrated to a residue which was purified by Prep-HPLC to afford (E)-N-(4-(2-(6-(2,6-dichloro-3,5-dimethoxyphenyl)-2-(methylamino)-7-oxopyrido[2,3-d]pyrimidin-8(7H)-yl)ethyl)phenyl)-4-(dimethylamino)but-2-enamide (35 mg, 20%) as a white solid. LCMS (ESI, pos. ion) m/z: 611.0 (M+1).

BIOLOGICAL EXAMPLES

Example 1

FGFR Family Enzymatic Activity Assay

A Caliper-based kinase assay (Caliper Life Sciences, Hopkinton, Mass.) was used to measure inhibition of FGFR family (FGFR1, FGFR2, FGFR3, FGFR4) kinase activity of a compound of Formula (I') or (I). Serial dilutions of test compounds, i.e., compounds of the present disclosure, were incubated with either human recombinant FGFR1 (0.5 nM), FGFR2 (0.1 nM, FGFR3 (0.9 nM), or FGFR4 (2 nM), ATP (FGFR1: 100 µM; FGFR2: 75 µM; FGFR3: 120 µM; FGFR4: 250 µM) and a phosphoacceptor peptide substrate FAM-KKKKEEIYFFF-CONH$_2$ (1 µM) at room temperature for 3 h. The reaction was then terminated with EDTA, final concentration 20 mM and the phosphorylated reaction product was quantified on a Caliper Desktop Profiler (Caliper LabChip 3000). Percent inhibition was calculated for each compound dilution and the concentration that produced 50% inhibition was calculated. This value is presented as the IC$_{50}$. The IC$_{50}$ values for a representative no. of compounds of the disclosure are provided below.

| Example No. | FGFR1 | FGFR2 | FGFR3 | FGFR4 |
|---|---|---|---|---|
| 1 | 0.0380 | 0.0344 | 0.2690 | 0.5263 |
| 2 | 0.8402 | 0.7011 | 1.042 | >5 |
| 3 | 0.2504 | 0.3685 | 0.8203 | 2.7716 |
| 4 | 0.0013 | 0.0016 | 0.0031 | 0.0104 |
| 5 | 0.0011 | 0.0015 | 0.0055 | 0.0324 |
| 6 | 0.0013 | 0.0010 | 0.0031 | 0.0332 |
| 8 | 0.0312 | | 0.0190 | |
| 11 | 0.0222 | | | |
| 12 | 0.0028 | | | |
| 13 | 0.0013 | 0.0014 | 0.0023 | 0.0256 |
| 16 | 0.0013 | 0.0017 | 0.0023 | 0.0069 |
| 17 | 0.0047 | | | |
| 18 | 0.0094 | | | |
| 19 | 0.0053 | | | |
| 20 | 0.0034 | | | |
| 21 | 0.0067 | | | |
| 22 | 0.0004 | | | |
| 23 | 0.0012 | | | |
| 24 | 0.0017 | | | |
| 25 | 0.024 | | | |
| 26 | 0.0010 | | | |
| 27 | 0.0009 | | | |
| 28 | 0.0043 | | | |
| 29 | 0.0493 | | | |
| 30 | 0.0051 | | | |
| 31 | 0.0014 | | | |
| 32 | 0.0012 | | | |
| 33 | 0.0041 | | | |
| 34 | 0.0013 | | | |
| 35 | 0.006 | | | |
| 36 | 0.013 | | | |
| 37 | 0.0015 | | | |
| 38 | 0.0012 | 0.002 | 0.0033 | 0.0063 |
| 39 | 0.0009 | 0.0055 | 0.0054 | 0.042 |
| 40 | 0.0024 | | | |
| 41 | 0.005 | | | |
| 42 | 0.0018 | | | |
| 43 | 0.002 | 0.0026 | 0.0096 | 0.071 |
| 44 | 0.001 | 0.0025 | 0.004 | 0.014 |
| 45 | 0.004 | | | |
| 46 | 0.002 | | | |
| 47 | 0.003 | | | |
| 48 | 0.048 | | | |
| 49 | 0.0008 | | | |
| 50 | 0.0074 | | | |
| 51 | 0.0018 | 0.0042 | 0.0054 | 0.0128 |
| 52 | 0.0054 | | | |
| 53 | 0.0289 | | | |
| 54 | 0.0117 | | | |
| 55 | 0.0022 | | | |
| 56 | 0.0037 | | | |
| 57 | 0.0004 | | | |
| 58 | 0.0013 | | | |
| 59 | 0.0005 | | | |
| 60 | 0.0002 | | | |
| 61 | 0.0015 | 0.0034 | 0.0092 | 0.0644 |
| 62 | 0.0007 | 0.0020 | 0.0099 | 0.0541 |
| 63 | 0.0007 | 0.0009 | 0.0032 | 0.0097 |
| 64 | 0.0005 | 0.0022 | 0.0055 | 0.0199 |
| 65 | 0.0006 | 0.0017 | 0.0046 | 0.0138 |
| 66 | 0.0011 | 0.0020 | 0.0063 | 0.0410 |
| 67 | 0.0023 | | | |
| 68 | 0.0007 | 0.0016 | 0.0081 | 0.0538 |
| 69 | 0.0010 | 0.0020 | 0.0060 | 0.0424 |
| 70 | 0.0047 | | | |
| 71 | 0.0010 | 0.0013 | 0.0059 | 0.0958 |
| 72 | 0.0008 | 0.0015 | 0.0068 | 0.0433 |
| 73 | 0.0039 | | | |
| 74 | 0.0022 | | | |
| 75 | 0.0004 | 0.0006 | 0.0033 | 0.0147 |
| 76 | 0.0008 | 0.0016 | 0.0067 | 0.0096 |
| 77 | 0.0023 | | | |
| 78 | 0.0009 | | | |
| 79 | 0.0002 | | | |
| 80 | 0.0005 | | | |
| 81 | 0.0003 | | | |
| 82 | 0.0005 | | | |
| 83 | 0.0006 | | | |
| 84 | 0.0007 | | | |
| 85 | 0.0012 | | | |
| 86 | 0.0006 | | | |
| 87 | 0.0012 | | | |
| 88 | 0.0006 | | | |
| 89 | 0.0002 | | | |
| 90 | 0.0018 | | | |
| 91 | 0.0006 | | | |
| 92 | 0.0011 | | | |
| 93 | 0.0007 | | | |
| 94 | 0.0021 | | | |
| 95 | 0.0062 | | | |
| 96 | 0.0098 | | | |
| 97 | 0.0015 | | | |
| 98 | 0.0003 | | | |
| 99 | 0.0012 | | | |
| 100 | 0.0014 | | | |
| 101 | 0.0003 | | | |
| 102 | 0.001 | | | |
| 103 | 0.0006 | | | |
| 104 | 0.0008 | | | |
| 105 | 0.0012 | | | |
| 106 | 0.0296 | | | |
| 107 | 0.0125 | | | |
| 108 | 0.0082 | | | |
| 109 | 0.0016 | | | |
| 110 | 0.0019 | | | |
| 111 | 0.0034 | | | |

Example 2

Inhibition of FGFR2-Dependent Cell Growth

The cell-based effects of FGFR inhibitors were determined by measuring inhibition of FGFR-dependent cell line growth. Two FGFR2-dependent cell lines, NCI H-716 and SNU-16 were used for these assays. NCI H-716 or SNU-16 cells were seeded in a 96-well plate at 5,000 cells per well in RPMI 1640 high glucose medium with 10% fetal bovine serum (FBS. Cells were incubated at 37° C. for 24 hrs in 5% CO$_2$. Compound dilutions were added to cells starting at a concentration of 30 uM and decreasing in tripling dilutions to a final concentration of 9 nM. The final DMSO concentration was 0.1%. The concentration range was adjusted as needed for compounds of different potencies. The cells treated with compounds of the present disclosure were incubated for 72 hrs at 37° C. in 5% $CO_2$. At the end of the 72 hour incubation period, cell viability was determined using the Cell-titer Glo Luminescence assay from Promega. Percent inhibition of cell growth was calculated as a percentage of untreated cell viability. The percent inhibition was plotted as a function of log compound concentration. The $IC_{50}$ was then calculated for each compound using Prism software from GraphPad. The $IC_{50}$ values for a representative no. of compounds of the disclosure in SNU16 cells are provided below.

| Synthetic Example No. | SNU16 |
|---|---|
| 4 | 0.0014 |
| 5 | 0.0056 |
| 8 | 0.083 |
| 11 | 0.0942 |
| 12 | 0.0053 |
| 13 | 0.0015 |
| 16 | 0.0014 |
| 20 | 0.0243 |
| 21 | 0.1149 |
| 22 | 0.001 |
| 23 | 0.001 |
| 24 | 0.0018 |
| 25 | 0.0174 |
| 26 | 0.0019 |
| 27 | 0.0074 |
| 28 | 0.0038 |
| 30 | 0.005 |
| 31 | 0.0036 |
| 32 | 0.0067 |
| 33 | 0.0327 |
| 34 | 0.0068 |
| 35 | 0.0036 |
| 36 | 0.0257 |
| 37 | 0.0012 |
| 38 | 0.0025 |
| 39 | 0.0012 |
| 40 | 0.003 |
| 41 | >0.3300 |
| 43 | 0.0037 |
| 44 | 0.0031 |
| 45 | 0.048 |
| 46 | 0.0344 |
| 47 | 0.0824 |
| 49 | 0.0021 |
| 50 | 0.0117 |
| 51 | 0.0024 |
| 52 | 0.015 |
| 53 | 0.0713 |
| 54 | 0.0333 |
| 55 | 0.0043 |
| 56 | 0.005 |
| 57 | 0.0004 |
| 58 | 0.0008 |
| 59 | 0.0006 |
| 60 | 0.0003 |
| 61 | 0.0068 |
| 62 | 0.0021 |
| 63 | 0.0031 |
| 64 | 0.0032 |
| 65 | 0.003 |
| 66 | 0.0041 |
| 67 | 0.0097 |
| 68 | 0.0031 |
| 69 | 0.0038 |
| 70 | 0.0266 |
| 71 | 0.0049 |
| 72 | 0.0113 |
| 73 | 0.0513 |
| 74 | 0.0133 |
| 75 | 0.0022 |
| 76 | 0.0074 |
| 77 | 0.007 |
| 78 | 0.003 |
| 79 | 0.0034 |
| 80 | 0.0096 |
| 81 | 0.0041 |
| 82 | 0.0704 |
| 83 | 0.0042 |
| 84 | 0.0145 |
| 86 | 0.0114 |
| 87 | 0.169 |
| 88 | 0.0246 |
| 89 | 0.0048 |
| 90 | 0.0046 |
| 91 | 0.0029 |
| 92 | 0.0063 |
| 93 | 0.0015 |
| 94 | 0.0074 |
| 97 | 0.0064 |
| 98 | 0.0164 |
| 99 | 0.0026 |
| 100 | 0.0262 |
| 101 | 0.0016 |
| 102 | 0.0039 |
| 103 | 0.0036 |
| 104 | 0.0134 |
| 105 | 0.0078 |
| 109 | 0.0035 |

Example 3

FGFR1 Cell-Based Activity Assay Utilizing IL3-Dependent BA/F3 Cells

An engineered, cell-based assay was utilized to test the potency of FGFR1 inhibitors in a cellular context. In this system, IL3-dependent Ba/F3 cells were modified to express an activated form of FGFR1 kinase domain. Following removal of IL3 from the culture media, the modified cells were dependent on the activity of the recombinant kinase for proliferation and survival. In these studies, Ba/F3 cells were transformed by inducting TEL fusions using viral vectors. If the compound of interest specifically blocked the activity of FGFR1, the modified cells underwent programmed cell death. The amount of cell survival was quantified using CellTiter-Glo, a well-established luminescent cell viability method. Compounds were evaluated at multiple doses using a maximum compound concentration of 5 uM and a 3-fold dilution series from this concentration.

Example 4

Tumor Xenograft Models for Assessing Efficacy of FGFR Inhibitors

Figure 2:
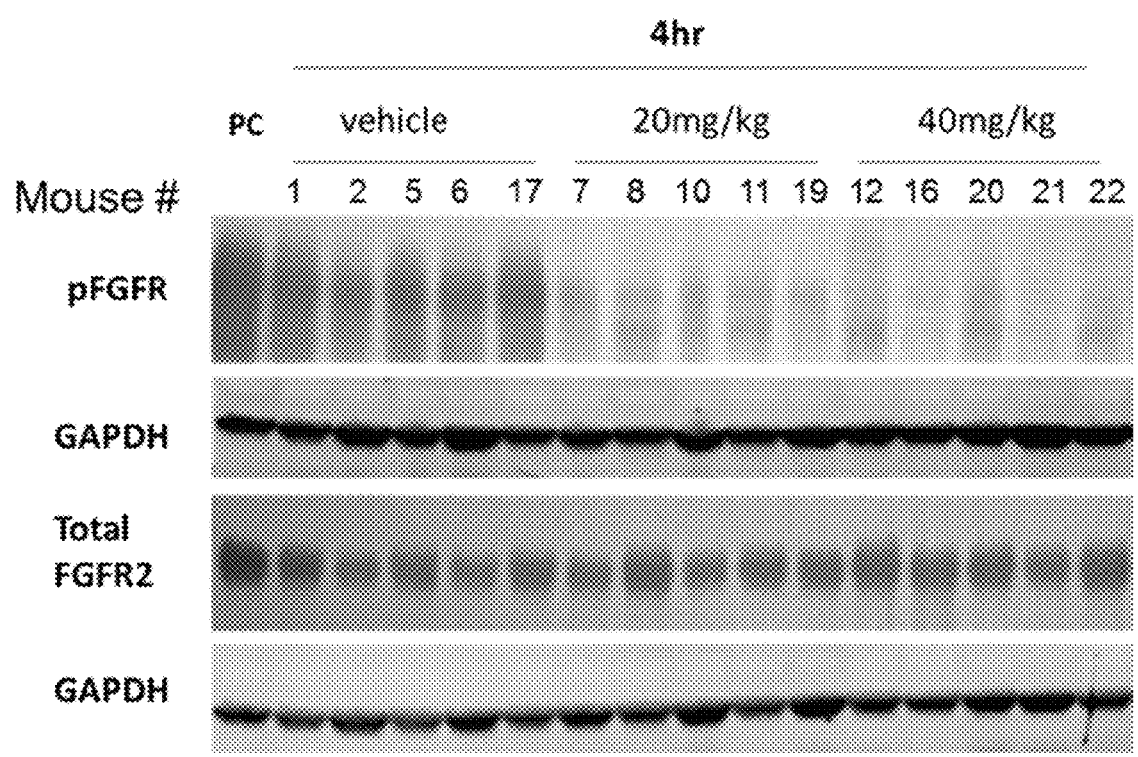

SNU-16 human gastric cancer cell line was used to generate a xenograft model to determine the effects of a present disclosure FGFR inhibitor as a single agent treatment to target FGFR-dependent tumor growth. SNU-16 cells were grown in tissue culture as described above. For tumor inoculation, approximately $1 \times 10^7$ cells were mixed with Matrigel (1:1) and were implanted into the rear flank of immunocompromised Balb/c nu/nu mice. Tumor-bearing mice were monitored twice weekly. Once tumor volume reached a mean average of 175 mm³ mice were randomized into 3 groups (n=9-10 per group) receiving either vehicle control or the present disclosure compound at 40 mg/kg QD or 20 mg/kg BID by oral gavage. Tumor volumes were measured twice weekly to determine efficacy. In addition to anti-tumor response study, SNU-16 xenograft model was used to access in vivo pharmacodynamics activity of disclosure compound. Subcutaneous tumors of SNU-16 cells were grown in mice as described above. Once the tumors reached approximately 300 mm$^3$, tumor bearing mice (n=5 per group) were dosed with control vehicle or disclosure compound at 20 mg/kg/day or 40 mg/kg/day by oral gavage. When the experiment was terminated, tumors were excised at 4 hr after the last dose. The inhibition of FGFR pathway was assessed by detection of FGFR autophosphorylation activity. Tumor growth inhibition and pFGFR inhibition in a SNU-16 xenograft model for a representative compound (Synthetic Example No. 26) of the disclosure is shown in FIGS. 1 and 2.

Example 5

Recovery of Kinase Activity Upon Dialysis

Standard experimental methods to establish irreversible inhibition are known in the art. Protein dialysis is one such method. A solution containing a protein kinase, such as FGFR, that is inhibited by a compound of the present disclosure may be subjected to extensive dialysis to establish if the compound of the present disclosure is irreversible (i.e. forms an irreversible covalent bond). Partial or complete recovery of protein kinase activity over time during dialysis is indicative of reversibility of the covalent bond.

Method:

A compound of the present disclosure and/or a pharmaceutically acceptable salt thereof described herein (1 uM) is added to a solution of protein kinase (50 nM, pre-activated if necessary) in a buffer containing 20 mM Hepes [pH 8.0], 10 mM MgCl$_2$, 2.5 mM tris(2-carboxyethyl)phosphine (TCEP), 0.25 mg/mL BSA, and 100 uM ATP. After 60 min at rt, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM MgCl$_2$, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results: For an irreversible kinase inhibitor, kinase enzymatic activity will not return upon dialysis. Upon extensive dialysis at 4° C. or at room temperature, kinase activity will recover either partially or completely in a time-dependent manner from inhibition by an excess (20 equiv, 1.0 uM) of reversible kinase inhibitor.

Example 6

Mass Spectral Analysis

A protein kinase that is inhibited by compound of the present disclosure and/or a pharmaceutically acceptable salt thereof may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase

Method (a):

A protein kinase (5 uM) is incubated with a compound of the present disclosure and/or a pharmaceutically acceptable salt thereof (25 uM, 5 equiv) for 1 h at room temperature in buffer (20 mM Hepes [pH 8.0], 100 mM NaCl, 10 mM MgCl$_2$). A control sample is also prepared which does not have a compound of the present disclosure. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results: High-resolution intact mass spectrometry analysis of a kinase that is inhibited by a compound of the present disclosure and/or a pharmaceutically acceptable salt thereof will reveal a spectrum containing a peak corresponding to the molecular mass of the kinase plus the molecular mass of the compound of the present disclosure. On the basis of this experiment a permanent, irreversible protein adduct will be apparent to one skilled in the art. Mass spectral analysis of kinase tryptic digest Method (b):

A protein (10-100 pmols) is incubated with a compound of the present disclosure and/or a pharmaceutically acceptable salt thereof (100-1000 pmols, 10 equiv) for 3 hrs prior to tryptic digestion. Iodoacetamide may be used as the alkylating agent after compound incubation. A control sample is also prepared which does not the compound of the present disclosure. For tryptic digests a 1 ul aliquot (3.3 pmols) is diluted with 10 ul of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50).

Results: High-resolution mass spectrometry analysis of the tryptic fragments of a kinase that is irreversibly and covalently inhibited by a compound of the present disclosure and/or a pharmaceutically acceptable salt thereof will reveal a mass spectrum of a fragment that corresponds to a molecular weight of the tryptic fragment plus the molecular mass of the compound of the present disclosure. On the basis of this experiment, permanent, irreversible protein adducts will be apparent to one skilled in the art.

Cellular assays are also optionally used to assess the inhibiting properties of a compound of the present disclosure and/or a pharmaceutically acceptable salt thereof provided herein or embodiments thereof. Cellular assays include cells from any appropriate source, including plant and animal cells (such as mammalian cells). The cellular assays are also optionally conducted in human cells. Cellular assays of FGFR inhibition are well known in the art, and include methods in which an inhibitor is delivered into the cell (e.g. by electroporation, passive diffusion, microinjection and the like) and an activity endpoint is measured, such as the amount of phosphorylation of a cellular substrate, the amount of expression of a cellular protein, or some other change in the cellular phenotype known to be affected by the catalytic activity of FGFR. For example, phosphorylation of a particular cellular substrate is optionally assessed using a detection antibody specific or the phosphorylated cellular substrate followed by western blotting techniques and visualization using any appropriate means (e.g. fluorescent detection of a fluorescently labeled antibody).

Measuring the reduction in the FGFR catalytic activity in the presence of a compound of the present disclosure relative to the activity in the absence of the compound of the present disclosure is optionally performed using a variety of methods known in the art, such as the assays described in the Examples section below. Other methods for assaying FGFR activity are known in the art.

Example 7

Determination of Drug-Kinase Residence Time for FGFR1

The following is a protocol to distinguish whether a compound and/or a pharmaceutically acceptable salt thereof disclosed herein displays a slow or non-existent dissociation rate from FGFR1, such as typically would occur if an irreversible covalent bond is formed between the compound and the target. The read-out for slow or non-existent dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM $MgCl_2$, 0.01% Triton X-100, and 1 mM EGTA.

The first step of the procedure was incubation of 500 nM FGFR1 (Invitrogen Cat. #PV3146) with 1.5 uM of a compound of the present disclosure for 60 minutes in a volume of 10 uL. The mixture was then diluted 40-fold by mixture of 2 uL FGFR1/cmpd with 78 uL buffer. A 10 uL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For FGFR1, the competition solution contained 8 uM Tracer 236 (Invitrogen Cat. #PV5592), which is a proprietary high affinity ligand for FGFR1 coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in FGFR1.

After addition of 10 uL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to FGFR1 was detected using TR-FRET between the Europium moiety of the Anti-histidine antibody and the AlexaFluor 647 group of Tracer 236. Binding was evaluated using a Perkin Elmer Envision instrument (Model 2101) equipped with filters and mirrors compatible with LANCE-type TR-FRET experiments. Data were plotted as percentage of signal obtained in the absence of a compound. The background signal was obtained by omission of FGFR1 from the reaction. Results: Tracer was prevented from binding when an irreversible covalent inhibitor of the present disclosure and/or a pharmaceutically acceptable salt thereof described herein binds to the kinase and occupies the tracer binding site.

Example 8

Durability of Binding in Cells

In addition to durability of binding of irreversible inhibitors to FGFR to recombinant protein, the durability can be assessed in FGFR containing cells. A system to test the durability of binding in cells involves treating the cells with compound for a time period adequate for complete binding to occur (e.g., one hour), followed by removal of the compound from the cell culture medium by extensive washing. Then at predetermined time points, for instance 1, 6, 14 and 24 hours after washing away the compound, the FGF-sensitive cells, (e.g., human umbilical vein endothelial cells), are stimulated with FGF to initiate FGFR signaling. Then a downstream readout of FGFR signaling such as phosphoERK can be monitored to determine how long the inhibition of FGFR continues after washing. Cellular durability of action will be detectable by inhibition of signaling at later time points. Long cellular durability is a property of covalent irreversible binding of the inhibitor to FGFR in cells.

Example 9

Irreversibility of Binding

The following approach was developed to differentiate compounds that form irreversible covalent bond with their targets from compounds that bind reversibly. Reactions are prepared with the protein target at a higher concentration than the compounds of interest. Irreversible and reversible compounds bind the target and become depleted from solution. The reactions are then treated with perturbations including both denaturation with 5 M guanidine hydrochloride or digestion with trypsin, disrupting proper folding of the target. It is found that the perturbation returns reversible compounds to solution due to dissociation from the target while irreversible covalent compounds remained bound to the target. The concentration of compound in solution is assessed both preceding and following perturbation using high performance liquid chromatography (HPLC) coupled to tandem mass spectrometry. Compounds of the present disclosure are expected to be depleted from solution in both the native state and in the perturbed state indicating that they are irreversible i.e., the covalent bond formed between the compounds and the target protein does not break.

Example 10

FGFR Cell-Based Activity Assay Utilizing HUVECs Cells

The data herein demonstrate the use of human umbilical vein endothelial cells (HUVECs) to determine compound potency to FGFR pathway activity. Extracellular-signal-regulated kinases (ERKs) activity, effectors of FGFR pathway, was utilized to develop a FGFR-targeted assay to determine compound potency. Human umbilical vein endothelial cells (HUVECs) cell-based effects of FGFR inhibitors were determined by measuring inhibition of compounds on FGF-induced MAP kinases activation, (phosphorylation of p44 and p42 MAP Kinase or phospho-Erk1/2) using PerkinElmer pERK SureFire Kit. Approximately 30,000 HUVECs were seeded per well in a 96-well cell culture plate at 37° C. overnight. Cells were incubated in recommended HUVECs media with 10% fetal bovine serum (Cells were incubated at 37° C. for 24 hrs in 5% CO2). After 24 h, media were removed and replaced by serum free media for 1 hr prior to compound treatment. Compound dilutions were added to cells starting at a concentration of 1 uM and decreasing in tripling dilutions to a final concentration of 0.05 nM. The cells treated with compounds of the present disclosure were incubated for 1 hr at 37° C. in 5% $CO_2$. At the end of the 1 h incubation period, cells were stimulated with 50 ng/ml of FGF2 for 10 mins. The reaction was stopped with 100 ul of ice cold PBS and washed once with cold PBS. After washing, cells were lysed with 50 uL of 1× lysis buffer from pERK SureFire kit (Perkin Elmer). Lysates were incubated in a pERK SureFire reaction mixture for a total of 4 hrs. At the end of the incubation period, pERK activity was measured using an Envision multilabel reader (Perkin Elmer). The raw signals for pERK activity were used to calculate $IC_{50}$ inhibition value as a function of log compound concentration for each compound using Prism software from GraphPad.

Formulation Examples

The following are representative pharmaceutical formulations containing a compound of present disclosure.

Tablet Formulation

The following ingredients are mixed intimately and pressed into single scored tablets.

| Ingredient | Quantity per tablet mg |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
| --- | --- |
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/mL Inhalation Composition To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 μl of spray for each application.

What is claimed is:
1. A compound of Formula (I'):

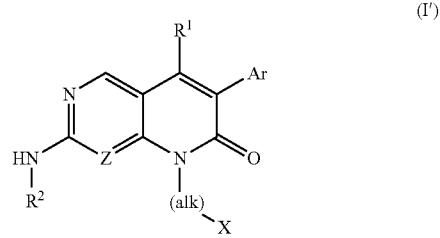

or a pharmaceutically acceptable salt thereof; wherein:
  Z is N;
  Ar is phenyl optionally substituted with one, two, three, or four substituents independently selected from alkyl, cycloalkyl, hydroxy, alkoxy, halo, haloalkyl, alkyl sulfonyl, haloalkoxy, and cyano;
  $R^1$ is hydrogen;
  $R^2$ is hydrogen, alkyl, alkynyl, cycloalkylalkyl, hydroxyalkyl, alkoxyalkyl, aminoalkyl, heterocyclyl (wherein the heterocyclyl is optionally substituted with one or two substituents independently selected from alkyl, hydroxyalkyl, alkoxyalkyl, aminoalkyl, optionally substituted aryl, optionally substituted heteroaryl, and optionally substituted heterocyclyl), heterocyclylalkyl (wherein the heterocyclyl ring in heterocyclylalkyl is optionally substituted with one or two substituents independently selected from alkyl, hydroxy, hydroxyalkyl, aminoalkyl, optionally substituted aryl, optionally substituted heteroaryl, and optionally substituted heterocyclyl), heteroaryl (where the heteroaryl is optionally substituted with one, two, or three substituents where two of the heteroaryl optional substituents are independently selected from alkyl, hydroxy, alkoxy, halo, haloalkyl, haloalkoxy, and cyano and one of the heteroaryl optional substituents is alkyl, cycloalkyl, hydroxy, alkoxy, halo, haloalkyl, haloalkoxy, cyano, hydroxyalkyl, alkoxyalkyl, aminoalkyl, optionally substituted aryl, optionally substituted heteroaryl or optionally substituted heterocyclyl), or heteroaralkyl where the heteroaryl ring in the heteroaralkyl is optionally substituted with one, two, or three substituents independently selected from halo, alkyl, hydroxy, alkoxy, and haloalkoxy;

alk is alkylene;

X is a group of formula (a) or (b):

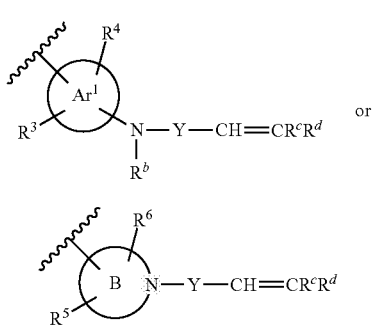

wherein:
Ar$^1$ is phenylene, pyridinylene, thiazolylene, pyrazinylene or imidazolylene;
Ring B is piperidinyl, where the nitrogen atom of the piperidinyl ring is attached to Y;
R$^3$ is hydrogen, alkyl, hydroxy, alkoxy, halo, haloalkyl, haloalkoxy, or cyano;
R$^4$ is hydrogen, alkyl, cycloalkyl, hydroxy, alkoxy, halo, haloalkyl, haloalkoxy, or cyano;
R$^5$ and R$^6$ are independently hydrogen, alkyl, or halo;
Y is CO— or —SO$_2$—;
R$^b$ is hydrogen or alkyl;
R$^c$ is hydrogen, alkyl, or substituted alkyl; and
R$^d$ is hydrogen or alkyl;
provided that (i) alk and —NR$^b$—Y—CH=CR$^c$R$^d$ are meta or para to each other and (ii) alk and —Y—CH=CR$^c$R$^d$ are meta or para to each other.

2. The compound of claim 1 or a pharmaceutically acceptable salt thereof wherein the compound has the structure (Ib):

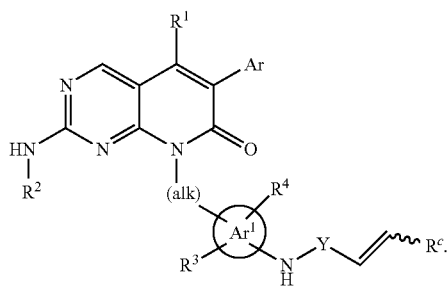

3. The compound of claim 1 or a pharmaceutically acceptable salt thereof where Ar is 2-chloro-3,5-dimethoxyphenyl, 3,5-dimethoxyphenyl, 2-chlorophenyl, or 2,6-dichloro-3,5-dimethoxyphenyl.

4. The compound of claim 1 or a pharmaceutically acceptable salt thereof where R$^2$ is alkyl.

5. The compound of claim 1 and/or a pharmaceutically acceptable salt thereof where R$^2$ is aminoalkyl.

6. The compound of claim 1 or a pharmaceutically acceptable salt thereof where R$^2$ is methyl, ethyl, prop-2-yl, 2,2-dimethylprop-1-yl, 2-hydroxy-2-methylprop-1-yl, 2,3-dihydroxyprop-1-yl, 2-hydroxyethyl, 1,3-dihydroxyprop-2-yl, 3-hydroxy-2-methylprop-2-yl, 3-hydroxy-2,2-dimethylprop-1-yl, 1,3-dihydroxy-2-methylprop-2-yl, 1,3-dihydroxy-2-ethylprop-2-yl, dimethylaminoethyl, ethylaminoethyl, 3-dimethylaminopropyl, 3-ethylaminopropyl, 4-dimethylaminobutyl, 4-ethylaminobutyl, methyl, ethyl, propyl or butyl substituted with: morpholin-4-yl, 2,6-dimethylmorpholin-4-yl, piperazin-1-yl, 4-methylpiperazin-1-yl, 4-ethylpiperazin-1-yl, 4-acetylpiperazin-1-yl, 4-isopropylpiperazin-1-yl, 4-(2-hydroxy-2-methylprop-2-yl)piperazin-1-yl, piperidin-1-yl, 1-methylpiperidin-4-yl, 1,2-dioxothiomorpholin-4-yl, 4-oxetan-3-ylpiperazin-1-yl, 2,6-dimethylpiperazin-1-yl, 3,5-dimethylpiperazin-1-yl, 4-hydroxy-1-methylpiperidin-4-yl, 4,4-difluoropiperidin-1-yl, or 1,4-dimethylpiperidin-4-yl.

7. The compound of claim 1 or a pharmaceutically acceptable salt thereof where Ar$^1$ is phenylene where the alk and —NHYCH=CHR$^c$ group are meta or para to each other on the phenylene ring.

8. The compound of claim 1 and/or a pharmaceutically acceptable salt thereof where Ar$^1$ is pyridinylene and the nitrogen atom of the pyridinylene ring is position #1 and where (i) alk is attached to the C-2 or C-3 carbon of the pyridinylene ring and the —NHYCH=CHR$^c$ group is attached to the C-6 position of the pyridinylene ring or (ii) alk is attached to the C-4 carbon of the pyridinylene ring and the —NHYCH=CHR$^c$ group is at C-2 position of the pyridinylene ring.

9. The compound of claim 1 or a pharmaceutically acceptable salt thereof where Y is —CO—.

10. The compound of claim 1 or a pharmaceutically acceptable salt thereof where R$^c$ is hydrogen.

11. The compound of claim 1 or a pharmaceutically acceptable salt thereof where R$^c$ is —CH$_2$NRR', where R is hydrogen, alkyl, hydroxyalkyl, alkoxyalkyl, or heterocyclyl optionally substituted with one or two groups independently selected from alkyl, hydroxyl, alkoxy, or halo and R' is hydrogen, alkyl, or cycloalkyl.

12. A compound selected from the group consisting of:
N-(4-(2-(6-(2-chlorophenyl)-2-((4-(diethylamino)butyl)amino)-7-oxopyrido[2,3-d]-pyrimidin-8(7H)-yl)ethyl)phenyl)prop-2-enamide;
8-(2-(1-acryloylpiperidin-3-yl)ethyl)-6-(2-chlorophenyl)-2-(4-(diethylamino)butylamino)pyrido[2,3-d]pyrimidin-7(8H)-one;
N-(3-(2-(6-(2-chlorophenyl)-2-((4-(diethylamino)butyl)amino)-7-oxopyrido[2,3-d]-pyrimidin-8(7H)-yl)ethyl)phenyl)acrylamide;
N-(4-(2-(6-(2,6-dichloro-3,5-dimethoxyphenyl)-2-(methylamino)-7-oxopyrido[2,3-d]-pyrimidin-8(7H)-yl)ethyl)phenyl)acrylamide;
N-(4-(2-(6-(2,6-dichloro-3,5-dimethoxyphenyl)-2-((4-(diethylamino)butyl)amino)-7-oxopyrido[2,3-d]pyrimidin-8(7H)-yl)ethyl)phenyl)acrylamide;

N-(3-((6-(2,6-dichloro-3,5-dimethoxyphenyl)-2-((4-(diethylamino)butyl)amino)-7-oxo-pyrido[2,3-d]pyrimidin-8(7H)-yl)methyl)phenyl)acrylamide;

N-(3-(2-(6-(2,6-dichloro-3,5-dimethoxyphenyl)-2-((4-(diethylamino)butyl)amino)-7-oxo-pyrido[2,3-d]pyrimidin-8(7H)-yl)ethyl)phenyl)acrylamide;

N-(3-(2-(6-(3,5-dimethoxyphenyl)-2-(methylamino)-7-oxopyrido[2,3-d]pyrimidin-8(7H)-yl)ethyl)phenyl)acrylamide;

N-(4-(2-(6-(3,5-dimethoxyphenyl)-2-(methylamino)-7-oxopyrido[2,3-d]pyrimidin-8(7H)-yl)ethyl)phenyl)acrylamide;

N-(4-(2-(6-(3,5-dimethoxyphenyl)-2-(methylamino)-7-oxopyrido[2,3-d]pyrimidin-8(7H)-yl)ethylpyridinyl-2-yl)acrylamide;

N-(6-(2-(6-(3,5-dimethoxyphenyl)-2-(methylamino)-7-oxopyrido[2,3-d]pyrimidin-8(7H)-yl)ethylpyridinyl-2-yl)acrylamide;

N-(3-(2-(6-(2-chloro-3,5-dimethoxyphenyl)-2-(methylamino)-7-oxopyrido[2,3-d]-pyrimidin-8(7H)-yl)ethyl)phenyl)acrylamide;

N-(4-(2-(6-(2-chloro-3,5-dimethoxyphenyl)-2-(methylamino)-7-oxopyrido[2,3-d]-pyrimidin-8(7H)-yl)ethyl)phenyl)acrylamide;

N-(4-(2-(6-(2-chloro-3,5-dimethoxyphenyl)-2-(methylamino)-7-oxopyrido[2,3-d]-pyrimidin-8(7H)-yl)ethyl)pyridin-2-yl)acrylamide;

N-(6-(2-(6-(2-chloro-3,5-dimethoxyphenyl)-2-(methylamino)-7-oxopyrido[2,3-d]-pyrimidin-8(7H)-yl)ethyl-pyridin-2-yl)acrylamide;

N-(5-(2-(6-(2-chloro-3,5-dimethoxyphenyl)-2-(methylamino)-7-oxopyrido[2,3-d]-pyrimidin-8(7H)-yl)ethyl-pyridin-2-yl)acrylamide;

N-(4-(2-(6-(2-chloro-3,5-dimethoxyphenyl)-2-(methylamino)-7-oxopyrido[2,3-d]-pyrimidin-8(7H)-yl)ethyl)phenyl)-N-methylacrylamide;

N-(3-(2-(6-(2-chloro-3,5-dimethoxyphenyl)-2-(methylamino)-7-oxopyrido[2,3-d]-pyrimidin-8(7H)-yl)ethyl)phenyl)-N-methylacrylamide;

N-(3-((6-(2-chloro-3,5-dimethoxyphenyl)-2-(methylamino)-7-oxopyrido[2,3-d]-pyrimidin-8(7H)-yl)methyl)phenyl)acrylamide;

N-(4-(2-(6-(2-chloro-3,5-dimethoxyphenyl)-2-(methylamino)-7-oxopyrido[2,3-d]pyrimidin-8(7H)-yl)ethyl)phenyl)ethenesulfonamide;

N-(3-(2-(6-(2-chloro-3,5-dimethoxyphenyl)-2-(methylamino)-7-oxopyrido[2,3-d]-pyrimidin-8(7H)-yl)ethyl)phenyl)ethenesulfonamide;

(E)-N-(4-(2-(6-(2-chloro-3,5-dimethoxyphenyl)-2-(methylamino)-7-oxopyrido[2,3-d]-pyrimidin-8(7H)-yl)ethyl)phenyl)-4-(dimethylamino)but-2-enamide;

(E)-N-(3-(2-(6-(2-chloro-3,5-dimethoxyphenyl)-2-(methylamino)-7-oxopyrido[2,3-d]-pyrimidin-8(7H)-yl)ethyl)phenyl)-4-(dimethylamino)but-2-enamide;

N-(4-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)phenyl)acrylamide;

N-(4-(2-(6-(2-chloro-3,5-dimethoxyphenyl)-2-((2-(diethylamino)ethyl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide;

N-(4-(2-(2-amino-6-(2-chloro-3,5-dimethoxyphenyl)-7-oxopyrido[2,3-d]pyrimidin-8(7H)-yl)ethyl)phenyl)acrylamide;

N-(5-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)pyridin-2-yl)acrylamide;

N-(5-(2-(6-(2-chloro-3,5-dimethoxyphenyl)-2-((2-(diethylamino)ethyl)amino)-7-oxo-pyrido[2,3-d]pyrimidin-8(7H)-yl)ethyl)pyridin-2-yl)acrylamide;

N-(5-(2-(6-(2-chloro-3,5-dimethoxyphenyl)-2-(neopentylamino)-7-oxopyrido[2,3-d]-pyrimidin-8(7H)-yl)ethyl)pyridin-2-yl)acrylamide;

N-(5-(2-(6-(2-chloro-3,5-dimethoxyphenyl)-2-(2-morpholinoethylamino)-7-oxopyrido[2,3-d]pyrimidin-8(7H)-yl)ethyl)pyridin-2-yl)acrylamide;

N-(5-(2-(6-(2-chloro-3,5-dimethoxyphenyl)-2-((4-(diethylamino)butyl)amino)-7-oxo-pyrido[2,3-d]pyrimidin-8(7H)-yl)ethyl)pyridin-2-yl)acrylamide;

N-(4-(2-(6-(2-chloro-3,5-dimethoxyphenyl)-2-(methylamino)-7-oxopyrido[2,3-d]-pyrimidin-8(7H)-yl)ethyl)thiazol-2-yl)acrylamide;

N-(6-(2-(6-(2-chloro-3,5-dimethoxyphenyl)-2-(methylamino)-7-oxopyrido[2,3-d]-pyrimidin-8(7H)-yl)ethyl)pyridin-3-yl)acrylamide;

N-(3-(2-(6-(2-chloro-3,5-dimethoxyphenyl)-2-((2-morpholinoethyl)amino)-7-oxo-pyrido[2,3-d]pyrimidin-8(7H)-yl)ethyl)phenyl)acrylamide;

N-(3-(2-(6-(2-chloro-3,5-dimethoxyphenyl)-2-((2-piperidin-1-ylethyl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((3-morpholinopropyl)amino)-7-oxo-pyrido[2,3-d]pyrimidin-8(7H)-yl)ethyl)phenyl)acrylamide;

N-(6-(2-(6-(2,6-dichloro-3,5-dimethoxyphenyl)-2-(methylamino)-7-oxopyrido[2,3-d]-pyrimidin-8(7H)-yl)ethyl)pyridin-3-yl)acrylamide;

N-(6-(2-(6-(2-chloro-3,5-dimethoxyphenyl)-2-((2-morpholinoethyl)amino)-7-oxo-pyrido[2,3-d]pyrimidin-8(7H)-yl)ethyl)pyridin-3-yl)acrylamide;

N-(4-(2-(6-(2-chloro-3,5-dimethoxyphenyl)-2-((3-(diethylamino)propyl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-(methylamino)-7-oxopyrido[2,3-d]-pyrimidin-8(7H)-yl)ethyl)thiazol-2-yl)acrylamide;

N-(3-(2-(6-(2-fluoro-3,5-dimethoxyphenyl)-2-(4-diethylaminobutylamino)-7-oxopyrido[2,3-d]pyrimidin-8(7H)-yl)ethyl)phenyl)acrylamide;

N-(4-(2-(6-(2-fluoro-3,5-dimethoxyphenyl)-2-((2-morpholinoethyl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((2-morpholinoethyl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-(methylamino)-7-oxopyrido[2,3-d]-pyrimidin-8(7H)-yl)ethyl)phenyl)-2-methylprop-1-ene-1-sulfonamide;

N-(5-(2-(6-(2-chloro-3,5-dimethoxyphenyl)-2-(methylamino)-7-oxopyrido[2,3-d]-pyrimidin-8(7H)-yl)ethyl)pyrazin-2-yl)acrylamide;

N-(5-(2-(6-(2-chloro-3,5-dimethoxyphenyl)-2-((2-morpholinoethyl)amino)-7-oxo-pyrido[2,3-d]pyrimidin-8(7H)-yl)ethyl)pyrazin-2-yl)acrylamide;

N-(1-(2-(6-(2-chloro-3,5-dimethoxyphenyl)-2-(methylamino)-7-oxopyrido[2,3-d]-pyrimidin-8(7H)-yl)ethyl)-1H-imidazol-4-yl)acrylamide;

N-(4-(2-(6-(2-chloro-3,5-dimethoxyphenyl)-2-((2-(4-methylpiperazin-1-yl)ethyl)-amino)-7-oxopyrido[2,3-d]pyrimidin-8(7H)-yl)ethyl)phenyl)acrylamide;

N-(4-(2-(2-((2-(1H-imidazol-1-yl)ethyl)amino)-6-(2-chloro-3,5-dimethoxyphenyl)-7-oxo-pyrido[2,3-d]pyrimidin-8(7H)-yl)ethyl)phenyl)acrylamide;

N-(6-(2-(6-(2,6-dichloro-3,5-dimethoxyphenyl)-2-(2-morpholinoethylamino)-7-oxopyrido[2,3-d]pyrimidin-8(7H)-yl)ethyl)pyridin-3-yl)acrylamide;

N-(3-(2-(6-(2-fluoro-3,5-dimethoxyphenyl)-2-(2-morpholin-4-ylethyllamino)-7-oxopyrido[2,3-d]pyrimidin-8(7H)-yl)ethyl)phenyl)acrylamide;

N-(2-fluoro-4-(2-(6-(2-fluoro-3,5-dimethoxyphenyl)-2-((2-morpholinoethyl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((2-morpholinoethyl)amino)-7-oxopyrido-[2,3-d]pyrimidin-8(7H)-yl)ethyl)-2-fluorophenyl)acrylamide;

N-(4-(2-(6-(2-chloro-3,5-dimethoxyphenyl)-2-((2-morpholinoethyl)amino)-7-oxopyrido-[2,3-d]pyrimidin-8(7H)-yl)ethyl)-3-fluorophenyl)acrylamide;

N-(4-(2-(6-(2-chloro-3,5-dimethoxyphenyl)-2-((2-morpholinoethyl)amino)-7-oxopyrido-[2,3-d]pyrimidin-8(7H)-yl)ethyl)-2-chlorophenyl)acrylamide;

N-(4-(2-(6-(2-chloro-3,5-dimethoxyphenyl)-2-((4-isopropylpiperazin-1-ethyl)amino)-7-oxopyrido[2,3-d]pyrimidin-8(7H)-yl)ethyl)-phenyl)acylamide;

N-(4-(2-(6-(2-chloro-3,5-dimethoxyphenyl)-2-((2-((2R,6S)-2,6-dimethyl-morpholino)-ethyl)-amino)-7-oxopyrido[2,3-d]pyrimidin-8(7H)-yl)ethyl)phenyl)acrylamide;

N-(6-(2-(6-(2-chloro-3,5-dimethoxyphenyl)-7-oxo-2-(prop-2-yn-1-ylamino)pyrido-[2,3-d]-pyrimidin-8(7H)-yl)ethyl)pyridin-3-yl)acrylamide;

N-(4-(2-(6-(2-chloro-3,5-dimethoxyphenyl)-2-((2-(4-ethylpiperazin-1-yl)ethyl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-((1-hydroxy-2-methylpropan-2-yl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((1-methylpiperidin-4-yl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((2,3-dihydroxypropyl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((2-hydroxy-2-methylpropyl)-amino)-7-oxopyrido[2,3-d]pyrimidin-8(7H)-yl)ethyl)phenyl)acrylamide;

N-(4-(2-(6-(2,6-dichloro-3,5-dimethoxyphenyl)-2-((2-hydroxyethyl)amino)-7-oxo-pyrido[2,3-d]pyrimidin-8(7H)-yl)ethyl)phenyl)acrylamide;

N-(4-(2-(2-((2-(4-acetylpiperazin-1-yl)ethyl)amino)-6-(2-chloro-3,5-dimethoxy-phenyl)-7-oxopyrido[2,3-d]pyrimidin-8(7H)-yl)ethyl)phenyl)acrylamide;

N-(4-(2-(6-(2-chloro-3,5-dimethoxyphenyl)-2-((2-methyl-1-morpholinopropan-2-yl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-((2-(4-(2-hydroxy-2-methylpropyl)-piperazin-1-yl)ethyl)amino)-7-oxopyrido[2,3-d]pyrimidin-8(7H)-yl)ethyl)-phenyl)acrylamide;

N-(4-(2-(6-(2-chloro-3,5-dimethoxyphenyl)-2-((2-hydroxyethyl)amino)-7-oxopyrido[2,3-d]-pyrimidin-8(7H)-yl)ethyl)phenyl)acrylamide;

N-(4-(2-(6-(2-chloro-3,5-dimethoxyphenyl)-2-((1-methylpiperidin-4-yl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((1-methylpiperidin-4-yl)methyl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-((1,3-dihydroxypropan-2-yl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((2,3-dihydroxypropyl)amino)-7-oxo-pyrido[2,3-d]pyrimidin-8(7H)-yl)ethyl)phenyl)acrylamide;

N-(4-(2-(6-(2-chloro-3,5-dimethoxyphenyl)-2-((2-(1,1-dioxidothiomorpholino)-ethyl)amino)-7-oxopyrido[2,3-d]pyrimidin-8(7H)-yl)ethyl)phenyl)acrylamide;

N-(4-(2-(6-(2,6-dichloro-3,5-dimethoxyphenyl)-2-(((1-methylpiperidin-4-yl)-methyl)amino)-7-oxopyrido[2,3-d]pyrimidin-8(7H)-yl)ethyl)phenyl)acrylamide;

N-(4-(2-(6-(2,6-dichloro-3,5-dimethoxyphenyl)-2-((1,3-dihydroxypropan-2-yl)amino)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((1-hydroxy-2-methylpropan-2-yl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-((2-(4-(oxetan-3-yl)piperazin-1-yl)-ethyl)amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-(ethylamino)-7-oxopyrido[2,3-d]-pyrimidin-8(7H)-yl)ethyl)pyridin-3-yl)acrylamide;

N-(6-(2-(6-(2,6-dichloro-3,5-dimethoxyphenyl)-2-(isopropylamino)-7-oxopyrido[2,3-d]-pyrimidin-8(7H)-yl)ethyl)pyridin-3-yl)acrylamide;

N-(6-(2-(6-(2,6-dichloro-3,5-dimethoxyphenyl)-7-oxo-2-((tetrahydro-2H-pyran-4-yl)-amino)-pyrido[2,3-d]pyrimidin-8(7H)-yl)ethyl)pyridin-3-yl)acrylamide;

N-(4-(2-(6-(2-chloro-3,5-dimethoxyphenyl)-2-((2-((2R,6S)-2,6-dimethylpiperazin-1-yl)-ethyl)amino)-7-oxopyrido[2,3-d]pyrimidin-8(7H)-yl)ethyl)phenyl)acrylamide;

N-(4-(2-(6-(2-chloro-3,5-dimethoxyphenyl)-2-((3-hydroxy-2,2-dimethylpropyl)amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-((2-hydroxy-2-methylpropyl)-amino)-7-oxopyrido[2,3-d]pyrimidin-8(7H)-yl)ethyl)pyridin-3-yl)acrylamide;

N-(4-(2-(6-(2-chloro-3,5-dimethoxyphenyl)-2-((2-((3 S,5R)-3,5-dimethylpiperazin-1-yl)-ethyl)amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-((2-hydroxyethyl)amino)-7-oxo-pyrido[2,3-d]pyrimidin-8(7H)-yl)ethyl)pyridin-3-yl)acrylamide;

N-(6-(2-(6-(2,6-dichloro-3,5-dimethoxyphenyl)-2-((1,3-dihydroxypropan-2-yl)amino)-7-oxopyrido[2,3-d]pyrimidin-8(7H)-yl)ethyl)pyridin-3-yl)acrylamide;

N-(6-(2-(6-(2,6-dichloro-3,5-dimethoxyphenyl)-2-((2,3-dihydroxypropyl)amino)-7-oxo-pyrido[2,3-d]pyrimidin-8(7H)-yl)ethyl)pyridin-3-yl)acrylamide;

N-(4-(2-(6-(2,6-dichloro-3,5-dimethoxyphenyl)-7-oxo-2-((tetrahydro-2H-pyran-4-yl)-amino)pyrido[2,3-d]pyrimidin-8(7H)-yl)ethyl)phenyl)acrylamide;

N-(4-(2-(2-((cyclopropylmethyl)amino)-6-(2,6-dichloro-3,5-dimethoxyphenyl)-7-oxo-pyrido[2,3-d]pyrimidin-8(7H)-yl)ethyl)phenyl)acrylamide;

N-(4-(2-(6-(2,6-dichloro-3,5-dimethoxyphenyl)-2-((1,3-dihydroxy-2-methylpropan-2-yl)amino)-7-oxopyrido[2,3-d]pyrimidin-8(7H)-yl)ethyl)phenyl)acrylamide;

N-(4-(2-(6-(2,6-dichloro-3,5-dimethoxyphenyl)-2-((1-hydroxy-2-(hydroxymethyl)-butan-2-yl)-amino)-7-oxopyrido[2,3-d]pyrimidin-8(7H)-yl)ethyl)phenyl)acrylamide;

N-(4-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-((1-hydroxy-2-methylpropan-2-yl)-amino)-7-oxopyrido[2,3-d]pyrimidin-8(7H)-yl)ethyl)pyridin-3-yl)acrylamide;

N-(4-(2-(6-(2-chloro-3,5-dimethoxyphenyl)-2-((1,3-dihydroxy-2-methylpropan-2-yl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-(((4-hydroxy-1-methylpiperidin-4-yl)-methyl)-amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-((3-hydroxy-2,2-dimethylpropyl)-amino)-7-oxopyrido[2,3-d]pyrimidin-8(7H)-yl)ethyl)pyridin-3-yl)acrylamide;

N-(4-(2-(6-(2,6-dichloro-3,5-dimethoxyphenyl)-2-(((4-hydroxy-1-methylpiperidin-4-yl)-methyl)-amino)-7-oxopyrido[2,3-d]pyrimidin-8(7H)-yl)ethyl)phenyl)acrylamide;

N-(6-(2-(6-(2,6-dichloro-3,5-dimethoxyphenyl)-2-((1,3-dihydroxy-2-methylpropan-2-yl)amino)-7-oxopyrido[2,3-d]pyrimidin-8(7H)-yl)ethyl)pyridin-3-yl)acrylamide;

N-(6-(2-(6-(2,6-dichloro-3,5-dimethoxyphenyl)-2-((1-hydroxy-2-(hydroxymethyl)-butan-2-yl)amino)-7-oxopyrido[2,3-d]pyrimidin-8(7H)-yl)ethyl)pyridin-3-yl)acrylamide;

N-(6-(2-(6-(2,6-dichloro-3,5-dimethoxyphenyl)-7-oxo-2-(prop-2-yn-1-ylamino)pyrido[2,3-d]pyrimidin-8(7H)-yl)ethyl)pyridin-3-yl)acrylamide;

N-(3-((6-(2-chloro-3,5-dimethoxyphenyl)-2-((2-morpholinoethyl)amino)-7-oxopyrido[2,3-d]pyrimidin-8(7H)-yl)methyl)phenyl)acrylamide;

N-(6-(2-(6-(2-chloro-3,5-dimethoxyphenyl)-2-((cyclopropylmethyl)amino)-7-oxopyrido-[2,3-d]pyrimidin-8(7H)-yl)ethyl)pyridin-3-yl)acrylamide;

N-(6-(2-(6-(2-chloro-3,5-dimethoxyphenyl)-2-((2-hydroxyethyl)amino)-7-oxopyrido[2,3-d]pyrimidin-8(7H)-yl)ethyl)pyridin-3-yl)acrylamide;

N-(4-(2-(6-(2,6-dichloro-3,5-dimethoxyphenyl)-2-((4-methylpiperazin-1-yl)amino)-7-oxopyrido[2,3-d]pyrimidin-8(7H)-yl)ethyl)phenyl)acrylamide;

N-(4-(2-(6-(2,6-dichlorophenyl)-2-(methylamino)-7-oxopyrido[2,3-d]pyrimidin-8(7H)-yl)ethyl)phenyl)acrylamide;

N-(6-(2-(6-(2,6-dichlorophenyl)-2-(methylamino)-7-oxopyrido[2,3-d]pyrimidin-8(7H)-yl)ethyl)pyridin-3-yl)acrylamide;

N-(6-(2-(6-(2-chloro-3,5-dimethoxyphenyl)-7-oxo-2-(pyridin-2-ylamino)pyrido[2,3-d]pyrimidin-8(7H)-yl)ethyl)pyridin-3-yl)acrylamide;

N-(6-(2-(6-(2-chloro-3,5-dimethoxyphenyl)-2-((2-hydroxy-2-methylpropyl)amino)-7-oxopyrido[2,3-d]pyrimidin-8(7H)-yl)ethyl)pyridin-3-yl)acrylamide;

N-(4-(2-(6-(2-chloro-3,5-dimethoxyphenyl)-2-((2-methyl-2-morpholinopropyl)-amino)-7-oxopyrido[2,3-d]pyrimidin-8(7H)-yl)ethyl)phenyl)acrylamide;

N-(4-(2-(6-(2-chloro-3,5-dimethoxyphenyl)-2-((2-(4,4-difluoropiperidin-1-yl)ethyl)amino)-7-oxopyrido[2,3-d]pyrimidin-8(7H)-yl)ethyl)phenyl)acrylamide;

N-(4-(2-(6-(2-chloro-3,5-dimethoxyphenyl)-2-((1,4-dimethylpiperidin-4-yl)methyl)-amino)-7-oxopyrido[2,3-d]pyrimidin-8(7H)-yl)ethyl)phenyl)acrylamide;

N-(4-(1-(6-(2-chloro-3,5-dimethoxyphenyl)-2-(methylamino)-7-oxopyrido[2,3-d]-pyrimidin-8(7H)-yl)-2-methylpropan-2-yl)phenyl)acrylamide; and (E)-N-(4-(2-(6-(2,6-dichloro-3,5-dimethoxyphenyl)-2-(methylamino)-7-oxopyrido-[2,3-d]pyrimidin-8(7H)-yl)ethyl)phenyl)-4-(dimethylamino)but-2-enamide;

an individual E or Z isomer thereof; or a pharmaceutically acceptable salt of any of the above compounds.

13. A pharmaceutical composition comprising a compound of claim 1 or a pharmaceutically acceptable salt thereof; and a pharmaceutically acceptable excipient.

14. A pharmaceutical composition comprising a compound of claim 12 or a pharmaceutically acceptable salt thereof; and a pharmaceutically acceptable excipient.

* * * * *